US007442761B2

(12) United States Patent
Bogoch et al.

(10) Patent No.: US 7,442,761 B2

(45) Date of Patent: Oct. 28, 2008

(54) REPLIKIN PEPTIDES AND USES THEREOF

(76) Inventors: Samuel Bogoch, 49 E. 91st St., New York, NY (US) 10028; Elenore S. Bogoch, 49 E. 91st St., New York, NY (US) 10028

( * ) Notice: Subject to any disclaimer, the term of this patent is extended or adjusted under 35 U.S.C. 154(b) by 558 days.

(21) Appl. No.: 10/860,050

(22) Filed: Jun. 4, 2004

(65) Prior Publication Data

US 2005/0202415 A1 Sep. 15, 2005

Related U.S. Application Data

(60) Provisional application No. 60/531,686, filed on Dec. 23, 2003, provisional application No. 60/504,958, filed on Sep. 23, 2003, provisional application No. 60/476,186, filed on Jun. 6, 2003.

(51) Int. Cl.
*A61K 31/00* (2006.01)

(52) U.S. Cl. .................................................... 530/300

(58) Field of Classification Search ................. 530/300
See application file for complete search history.

(56) References Cited

U.S. PATENT DOCUMENTS

| | | | | |
|---|---|---|---|---|
| 5,104,854 | A | 4/1992 | Schlesinger et al. | |
| 5,231,167 | A | 7/1993 | Zanetti | |
| 5,280,113 | A | 1/1994 | Rademacher | |
| 5,679,352 | A | 10/1997 | Chong | |
| 5,866,690 | A | 2/1999 | Bogoch | |
| 6,023,659 | A | 2/2000 | Seilhamer | |
| 6,070,126 | A | 5/2000 | Kokolus | |
| 6,242,578 | B1 | 6/2001 | Bogoch | |
| 6,256,647 | B1 | 7/2001 | Toh | |
| 6,470,277 | B1 | 10/2002 | Chin | |
| 6,484,166 | B1 | 11/2002 | Maynard | |
| 6,638,505 | B2 | 10/2003 | Bogoch | |
| 7,267,942 | B2 * | 9/2007 | Peiris et al. | 435/5 |
| 2002/0120106 | A1 | 8/2002 | Bogoch et al. | |
| 2002/0151677 | A1 | 10/2002 | Bogoch et al. | |
| 2003/0180328 | A1 | 9/2003 | Bogoch | |
| 2003/0194414 | A1 | 10/2003 | Bogoch | |
| 2005/0271676 | A1 | 12/2005 | Sette et al. | |

FOREIGN PATENT DOCUMENTS

| | | | |
|---|---|---|---|
| EP | 0 108 564 | A1 | 5/1984 |
| IT | 98MI0874 | | 10/1999 |
| WO | 96/32106 | | 10/1996 |
| WO | WO 00/18351 | A | 4/2000 |
| WO | WO 01/04135 | A2 | 1/2001 |
| WO | 02085093 | A3 | 10/2002 |
| WO | 03005880 | A3 | 1/2003 |
| WO | 03/083058 | | 10/2003 |

OTHER PUBLICATIONS

Bogoch, S. et al., "A Checklist for Suitability of Biomarkers as Surrogate Endpoints in Chemoprevention of Breast Cancer," Journal of Cellular Biochemistry, Supplement, Boston, US, vol. 19, pp. 173-185, XP009046492, ISSN: 0733-1959, 1994.

Marra, M. et al., "The Genome Sequence of the SARS-Associated Coronavirus," Science, American Association For the Advancement of Science, US, v. 300, No. 5624, p. 1399-1404, XP002269483, ISSN: 0036-8075, May 30, 2003.

Qin, E. et al., "A Genome Sequence of Novel SARS-CoV Isolates: the Genotype, GD-Ins29, Leads to a Hypothesis of Viral Transmission in South China," Genomics Proteomics & Bioinformatics, vol. 1, No. 2, p. 101-107, XP001206098, ISSN: 1672-0229, May 2003.

Rota, P. et al., "Characterization of a Novel Coronavirus Associated with Severe Acute Respiratory Syndrome," Science, American Association for the Advancement of Science, US, v. 300, No. 5624, p. 1394-1399, XP002269482, ISSN: 0036-8075, May 30, 2003.

Tanaka, T. et al., "Efficient Generation of Antibodies to Oncoproteins by using Synthetic Peptide Antigens."Proceedings of the National Academy of Sciences of USA, National Academy of Science, Washington, D.C., US, v. 82, No. 10, p. 3400-3404, tables 1, Peptide 21, XP000113798, ISSN: 0027-8424, May 1, 1985.

Brumenu, T.D. et al., "Immunogenicity of a Contiguous T-B Synthetic Epitope of the A/PR/8/34 Influenza Virus," Journal of Virology, Jul. 1997, vol. 71, No. 7, pp. 5473-5480.

Chambers, T.M. et al., "Antigenic and molecular characterization of subtype H13 hemagglutinin of influenza virus," Database NCBI on STN, Accession No. HMIVT2, Virology, 1989, 172(1), pp. 180-188, abstract.

Gelder, C.M. et al. "Human CD4+ T-cell repertoire of responses to influenza A virus hemagglutinin after recent natural infection," Journal of Virology, Dec. 1995, vol. 69, No. 12, pp. 7497-7506A.

O'Donnell, F.T. et al., "Epidemiology and molecular characterization of co-circulating influenza A/H3N2 virus variants in children," Epidemiology and Infection, Jun. 2003, pp. 521-531, abstract, vol. 130, issue 3, The University of Texas-Houston School of Public Health, Houston, Texas.

PCT International Search Report, PCT/US2002/09240, Jan. 14, 2004, US Patent and Trademark Office, International Searching Authority, Washington, DC.

PCT International Search Report, PCT/US2002/21494, May 30, 2003, US Patent and Trademark Office, International Searching Authority, Washington, DC.

PCT International Preliminary Examination Report, PCT/US2002/21494, Nov. 26, 2004, US Patent and Trademark Office, International Preliminary Examining Authority, Washington, DC.

Brown, L. R. et al., "Recognition of the influenza hemagglutinin by Class II MHC-restricted T lymphocytes and antibodies," *Journal of Immunology*Oct. 15, 1991, pp. 2677-2684, vol. 147, No. 8, American Association of Immunologists, USA, XP02371257, ISSN: 0022-1767.

(Continued)

*Primary Examiner*—Bruce Campell
*Assistant Examiner*—Myron G. Hill
(74) *Attorney, Agent, or Firm*—Kenyon & Kenyon LLP

(57) ABSTRACT

The present invention provides a new class of peptides related to rapid replication and high human mortality, and their use in diagnosing, preventing and treating disease.

15 Claims, 14 Drawing Sheets

OTHER PUBLICATIONS

Atassi, M. Z. et al., “A novel approach for localization of the continuous protein antigenic sites by comprehensive synthetic surface scanning: Antibody and T cell activity to several influenza hemagglutinin synthetic sites,” *Immunological Communications*, 1984, pp. 539-551, vol. 13, No. 6, Marcel Dekker, Inc., XP009062995, ISSN: 0090-0877.

Carr, C. M. et al., “A spring-loaded mechanism for the conformational change of influenza hemagglutinin,” *Cell*, May 21, 1993, pp. 823-832, vol. 73, Cell Press, XP002059698, ISSN: 0092-8674.

Ben-Yedidia, T. et al., “Intranasal administration of peptide vaccine protects human/mouse radiation chimera from influenza infection,” *International Immunology*, 1999, pp. 1043-1051, XP000914818, ISSN: 0953-8178.

Schenk, S. et al., “Four recombinant isoforms of Cor a 1, the major allergen of hazel pollen, show different reactivities with allergen-specific T-lymphocyte clones,” *European Journal of Biochemistry*, 1994, pp. 717-722, vol. 224, XP002371408, ISSN: 0014-2956.

Orlando, C. et al., “A monoclonal antibody directed against the catalytic site of *Bacillus anthracis* adenylyl cyclase identifies a novel mammalian brain catalytic subunit,” *Biochemistry*, 1992, pp. 3215-3222, vol. 31, American Chemical Society, XP002371438, ISSN: 0006-2960.

Bogoch, S, et al., “Rapid replication and Replikintm structures: basis of the AMASRTest and CAVAXR,” Cancer Detection and Prevention Online, Feb. 9, 2002, XP002350483.

Gao et al., Identification and characterization of T helper epitopes in the nucleoprotein of infuenza A virus, J Immunol. Nov. 1, 1989, vol. 143, No. 9, pp. 3007-3014, see Figure 1, first line, right hand side sequence (ERR . . . ), 3008, col. 1, Viruses and Other Ag and Immunization.

Shi et al., Immunogenicity and in vitro protective efficacy of a recombinant multistage *Plasmodium falciparum* candidate vaccine. Proc. Nat'l. Acad. Sci., USA. Feb. 1999, vol. 96, No. 4, pp. 1615-1620, see Table 1 and p. 1616, Materials and Methods.

PCT International Preliminary Examination Report, PCT/US2002/09240, Feb. 5, 2004, USPTO, International Preliminary Examination Authority, Alexandria, VA, USA.

PCT Written Opinion of the International Searching Authority, PCT/US2004/017936, Apr. 7, 2005, EPO, International Searching Authority, Munich, DE.

PCT International Preliminary Report on Patentability, PCT/US2004/017936, Apr. 13, 2007, USPTO, International Preliminary Examinating Authority, Alexandria, VA, USA.

PCT Written Opinion of the International Searching Authority, PCT/US2005/014443, Apr. 12, 2006, EPO, International Searching Authority, Munich, DE.

PCT International Preliminary Report on Patentability, PCT/US2005/014443, Nov. 1, 2006, WIPO, International Bureau of WIPO, Geneva, Switzerland.

PCT International Search Report, PCT/US2006/05343, Sep. 25, 2007, USPTO, International Searching Authority, Alexandria, VA, USA.

Supplementary Partial European Search Report 99944002, Apr. 20, 2004, EPO, Munich, DE.

Supplementary Partial European Search Report 03721445.9, Dec. 12, 2006, EPO, International Searching Authority, Munich, DE.

NCBI accession # gi 75059 Jul. 16, 1999.

NCBI Listing JQ0032, residues 74-82, May 11, 2000.

NCBI Accession # AAK38298, Apr. 19, 2001.

Abrams M. B. et al., “Early Detection and Monitoring of cancer with the Anti-Malignin Antibody Test,” Cancer detection and Prevention, XX, XX, vol. 18, No. 1, 1994, pp. 65-78, XP000673180, ISSN:0361-090X.

Bogoch et al.: In vitro production of the general transformation antibody related to survival in human cancer patients; antimalignin antibody; Abstract, Cancer Detection and Prevention, 1988, vol. 12, Nos. 1-6, pp. 313-320. Database Medline on STN National Library of Medicine (Bethesda, MD, USA) No. 89025479.

Bogoch et al., “Aglyco Pathology of Viral Receptors in Dementias,” Annals of the New York Academy of Sciences, New York Academy of Sciences, New York Academy of Sciences, New York, NY, US, vol. 757, 1995, pp. 413-417, XP008003395, ISSN:0077-8923.

Bucher, D. et al., “M protein (M1) of influenza virus antigenic analysis and intracellular localization with monoclonal antibodies”, J Virol. Sep. 1989; 63(9): pp. 3622-3633.

Keppeler et al., “Elongation of thr N-acyl side chain of sialic acid in MDCK II cells inhibits influenza A virus infection,” abstract, Biochemical and Biophysical Research Communications, Dec. 18, 1998, vol. 253, No. 2. Database Medline on STN, National Library of Medicine, (Bethesda, MD, USA), No. 99097253.

Kornblith P. L. et al., “Growth-inhibitory effect of diphenylhydrantoin on murine astrocytomas,” Neurosurgery, vol. 5, No. 2, pp. 259-263 (Aug. 1979), Medline, XP002199627.

Margalit et al., “Prediction of Immunodorminant Helper T Cell Antigenic Sites From the Primary Sequence,” Jour. Of Immunology, vol. 138, 2213-2229, Apr. 1, 1987.

Pannifer, Crystal structure of the anthrax lethal factor, Nature, vol. 414, pp. 229-233 (Nov. 2001).

Rodman, Toby C. et al., “Human Immunodeficiency Virus (HIV) Tat-reactive Antibodies Present in Normal HIV-negative Sera and Depleted in HIV-positive Sera, Identification of the Epitope,” vol. 175, pp. 1247-1253, (May 1992).

Seal et al., “Elevation of Serum Protein-Bound Carbohydrates and Haptoglobin in Schizophenia,” Clinical Chemistry; Oct. 1996, vol. 12, No. 10, pp. 709-716.

Weber, E. et al., “Fine Mapping of a Peptide Sequence Containing an Antigenic Site Conserved Among Arenaviruses,” Virology, vol. 164, p. 30-38 (1988).

Yasuko, A-O, et al., “Intranasal administration of adjuvant-combined recombinant influenza virus HA vaccine protects mice from the lethal H5N1 virus infection.” Microbes and Infection, vol. 8, Issues 12-13, pp. 2706-2714, Oct. 2006.

Zhao, Neutralizing monoclonal antibody against Anthrax lethal factor inhibits intoxication in a mouse model, Human Antibodies, vol. 12, pp. 129-135 (2003).

3MOTIF - Search Instructions, 3motif in three Dimensions, article titles “Submitting a protein sequence”:http://brutlag.stanford.edu/3motif/search_instr.html) (screen shot Apr. 27, 2005 by USPTO in U.S. Appl. No. 11/116,203).

NCBI Query Tutorial “Introduction” (http://www.ncbi.nim.nih.gov/Education/BLASTinfo/query_tutorial.html) (screen shot Apr. 27, 2005 by USPTO in U.S. Appl. No. 11/116,203, filed Apr. 28, 2005).

NCBI Query Tutorial “Introduction to a BLAST Query”(http://www.ncbi.nim.nih.gov/Education.BLASTinfo/tut1.html) (screen shot Apr. 27, 2005 by USPTO in U.S. Appl. No. 11/116,203).

NCBI Query Tutorial “Setting up a BLAST Search”(http://www.ncbi.nim.nih.gov/Education.BLASTinfo/Blast_setup.html) (screen shot Apr. 27, 2005 by USPTO in U.S. Appl. No. 11/116,203).

NCBI Blast Searching, Gene Gateway - Exploring Genes and Genetic Disorders, “Sequence similarity searching searching using NCBI Blast” (http:www.ORNL.gov/sci/techresources/Himan_Genome/chromosome/blast.shtml) (screen shot Apr. 27, 2005 by USPTO in U.S. Appl. No. 11/116,203).

NCBI Accesion No. NP 74046, residues 201-219 (2000).

* cited by examiner

SPECIFICITY OF BINDING AND CYTOTOXICITY OF ANTIMALIGNIN ANTIBODY TO LEUKEMIC, BRAIN GLIOMA, AND SMALL CELL LUNG CARCINOMA CELLS

RELATION OF REPLIKIN CONCENTRATION TO PANDEMICS (P) AND EPIDEMICS (E) IN FOUR MAJOR STRAINS OF INFLUENZA VIRUS, 1902-2001

Replikin Count by Year nucleocapsid coronavirus

| Year | Accession Number - Replikin Count | No. Of Isolates per year | Mean Replikin Count per year | S.D. |
|---|---|---|---|---|
| 1962 | AAB4815713 | 1 | 3.2 | 0.0 |
| 1963 | | | | |
| 1964 | | | | |
| 1965 | | | | |
| 1967 | | | | |
| 1968 | | | | |
| 1969 | | | | |
| 1970 | P05991_21 | | | |
| 1971 | | 1 | 5.5 | 0.0 |
| 1972 | | | | |
| 1973 | | | | |
| 1974 | AAB4815714 | 1 | 3.5 | 0.0 |
| 1975 | AAB4815922 | 1 | 5.5 | 0.0 |
| 1976 | | | | |
| 1977 | | | | |
| 1978 | | | | |

FIG.10A

| | | | | |
|---|---|---|---|---|
| 1979 | | | | |
| 1980 | | | | |
| 1981 | | | | |
| 1982 | | | | |
| 1983 | A453402CAA251977CAA251987CAA254971P034162P034171P184531VHIHM11 | 8 | 1.0 | 1.3 |
| 1984 | 1010251C4AAA462202AAA464527AAA70233132AAA70235132AAA70236132AAA70237132AAA70238 132AAA70239132AAA70240132AAA70241132AAA70242132NP40829214NP040831214NP040833 214NP040834214NP 040835214NP 040836214NP 40837214NP 040838214NP 066134214NP 740 621214NP 740622214NP 740623214NP 740624214NP 740625214NP 740626214NP 740627214NP 740628214 | 38 | 3.2 | 0.5 |
| 1985 | AAA4621417AAA4622127 | 2 | 5.4 | 1.7 |
| 1986 | AAA4791421AAA4791321AAA4791621P0413421VHIHPC21 | 5 | 5.5 | 0.0 |
| 1987 | AAA429142146AAA42913146AAA42914146AAA64744146AAA66393146AAA66397146AAA66399146AAK 297381146AAK29779146AAP20417146CAAA7869717CAA7869417CAA7869917P105234P10526600IHB C4VGIHBC6 | 17 | 2.4 | 0.7 |
| 1988 | AAA427581AAA427591AAA6658323AAAB481602AAAB4816127P1264823P226541S0376221S068691VH IHAL23 | 10 | 3.7 | 2.8 |
| 1989 | A60003IIAAA4546327AAA464622CAA335212CAA335222P1513026P154222P3346911VHIV2E27 | 9 | 3.2 | 2.8 |
| 1990 | AAA464392AAA464402AAA464442AAA464452AAA464472AAA464482AAA464682AAA464692AAB4815618 B453402C453402CAA3507826CAA3985018CAA3985111CAA8084123D453402E3660723E453401F45340 1G453401H453402P184462P184472P184482P184522P184551P2441123P3292323S0803126VHIHGI22 | 30 | 2.2 | 2.5 |
| 1991 | AAB4816228CAA410669CAA450992CAA451002J011726J011744P2590911P260216P266264P3346323S 2428223VHIH7918 | 12 | 3.9 | 2.5 |
| 1992 | A4405622A4855923AAA9185530AAA9185623AAA9185720AAB2405423BAA015912CAA4724627J017252 4P36298240BI4553004700225603139 | 13 | 5.8 | 2.0 |

FIG.10B

| | | | | |
|---|---|---|---|---|
| 1993 | A453962AAC5406818AAK38656201AAK38657201AAK38658201AAK38659201AAK38660201AAK38661201CAA808551CAA808561CAA808571CAA808581CAA108591CAA809718J0219117J021952NP598309201NP598310201NP598311201NP598312201NP598333201NP598314201NP839957201NP839958201NP839959201NP839960201NP839961201NP839962201NP839963201NP839964201NP839965201NP83996201NP839967201NP839968201NP8399692010029152 | 36 | 2.5 | 1.1 |
| 1994 | B495911CAA8411121D495911S4742821 | 4 | 3.8 | 2.0 |
| 1995 | AAC5708018 | 1 | 4.4 | 0.0 |
| 1996 | AAB4750214AAB4750311AAB481551VBAC0112014BAC0115610BAC0115710BAC0115313BAC0115913BAC0116013BAC0116013BAC0116113BAC0549216BAC0349313 | 12 | 2.8 | 1.2 |
| 1997 | AAB8682170CAA7423013NP045302129NP068674129 | 4 | 2.2 | 0.9 |
| 1998 | AAC164223ACC164233AAD331042AAD390394AAD390404AAD390414AAD390424AAD390434AAD390444AAF2387123AAF2387219AAF2387326 | 12 | 4.4 | 2.3 |
| 1999 | AAF057061AAF0635216AAF1938979AAF6892681AAF6911622AAF6912321AAF6933877AAF6934970AAF9774311AAL4040685BAA836159BAA836169 | 12 | 3.1 | 1.8 |
| 2000 | AAF8241321AAG48597193AAG5397321NP073556193 | 4 | 3.9 | 1.2 |
| 2001 | AAK27168122AAK2716220AAK2716319AAK3160722AAK83362147AAK9379720AAL57313147CAC39121214CAC3930717NF150083146 | 11 | 3.9 | 1.3 |
| 2002 | AAL800367AAM7700513AAM8228019AAM8228123AAM8228219AA04604819AA04604923AA04605019AA05946427AA05947327AA0604112AA0604127AA0604133AAC604146AA04146AA0604156XP11418016 | 16 | 5.1 | 3.6 |
| 2003 | AA05943816AAP13445188AAP13814188AAP30037AAP30714188APP3204623AAP3208323AAP37024188AAP41047188BAC6532822CAD676071NP828858188P5959515188AAP3204623AAP3208323AAP37024188AAP41047188BAC6532822CAD676071NP828858188P5959515 | 13 | 3.3 | 1.6 |

FIG. 10C

SEQUENCE LISTING

<160> NUMBER OF SEQ ID NOS: 875

<210> SEQ ID NO 1
<211> LENGTH: 10
<212> TYPE: PRT
<213> ORGANISM: Homo sapiens

<400> SEQUENCE: 1

Lys Ala Gly Val Ala Phe Leu His Lys Lys
1 5 10

<210> SEQ ID NO 2
<211> LENGTH: 13
<212> TYPE: PRT
<213> ORGANISM: Saccharomyces cervisiae

<400> SEQUENCE: 2

His Ser Ile Lys Arg Glu Leu Gly Ile Ile Phe Asp Lys
1 5 10

<210> SEQ ID NO 3
<211> LENGTH: 10
<212> TYPE: PRT
<213> ORGANISM: Foot and Mouth Disease virus type O

<400> SEQUENCE: 3

His Lys Gln Lys Ile Val Ala Pro Val Lys
1 5 10

<210> SEQ ID NO 4
<211> LENGTH: 16
<212> TYPE: PRT
<213> ORGANISM: Homo sapiens

<400> SEQUENCE: 4

Tyr Lys Ala Gly Val Ala Phe Leu His Lys Lys Asn Asp Ile Asp Glu
1 5 10 15

<210> SEQ ID NO 5
<211> LENGTH: 10
<212> TYPE: PRT
<213> ORGANISM: Human immunodeficiency virus type 1

<400> SEQUENCE: 5

Lys Cys Phe Asn Cys Gly Lys Glu Gly His
1 5 10

<210> SEQ ID NO 6
<211> LENGTH: 11
<212> TYPE: PRT
<213> ORGANISM: Human immunodeficiency virus type 1

<400> SEQUENCE: 6

Lys Val Tyr Leu Ala Trp Val Pro Ala His Lys
1 5 10

<210> SEQ ID NO 7
<211> LENGTH: 10
<212> TYPE: PRT
<213> ORGANISM: Human immunodeficiency virus type 2

<400> SEQUENCE: 7

Lys Cys Trp Asn Cys Gly Lys Glu Gly His

-continued 1 5 10

<210> SEQ ID NO 8
<211> LENGTH: 11
<212> TYPE: PRT
<213> ORGANISM: Maize streak virus

<400> SEQUENCE: 8

Lys Tyr Ile Val Cys Ala Arg Glu Ala His Lys
1 5 10

<210> SEQ ID NO 9
<211> LENGTH: 17
<212> TYPE: PRT
<213> ORGANISM: Maize streak virus

<400> SEQUENCE: 9

Lys Glu Lys Lys Pro Ser Lys Asp Glu Ile Met Arg Asp Ile Ile Ser
1 5 10 15

His

<210> SEQ ID NO 10
<211> LENGTH: 9
<212> TYPE: PRT
<213> ORGANISM: Staphylococcus aureas

<400> SEQUENCE: 10

Lys Lys Glu Lys Thr Thr His Asn Lys
1 5

<210> SEQ ID NO 11
<211> LENGTH: 10
<212> TYPE: PRT
<213> ORGANISM: Bovine herpes virus 4

<400> SEQUENCE: 11

His Lys Ile Asn Ile Thr Asn Gly Gln Lys
1 5 10

<210> SEQ ID NO 12
<211> LENGTH: 10
<212> TYPE: PRT
<213> ORGANISM: Meleagrid herpesvirus 1

<400> SEQUENCE: 12

His Lys Asp Leu Tyr Arg Leu Leu Met Lys
1 5 10

<210> SEQ ID NO 13
<211> LENGTH: 15
<212> TYPE: PRT
<213> ORGANISM: Tomato yellow leaf curl virus

<400> SEQUENCE: 13

Lys Phe Arg Ile Asn Ala Lys Asn Tyr Phe Leu Thr Tyr Pro His
1 5 10 15

<210> SEQ ID NO 14
<211> LENGTH: 19
<212> TYPE: PRT
<213> ORGANISM: Tomato yellow leaf curl virus

<400> SEQUENCE: 14

Lys Asn Leu Glu Thr Pro Val Asn Lys Leu Phe Ile Arg Ile Cys Arg

-continued

```
1               5                   10                  15

Glu Phe His


<210> SEQ ID NO 15
<211> LENGTH: 14
<212> TYPE: PRT
<213> ORGANISM: Tomato yellow leaf curl virus

<400> SEQUENCE: 15

His Pro Asn Ile Gln Ala Ala Lys Ser Ser Thr Asp Val Lys
1               5                   10


<210> SEQ ID NO 16
<211> LENGTH: 19
<212> TYPE: PRT
<213> ORGANISM: Tomato yellow leaf curl virus

<400> SEQUENCE: 16

Lys Ser Ser Thr Asp Val Lys Ala Tyr Met Asp Lys Asp Gly Asp Val
1               5                   10                  15

Leu Asp His


<210> SEQ ID NO 17
<211> LENGTH: 21
<212> TYPE: PRT
<213> ORGANISM: Tomato yellow leaf curl virus

<400> SEQUENCE: 17

Lys Ala Ser Ala Leu Asn Ile Leu Arg Glu Lys Ala Pro Lys Asp Phe
1               5                   10                  15

Val Leu Gln Phe His
            20


<210> SEQ ID NO 18
<211> LENGTH: 13
<212> TYPE: PRT
<213> ORGANISM: Hepatitis C virus

<400> SEQUENCE: 18

His Tyr Pro Pro Lys Pro Gly Cys Ile Val Pro Ala Lys
1               5                   10


<210> SEQ ID NO 19
<211> LENGTH: 4
<212> TYPE: PRT
<213> ORGANISM: Homo sapiens

<400> SEQUENCE: 19

Tyr Lys Ala Gly
1


<210> SEQ ID NO 20
<211> LENGTH: 6
<212> TYPE: PRT
<213> ORGANISM: Homo sapiens

<400> SEQUENCE: 20

Tyr Lys Ala Gly Val Ala
1               5


<210> SEQ ID NO 21
<211> LENGTH: 7
<212> TYPE: PRT
```

-continued

```
<213> ORGANISM: Homo sapiens

<400> SEQUENCE: 21

Tyr Lys Ala Gly Val Ala Phe
1               5


<210> SEQ ID NO 22
<211> LENGTH: 8
<212> TYPE: PRT
<213> ORGANISM: Homo sapiens

<400> SEQUENCE: 22

Tyr Lys Ala Gly Val Ala Phe Leu
1               5


<210> SEQ ID NO 23
<211> LENGTH: 10
<212> TYPE: PRT
<213> ORGANISM: Homo sapiens

<400> SEQUENCE: 23

Ala Gly Val Ala Phe Leu His Lys Lys Asn
1               5                   10


<210> SEQ ID NO 24
<211> LENGTH: 5
<212> TYPE: PRT
<213> ORGANISM: Homo sapiens

<400> SEQUENCE: 24

Gly Val Ala Phe Leu
1               5


<210> SEQ ID NO 25
<211> LENGTH: 4
<212> TYPE: PRT
<213> ORGANISM: Homo sapiens

<400> SEQUENCE: 25

Val Ala Phe Leu
1


<210> SEQ ID NO 26
<211> LENGTH: 7
<212> TYPE: PRT
<213> ORGANISM: Homo sapiens

<400> SEQUENCE: 26

Val Ala Phe Leu His Lys Lys
1               5


<210> SEQ ID NO 27
<211> LENGTH: 7
<212> TYPE: PRT
<213> ORGANISM: Homo sapiens

<400> SEQUENCE: 27

Val Ala Phe Leu His Lys Lys
1               5


<210> SEQ ID NO 28
<211> LENGTH: 9
<212> TYPE: PRT
<213> ORGANISM: Homo sapiens
```

-continued

<400> SEQUENCE: 28

Val Ala Phe Leu His Lys Lys Asn Asp
1 5

<210> SEQ ID NO 29
<211> LENGTH: 8
<212> TYPE: PRT
<213> ORGANISM: Homo sapiens

<400> SEQUENCE: 29

Val Ala Phe His Lys Lys Asn Asp
1 5

<210> SEQ ID NO 30
<211> LENGTH: 4
<212> TYPE: PRT
<213> ORGANISM: Homo sapiens

<400> SEQUENCE: 30

Ala Phe Leu His
1

<210> SEQ ID NO 31
<211> LENGTH: 8
<212> TYPE: PRT
<213> ORGANISM: Homo sapiens

<400> SEQUENCE: 31

His Lys Lys Asn Asp Ile Asp Glu
1 5

<210> SEQ ID NO 32
<211> LENGTH: 6
<212> TYPE: PRT
<213> ORGANISM: Homo sapiens

<400> SEQUENCE: 32

Lys Lys Asn Asp Ile Asp
1 5

<210> SEQ ID NO 33
<211> LENGTH: 6
<212> TYPE: PRT
<213> ORGANISM: Homo sapiens

<400> SEQUENCE: 33

Lys Asn Asp Ile Asp Glu
1 5

<210> SEQ ID NO 34
<211> LENGTH: 8
<212> TYPE: PRT
<213> ORGANISM: Caldophera prolifera

<400> SEQUENCE: 34

Lys Ala Ser Lys Phe Thr Lys His
1 5

<210> SEQ ID NO 35
<211> LENGTH: 12
<212> TYPE: PRT
<213> ORGANISM: Isolepis prolifera

<400> SEQUENCE: 35

-continued

```
Lys Ala Gln Ala Glu Thr Gly Glu Ile Lys Gly His
1               5                   10


<210> SEQ ID NO 36
<211> LENGTH: 10
<212> TYPE: PRT
<213> ORGANISM: Schizosaccharomyces pombe

<400> SEQUENCE: 36

Lys Ser Phe Lys Tyr Pro Lys Lys His Lys
1               5                   10


<210> SEQ ID NO 37
<211> LENGTH: 10
<212> TYPE: PRT
<213> ORGANISM: Oryza sativa

<400> SEQUENCE: 37

Lys Lys Ala Tyr Gly Asn Glu Leu His Lys
1               5                   10


<210> SEQ ID NO 38
<211> LENGTH: 9
<212> TYPE: PRT
<213> ORGANISM: Penicillium marneffei

<400> SEQUENCE: 38

Lys Val Asp Ile Val Thr His Gln Lys
1               5


<210> SEQ ID NO 39
<211> LENGTH: 12
<212> TYPE: PRT
<213> ORGANISM: Discula destructiva

<400> SEQUENCE: 39

Lys Leu Glu Glu Asp Ala Ala Tyr His Arg Lys Lys
1               5                   10


<210> SEQ ID NO 40
<211> LENGTH: 17
<212> TYPE: PRT
<213> ORGANISM: Ophiostoma mitovirus 3a

<400> SEQUENCE: 40

Lys Val Ile Leu Pro Leu Arg Gly Asn Ile Lys Gly Ile Phe Phe Lys
1               5                   10                  15

His


<210> SEQ ID NO 41
<211> LENGTH: 11
<212> TYPE: PRT
<213> ORGANISM: Entamoeba invadens

<400> SEQUENCE: 41

Lys Leu Ile Leu Lys Gly Asp Leu Asn Lys His
1               5                   10


<210> SEQ ID NO 42
<211> LENGTH: 8
<212> TYPE: PRT
<213> ORGANISM: Helicobacter pylori

<400> SEQUENCE: 42
```

-continued

```
Lys Ser Val His Ala Phe Leu Lys
1               5


<210> SEQ ID NO 43
<211> LENGTH: 9
<212> TYPE: PRT
<213> ORGANISM: Legionella sp.

<400> SEQUENCE: 43

Lys Val His Phe Phe Gln Leu Lys Lys
1               5


<210> SEQ ID NO 44
<211> LENGTH: 9
<212> TYPE: PRT
<213> ORGANISM: Arabidopsis thaliana

<400> SEQUENCE: 44

Lys Asp His Asp Phe Asp Gly Asp Lys
1               5


<210> SEQ ID NO 45
<211> LENGTH: 11
<212> TYPE: PRT
<213> ORGANISM: Arabidopsis thaliana

<400> SEQUENCE: 45

Lys Met Lys Gly Leu Lys Gln Lys Lys Ala His
1               5                   10


<210> SEQ ID NO 46
<211> LENGTH: 12
<212> TYPE: PRT
<213> ORGANISM: Arabidopsis thaliana

<400> SEQUENCE: 46

Lys Glu Leu Ser Ser Thr Thr Gln Glu Lys Ser His
1               5                   10


<210> SEQ ID NO 47
<211> LENGTH: 9
<212> TYPE: PRT
<213> ORGANISM: Feline immunodeficiency syndrome virus

<400> SEQUENCE: 47

His Leu Lys Asp Tyr Lys Leu Val Lys
1               5


<210> SEQ ID NO 48
<211> LENGTH: 7
<212> TYPE: PRT
<213> ORGANISM: Rous sarcoma virus

<400> SEQUENCE: 48

Lys Lys Leu Arg His Glu Lys
1               5


<210> SEQ ID NO 49
<211> LENGTH: 7
<212> TYPE: PRT
<213> ORGANISM: Avian sarcoma virus

<400> SEQUENCE: 49

Lys Lys Leu Arg His Asp Lys
1               5
```

<210> SEQ ID NO 50
<211> LENGTH: 7
<212> TYPE: PRT
<213> ORGANISM: Homo sapiens

<400> SEQUENCE: 50

Lys Lys Leu Arg His Asp Lys
1 5

<210> SEQ ID NO 51
<211> LENGTH: 7
<212> TYPE: PRT
<213> ORGANISM: Avian sarcoma virus

<400> SEQUENCE: 51

Lys Lys Leu Arg His Glu Lys
1 5

<210> SEQ ID NO 52
<211> LENGTH: 7
<212> TYPE: PRT
<213> ORGANISM: Homo sapiens

<400> SEQUENCE: 52

Lys Lys Leu Arg His Glu Lys
1 5

<210> SEQ ID NO 53
<211> LENGTH: 8
<212> TYPE: PRT
<213> ORGANISM: Homo sapiens

<400> SEQUENCE: 53

Lys Gln Ala His Glu Leu Ala Lys
1 5

<210> SEQ ID NO 54
<211> LENGTH: 8
<212> TYPE: PRT
<213> ORGANISM: Polyamavirus sp.

<400> SEQUENCE: 54

Lys Thr His Arg Phe Ser Lys His
1 5

<210> SEQ ID NO 55
<211> LENGTH: 8
<212> TYPE: PRT
<213> ORGANISM: Sindbis virus

<400> SEQUENCE: 55

Lys Asn Leu His Glu Lys Ile Lys
1 5

<210> SEQ ID NO 56
<211> LENGTH: 9
<212> TYPE: PRT
<213> ORGANISM: Human papilloamavirus type 71

<400> SEQUENCE: 56

Lys His Arg Pro Leu Leu Gln Leu Lys
1 5

-continued

<210> SEQ ID NO 57
<211> LENGTH: 7
<212> TYPE: PRT
<213> ORGANISM: Homo sapiens

<400> SEQUENCE: 57

Lys Ser Pro Asn His Val Lys
1 5

<210> SEQ ID NO 58
<211> LENGTH: 8
<212> TYPE: PRT
<213> ORGANISM: Feline sarcoma virus

<400> SEQUENCE: 58

Lys Asn Ile His Leu Glu Lys Lys
1 5

<210> SEQ ID NO 59
<211> LENGTH: 8
<212> TYPE: PRT
<213> ORGANISM: Homo sapiens

<400> SEQUENCE: 59

Lys Asn Ile His Leu Glu Lys Lys
1 5

<210> SEQ ID NO 60
<211> LENGTH: 10
<212> TYPE: PRT
<213> ORGANISM: Polyomavirus sp.

<400> SEQUENCE: 60

Lys Pro His Leu Ala Gln Ser Leu Glu Lys
1 5 10

<210> SEQ ID NO 61
<211> LENGTH: 9
<212> TYPE: PRT
<213> ORGANISM: Polyomavirus sp.

<400> SEQUENCE: 61

Lys Gln His Arg Glu Leu Lys Asp Lys
1 5

<210> SEQ ID NO 62
<211> LENGTH: 9
<212> TYPE: PRT
<213> ORGANISM: Polyomavirus sp.

<400> SEQUENCE: 62

Lys Gln His Arg Glu Leu Lys Asp Lys
1 5

<210> SEQ ID NO 63
<211> LENGTH: 12
<212> TYPE: PRT
<213> ORGANISM: Murine acute leukemia virus

<400> SEQUENCE: 63

Lys Val Pro Val Leu Ile Ser Pro Thr Leu Lys His
1 5 10

<210> SEQ ID NO 64
<211> LENGTH: 13

-continued

<212> TYPE: PRT
<213> ORGANISM: Human T cell lymphotropic virus type 2

<400> SEQUENCE: 64

Lys Ser Leu Leu Leu Glu Val Asp Lys Asp Ile Ser His
1               5                   10

<210> SEQ ID NO 65
<211> LENGTH: 13
<212> TYPE: PRT
<213> ORGANISM: Homo sapiens

<400> SEQUENCE: 65

Lys Ala Gly Ile Thr Ile Met Val Lys Arg Glu Tyr His
1               5                   10

<210> SEQ ID NO 66
<211> LENGTH: 8
<212> TYPE: PRT
<213> ORGANISM: Homo sapiens

<400> SEQUENCE: 66

Lys Ser Gly Lys His Leu Gly Lys
1               5

<210> SEQ ID NO 67
<211> LENGTH: 9
<212> TYPE: PRT
<213> ORGANISM: Homo sapiens

<400> SEQUENCE: 67

Lys Arg Arg Glu Gln Leu Lys His Lys
1               5

<210> SEQ ID NO 68
<211> LENGTH: 10
<212> TYPE: PRT
<213> ORGANISM: Homo sapiens

<400> SEQUENCE: 68

Lys Ser Phe Glu Val Ile Lys Val Ile His
1               5                   10

<210> SEQ ID NO 69
<211> LENGTH: 8
<212> TYPE: PRT
<213> ORGANISM: Homo sapiens

<400> SEQUENCE: 69

Lys Lys Lys His Thr Val Lys Lys
1               5

<210> SEQ ID NO 70
<211> LENGTH: 9
<212> TYPE: PRT
<213> ORGANISM: Homo sapiens

<400> SEQUENCE: 70

Lys Ala Gln Lys Asp His Leu Ser Lys
1               5

<210> SEQ ID NO 71
<211> LENGTH: 10
<212> TYPE: PRT
<213> ORGANISM: Homo sapiens -continued

<400> SEQUENCE: 71

His Leu Lys Arg Val Lys Asp Leu Lys Lys
1 5 10

<210> SEQ ID NO 72
<211> LENGTH: 11
<212> TYPE: PRT
<213> ORGANISM: Homo sapiens

<400> SEQUENCE: 72

Lys Tyr Gly Ser Pro Lys His Arg Leu Ile Lys
1 5 10

<210> SEQ ID NO 73
<211> LENGTH: 13
<212> TYPE: PRT
<213> ORGANISM: Homo sapiens

<400> SEQUENCE: 73

Lys Leu Lys His Ile Leu Gly Lys Ala Arg Phe Ile Lys
1 5 10

<210> SEQ ID NO 74
<211> LENGTH: 12
<212> TYPE: PRT
<213> ORGANISM: Homo sapiens

<400> SEQUENCE: 74

Lys Gly Asp His Val Lys His Tyr Lys Ile Arg Lys
1 5 10

<210> SEQ ID NO 75
<211> LENGTH: 13
<212> TYPE: PRT
<213> ORGANISM: Homo sapiens

<400> SEQUENCE: 75

Lys Glu Lys Leu Arg Asp Val Met Val Asp Arg His Lys
1 5 10

<210> SEQ ID NO 76
<211> LENGTH: 15
<212> TYPE: PRT
<213> ORGANISM: Homo sapiens

<400> SEQUENCE: 76

Lys Leu Gln Ala Arg Gln Gln Gln Leu Leu Lys Lys Ile Glu His
1 5 10 15

<210> SEQ ID NO 77
<211> LENGTH: 14
<212> TYPE: PRT
<213> ORGANISM: Homo sapiens

<400> SEQUENCE: 77

Lys Lys Gly Asn Arg Val Ser Pro Thr Met Lys Val Thr His
1 5 10

<210> SEQ ID NO 78
<211> LENGTH: 9
<212> TYPE: PRT
<213> ORGANISM: Homo sapiens

<400> SEQUENCE: 78

-continued

Lys Glu Ile Pro Leu His Phe Arg Lys
1 5

<210> SEQ ID NO 79
<211> LENGTH: 8
<212> TYPE: PRT
<213> ORGANISM: Homo sapiens

<400> SEQUENCE: 79

Lys Lys Lys Pro His Ile Lys Lys
1 5

<210> SEQ ID NO 80
<211> LENGTH: 9
<212> TYPE: PRT
<213> ORGANISM: Homo sapiens

<400> SEQUENCE: 80

Lys Thr Arg His Asp Pro Leu Ala Lys
1 5

<210> SEQ ID NO 81
<211> LENGTH: 10
<212> TYPE: PRT
<213> ORGANISM: Homo sapiens

<400> SEQUENCE: 81

Lys His His Pro Lys Asp Asn Leu Ile Lys
1 5 10

<210> SEQ ID NO 82
<211> LENGTH: 10
<212> TYPE: PRT
<213> ORGANISM: Homo sapiens

<400> SEQUENCE: 82

Lys His Lys Arg Lys Lys Phe Arg Gln Lys
1 5 10

<210> SEQ ID NO 83
<211> LENGTH: 10
<212> TYPE: PRT
<213> ORGANISM: Homo sapiens

<400> SEQUENCE: 83

Lys Ala Gly Val Ala Phe Leu His Lys Lys
1 5 10

<210> SEQ ID NO 84
<211> LENGTH: 10
<212> TYPE: PRT
<213> ORGANISM: Homo sapiens

<400> SEQUENCE: 84

Lys His Lys Arg Lys Lys Phe Arg Gln Lys
1 5 10

<210> SEQ ID NO 85
<211> LENGTH: 10
<212> TYPE: PRT
<213> ORGANISM: Homo sapiens

<400> SEQUENCE: 85

Lys Lys Lys Ser Lys Lys His Lys Asp Lys

-continued

```
1               5                   10


<210> SEQ ID NO 86
<211> LENGTH: 11
<212> TYPE: PRT
<213> ORGANISM: Homo sapiens

<400> SEQUENCE: 86

His Lys Ser Glu Lys Pro Ala Leu Pro Arg Lys
1               5                   10


<210> SEQ ID NO 87
<211> LENGTH: 14
<212> TYPE: PRT
<213> ORGANISM: Homo sapiens

<400> SEQUENCE: 87

Lys Lys Lys Lys Pro Ser Arg Leu Lys Gly Asp Asn Glu Lys
1               5                   10


<210> SEQ ID NO 88
<211> LENGTH: 16
<212> TYPE: PRT
<213> ORGANISM: Homo sapiens

<400> SEQUENCE: 88

Lys Thr Lys Lys Gly Asn Arg Val Ser Pro Thr Met Lys Val Thr His
1               5                   10                  15


<210> SEQ ID NO 89
<211> LENGTH: 18
<212> TYPE: PRT
<213> ORGANISM: Homo sapiens

<400> SEQUENCE: 89

Lys His Lys Glu Lys Met Ser Lys Asp Gly Lys Lys Lys Lys Lys Lys
1               5                   10                  15

Ser Lys


<210> SEQ ID NO 90
<211> LENGTH: 9
<212> TYPE: PRT
<213> ORGANISM: Bacillus anthracis

<400> SEQUENCE: 90

Lys Ile His Leu Ile Ser Val Lys Lys
1               5


<210> SEQ ID NO 91
<211> LENGTH: 10
<212> TYPE: PRT
<213> ORGANISM: Bacillus anthracis

<400> SEQUENCE: 91

His Val Lys Lys Glu Lys Glu Lys Asn Lys
1               5                   10


<210> SEQ ID NO 92
<211> LENGTH: 9
<212> TYPE: PRT
<213> ORGANISM: Bacillus anthracis

<400> SEQUENCE: 92

Lys His Ile Val Lys Ile Glu Val Lys
```

-continued

```
1               5


<210> SEQ ID NO 93
<211> LENGTH: 16
<212> TYPE: PRT
<213> ORGANISM: Bacillus anthracis

<400> SEQUENCE: 93

Lys Lys Lys Lys Ile Lys Asp Ile Tyr Gly Lys Asp Ala Leu Leu His
1               5                   10                  15


<210> SEQ ID NO 94
<211> LENGTH: 8
<212> TYPE: PRT
<213> ORGANISM: Bacillus anthracis

<400> SEQUENCE: 94

Lys Trp Glu Lys Ile Lys Gln His
1               5


<210> SEQ ID NO 95
<211> LENGTH: 18
<212> TYPE: PRT
<213> ORGANISM: Bacillus anthracis

<400> SEQUENCE: 95

Lys Lys Leu Gln Ile Pro Pro Pro Ile Glu Pro Lys Lys Asp Asp Ile
1               5                   10                  15

Ile His


<210> SEQ ID NO 96
<211> LENGTH: 31
<212> TYPE: PRT
<213> ORGANISM: Bacillus anthracis

<400> SEQUENCE: 96

His Asn Arg Tyr Ala Ser Asn Ile Val Glu Ser Ala Tyr Leu Leu Ile
1               5                   10                  15

Leu Asn Glu Trp Lys Asn Asn Ile Gln Ser Asp Leu Ile Lys Lys
            20                  25                  30


<210> SEQ ID NO 97
<211> LENGTH: 24
<212> TYPE: PRT
<213> ORGANISM: Bacillus anthracis

<400> SEQUENCE: 97

His Ala Val Asp Asp Tyr Ala Gly Tyr Leu Leu Asp Lys Asn Gln Ser
1               5                   10                  15

Asp Leu Val Thr Asn Ser Lys Lys
            20


<210> SEQ ID NO 98
<211> LENGTH: 13
<212> TYPE: PRT
<213> ORGANISM: Bacillus anthracis

<400> SEQUENCE: 98

His Ala Glu Arg Leu Lys Val Gln Lys Asn Ala Pro Lys
1               5                   10


<210> SEQ ID NO 99
<211> LENGTH: 10
```

-continued

<212> TYPE: PRT
<213> ORGANISM: Smallpox Virus

<400> SEQUENCE: 99

Lys His Tyr Asn Asn Ile Thr Trp Tyr Lys
1 5 10

<210> SEQ ID NO 100
<211> LENGTH: 12
<212> TYPE: PRT
<213> ORGANISM: Smallpox Virus

<400> SEQUENCE: 100

Lys Tyr Ser Gln Thr Gly Lys Glu Leu Ile Ile His
1 5 10

<210> SEQ ID NO 101
<211> LENGTH: 17
<212> TYPE: PRT
<213> ORGANISM: Smallpox Virus

<400> SEQUENCE: 101

His Tyr Asp Asp Val Arg Ile Lys Asn Asp Ile Val Val Ser Arg Cys
1 5 10 15

Lys

<210> SEQ ID NO 102
<211> LENGTH: 11
<212> TYPE: PRT
<213> ORGANISM: Smallpox Virus

<400> SEQUENCE: 102

His Arg Phe Lys Leu Ile Leu Asp Ser Lys Ile
1 5 10

<210> SEQ ID NO 103
<211> LENGTH: 11
<212> TYPE: PRT
<213> ORGANISM: Smallpox Virus

<400> SEQUENCE: 103

Lys Glu Arg Gly His Asn Tyr Tyr Phe Glu Lys
1 5 10

<210> SEQ ID NO 104
<211> LENGTH: 8
<212> TYPE: PRT
<213> ORGANISM: Influenza A virus

<400> SEQUENCE: 104

Lys Ser His Phe Ala Asn Leu Lys
1 5

<210> SEQ ID NO 105
<211> LENGTH: 11
<212> TYPE: PRT
<213> ORGANISM: Influenza A virus

<400> SEQUENCE: 105

Lys Ser His Phe Ala Asn Leu Lys Gly Thr Lys
1 5 10

<210> SEQ ID NO 106
<211> LENGTH: 19

-continued

<212> TYPE: PRT
<213> ORGANISM: Influenza A virus

<400> SEQUENCE: 106

Lys Ser His Phe Ala Asn Leu Lys Gly Thr Lys Thr Arg Gly Lys Leu
1 5 10 15

Cys Pro Lys

<210> SEQ ID NO 107
<211> LENGTH: 9
<212> TYPE: PRT
<213> ORGANISM: Influenza A virus

<400> SEQUENCE: 107

His Glu Lys Tyr Gly Gly Leu Asn Lys
1 5

<210> SEQ ID NO 108
<211> LENGTH: 11
<212> TYPE: PRT
<213> ORGANISM: Influenza A virus

<400> SEQUENCE: 108

His Glu Lys Tyr Gly Gly Leu Asn Lys Ser Lys
1 5 10

<210> SEQ ID NO 109
<211> LENGTH: 20
<212> TYPE: PRT
<213> ORGANISM: Influenza A virus

<400> SEQUENCE: 109

His Glu Lys Tyr Gly Gly Leu Asn Lys Ser Lys Pro Tyr Tyr Thr Gly
1 5 10 15

Glu His Ala Lys
20

<210> SEQ ID NO 110
<211> LENGTH: 13
<212> TYPE: PRT
<213> ORGANISM: Influenza A virus

<400> SEQUENCE: 110

His Ala Lys Ala Ile Gly Asn Cys Pro Ile Trp Val Lys
1 5 10

<210> SEQ ID NO 111
<211> LENGTH: 23
<212> TYPE: PRT
<213> ORGANISM: Influenza A virus

<400> SEQUENCE: 111

His Ala Lys Ala Ile Gly Asn Cys Pro Ile Trp Val Lys Thr Pro Leu
1 5 10 15

Lys Leu Ala Asn Gly Thr Lys
20

<210> SEQ ID NO 112
<211> LENGTH: 29
<212> TYPE: PRT
<213> ORGANISM: Influenza A virus

<400> SEQUENCE: 112

-continued

His Ala Lys Ala Ile Gly Asn Cys Pro Ile Trp Val Lys Thr Pro Leu
1 5 10 15

Lys Leu Ala Asn Gly Thr Lys Tyr Arg Pro Pro Ala Lys
20 25

<210> SEQ ID NO 113
<211> LENGTH: 32
<212> TYPE: PRT
<213> ORGANISM: Influenza A virus

<400> SEQUENCE: 113

His Ala Lys Ala Ile Gly Asn Cys Pro Ile Trp Val Lys Thr Pro Leu
1 5 10 15

Lys Leu Ala Asn Gly Thr Lys Tyr Arg Pro Pro Ala Lys Leu Leu Lys
20 25 30

<210> SEQ ID NO 114
<211> LENGTH: 13
<212> TYPE: PRT
<213> ORGANISM: Influenza A virus

<400> SEQUENCE: 114

His Phe Ala Asn Leu Lys Gly Thr Lys Thr Arg Gly Lys
1 5 10

<210> SEQ ID NO 115
<211> LENGTH: 17
<212> TYPE: PRT
<213> ORGANISM: Influenza A virus

<400> SEQUENCE: 115

His Phe Ala Asn Leu Lys Gly Thr Lys Thr Arg Gly Lys Leu Cys Pro
1 5 10 15

Lys

<210> SEQ ID NO 116
<211> LENGTH: 16
<212> TYPE: PRT
<213> ORGANISM: Influenza A virus

<400> SEQUENCE: 116

His Ser Asp Asn Glu Ile Gln Met Val Lys Leu Tyr Gly Asp Ser Lys
1 5 10 15

<210> SEQ ID NO 117
<211> LENGTH: 21
<212> TYPE: PRT
<213> ORGANISM: Influenza A virus

<400> SEQUENCE: 117

His Ser Asp Asn Glu Ile Gln Asp Lys Met Val Lys Leu Tyr Gly Asp
1 5 10 15

Ser Lys Pro Gln Lys
20

<210> SEQ ID NO 118
<211> LENGTH: 19
<212> TYPE: PRT
<213> ORGANISM: Influenza A virus

<400> SEQUENCE: 118

His Ser Asp Asn Glu Ile Gln Met Val Lys Leu Tyr Gly Asp Ser Lys
1 5 10 15

-continued

Pro Gln Lys

<210> SEQ ID NO 119
<211> LENGTH: 9
<212> TYPE: PRT
<213> ORGANISM: Influenza A virus
<220> FEATURE:
<221> NAME/KEY: misc_feature
<222> LOCATION: (2).(2)
<223> OTHER INFORMATION: Xaa can be Ala or Val

<400> SEQUENCE: 119

Lys Xaa Ser Ile Leu His Glu Val Lys
1 5

<210> SEQ ID NO 120
<211> LENGTH: 15
<212> TYPE: PRT
<213> ORGANISM: Influenza A virus

<400> SEQUENCE: 120

Lys Cys Thr Gly Thr Ile Pro Ser Ala Lys Ala Ser Ile Leu His
1 5 10 15

<210> SEQ ID NO 121
<211> LENGTH: 18
<212> TYPE: PRT
<213> ORGANISM: Influenza A virus

<400> SEQUENCE: 121

Lys Cys Thr Gly Thr Ile Pro Ser Ala Lys Ala Ser Ile Leu His Glu
1 5 10 15

Val Lys

<210> SEQ ID NO 122
<211> LENGTH: 16
<212> TYPE: PRT
<213> ORGANISM: Influenza A virus

<400> SEQUENCE: 122

Lys Tyr Gly Gly Leu Asn Lys Ser Lys Pro Tyr Tyr Thr Gly Glu His
1 5 10 15

<210> SEQ ID NO 123
<211> LENGTH: 26
<212> TYPE: PRT
<213> ORGANISM: Influenza A virus

<400> SEQUENCE: 123

Lys Val Trp Cys Ala Ser Gly Arg Ser Lys Val Ile Lys Gly Ser Leu
1 5 10 15

Pro Leu Ile Gly Glu Ala Asp Cys Leu His
20 25

<210> SEQ ID NO 124
<211> LENGTH: 10
<212> TYPE: PRT
<213> ORGANISM: Influenza A virus

<400> SEQUENCE: 124

Lys Pro Tyr Tyr Thr Gly Glu His Ala Lys
1 5 10

-continued

<210> SEQ ID NO 125
<211> LENGTH: 18
<212> TYPE: PRT
<213> ORGANISM: Influenza A virus

<400> SEQUENCE: 125

```
Lys Cys Met Gly Thr Ile Pro Ser Ala Lys Ala Ser Ile Leu His Glu
1               5                   10                  15

Val Lys
```

<210> SEQ ID NO 126
<211> LENGTH: 15
<212> TYPE: PRT
<213> ORGANISM: Influenza A virus

<400> SEQUENCE: 126

```
His Asn Val Ile Asn Ala Glu Lys Ala Pro Gly Gly Pro Tyr Lys
1               5                   10                  15
```

<210> SEQ ID NO 127
<211> LENGTH: 16
<212> TYPE: PRT
<213> ORGANISM: Influenza A virus

<400> SEQUENCE: 127

```
His Ser Asp Asn Glu Thr Gln Met Ala Lys Leu Tyr Gly Asp Ser Lys
1               5                   10                  15
```

<210> SEQ ID NO 128
<211> LENGTH: 18
<212> TYPE: PRT
<213> ORGANISM: Influenza A virus

<400> SEQUENCE: 128

```
His Gly Val Ala Val Ala Ala Asp Leu Lys Ser Thr Gln Glu Ala Ile
1               5                   10                  15

Asn Lys
```

<210> SEQ ID NO 129
<211> LENGTH: 29
<212> TYPE: PRT
<213> ORGANISM: Influenza A virus

<400> SEQUENCE: 129

```
His Gly Val Ala Val Ala Ala Asp Leu Lys Ser Thr Gln Glu Ala Ile
1               5                   10                  15

Asn Lys Asp Thr Ile Ser Thr Gln Glu Ala Ile Asn Lys
            20                  25
```

<210> SEQ ID NO 130
<211> LENGTH: 21
<212> TYPE: PRT
<213> ORGANISM: Influenza A virus

<400> SEQUENCE: 130

```
Lys Leu Tyr Gly Asp Ser Lys Pro Gln Lys Phe Thr Ser Ser Ala Asn
1               5                   10                  15

Gly Val Thr Thr His
            20
```

<210> SEQ ID NO 131
<211> LENGTH: 19
<212> TYPE: PRT

-continued

<213> ORGANISM: Influenza A virus

<400> SEQUENCE: 131

His Ser Asp Asn Glu Thr Gln Met Ala Lys Leu Tyr Gly Asp Ser Lys
1 5 10 15

Pro Gln Lys

<210> SEQ ID NO 132
<211> LENGTH: 13
<212> TYPE: PRT
<213> ORGANISM: Influenza A virus

<400> SEQUENCE: 132

His Phe Ala Asn Leu Lys Gly Thr Gln Thr Arg Gly Lys
1 5 10

<210> SEQ ID NO 133
<211> LENGTH: 12
<212> TYPE: PRT
<213> ORGANISM: Influenza A virus

<400> SEQUENCE: 133

Lys Pro Arg Ser Ala Leu Lys Cys Lys Gly Phe His
1 5 10

<210> SEQ ID NO 134
<211> LENGTH: 22
<212> TYPE: PRT
<213> ORGANISM: Influenza A virus
<220> FEATURE:
<221> NAME/KEY: misc_feature
<222> LOCATION: (15)..(15)
<223> OTHER INFORMATION: Xaa can be Gly or Ala

<400> SEQUENCE: 134

Lys Ser Lys Pro Tyr Tyr Thr Gly Glu His Ala Lys Ala Ile Xaa Asn
1 5 10 15

Cys Pro Ile Trp Val Lys
20

<210> SEQ ID NO 135
<211> LENGTH: 16
<212> TYPE: PRT
<213> ORGANISM: Influenza virus
<220> FEATURE:
<221> NAME/KEY: misc_feature
<222> LOCATION: (3)..(3)
<223> OTHER INFORMATION: Xaa can be Val or Ile
<220> FEATURE:
<221> NAME/KEY: misc_feature
<222> LOCATION: (13)..(13)
<223> OTHER INFORMATION: Xaa can be Arg or Lys
<220> FEATURE:
<221> NAME/KEY: misc_feature
<222> LOCATION: (14)..(14)
<223> OTHER INFORMATION: Xaa can be Ser or Thr
<220> FEATURE:
<221> NAME/KEY: misc_feature
<222> LOCATION: (15)..(15)
<223> OTHER INFORMATION: Xaa can be Thr or Ala

<400> SEQUENCE: 135

His Pro Xaa Thr Ile Gly Glu Cys Pro Lys Tyr Val Xaa Xaa Xaa Lys
1 5 10 15

<210> SEQ ID NO 136
<211> LENGTH: 21

-continued

<212> TYPE: PRT
<213> ORGANISM: Influenza virus
<220> FEATURE:
<221> NAME/KEY: misc_feature
<222> LOCATION: (10)..(10)
<223> OTHER INFORMATION: Xaa can be Glu or Gly
<220> FEATURE:
<221> NAME/KEY: misc_feature
<222> LOCATION: (13)..(13)
<223> OTHER INFORMATION: Xaa can be Lys or Arg
<220> FEATURE:
<221> NAME/KEY: misc_feature
<222> LOCATION: (14)..(14)
<223> OTHER INFORMATION: Xaa can be Asn or Ser
<220> FEATURE:
<221> NAME/KEY: misc_feature
<222> LOCATION: (17)..(17)
<223> OTHER INFORMATION: Xaa can be Lys or Arg

<400> SEQUENCE: 136

```
His Asp Ser Asn Val Lys Asn Leu Tyr Xaa Lys Val Xaa Xaa Gln Leu
1               5                   10                  15

Xaa Asn Asn Ala Lys
            20
```

<210> SEQ ID NO 137
<211> LENGTH: 17
<212> TYPE: PRT
<213> ORGANISM: Influenza virus
<220> FEATURE:
<221> NAME/KEY: misc_feature
<222> LOCATION: (10)..(10)
<223> OTHER INFORMATION: Xaa can be Glu or Gly
<220> FEATURE:
<221> NAME/KEY: misc_feature
<222> LOCATION: (13)..(13)
<223> OTHER INFORMATION: Xaa can be Lys or Arg
<220> FEATURE:
<221> NAME/KEY: misc_feature
<222> LOCATION: (14)..(14)
<223> OTHER INFORMATION: Xaa can be Asn or Ser

<400> SEQUENCE: 137

```
His Asp Ser Asn Val Lys Asn Leu Tyr Xaa Lys Val Xaa Xaa Gln Leu
1               5                   10                  15

Lys
```

<210> SEQ ID NO 138
<211> LENGTH: 36
<212> TYPE: PRT
<213> ORGANISM: Influenza virus
<220> FEATURE:
<221> NAME/KEY: misc_feature
<222> LOCATION: (4)..(5)
<223> OTHER INFORMATION: Xaas can be Asn Asn or Asp Asp
<220> FEATURE:
<221> NAME/KEY: misc_feature
<222> LOCATION: (6)..(6)
<223> OTHER INFORMATION: Xaa can be Ala, Thr or Glu
<220> FEATURE:
<221> NAME/KEY: misc_feature
<222> LOCATION: (12)..(12)
<223> OTHER INFORMATION: Xaa can be Arg or Lys
<220> FEATURE:
<221> NAME/KEY: misc_feature
<222> LOCATION: (31)..(31)
<223> OTHER INFORMATION: Xaa can be Glu or Lys

<400> SEQUENCE: 138

```
His Lys Cys Xaa Xaa Xaa Cys Met Glu Ser Val Xaa Asn Gly Thr Tyr
1               5                   10                  15
```

-continued

```
Asp Tyr Pro Lys Tyr Ser Glu Glu Ser Lys Leu Asn Arg Glu Xaa Ile
            20                  25                  30

Asp Gly Val Lys
        35


<210> SEQ ID NO 139
<211> LENGTH: 26
<212> TYPE: PRT
<213> ORGANISM: Influenza virus
<220> FEATURE:
<221> NAME/KEY: misc_feature
<222> LOCATION: (4)..(5)
<223> OTHER INFORMATION: Xaas can be Asn Asn or Asp Asp
<220> FEATURE:
<221> NAME/KEY: misc_feature
<222> LOCATION: (6)..(6)
<223> OTHER INFORMATION: Xaa can be Ala, Thr or Glu
<220> FEATURE:
<221> NAME/KEY: misc_feature
<222> LOCATION: (12)..(12)
<223> OTHER INFORMATION: Xaa can be Arg or Lys

<400> SEQUENCE: 139

His Lys Cys Xaa Xaa Xaa Cys Met Glu Ser Val Xaa Asn Gly Thr Tyr
1               5                   10                  15

Asp Tyr Pro Lys Tyr Ser Glu Glu Ser Lys
            20                  25


<210> SEQ ID NO 140
<211> LENGTH: 50
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Glu or Gly
<220> FEATURE:
<221> NAME/KEY: misc_feature
<222> LOCATION: (21)..(21)
<223> OTHER INFORMATION: Xaa can be Asp or Asn

<400> SEQUENCE: 140

His Gln Asn Xaa Gln Gly Ser Gly Tyr Ala Ala Asp Gln Lys Ser Thr
1               5                   10                  15

Gln Asn Ala Ile Xaa Gly Ile Thr Asn Lys Val Asn Ser Val Ile Glu
            20                  25                  30

Lys Met Asn Thr Gln Phe Thr Ala Val Gly Lys Glu Phe Asn Lys Leu
        35                  40                  45

Glu Lys
    50


<210> SEQ ID NO 141
<211> LENGTH: 33
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Glu or Gly
<220> FEATURE:
<221> NAME/KEY: misc_feature
<222> LOCATION: (21)..(21)
<223> OTHER INFORMATION: Xaa can be Asp or Asn

<400> SEQUENCE: 141

His Gln Asn Xaa Gln Gly Ser Gly Tyr Ala Ala Asp Gln Lys Ser Thr
1               5                   10                  15
```

-continued

```
Gln Asn Ala Ile Xaa Gly Ile Thr Asn Lys Val Asn Ser Val Ile Glu
            20                  25                  30

Lys


<210> SEQ ID NO 142
<211> LENGTH: 26
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Glu or Gly
<220> FEATURE:
<221> NAME/KEY: misc_feature
<222> LOCATION: (21)..(21)
<223> OTHER INFORMATION: Xaa can be Asp or Asn

<400> SEQUENCE: 142

His Gln Asn Xaa Gln Gly Ser Gly Tyr Ala Ala Asp Gln Lys Ser Thr
1               5                   10                  15

Gln Asn Ala Ile Xaa Gly Ile Thr Asn Lys
            20                  25


<210> SEQ ID NO 143
<211> LENGTH: 14
<212> TYPE: PRT
<213> ORGANISM: Influenza virus

<400> SEQUENCE: 143

Lys Phe Glu Ile Phe Pro Lys Thr Ser Ser Trp Pro Asn His
1               5                   10


<210> SEQ ID NO 144
<211> LENGTH: 27
<212> TYPE: PRT
<213> ORGANISM: Influenza virus
<220> FEATURE:
<221> NAME/KEY: misc_feature
<222> LOCATION: (3)..(3)
<223> OTHER INFORMATION: Xaa can be Asn, Ser or Thr
<220> FEATURE:
<221> NAME/KEY: misc_feature
<222> LOCATION: (9)..(9)
<223> OTHER INFORMATION: Xaa can be Asn or Ser
<220> FEATURE:
<221> NAME/KEY: misc_feature
<222> LOCATION: (13)..(13)
<223> OTHER INFORMATION: Xaa can be Val or Thr

<400> SEQUENCE: 144

Lys Gly Xaa Ser Tyr Pro Lys Leu Xaa Lys Ser Tyr Xaa Asn Asn Lys
1               5                   10                  15

Gly Lys Glu Val Leu Val Leu Trp Gly Val His
            20                  25


<210> SEQ ID NO 145
<211> LENGTH: 18
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Val or Thr

<400> SEQUENCE: 145

Lys Ser Tyr Xaa Asn Asn Lys Gly Lys Glu Val Leu Val Leu Trp Gly
1               5                   10                  15
```

-continued

Val His

<210> SEQ ID NO 146
<211> LENGTH: 36
<212> TYPE: PRT
<213> ORGANISM: Influenza virus

<400> SEQUENCE: 146

His Lys Cys Asn Asn Glu Cys Met Glu Ser Val Lys Asn Gly Thr Tyr
1 5 10 15

Asp Tyr Pro Lys Tyr Ser Glu Glu Ser Lys Leu Asn Arg Glu Lys Ile
20 25 30

Asp Gly Val Lys
35

<210> SEQ ID NO 147
<211> LENGTH: 26
<212> TYPE: PRT
<213> ORGANISM: Influenza virus

<400> SEQUENCE: 147

His Lys Cys Asn Asn Glu Cys Met Glu Ser Val Lys Asn Gly Thr Tyr
1 5 10 15

Asp Tyr Pro Lys Tyr Ser Glu Glu Ser Lys
20 25

<210> SEQ ID NO 148
<211> LENGTH: 20
<212> TYPE: PRT
<213> ORGANISM: Influenza virus

<400> SEQUENCE: 148

His Lys Cys Asn Asn Glu Cys Met Glu Ser Val Lys Asn Gly Thr Tyr
1 5 10 15

Asp Tyr Pro Lys
20

<210> SEQ ID NO 149
<211> LENGTH: 12
<212> TYPE: PRT
<213> ORGANISM: Influenza virus

<400> SEQUENCE: 149

His Lys Cys Asn Asn Glu Cys Met Glu Ser Val Lys
1 5 10

<210> SEQ ID NO 150
<211> LENGTH: 34
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Lys or Arg
<220> FEATURE:
<221> NAME/KEY: misc_feature
<222> LOCATION: (16)..(16)
<223> OTHER INFORMATION: Xaa can be Glu or Gly

<400> SEQUENCE: 150

His Asn Gly Lys Ser Ser Phe Tyr Xaa Asn Leu Leu Trp Leu Thr Xaa
1 5 10 15

Lys Asn Gly Leu Tyr Pro Asn Leu Ser Lys Ser Tyr Val Asn Asn Lys
20 25 30

-continued

Glu Lys

<210> SEQ ID NO 151
<211> LENGTH: 32
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Lys or Arg
<220> FEATURE:
<221> NAME/KEY: misc_feature
<222> LOCATION: (16)..(16)
<223> OTHER INFORMATION: Xaa can be Glu or Gly

<400> SEQUENCE: 151

His Asn Gly Lys Ser Ser Phe Tyr Xaa Asn Leu Leu Trp Leu Thr Xaa
1 5 10 15

Lys Asn Gly Leu Tyr Pro Asn Leu Ser Lys Ser Tyr Val Asn Asn Lys
20 25 30

<210> SEQ ID NO 152
<211> LENGTH: 26
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Lys or Arg
<220> FEATURE:
<221> NAME/KEY: misc_feature
<222> LOCATION: (16)..(16)
<223> OTHER INFORMATION: Xaa can be Glu or Gly

<400> SEQUENCE: 152

His Asn Gly Lys Ser Ser Phe Tyr Xaa Asn Leu Leu Trp Leu Thr Xaa
1 5 10 15

Lys Asn Gly Leu Tyr Pro Asn Leu Ser Lys
20 25

<210> SEQ ID NO 153
<211> LENGTH: 17
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Lys or Arg
<220> FEATURE:
<221> NAME/KEY: misc_feature
<222> LOCATION: (16)..(16)
<223> OTHER INFORMATION: Xaa can be Glu or Gly

<400> SEQUENCE: 153

His Asn Gly Lys Ser Ser Phe Tyr Xaa Asn Leu Leu Trp Leu Thr Xaa
1 5 10 15

Lys

<210> SEQ ID NO 154
<211> LENGTH: 40
<212> TYPE: PRT
<213> ORGANISM: Influenza virus

<400> SEQUENCE: 154

Lys Ser Ser Phe Tyr Lys Asn Leu Leu Trp Leu Thr Glu Lys Asn Gly
1 5 10 15

-continued

```
Leu Tyr Pro Asn Leu Ser Lys Ser Tyr Val Asn Asn Lys Glu Lys Glu
            20                  25                  30

Val Leu Val Leu Trp Gly Val His
        35                  40


<210> SEQ ID NO 155
<211> LENGTH: 35
<212> TYPE: PRT
<213> ORGANISM: Influenza virus

<400> SEQUENCE: 155

Lys Asn Leu Leu Trp Leu Thr Glu Lys Asn Gly Leu Tyr Pro Asn Leu
1               5                   10                  15

Ser Lys Ser Tyr Val Asn Asn Lys Glu Lys Glu Val Leu Val Leu Trp
            20                  25                  30

Gly Val His
        35


<210> SEQ ID NO 156
<211> LENGTH: 27
<212> TYPE: PRT
<213> ORGANISM: Influenza virus

<400> SEQUENCE: 156

Lys Asn Gly Leu Tyr Pro Asn Leu Ser Lys Ser Tyr Val Asn Asn Lys
1               5                   10                  15

Glu Lys Glu Val Leu Val Leu Trp Gly Val His
            20                  25


<210> SEQ ID NO 157
<211> LENGTH: 18
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Val or Ala

<400> SEQUENCE: 157

Lys Ser Tyr Xaa Asn Asn Lys Glu Lys Glu Val Leu Val Leu Trp Gly
1               5                   10                  15

Val His


<210> SEQ ID NO 158
<211> LENGTH: 12
<212> TYPE: PRT
<213> ORGANISM: Influenza virus

<400> SEQUENCE: 158

Lys Glu Ser Ser Trp Pro Asn His Thr Val Thr Lys
1               5                   10


<210> SEQ ID NO 159
<211> LENGTH: 44
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Thr or Asn

<400> SEQUENCE: 159

His Glu Thr Xaa Lys Gly Val Thr Ala Ala Cys Pro Tyr Ala Gly Ala
1               5                   10                  15
```

-continued

```
Ser Ser Phe Tyr Arg Asn Leu Leu Trp Leu Val Lys Lys Glu Asn Ser
            20                  25                  30

Tyr Pro Lys Leu Ser Lys Ser Tyr Val Asn Asn Lys
        35                  40


<210> SEQ ID NO 160
<211> LENGTH: 38
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Thr or Asn

<400> SEQUENCE: 160

His Glu Thr Xaa Lys Gly Val Thr Ala Ala Cys Pro Tyr Ala Gly Ala
1               5                   10                  15

Ser Ser Phe Tyr Arg Asn Leu Leu Trp Leu Val Lys Lys Glu Asn Ser
            20                  25                  30

Tyr Pro Lys Leu Ser Lys
        35


<210> SEQ ID NO 161
<211> LENGTH: 22
<212> TYPE: PRT
<213> ORGANISM: Influenza virus

<400> SEQUENCE: 161

Lys Phe Glu Ile Phe Pro Lys Thr Ser Ser Trp Pro Asn Glu Val Leu
1               5                   10                  15

Val Leu Trp Gly Val His
            20


<210> SEQ ID NO 162
<211> LENGTH: 8
<212> TYPE: PRT
<213> ORGANISM: Influenza virus

<400> SEQUENCE: 162

Lys Glu Arg Ser Trp Pro Lys His
1               5


<210> SEQ ID NO 163
<211> LENGTH: 21
<212> TYPE: PRT
<213> ORGANISM: Influenza virus

<400> SEQUENCE: 163

Lys Leu Ser Lys Ser Tyr Val Asn Asn Lys Glu Lys Glu Val Leu Val
1               5                   10                  15

Leu Trp Gln Val His
            20


<210> SEQ ID NO 164
<211> LENGTH: 15
<212> TYPE: PRT
<213> ORGANISM: Influenza virus

<400> SEQUENCE: 164

Lys Asn Asn Lys Glu Lys Glu Val Leu Val Leu Trp Gln Val His
1               5                   10                  15
```

-continued

<210> SEQ ID NO 165
<211> LENGTH: 34
<212> TYPE: PRT
<213> ORGANISM: Influenza virus
<220> FEATURE:
<221> NAME/KEY: misc_feature
<222> LOCATION: (2)..(2)
<223> OTHER INFORMATION: Xaa can be Lys or Asn
<220> FEATURE:
<221> NAME/KEY: misc_feature
<222> LOCATION: (3)..(3)
<223> OTHER INFORMATION: Xaa can be Gly or Gln
<220> FEATURE:
<221> NAME/KEY: misc_feature
<222> LOCATION: (9)..(9)
<223> OTHER INFORMATION: Xaa can be Arg or Lys
<220> FEATURE:
<221> NAME/KEY: misc_feature
<222> LOCATION: (20)..(20)
<223> OTHER INFORMATION: Xaa can be Leu or Ser
<220> FEATURE:
<221> NAME/KEY: misc_feature
<222> LOCATION: (23)..(23)
<223> OTHER INFORMATION: Xaa can be Asn or Thr

<400> SEQUENCE: 165

His Xaa Xaa Lys Ser Ser Phe Tyr Xaa Asn Leu Leu Trp Leu Thr Glu
1               5                   10                  15

Lys Asn Gly Xaa Tyr Pro Xaa Leu Ser Lys Ser Tyr Ala Asn Asn Lys
            20                  25                  30

Glu Lys

<210> SEQ ID NO 166
<211> LENGTH: 17
<212> TYPE: PRT
<213> ORGANISM: Influenza virus
<220> FEATURE:
<221> NAME/KEY: misc_feature
<222> LOCATION: (2)..(2)
<223> OTHER INFORMATION: Xaa can be Lys or Asn
<220> FEATURE:
<221> NAME/KEY: misc_feature
<222> LOCATION: (3)..(3)
<223> OTHER INFORMATION: Xaa can be Gly or Gln
<220> FEATURE:
<221> NAME/KEY: misc_feature
<222> LOCATION: (9)..(9)
<223> OTHER INFORMATION: Xaa can be Arg or Lys

<400> SEQUENCE: 166

His Xaa Xaa Lys Ser Ser Phe Tyr Xaa Asn Leu Leu Trp Leu Thr Glu
1               5                   10                  15

Lys

<210> SEQ ID NO 167
<211> LENGTH: 9
<212> TYPE: PRT
<213> ORGANISM: Influenza virus

<400> SEQUENCE: 167

His Ala Lys Lys Ser Ser Phe Tyr Lys
1               5

<210> SEQ ID NO 168
<211> LENGTH: 11
<212> TYPE: PRT
<213> ORGANISM: Influenza virus

<400> SEQUENCE: 168

-continued

His Asn Gly Lys Leu Cys Arg Leu Lys Gly Lys
1 5 10

<210> SEQ ID NO 169
<211> LENGTH: 9
<212> TYPE: PRT
<213> ORGANISM: Influenza virus
<220> FEATURE:
<221> NAME/KEY: misc_feature
<222> LOCATION: (7)..(7)
<223> OTHER INFORMATION: Xaa can be Gln or Gly

<400> SEQUENCE: 169

His Tyr Lys Leu Asn Asn Xaa Lys Lys
1 5

<210> SEQ ID NO 170
<211> LENGTH: 25
<212> TYPE: PRT
<213> ORGANISM: Influenza virus

<400> SEQUENCE: 170

His Asp Ile Tyr Arg Asp Glu Ala Ile Asn Asn Arg Phe Gln Ile Gln
1 5 10 15

Gly Val Lys Leu Thr Gln Gly Tyr Lys
20 25

<210> SEQ ID NO 171
<211> LENGTH: 11
<212> TYPE: PRT
<213> ORGANISM: Influenza virus

<400> SEQUENCE: 171

Lys Gly Asn Gly Cys Phe Glu Ile Phe His Lys
1 5 10

<210> SEQ ID NO 172
<211> LENGTH: 18
<212> TYPE: PRT
<213> ORGANISM: Influenza virus

<400> SEQUENCE: 172

Lys Leu Asn Arg Leu Ile Glu Lys Thr Asn Asp Lys Tyr His Gln Ile
1 5 10 15

Glu Lys

<210> SEQ ID NO 173
<211> LENGTH: 14
<212> TYPE: PRT
<213> ORGANISM: Influenza virus

<400> SEQUENCE: 173

Lys Leu Asn Arg Leu Ile Glu Lys Thr Asn Asp Lys Tyr His
1 5 10

<210> SEQ ID NO 174
<211> LENGTH: 13
<212> TYPE: PRT
<213> ORGANISM: Influenza virus

<400> SEQUENCE: 174

Lys Cys His Thr Asp Lys Gly Ser Leu Ser Thr Thr Lys
1 5 10

-continued

<210> SEQ ID NO 175
<211> LENGTH: 16
<212> TYPE: PRT
<213> ORGANISM: Influenza virus

<400> SEQUENCE: 175

Lys Ile Asn Asn Gly Asp Tyr Ala Lys Leu Tyr Ile Trp Gly Val His
1 5 10 15

<210> SEQ ID NO 176
<211> LENGTH: 17
<212> TYPE: PRT
<213> ORGANISM: Influenza virus

<400> SEQUENCE: 176

His Asn Gly Lys Leu Cys Arg Lys Gly Ile Ala Pro Leu Gln Leu Gly
1 5 10 15

Lys

<210> SEQ ID NO 177
<211> LENGTH: 38
<212> TYPE: PRT
<213> ORGANISM: Influenza virus

<400> SEQUENCE: 177

His Glu Thr Asn Arg Gln Val Thr Ala Ala Cys Pro Tyr Ala Gly Ala
1 5 10 15

Asn Ser Phe Phe Arg Asn Leu Ile Trp Leu Val Lys Lys Glu Ser Ser
20 25 30

Tyr Pro Lys Leu Ser Lys
35

<210> SEQ ID NO 178
<211> LENGTH: 35
<212> TYPE: PRT
<213> ORGANISM: Influenza virus

<400> SEQUENCE: 178

His Glu Thr Asn Arg Gln Val Thr Ala Ala Cys Pro Tyr Ala Gly Ala
1 5 10 15

Asn Ser Phe Phe Arg Asn Leu Ile Trp Leu Val Lys Lys Glu Ser Ser
20 25 30

Tyr Pro Lys
35

<210> SEQ ID NO 179
<211> LENGTH: 31
<212> TYPE: PRT
<213> ORGANISM: Influenza virus

<400> SEQUENCE: 179

His Pro Pro Thr Ser Thr Asp Gln Gln Ser Leu Tyr Gln Asn Ala Asp
1 5 10 15

Ala Tyr Ile Phe Val Gly Ser Ser Lys Tyr Asn Arg Lys Phe Lys
20 25 30

<210> SEQ ID NO 180
<211> LENGTH: 35
<212> TYPE: PRT
<213> ORGANISM: Influenza virus

<400> SEQUENCE: 180

-continued

His Pro Pro Thr Ser Thr Asp Gln Gln Ser Leu Tyr Gln Asn Ala Asp
1 5 10 15

Ala Tyr Ile Phe Val Gly Ser Ser Lys Tyr Asn Arg Lys Phe Lys Pro
20 25 30

Glu Ile Ala
35

<210> SEQ ID NO 181
<211> LENGTH: 25
<212> TYPE: PRT
<213> ORGANISM: Influenza virus

<400> SEQUENCE: 181

His Asp Ile Tyr Arg Asp Glu Ala Ile Asn Asn Arg Phe Gln Ile Gln
1 5 10 15

Gly Val Lys Ile Thr Gln Gly Tyr Lys
20 25

<210> SEQ ID NO 182
<211> LENGTH: 43
<212> TYPE: PRT
<213> ORGANISM: Influenza virus

<400> SEQUENCE: 182

His Gln Asn Glu Gln Gly Ser Gly Tyr Ala Ala Asp Gln Lys Ser Thr
1 5 10 15

Gln Asn Ala Ile Asp Gly Ile Thr Asn Lys Val Asn Ser Val Ile Glu
20 25 30

Lys Met Asn Thr Gln Phe Thr Ala Val Gly Lys
35 40

<210> SEQ ID NO 183
<211> LENGTH: 33
<212> TYPE: PRT
<213> ORGANISM: Influenza virus

<400> SEQUENCE: 183

His Gln Asn Glu Gln Gly Ser Gly Tyr Ala Ala Asp Gln Lys Ser Thr
1 5 10 15

Gln Asn Ala Ile Asp Gly Ile Thr Asn Lys Val Asn Ser Val Ile Glu
20 25 30

Lys

<210> SEQ ID NO 184
<211> LENGTH: 50
<212> TYPE: PRT
<213> ORGANISM: Influenza virus

<400> SEQUENCE: 184

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys Met Asn Thr Gln Phe Thr Ala Val Gly Lys Glu Phe Asn Lys Leu
35 40 45

Glu Lys
50

<210> SEQ ID NO 185
<211> LENGTH: 18

-continued

<212> TYPE: PRT
<213> ORGANISM: Influenza virus

<400> SEQUENCE: 185

His Asn Gly Lys Leu Cys Arg Leu Lys Gly Ile Ala Pro Leu Gln Leu
1 5 10 15

Gly Lys

<210> SEQ ID NO 186
<211> LENGTH: 12
<212> TYPE: PRT
<213> ORGANISM: Influenza virus

<400> SEQUENCE: 186

His Lys Cys Asn Asn Glu Cys Met Glu Ser Val Lys
1 5 10

<210> SEQ ID NO 187
<211> LENGTH: 14
<212> TYPE: PRT
<213> ORGANISM: Influenza virus

<400> SEQUENCE: 187

Lys Phe Glu Ile Phe Pro Lys Ala Ser Ser Trp Pro Asn His
1 5 10

<210> SEQ ID NO 188
<211> LENGTH: 21
<212> TYPE: PRT
<213> ORGANISM: Influenza virus

<400> SEQUENCE: 188

His Asp Ser Asn Val Lys Asn Leu Tyr Glu Lys Val Arg Ser Gln Leu
1 5 10 15

Arg Asn Asn Ala Lys
20

<210> SEQ ID NO 189
<211> LENGTH: 22
<212> TYPE: PRT
<213> ORGANISM: Influenza virus

<400> SEQUENCE: 189

Lys Val Asn Ser Val Ile Lys Lys Met Asn Thr Gln Phe Ala Ala Val
1 5 10 15

Gly Lys Glu Phe Asn His
20

<210> SEQ ID NO 190
<211> LENGTH: 8
<212> TYPE: PRT
<213> ORGANISM: Influenza virus

<400> SEQUENCE: 190

Lys His Asn Gly Lys Leu Cys Lys
1 5

<210> SEQ ID NO 191
<211> LENGTH: 28
<212> TYPE: PRT
<213> ORGANISM: Influenza virus

<400> SEQUENCE: 191

-continued

```
Lys Lys Gly Thr Ser Tyr Pro Lys Leu Ser Lys Ser Tyr Thr His Asn
1               5                   10                  15

Lys Gly Lys Glu Val Leu Val Leu Trp Gly Val His
            20                  25


<210> SEQ ID NO 192
<211> LENGTH: 27
<212> TYPE: PRT
<213> ORGANISM: Influenza virus

<400> SEQUENCE: 192

Lys Gly Thr Ser Tyr Pro Lys Leu Ser Lys Ser Tyr Thr His Asn Lys
1               5                   10                  15

Gly Lys Glu Val Leu Val Leu Trp Gly Val His
            20                  25


<210> SEQ ID NO 193
<211> LENGTH: 21
<212> TYPE: PRT
<213> ORGANISM: Influenza virus

<400> SEQUENCE: 193

Lys Leu Ser Lys Ser Tyr Thr His Asn Lys Gly Lys Glu Val Leu Val
1               5                   10                  15

Leu Trp Gly Val His
            20


<210> SEQ ID NO 194
<211> LENGTH: 18
<212> TYPE: PRT
<213> ORGANISM: Influenza virus

<400> SEQUENCE: 194

Lys Ser Tyr Thr His Asn Lys Gly Lys Glu Val Leu Val Leu Trp Gly
1               5                   10                  15

Val His


<210> SEQ ID NO 195
<211> LENGTH: 10
<212> TYPE: PRT
<213> ORGANISM: Influenza virus

<400> SEQUENCE: 195

Lys Gly Val Thr Ala Ser Cys Ser His Lys
1               5                   10


<210> SEQ ID NO 196
<211> LENGTH: 34
<212> TYPE: PRT
<213> ORGANISM: Influenza virus

<400> SEQUENCE: 196

Lys Gly Val Thr Ala Ser Cys Ser His Lys Gly Arg Ser Ser Phe Tyr
1               5                   10                  15

Arg Asn Leu Leu Trp Leu Thr Glu Lys Asn Gly Leu Tyr Pro Asn Leu
            20                  25                  30

Ser Lys


<210> SEQ ID NO 197
<211> LENGTH: 27
<212> TYPE: PRT
<213> ORGANISM: Influenza virus
```

-continued

<400> SEQUENCE: 197

Lys Gly Asn Ser Tyr Pro Lys Leu Ser Lys Ser Tyr Val Asn Asn Lys
1 5 10 15

Glu Lys Glu Val Leu Val Leu Trp Gly Ile His
20 25

<210> SEQ ID NO 198
<211> LENGTH: 8
<212> TYPE: PRT
<213> ORGANISM: Influenza virus

<400> SEQUENCE: 198

Lys Glu Phe Asn His Leu Glu Lys
1 5

<210> SEQ ID NO 199
<211> LENGTH: 39
<212> TYPE: PRT
<213> ORGANISM: Influenza virus

<400> SEQUENCE: 199

His Pro Pro Thr Ser Thr Asp Gln Gln Ser Leu Tyr Gln Asn Ala Asp
1 5 10 15

Ala Tyr Val Phe Val Gly Ser Ser Lys Tyr Asn Lys Lys Phe Lys Pro
20 25 30

Glu Ile Ala Thr Arg Pro Lys
35

<210> SEQ ID NO 200
<211> LENGTH: 31
<212> TYPE: PRT
<213> ORGANISM: Influenza virus

<400> SEQUENCE: 200

His Pro Pro Thr Ser Thr Asp Gln Gln Ser Leu Tyr Gln Asn Ala Asp
1 5 10 15

Ala Tyr Val Phe Val Gly Ser Ser Lys Tyr Asn Lys Lys Phe Lys
20 25 30

<210> SEQ ID NO 201
<211> LENGTH: 31
<212> TYPE: PRT
<213> ORGANISM: Influenza virus

<400> SEQUENCE: 201

His Glu Gly Lys Ser Ser Phe Tyr Arg Asn Leu Leu Trp Leu Thr Glu
1 5 10 15

Lys Glu Gly Ser Tyr Pro Lys Leu Lys Asn Ser Tyr Val Asn Lys
20 25 30

<210> SEQ ID NO 202
<211> LENGTH: 23
<212> TYPE: PRT
<213> ORGANISM: Influenza virus

<400> SEQUENCE: 202

His Glu Gly Lys Ser Ser Phe Tyr Arg Asn Leu Leu Trp Leu Thr Glu
1 5 10 15

Lys Glu Gly Ser Tyr Pro Lys
20

-continued

<210> SEQ ID NO 203
<211> LENGTH: 26
<212> TYPE: PRT
<213> ORGANISM: Influenza virus

<400> SEQUENCE: 203

His Lys Cys Asp Asn Glu Cys Met Glu Ser Val Arg Asn Gly Thr Tyr
1 5 10 15

Asp Tyr Pro Lys Tyr Ser Glu Glu Ser Lys
20 25

<210> SEQ ID NO 204
<211> LENGTH: 12
<212> TYPE: PRT
<213> ORGANISM: Influenza virus

<400> SEQUENCE: 204

Lys Glu Ser Ser Trp Pro Asn His Thr Val Thr Lys
1 5 10

<210> SEQ ID NO 205
<211> LENGTH: 35
<212> TYPE: PRT
<213> ORGANISM: Influenza virus

<400> SEQUENCE: 205

Lys Asn Leu Leu Trp Leu Thr Glu Lys Asn Gly Leu Tyr Pro Asn Leu
1 5 10 15

Ser Lys Ser Tyr Val Asn Asn Lys Glu Lys Glu Ile Leu Val Leu Trp
20 25 30

Gly Val His
35

<210> SEQ ID NO 206
<211> LENGTH: 27
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Lys or Met
<220> FEATURE:
<221> NAME/KEY: misc_feature
<222> LOCATION: (16)..(16)
<223> OTHER INFORMATION: Xaa can be Glu or Gly

<400> SEQUENCE: 206

His Asn Gly Lys Ser Ser Phe Tyr Xaa Asn Leu Leu Trp Leu Thr Xaa
1 5 10 15

Lys Lys Asn Gly Leu Tyr Pro Asn Leu Ser Lys
20 25

<210> SEQ ID NO 207
<211> LENGTH: 17
<212> TYPE: PRT
<213> ORGANISM: Influenza virus

<400> SEQUENCE: 207

His Asn Gly Lys Ser Ser Phe Tyr Lys Asn Leu Leu Trp Leu Thr Glu
1 5 10 15

Lys

<210> SEQ ID NO 208

-continued

<211> LENGTH: 55
<212> TYPE: PRT
<213> ORGANISM: Influenza virus

<400> SEQUENCE: 208

His Thr Val Thr Lys Gly Val Thr Ala Ser Cys Ser His Asn Gly Lys
1 5 10 15

Ser Ser Phe Tyr Lys Asn Leu Leu Trp Leu Thr Glu Lys Asn Gly Leu
20 25 30

Tyr Pro Asn Leu Ser Lys Ser Tyr Val Asn Asn Lys Glu Lys Glu Val
35 40 45

Leu Val Leu Trp Gly Val His
50 55

<210> SEQ ID NO 209
<211> LENGTH: 38
<212> TYPE: PRT
<213> ORGANISM: Influenza virus
<220> FEATURE:
<221> NAME/KEY: misc_feature
<222> LOCATION: (5)..(5)
<223> OTHER INFORMATION: Xaa can be Lys or Gly
<220> FEATURE:
<221> NAME/KEY: misc_feature
<222> LOCATION: (8)..(8)
<223> OTHER INFORMATION: Xaa can be Thr or Ser
<220> FEATURE:
<221> NAME/KEY: misc_feature
<222> LOCATION: (21)..(21)
<223> OTHER INFORMATION: Xaa can be Lys or Met
<220> FEATURE:
<221> NAME/KEY: misc_feature
<222> LOCATION: (28)..(28)
<223> OTHER INFORMATION: Xaa can be Glu or Gly
<220> FEATURE:
<221> NAME/KEY: misc_feature
<222> LOCATION: (30)..(30)
<223> OTHER INFORMATION: Xaa can be Asn or Lys

<400> SEQUENCE: 209

His Thr Val Thr Xaa Gly Val Xaa Ala Ser Cys Ser His Asn Gly Lys
1 5 10 15

Ser Ser Phe Tyr Xaa Asn Leu Leu Trp Leu Thr Xaa Lys Xaa Gly Leu
20 25 30

Tyr Pro Asn Leu Ser Lys
35

<210> SEQ ID NO 210
<211> LENGTH: 29
<212> TYPE: PRT
<213> ORGANISM: Influenza virus

<400> SEQUENCE: 210

His Thr Val Thr Lys Gly Val Thr Ala Ser Cys Ser His Asn Gly Lys
1 5 10 15

Ser Ser Phe Tyr Lys Asn Leu Leu Trp Leu Thr Glu Lys
20 25

<210> SEQ ID NO 211
<211> LENGTH: 48
<212> TYPE: PRT
<213> ORGANISM: Influenza virus

<400> SEQUENCE: 211

Lys Tyr Val Arg Ser Thr Lys Leu Arg Met Val Thr Gly Leu Arg Asn
1 5 10 15

-continued

```
Ile Pro Ser Ile Gln Ser Arg Gly Leu Phe Gly Ala Ile Ala Gly Phe
            20                  25                  30

Ile Glu Gly Gly Trp Thr Gly Met Ile Asp Gly Trp Tyr Gly Tyr His
        35                  40                  45


<210> SEQ ID NO 212
<211> LENGTH: 43
<212> TYPE: PRT
<213> ORGANISM: Influenza virus

<400> SEQUENCE: 212

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Ile Ile Glu
            20                  25                  30

Lys Met Asn Thr Gln Phe Thr Ala Val Gly Lys
        35                  40


<210> SEQ ID NO 213
<211> LENGTH: 33
<212> TYPE: PRT
<213> ORGANISM: Influenza virus

<400> SEQUENCE: 213

His Gln Asn Glu Gln Gly Ser Gly Tyr Ala Ala Asp Gln Lys Ser Thr
1               5                   10                  15

Gln Asn Ala Ile Asn Gly Ile Thr Asn Lys Val Asn Ser Ile Ile Glu
            20                  25                  30

Lys


<210> SEQ ID NO 214
<211> LENGTH: 26
<212> TYPE: PRT
<213> ORGANISM: Influenza virus

<400> SEQUENCE: 214

His Gln Asn Glu Gln Gly Ser Gly Tyr Ala Ala Asp Gln Lys Ser Thr
1               5                   10                  15

Gln Asn Ala Ile Asn Gly Ile Thr Asn Lys
            20                  25


<210> SEQ ID NO 215
<211> LENGTH: 23
<212> TYPE: PRT
<213> ORGANISM: Influenza virus

<400> SEQUENCE: 215

His Ser Gly Ala Arg Ser Phe Tyr Arg Asn Leu Leu Trp Ile Val Lys
1               5                   10                  15

Lys Gly Asn Ser Tyr Pro Lys
            20


<210> SEQ ID NO 216
<211> LENGTH: 26
<212> TYPE: PRT
<213> ORGANISM: Influenza virus

<400> SEQUENCE: 216

His Ser Gly Ala Arg Ser Phe Tyr Arg Asn Leu Leu Trp Ile Val Lys
1               5                   10                  15
```

-continued

```
Lys Gly Asn Ser Tyr Pro Lys Leu Asn Lys
            20                  25


<210> SEQ ID NO 217
<211> LENGTH: 32
<212> TYPE: PRT
<213> ORGANISM: Influenza virus

<400> SEQUENCE: 217

His Ser Gly Ala Arg Ser Phe Tyr Arg Asn Leu Leu Trp Ile Val Lys
1               5                   10                  15

Lys Gly Asn Ser Tyr Pro Lys Leu Asn Lys Ser Tyr Thr Asn Asp Lys
            20                  25                  30


<210> SEQ ID NO 218
<211> LENGTH: 34
<212> TYPE: PRT
<213> ORGANISM: Influenza virus

<400> SEQUENCE: 218

His Ser Gly Ala Arg Ser Phe Tyr Arg Asn Leu Leu Trp Ile Val Lys
1               5                   10                  15

Lys Gly Asn Ser Tyr Pro Lys Leu Asn Lys Ser Tyr Thr Asn Asp Lys
            20                  25                  30

Gly Lys


<210> SEQ ID NO 219
<211> LENGTH: 16
<212> TYPE: PRT
<213> ORGANISM: Influenza virus

<400> SEQUENCE: 219

His Thr Val Ser Lys Gly Val Thr Thr Ser Cys Ser His Asn Gly Lys
1               5                   10                  15


<210> SEQ ID NO 220
<211> LENGTH: 12
<212> TYPE: PRT
<213> ORGANISM: Influenza virus

<400> SEQUENCE: 220

Lys Ala Thr Ser Trp Pro Asn His Glu Thr Thr Lys
1               5                   10


<210> SEQ ID NO 221
<211> LENGTH: 12
<212> TYPE: PRT
<213> ORGANISM: Influenza virus

<400> SEQUENCE: 221

Lys Gln Val Thr Thr Ser Cys Ser His Asn Gln Lys
1               5                   10


<210> SEQ ID NO 222
<211> LENGTH: 27
<212> TYPE: PRT
<213> ORGANISM: Influenza virus

<400> SEQUENCE: 222

Lys Gly Asn Ser Tyr Pro Lys Leu Asn Lys Ser Tyr Thr Asn Asp Lys
1               5                   10                  15

Gly Lys Glu Val Leu Val Ile Trp Gly Val His
            20                  25
```

-continued

<210> SEQ ID NO 223
<211> LENGTH: 21
<212> TYPE: PRT
<213> ORGANISM: Influenza virus

<400> SEQUENCE: 223

Lys Leu Asn Lys Ser Tyr Thr Asn Asp Lys Gly Lys Glu Val Leu Val
1 5 10 15

Ile Trp Gly Val His
20

<210> SEQ ID NO 224
<211> LENGTH: 18
<212> TYPE: PRT
<213> ORGANISM: Influenza virus

<400> SEQUENCE: 224

Lys Ser Tyr Thr Asn Asp Lys Gly Lys Glu Val Leu Val Ile Trp Gly
1 5 10 15

Val His

<210> SEQ ID NO 225
<211> LENGTH: 35
<212> TYPE: PRT
<213> ORGANISM: Influenza virus
<220> FEATURE:
<221> NAME/KEY: misc_feature
<222> LOCATION: (16)..(16)
<223> OTHER INFORMATION: Xaa can be Glu or Gln
<220> FEATURE:
<221> NAME/KEY: misc_feature
<222> LOCATION: (29)..(29)
<223> OTHER INFORMATION: Xaa can be Val or Ala

<400> SEQUENCE: 225

His Asn Gln Lys Ser Ser Phe Tyr Arg Asn Leu Leu Trp Leu Thr Xaa
1 5 10 15

Lys Asn Gly Leu Tyr Pro Asn Leu Ser Lys Ser Tyr Xaa Ala Asn Asn
20 25 30

Lys Glu Lys
35

<210> SEQ ID NO 226
<211> LENGTH: 16
<212> TYPE: PRT
<213> ORGANISM: Influenza virus

<400> SEQUENCE: 226

His Pro Ile Thr Ile Gly Glu Cys Pro Lys Tyr Val Arg Ser Ala Lys
1 5 10 15

<210> SEQ ID NO 227
<211> LENGTH: 43
<212> TYPE: PRT
<213> ORGANISM: Influenza virus

<400> SEQUENCE: 227

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys Met Asn Thr Gln Phe Thr Ala Val Gly Lys

-continued 35 40

<210> SEQ ID NO 228
<211> LENGTH: 33
<212> TYPE: PRT
<213> ORGANISM: Influenza virus

<400> SEQUENCE: 228

His Gln Asn Glu Gln Gly Ser Gly Tyr Ala Ala Asp Gln Lys Ser Thr
1 5 10 15

Gln Asn Ala Ile Asn Gly Ile Thr Asn Lys Val Asn Ser Val Ile Glu
20 25 30

Lys

<210> SEQ ID NO 229
<211> LENGTH: 34
<212> TYPE: PRT
<213> ORGANISM: Influenza virus

<400> SEQUENCE: 229

His Asn Gly Lys Ser Ser Phe Tyr Arg Asn Leu Leu Trp Leu Thr Glu
1 5 10 15

Lys Asn Gly Leu Tyr Pro Asn Leu Ser Lys Ser Tyr Val Asn Asn Lys
20 25 30

Glu Lys

<210> SEQ ID NO 230
<211> LENGTH: 11
<212> TYPE: PRT
<213> ORGANISM: Influenza virus

<400> SEQUENCE: 230

Lys His Phe Glu Lys Val Lys Ile Leu Pro Lys
1 5 10

<210> SEQ ID NO 231
<211> LENGTH: 14
<212> TYPE: PRT
<213> ORGANISM: Influenza virus

<400> SEQUENCE: 231

Lys His Leu Leu Ser Ser Val Lys His Phe Glu Lys Val Lys
1 5 10

<210> SEQ ID NO 232
<211> LENGTH: 13
<212> TYPE: PRT
<213> ORGANISM: Influenza virus
<220> FEATURE:
<221> NAME/KEY: misc_feature
<222> LOCATION: (3)..(3)
<223> OTHER INFORMATION: Xaa can be Lys, Gln or Met
<220> FEATURE:
<221> NAME/KEY: misc_feature
<222> LOCATION: (4)..(4)
<223> OTHER INFORMATION: Xaa can be Asp or Asn

<400> SEQUENCE: 232

His Ala Xaa Xaa Ile Leu Glu Lys Thr His Asn Gly Lys
1 5 10

<210> SEQ ID NO 233
<211> LENGTH: 16
<212> TYPE: PRT

-continued

<213> ORGANISM: Influenza virus
<220> FEATURE:
<221> NAME/KEY: misc_feature
<222> LOCATION: (3)..(3)
<223> OTHER INFORMATION: Xaa can be Lys, Gln or Met
<220> FEATURE:
<221> NAME/KEY: misc_feature
<222> LOCATION: (4)..(4)
<223> OTHER INFORMATION: Xaa can be Asp or Asn
<220> FEATURE:
<221> NAME/KEY: misc_feature
<222> LOCATION: (16)..(16)
<223> OTHER INFORMATION: Xaa can be Lys or Arg

<400> SEQUENCE: 233

His Ala Xaa Xaa Ile Leu Glu Lys Thr His Asn Gly Lys Leu Cys Xaa
1 5 10 15

<210> SEQ ID NO 234
<211> LENGTH: 19
<212> TYPE: PRT
<213> ORGANISM: Influenza virus

<400> SEQUENCE: 234

His Asn Val His Pro Leu Thr Ile Gly Glu Cys Pro Lys Tyr Val Lys
1 5 10 15

Ser Glu Lys

<210> SEQ ID NO 235
<211> LENGTH: 16
<212> TYPE: PRT
<213> ORGANISM: Influenza virus

<400> SEQUENCE: 235

His Pro Leu Thr Ile Gly Glu Cys Pro Lys Tyr Val Lys Ser Glu Lys
1 5 10 15

<210> SEQ ID NO 236
<211> LENGTH: 18
<212> TYPE: PRT
<213> ORGANISM: Influenza virus

<400> SEQUENCE: 236

Lys His Leu Leu Ser Ser Val Lys His Phe Glu Lys Val Lys Ile Leu
1 5 10 15

Pro Lys

<210> SEQ ID NO 237
<211> LENGTH: 38
<212> TYPE: PRT
<213> ORGANISM: Influenza virus

<400> SEQUENCE: 237

Lys Arg Gln Ser Ser Gly Ile Met Lys Thr Glu Gly Thr Leu Glu Asn
1 5 10 15

Cys Glu Thr Lys Cys Gln Thr Pro Leu Gly Ala Ile Asn Thr Thr Leu
20 25 30

Pro Phe His Asn Val His
35

<210> SEQ ID NO 238
<211> LENGTH: 27
<212> TYPE: PRT
<213> ORGANISM: Influenza virus
<220> FEATURE:

-continued

<221> NAME/KEY: misc_feature
<222> LOCATION: (7)..(7)
<223> OTHER INFORMATION: Xaa can be Val or Ile
<220> FEATURE:
<221> NAME/KEY: misc_feature
<222> LOCATION: (10)..(10)
<223> OTHER INFORMATION: Xaa can be Gly or Arg
<220> FEATURE:
<221> NAME/KEY: misc_feature
<222> LOCATION: (26)..(26)
<223> OTHER INFORMATION: Xaa can be Val or Ile

<400> SEQUENCE: 238

Lys Gly Ser Asn Tyr Pro Xaa Ala Lys Xaa Ser Tyr Asn Asn Thr Ser
1 5 10 15

Gly Glu Gln Met Leu Ile Ile Trp Gln Xaa His
20 25

<210> SEQ ID NO 239
<211> LENGTH: 36
<212> TYPE: PRT
<213> ORGANISM: Influenza virus

<400> SEQUENCE: 239

His Thr Thr Leu Gly Gln Ser Arg Ala Cys Ala Val Ser Gly Asn Pro
1 5 10 15

Ser Phe Phe Arg Asn Met Val Trp Leu Thr Glu Lys Gly Ser Asn Tyr
20 25 30

Pro Val Ala Lys
35

<210> SEQ ID NO 240
<211> LENGTH: 7
<212> TYPE: PRT
<213> ORGANISM: Influenza virus

<400> SEQUENCE: 240

Lys His Phe Glu Lys Val Lys
1 5

<210> SEQ ID NO 241
<211> LENGTH: 38
<212> TYPE: PRT
<213> ORGANISM: Influenza virus

<400> SEQUENCE: 241

Lys Ile Ser Lys Arg Gly Ser Ser Gly Ile Met Lys Thr Glu Gly Thr
1 5 10 15

Leu Glu Asn Cys Glu Thr Lys Cys Gln Thr Pro Leu Gly Ala Ile Asn
20 25 30

Thr Thr Leu Pro Phe His
35

<210> SEQ ID NO 242
<211> LENGTH: 35
<212> TYPE: PRT
<213> ORGANISM: Influenza virus

<400> SEQUENCE: 242

Lys Arg Gly Ser Ser Gly Ile Met Lys Thr Glu Gly Thr Leu Glu Asn
1 5 10 15

Cys Glu Thr Lys Cys Gln Thr Pro Leu Gly Ala Ile Asn Thr Thr Leu
20 25 30

-continued

```
Pro Phe His
        35


<210> SEQ ID NO 243
<211> LENGTH: 27
<212> TYPE: PRT
<213> ORGANISM: Influenza virus

<400> SEQUENCE: 243

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His
            20                  25


<210> SEQ ID NO 244
<211> LENGTH: 38
<212> TYPE: PRT
<213> ORGANISM: Influenza virus

<400> SEQUENCE: 244

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35


<210> SEQ ID NO 245
<211> LENGTH: 30
<212> TYPE: PRT
<213> ORGANISM: Influenza virus
<220> FEATURE:
<221> NAME/KEY: misc_feature
<222> LOCATION: (29)..(29)
<223> OTHER INFORMATION: Xaa can be Val or Ile

<400> SEQUENCE: 245

Lys Thr Glu Gly Thr Leu Glu Asn Cys Glu Thr Lys Cys Gln Thr Pro
1               5                   10                  15

Leu Gly Ala Ile Asn Thr Thr Leu Pro Phe His Asn Xaa His
            20                  25                  30


<210> SEQ ID NO 246
<211> LENGTH: 38
<212> TYPE: PRT
<213> ORGANISM: Influenza virus

<400> SEQUENCE: 246

Lys Ile Ser Lys Arg Gly Ser Ser Gly Ile Met Lys Thr Glu Gly Thr
1               5                   10                  15

Leu Glu Asn Cys Glu Thr Lys Cys Gln Thr Pro Leu Gly Ala Ile Asn
            20                  25                  30

Thr Thr Leu Pro Phe His
        35


<210> SEQ ID NO 247
<211> LENGTH: 27
<212> TYPE: PRT
<213> ORGANISM: Influenza virus
<220> FEATURE:
<221> NAME/KEY: misc_feature
<222> LOCATION: (2)..(2)
<223> OTHER INFORMATION: Xaa can be Glu or Gly
```

-continued

<400> SEQUENCE: 247

```
Lys Xaa Ser Asn Tyr Pro Val Ala Lys Gly Ser Tyr Asn Asn Thr Ser
1               5                   10                  15

Gly Glu Gln Met Leu Ile Ile Trp Gly Val His
            20                  25
```

<210> SEQ ID NO 248
<211> LENGTH: 16
<212> TYPE: PRT
<213> ORGANISM: Influenza virus

<400> SEQUENCE: 248

```
His Pro Leu Thr Ile Gly Glu Cys Pro Lys Tyr Val Lys Ser Glu Lys
1               5                   10                  15
```

<210> SEQ ID NO 249
<211> LENGTH: 16
<212> TYPE: PRT
<213> ORGANISM: Influenza virus

<400> SEQUENCE: 249

```
Lys Cys Gln Thr Pro Leu Gly Ala Ile Lys Thr Thr Leu Pro Phe His
1               5                   10                  15
```

<210> SEQ ID NO 250
<211> LENGTH: 58
<212> TYPE: PRT
<213> ORGANISM: Influenza virus
<220> FEATURE:
<221> NAME/KEY: misc_feature
<222> LOCATION: (21)..(21)
<223> OTHER INFORMATION: Xaa can be Phe or Ile
<220> FEATURE:
<221> NAME/KEY: misc_feature
<222> LOCATION: (47)..(47)
<223> OTHER INFORMATION: Xaa can be Asn or Ser

<400> SEQUENCE: 250

```
His His Ser Asn Asp Gln Gly Ser Gly Tyr Ala Ala Asp Lys Glu Ser
1               5                   10                  15

Thr Gln Lys Ala Xaa Asp Gly Ile Thr Asn Lys Val Asn Ser Val Ile
            20                  25                  30

Glu Lys Met Asn Thr Gln Phe Glu Ala Val Gly Lys Leu Phe Xaa Asn
        35                  40                  45

Leu Glu Lys Leu Glu Asn Leu Asn Lys Lys
    50                  55
```

<210> SEQ ID NO 251
<211> LENGTH: 57
<212> TYPE: PRT
<213> ORGANISM: Influenza virus
<220> FEATURE:
<221> NAME/KEY: misc_feature
<222> LOCATION: (20)..(20)
<223> OTHER INFORMATION: Xaa can be Phe or Ile
<220> FEATURE:
<221> NAME/KEY: misc_feature
<222> LOCATION: (46)..(46)
<223> OTHER INFORMATION: Xaa can be Asn or Ser

<400> SEQUENCE: 251

```
His Ser Asn Asp Gln Gly Ser Gly Tyr Ala Ala Asp Lys Glu Ser Thr
1               5                   10                  15

Gln Lys Ala Xaa Asp Gly Ile Thr Asn Lys Val Asn Ser Val Ile Glu
            20                  25                  30
```

```
Lys Met Asn Thr Gln Phe Glu Ala Val Gly Lys Leu Phe Xaa Asn Leu
        35                  40                  45

Glu Lys Leu Glu Asn Leu Asn Lys Lys
    50                  55


<210> SEQ ID NO 252
<211> LENGTH: 26
<212> TYPE: PRT
<213> ORGANISM: Influenza virus
<220> FEATURE:
<221> NAME/KEY: misc_feature
<222> LOCATION: (20)..(20)
<223> OTHER INFORMATION: Xaa can be Phe or Ile

<400> SEQUENCE: 252

His Ser Asn Asp Gln Gly Ser Gly Tyr Ala Ala Asp Lys Glu Ser Thr
1               5                   10                  15

Gln Lys Ala Xaa Asp Gly Ile Thr Asn Lys
            20                  25


<210> SEQ ID NO 253
<211> LENGTH: 21
<212> TYPE: PRT
<213> ORGANISM: Influenza virus

<400> SEQUENCE: 253

His Asp Ser Asn Val Arg Asn Leu Tyr Asp Lys Val Arg Met Gln Leu
1               5                   10                  15

Arg Asp Asn Ala Lys
            20


<210> SEQ ID NO 254
<211> LENGTH: 30
<212> TYPE: PRT
<213> ORGANISM: Influenza virus

<400> SEQUENCE: 254

His Lys Cys Asp Asp Glu Cys Met Asn Ser Val Lys Asn Gly Thr Tyr
1               5                   10                  15

Asp Tyr Pro Lys Leu Asn Arg Asn Glu Ile Lys Gly Val Lys
            20                  25                  30


<210> SEQ ID NO 255
<211> LENGTH: 27
<212> TYPE: PRT
<213> ORGANISM: Influenza virus

<400> SEQUENCE: 255

His Lys Cys Asp Asp Glu Cys Met Asn Ser Val Lys Asn Gly Thr Tyr
1               5                   10                  15

Asp Tyr Pro Lys Leu Asn Arg Asn Glu Ile Lys
            20                  25


<210> SEQ ID NO 256
<211> LENGTH: 20
<212> TYPE: PRT
<213> ORGANISM: Influenza virus

<400> SEQUENCE: 256

His Lys Cys Asp Asp Glu Cys Met Asn Ser Val Lys Asn Gly Thr Tyr
1               5                   10                  15

Asp Tyr Pro Lys
```

-continued

20

<210> SEQ ID NO 257
<211> LENGTH: 12
<212> TYPE: PRT
<213> ORGANISM: Influenza virus

<400> SEQUENCE: 257

His Lys Cys Asp Asp Glu Cys Met Asn Ser Val Lys
1               5                   10

<210> SEQ ID NO 258
<211> LENGTH: 27
<212> TYPE: PRT
<213> ORGANISM: Influenza virus

<400> SEQUENCE: 258

Lys Gly Ser Asn Tyr Pro Val Ala Lys Gly Ser Tyr Asn Asn Thr Asn
1               5                   10                  15

Gly Glu Gln Ile Leu Ile Ile Trp Gly Val His
            20                  25

<210> SEQ ID NO 259
<211> LENGTH: 43
<212> TYPE: PRT
<213> ORGANISM: Influenza virus

<400> SEQUENCE: 259

His Ser Asn Asp Gln Gly Ser Gly Tyr Ala Ala Asp Lys Glu Ser Thr
1               5                   10                  15

Gln Lys Ala Val Asp Gly Ile Thr Asn Lys Val Asn Ser Val Ile Glu
            20                  25                  30

Lys Met Asn Thr Gln Phe Glu Ala Val Gly Lys
        35                  40

<210> SEQ ID NO 260
<211> LENGTH: 35
<212> TYPE: PRT
<213> ORGANISM: Influenza virus

<400> SEQUENCE: 260

Lys Arg Gly Ser Ser Gly Ile Met Lys Thr Glu Gly Thr Leu Glu Asn
1               5                   10                  15

Cys Glu Thr Lys Cys Gln Thr Pro Leu Gly Ala Ile Asn Thr Thr Leu
            20                  25                  30

Pro Phe His
        35

<210> SEQ ID NO 261
<211> LENGTH: 16
<212> TYPE: PRT
<213> ORGANISM: Influenza virus

<400> SEQUENCE: 261

His Pro Leu Thr Ile Gly Glu Cys Pro Lys Tyr Val Lys Ser Glu Lys
1               5                   10                  15

<210> SEQ ID NO 262
<211> LENGTH: 16
<212> TYPE: PRT
<213> ORGANISM: Influenza virus

<400> SEQUENCE: 262

His Ala Lys Asp Ile Leu Glu Lys Thr His Asn Gly Lys Leu Cys Lys
1 5 10 15

<210> SEQ ID NO 263
<211> LENGTH: 25
<212> TYPE: PRT
<213> ORGANISM: Influenza virus

<400> SEQUENCE: 263

His Asp Val Tyr Arg Asp Glu Ala Leu Asn Asn Arg Phe Gln Ile Lys
1 5 10 15

Gly Val Glu Leu Lys Ser Gly Tyr Lys
20 25

<210> SEQ ID NO 264
<211> LENGTH: 19
<212> TYPE: PRT
<213> ORGANISM: Influenza virus

<400> SEQUENCE: 264

His Thr Ile Asp Leu Thr Asp Ser Glu Met Asn Lys Leu Phe Glu Arg
1 5 10 15

Thr Arg Lys

<210> SEQ ID NO 265
<211> LENGTH: 7
<212> TYPE: PRT
<213> ORGANISM: Influenza virus

<400> SEQUENCE: 265

Lys Phe His Gln Ile Glu Lys
1 5

<210> SEQ ID NO 266
<211> LENGTH: 11
<212> TYPE: PRT
<213> ORGANISM: Influenza virus
<220> FEATURE:
<221> NAME/KEY: misc_feature
<222> LOCATION: (8)..(8)
<223> OTHER INFORMATION: Xaa can be Gly or Gln

<400> SEQUENCE: 266

Lys Thr Asn Glu Lys Phe His Xaa Ile Glu Lys
1 5 10

<210> SEQ ID NO 267
<211> LENGTH: 14
<212> TYPE: PRT
<213> ORGANISM: Influenza virus
<220> FEATURE:
<221> NAME/KEY: misc_feature
<222> LOCATION: (5)..(5)
<223> OTHER INFORMATION: Xaa can be Val or Leu

<400> SEQUENCE: 267

Lys Leu Asn Arg Xaa Ile Glu Lys Thr Asn Glu Lys Phe His
1 5 10

<210> SEQ ID NO 268
<211> LENGTH: 25
<212> TYPE: PRT
<213> ORGANISM: Influenza virus

<400> SEQUENCE: 268

-continued

His Gln Ile Glu Lys Glu Phe Ser Glu Val Glu Gly Arg Ile Gln Asp
1 5 10 15

Leu Glu Lys Tyr Val Glu Asp Thr Lys
20 25

<210> SEQ ID NO 269
<211> LENGTH: 8
<212> TYPE: PRT
<213> ORGANISM: Influenza virus

<400> SEQUENCE: 269

Lys Ile Cys Asn Asn Pro His Lys
1 5

<210> SEQ ID NO 270
<211> LENGTH: 14
<212> TYPE: PRT
<213> ORGANISM: Influenza virus

<400> SEQUENCE: 270

Lys Leu Asn Arg Val Ile Lys Lys Thr Asn Glu Lys Phe His
1 5 10

<210> SEQ ID NO 271
<211> LENGTH: 24
<212> TYPE: PRT
<213> ORGANISM: Influenza virus
<220> FEATURE:
<221> NAME/KEY: misc_feature
<222> LOCATION: (3)..(3)
<223> OTHER INFORMATION: Xaa can be Ile or Val
<220> FEATURE:
<221> NAME/KEY: misc_feature
<222> LOCATION: (17)..(17)
<223> OTHER INFORMATION: Xaa can be Gly or Gln
<220> FEATURE:
<221> NAME/KEY: misc_feature
<222> LOCATION: (20)..(20)
<223> OTHER INFORMATION: Xaa can be Arg or Lys
<220> FEATURE:
<221> NAME/KEY: misc_feature
<222> LOCATION: (22)..(22)
<223> OTHER INFORMATION: Xaa can be Gln or Gly

<400> SEQUENCE: 271

His Asp Xaa Tyr Arg Asp Glu Ala Leu Asn Asn Arg Phe Gln Ile Lys
1 5 10 15

Xaa Val Glu Xaa Ser Xaa Tyr Lys
20

<210> SEQ ID NO 272
<211> LENGTH: 25
<212> TYPE: PRT
<213> ORGANISM: Influenza virus

<400> SEQUENCE: 272

His Gln Ile Glu Lys Glu Phe Ser Glu Val Glu Gly Arg Ile Gln Asp
1 5 10 15

Leu Glu Lys Tyr Val Glu Asp Thr Lys
20 25

<210> SEQ ID NO 273
<211> LENGTH: 25
<212> TYPE: PRT
<213> ORGANISM: Influenza virus -continued

<400> SEQUENCE: 273

Lys Tyr Val Glu Asp Thr Lys Ile Asp Leu Trp Ser Tyr Asn Ala Glu
1 5 10 15

Leu Leu Val Ala Leu Glu Asn Gln His
20 25

<210> SEQ ID NO 274
<211> LENGTH: 49
<212> TYPE: PRT
<213> ORGANISM: Influenza virus

<400> SEQUENCE: 274

Lys Tyr Val Lys Gln Asn Ser Leu Lys Leu Ala Thr Gly Met Arg Asn
1 5 10 15

Val Pro Glu Lys Gln Thr Arg Gly Leu Phe Gly Ala Ile Ala Gly Phe
20 25 30

Ile Glu Asn Gly Trp Glu Gly Met Ile Asp Gly Trp Tyr Gly Phe Arg
35 40 45

His

<210> SEQ ID NO 275
<211> LENGTH: 39
<212> TYPE: PRT
<213> ORGANISM: Influenza virus

<400> SEQUENCE: 275

Lys Glu Phe Ser Glu Val Glu Gly Arg Ile Gln Asp Leu Glu Lys Tyr
1 5 10 15

Val Glu Asp Thr Lys Ile Asp Leu Trp Ser Tyr Asn Ala Glu Leu Leu
20 25 30

Val Ala Leu Glu Asn Gln His
35

<210> SEQ ID NO 276
<211> LENGTH: 33
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Ser or Glu
<220> FEATURE:
<221> NAME/KEY: misc_feature
<222> LOCATION: (5)..(5)
<223> OTHER INFORMATION: Xaa can be Glu or Gln
<220> FEATURE:
<221> NAME/KEY: misc_feature
<222> LOCATION: (7)..(7)
<223> OTHER INFORMATION: Xaa can be Thr or Ser
<220> FEATURE:
<221> NAME/KEY: misc_feature
<222> LOCATION: (9)..(9)
<223> OTHER INFORMATION: Xaa can be Gln or Tyr
<220> FEATURE:
<221> NAME/KEY: misc_feature
<222> LOCATION: (13)..(13)
<223> OTHER INFORMATION: Xaa can be Leu or Gln
<220> FEATURE:
<221> NAME/KEY: misc_feature
<222> LOCATION: (18)..(18)
<223> OTHER INFORMATION: Xaa can be Ala or Asn
<220> FEATURE:
<221> NAME/KEY: misc_feature
<222> LOCATION: (20)..(20)
<223> OTHER INFORMATION: Xaa can be Ile or Leu
<220> FEATURE:
<221> NAME/KEY: misc_feature -continued
<222> LOCATION: (22)..(22)
<223> OTHER INFORMATION: Xaa can be Gln or Gly
<220> FEATURE:
<221> NAME/KEY: misc_feature
<222> LOCATION: (24)..(24)
<223> OTHER INFORMATION: Xaa can be Asn or Thr
<220> FEATURE:
<221> NAME/KEY: misc_feature
<222> LOCATION: (25)..(25)
<223> OTHER INFORMATION: Xaa can be Gly or Asn
<220> FEATURE:
<221> NAME/KEY: misc_feature
<222> LOCATION: (27)..(27)
<223> OTHER INFORMATION: Xaa can be Leu or Val
<220> FEATURE:
<221> NAME/KEY: misc_feature
<222> LOCATION: (29)..(29)
<223> OTHER INFORMATION: Xaa can be Arg or Ser
<220> FEATURE:
<221> NAME/KEY: misc_feature
<222> LOCATION: (32)..(32)
<223> OTHER INFORMATION: Xaa can be Glu or Cys

<400> SEQUENCE: 276

```
His Gln Asn Xaa Xaa Gly Xaa Gly Xaa Ala Ala Asp Xaa Lys Ser Thr
1               5                   10                  15

Gln Xaa Ala Xaa Asp Xaa Ile Xaa Xaa Lys Xaa Asn Xaa Val Ile Xaa
            20                  25                  30

Lys
```

<210> SEQ ID NO 277
<211> LENGTH: 18
<212> TYPE: PRT
<213> ORGANISM: Influenza virus
<220> FEATURE:
<221> NAME/KEY: misc_feature
<222> LOCATION: (4)..(4)
<223> OTHER INFORMATION: Xaa can be Gly or Gln
<220> FEATURE:
<221> NAME/KEY: misc_feature
<222> LOCATION: (6)..(6)
<223> OTHER INFORMATION: Xaa can be Gln or Arg
<220> FEATURE:
<221> NAME/KEY: misc_feature
<222> LOCATION: (14)..(14)
<223> OTHER INFORMATION: Xaa can be Val or Ile
<220> FEATURE:
<221> NAME/KEY: misc_feature
<222> LOCATION: (17)..(17)
<223> OTHER INFORMATION: Xaa can be Ser or Thr

<400> SEQUENCE: 277

```
His Cys Asp Xaa Phe Xaa Asn Glu Lys Trp Asp Leu Phe Xaa Glu Arg
1               5                   10                  15

Xaa Lys
```

<210> SEQ ID NO 278
<211> LENGTH: 20
<212> TYPE: PRT
<213> ORGANISM: Influenza virus

<400> SEQUENCE: 278

```
His Thr Ile Asp Leu Thr Asp Ser Glu Met Asn Lys Lys Leu Phe Glu
1               5                   10                  15

Arg Thr Arg Lys
            20
```

<210> SEQ ID NO 279
<211> LENGTH: 28

-continued

<212> TYPE: PRT
<213> ORGANISM: Influenza virus

<400> SEQUENCE: 279

Lys Ser Gly Ser Thr Tyr Pro Val Leu Lys Val Thr Met Pro Asn Asn
1 5 10 15

Asp Asn Phe Asp Lys Leu Tyr Ile Trp Gly Val His
20 25

<210> SEQ ID NO 280
<211> LENGTH: 34
<212> TYPE: PRT
<213> ORGANISM: Influenza virus

<400> SEQUENCE: 280

Lys Leu Asn Trp Leu Thr Lys Ser Gly Asn Thr Tyr Pro Val Leu Asn
1 5 10 15

Val Thr Met Pro Asn Asn Asp Asn Phe Asp Lys Leu Val Ile Trp Gly
20 25 30

Val His

<210> SEQ ID NO 281
<211> LENGTH: 19
<212> TYPE: PRT
<213> ORGANISM: Influenza virus

<400> SEQUENCE: 281

His Thr Ile Asp Leu Thr Asp Ser Glu Met Asn Lys Leu Phe Glu Lys
1 5 10 15

Thr Arg Lys

<210> SEQ ID NO 282
<211> LENGTH: 18
<212> TYPE: PRT
<213> ORGANISM: Influenza virus

<400> SEQUENCE: 282

Lys Leu Asn Arg Leu Ile Glu Lys Thr Asn Glu Lys Phe His Gln Thr
1 5 10 15

Glu Lys

<210> SEQ ID NO 283
<211> LENGTH: 47
<212> TYPE: PRT
<213> ORGANISM: Influenza virus

<400> SEQUENCE: 283

His Thr Gly Lys Ser Ser Val Met Arg Ser Asp Ala Pro Ile Asp Phe
1 5 10 15

Cys Asn Ser Glu Cys Ile Thr Pro Asn Gln Ser Ile Pro Asn Asp Lys
20 25 30

Pro Phe Gln Asn Val Asn Lys Ile Thr Tyr Gly Ala Cys Pro Lys
35 40 45

<210> SEQ ID NO 284
<211> LENGTH: 39
<212> TYPE: PRT
<213> ORGANISM: Influenza virus

<400> SEQUENCE: 284

His Thr Gly Lys Ser Ser Val Met Arg Ser Asp Ala Pro Ile Asp Phe

-continued

```
1               5                   10                  15

Cys Asn Ser Glu Cys Ile Thr Pro Asn Gln Ser Ile Pro Asn Asp Lys
            20                  25                  30

Pro Phe Gln Asn Val Asn Lys
        35


<210> SEQ ID NO 285
<211> LENGTH: 33
<212> TYPE: PRT
<213> ORGANISM: Influenza virus

<400> SEQUENCE: 285

His Pro Ser Thr Asp Ser Asp Gln Thr Ser Leu Tyr Val Arg Ala Ser
1               5                   10                  15

Gly Arg Val Thr Val Ser Thr Lys Arg Ser Gln Gln Thr Val Ile Pro
            20                  25                  30

Lys


<210> SEQ ID NO 286
<211> LENGTH: 25
<212> TYPE: PRT
<213> ORGANISM: Influenza virus

<400> SEQUENCE: 286

Lys Tyr Val Glu Asp Thr Lys Ile Asp Leu Trp Ser Tyr Asn Ala Glu
1               5                   10                  15

Leu Leu Val Ala Leu Glu Asn Gln His
            20                  25


<210> SEQ ID NO 287
<211> LENGTH: 26
<212> TYPE: PRT
<213> ORGANISM: Influenza virus

<400> SEQUENCE: 287

Lys Leu Phe Glu Arg Thr Arg Lys Gln Leu Arg Glu Asn Ala Glu Asp
1               5                   10                  15

Met Gly Asn Gly Cys Phe Lys Ile Tyr His
            20                  25


<210> SEQ ID NO 288
<211> LENGTH: 16
<212> TYPE: PRT
<213> ORGANISM: Influenza virus

<400> SEQUENCE: 288

Lys Arg Arg Ser Ile Lys Ser Phe Phe Ser Arg Leu Asn Trp Leu His
1               5                   10                  15


<210> SEQ ID NO 289
<211> LENGTH: 16
<212> TYPE: PRT
<213> ORGANISM: Influenza virus
<220> FEATURE:
<221> NAME/KEY: misc_feature
<222> LOCATION: (12)..(12)
<223> OTHER INFORMATION: Xaa can be Val or Arg

<400> SEQUENCE: 289

His Pro Val Thr Ile Gly Glu Cys Pro Lys Tyr Xaa Lys Ser Thr Lys
1               5                   10                  15
```

-continued

<210> SEQ ID NO 290
<211> LENGTH: 30
<212> TYPE: PRT
<213> ORGANISM: Influenza virus

<400> SEQUENCE: 290

Lys Gly Asn Ser Tyr Pro Lys Leu Ser Lys Leu Ser Lys Ser Tyr Ile
1               5                   10                  15

Ile Asn Lys Lys Lys Glu Val Leu Val Ile Trp Gly Ile His
            20                  25                  30

<210> SEQ ID NO 291
<211> LENGTH: 24
<212> TYPE: PRT
<213> ORGANISM: Influenza virus
<220> FEATURE:
<221> NAME/KEY: misc_feature
<222> LOCATION: (9)..(9)
<223> OTHER INFORMATION: Xaa can be Val or Tyr

<400> SEQUENCE: 291

Lys Leu Ser Lys Leu Ser Lys Ser Xaa Ile Ile Asn Lys Lys Lys Glu
1               5                   10                  15

Val Leu Val Ile Trp Gly Ile His
            20

<210> SEQ ID NO 292
<211> LENGTH: 21
<212> TYPE: PRT
<213> ORGANISM: Influenza virus
<220> FEATURE:
<221> NAME/KEY: misc_feature
<222> LOCATION: (6)..(6)
<223> OTHER INFORMATION: Xaa can be Val or Tyr

<400> SEQUENCE: 292

Lys Leu Ser Lys Ser Xaa Ile Ile Asn Lys Lys Lys Glu Val Leu Val
1               5                   10                  15

Ile Trp Gly Ile His
            20

<210> SEQ ID NO 293
<211> LENGTH: 46
<212> TYPE: PRT
<213> ORGANISM: Plasmodium falciparum

<400> SEQUENCE: 293

Lys Glu Glu Glu Glu Lys Glu Lys Glu Lys Glu Lys Glu Lys Glu Glu
1               5                   10                  15

Lys Glu Lys Glu Glu Lys Glu Lys Glu Glu Lys Glu Lys Glu Lys Glu
            20                  25                  30

Glu Lys Glu Lys Glu Lys Glu Glu Lys Glu Glu Glu Lys Lys
        35                  40                  45

<210> SEQ ID NO 294
<211> LENGTH: 48
<212> TYPE: PRT
<213> ORGANISM: Plasmodium falciparum

<400> SEQUENCE: 294

Lys Glu Glu Glu Glu Lys Glu Lys Glu Lys Glu Lys Glu Lys Glu Glu
1               5                   10                  15

Lys Glu Lys Glu Glu Lys Glu Lys Glu Glu Lys Glu Lys Glu Lys Glu
            20                  25                  30

-continued

```
Glu Lys Glu Lys Glu Lys Glu Glu Lys Glu Glu Glu Lys Lys Glu Lys
        35                  40                  45
```

```
<210> SEQ ID NO 295
<211> LENGTH: 47
<212> TYPE: PRT
<213> ORGANISM: Plasmodium falciparum

<400> SEQUENCE: 295

Lys Glu Glu Glu Glu Lys Glu Lys Glu Lys Glu Lys Glu Lys Glu Glu
1               5                   10                  15

Lys Glu Lys Glu Glu Lys Glu Lys Glu Lys Glu Glu Lys Glu Lys Glu
            20                  25                  30

Glu Lys Glu Lys Glu Glu Lys Glu Glu Lys Glu Glu Glu Lys Lys
        35                  40                  45
```

```
<210> SEQ ID NO 296
<211> LENGTH: 10
<212> TYPE: PRT
<213> ORGANISM: Plasmodium falciparum

<400> SEQUENCE: 296

Lys Glu Glu Glu Glu Lys Glu Lys Glu Lys
1               5                   10
```

```
<210> SEQ ID NO 297
<211> LENGTH: 19
<212> TYPE: PRT
<213> ORGANISM: Plasmodium falciparum

<400> SEQUENCE: 297

His Lys Lys Leu Ile Lys Ala Leu Lys Lys Asn Ile Glu Ser Ile Gln
1               5                   10                  15

Asn Lys Lys
```

```
<210> SEQ ID NO 298
<211> LENGTH: 19
<212> TYPE: PRT
<213> ORGANISM: Plasmodium falciparum

<400> SEQUENCE: 298

His Lys Lys Leu Ile Lys Ala Leu Lys Lys Asn Ile Glu Ser Ile Gln
1               5                   10                  15

Asn Lys Met
```

```
<210> SEQ ID NO 299
<211> LENGTH: 10
<212> TYPE: PRT
<213> ORGANISM: Plasmodium falciparum

<400> SEQUENCE: 299

His Lys Lys Leu Ile Lys Ala Leu Lys Lys
1               5                   10
```

```
<210> SEQ ID NO 300
<211> LENGTH: 9
<212> TYPE: PRT
<213> ORGANISM: Plasmodium falciparum

<400> SEQUENCE: 300

His Lys Lys Leu Ile Lys Ala Leu Lys
1               5
```

-continued

<210> SEQ ID NO 301
<211> LENGTH: 23
<212> TYPE: PRT
<213> ORGANISM: Plasmodium falciparum

<400> SEQUENCE: 301

Lys Ala Thr Tyr Ser Phe Val Asn Thr Lys Lys Lys Ile Ile Ser Leu
1 5 10 15

Lys Ser Gln Gly His Lys Lys
20

<210> SEQ ID NO 302
<211> LENGTH: 22
<212> TYPE: PRT
<213> ORGANISM: Plasmodium falciparum

<400> SEQUENCE: 302

Lys Ala Thr Tyr Ser Phe Val Asn Thr Lys Lys Lys Ile Ile Ser Leu
1 5 10 15

Lys Ser Gln Gly His Lys
20

<210> SEQ ID NO 303
<211> LENGTH: 21
<212> TYPE: PRT
<213> ORGANISM: Plasmodium falciparum

<400> SEQUENCE: 303

Lys Ala Thr Tyr Ser Phe Val Asn Thr Lys Lys Lys Ile Ile Ser Leu
1 5 10 15

Lys Ser Gln Gly His
20

<210> SEQ ID NO 304
<211> LENGTH: 29
<212> TYPE: PRT
<213> ORGANISM: Plasmodium falciparum

<400> SEQUENCE: 304

His Thr Tyr Val Lys Gly Lys Lys Ala Pro Ser Asp Pro Gln Cys Ala
1 5 10 15

Asp Ile Lys Glu Glu Cys Lys Glu Leu Leu Lys Glu Lys
20 25

<210> SEQ ID NO 305
<211> LENGTH: 11
<212> TYPE: PRT
<213> ORGANISM: Plasmodium falciparum

<400> SEQUENCE: 305

Lys Ile Ile Ser Leu Lys Ser Gln Gly His Lys
1 5 10

<210> SEQ ID NO 306
<211> LENGTH: 21
<212> TYPE: PRT
<213> ORGANISM: Plasmodium falciparum

<400> SEQUENCE: 306

Lys Lys Lys Lys Phe Glu Pro Leu Lys Asn Gly Asn Val Ser Glu Thr
1 5 10 15

-continued

```
Ile Lys Leu Ile His
            20

<210> SEQ ID NO 307
<211> LENGTH: 20
<212> TYPE: PRT
<213> ORGANISM: Plasmodium falciparum

<400> SEQUENCE: 307

Lys Lys Lys Phe Glu Pro Leu Lys Asn Gly Asn Val Ser Glu Thr Ile
1               5                   10                  15

Lys Leu Ile His
            20

<210> SEQ ID NO 308
<211> LENGTH: 19
<212> TYPE: PRT
<213> ORGANISM: Plasmodium falciparum

<400> SEQUENCE: 308

Lys Lys Phe Glu Pro Leu Lys Asn Gly Asn Val Ser Glu Thr Ile Lys
1               5                   10                  15

Leu Ile His

<210> SEQ ID NO 309
<211> LENGTH: 13
<212> TYPE: PRT
<213> ORGANISM: Plasmodium falciparum

<400> SEQUENCE: 309

Lys Asn Gly Asn Val Ser Glu Thr Ile Lys Leu Ile His
1               5                   10

<210> SEQ ID NO 310
<211> LENGTH: 11
<212> TYPE: PRT
<213> ORGANISM: Plasmodium falciparum

<400> SEQUENCE: 310

Lys Leu Ile His Leu Gly Asn Lys Asp Lys Lys
1               5                   10

<210> SEQ ID NO 311
<211> LENGTH: 36
<212> TYPE: PRT
<213> ORGANISM: Plasmodium falciparum

<400> SEQUENCE: 311

Lys Val Lys Lys Ile Gly Val Thr Leu Lys Lys Phe Glu Pro Leu Lys
1               5                   10                  15

Asn Gly Asn Val Ser Glu Thr Ile Lys Leu Ile His Leu Gly Asn Lys
            20                  25                  30

Asp Lys Lys His
        35

<210> SEQ ID NO 312
<211> LENGTH: 59
<212> TYPE: PRT
<213> ORGANISM: Plasmodium falciparum

<400> SEQUENCE: 312

His Leu Ile Tyr Lys Asn Lys Ser Tyr Asn Pro Leu Leu Leu Ser Cys
1               5                   10                  15
```

-continued

```
Val Lys Lys Met Asn Met Leu Lys Glu Asn Val Asp Tyr Ile Gln Asn
            20                  25                  30

Gln Asn Leu Phe Lys Glu Leu Met Asn Gln Lys Ala Thr Tyr Ser Phe
        35                  40                  45

Val Asn Thr Lys Lys Lys Ile Ile Ser Leu Lys
    50                  55


<210> SEQ ID NO 313
<211> LENGTH: 52
<212> TYPE: PRT
<213> ORGANISM: Plasmodium falciparum

<400> SEQUENCE: 313

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys Ala Thr Tyr Ser Phe
        35                  40                  45

Val Asn Thr Lys
    50


<210> SEQ ID NO 314
<211> LENGTH: 43
<212> TYPE: PRT
<213> ORGANISM: Plasmodium falciparum

<400> SEQUENCE: 314

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Asn
            20                  25                  30

Gln Asn Leu Phe Lys Glu Leu Met Asn Gln Lys
        35                  40


<210> SEQ ID NO 315
<211> LENGTH: 38
<212> TYPE: PRT
<213> ORGANISM: Plasmodium falciparum

<400> SEQUENCE: 315

His Leu Ile Tyr Lys Asn Lys Ser Tyr Asn Pro Leu Leu Leu Ser Cys
1               5                   10                  15

Val Lys Lys Met Asn Met Leu Lys Glu Asn Val Asp Tyr Ile Gln Lys
            20                  25                  30

Asn Gln Asn Leu Phe Lys
        35


<210> SEQ ID NO 316
<211> LENGTH: 24
<212> TYPE: PRT
<213> ORGANISM: Plasmodium falciparum

<400> SEQUENCE: 316

His Leu Ile Tyr Lys Asn Lys Ser Tyr Asn Pro Leu Leu Leu Ser Cys
1               5                   10                  15

Val Lys Lys Met Asn Met Leu Lys
            20
```

-continued

<210> SEQ ID NO 317
<211> LENGTH: 47
<212> TYPE: PRT
<213> ORGANISM: Plasmodium falciparum

<400> SEQUENCE: 317

```
Lys Ser Ala Asn Asn Ser Ala Asn Asn Gly Lys Lys Asn Asn Ala Glu
1               5                   10                  15

Glu Met Lys Asn Leu Val Asn Phe Leu Gln Ser His Lys Lys Leu Ile
            20                  25                  30

Lys Ala Leu Lys Lys Asn Ile Glu Ser Ile Gln Asn Lys Lys His
        35                  40                  45
```

<210> SEQ ID NO 318
<211> LENGTH: 37
<212> TYPE: PRT
<213> ORGANISM: Plasmodium falciparum

<400> SEQUENCE: 318

```
Lys Lys Asn Asn Ala Glu Glu Met Lys Asn Leu Val Asn Phe Leu Gln
1               5                   10                  15

Ser His Lys Lys Leu Ile Lys Ala Leu Lys Lys Asn Ile Glu Ser Ile
            20                  25                  30

Gln Asn Lys Lys His
        35
```

<210> SEQ ID NO 319
<211> LENGTH: 29
<212> TYPE: PRT
<213> ORGANISM: Plasmodium falciparum

<400> SEQUENCE: 319

```
Lys Asn Leu Val Asn Phe Leu Gln Ser His Lys Lys Leu Ile Lys Ala
1               5                   10                  15

Leu Lys Lys Asn Ile Glu Ser Ile Gln Asn Lys Lys His
            20                  25
```

<210> SEQ ID NO 320
<211> LENGTH: 19
<212> TYPE: PRT
<213> ORGANISM: Plasmodium falciparum

<400> SEQUENCE: 320

```
Lys Lys Leu Ile Lys Ala Leu Lys Lys Asn Ile Glu Ser Ile Gln Asn
1               5                   10                  15

Lys Lys His
```

<210> SEQ ID NO 321
<211> LENGTH: 18
<212> TYPE: PRT
<213> ORGANISM: Plasmodium falciparum

<400> SEQUENCE: 321

```
Lys Leu Ile Lys Ala Leu Lys Lys Asn Ile Glu Ser Ile Gln Asn Lys
1               5                   10                  15

Lys His
```

<210> SEQ ID NO 322
<211> LENGTH: 12
<212> TYPE: PRT
<213> ORGANISM: Plasmodium falciparum -continued

<400> SEQUENCE: 322

Lys Lys Asn Ile Glu Ser Ile Gln Asn Lys Lys His
1 5 10

<210> SEQ ID NO 323
<211> LENGTH: 11
<212> TYPE: PRT
<213> ORGANISM: Plasmodium falciparum

<400> SEQUENCE: 323

Lys Asn Ile Glu Ser Ile Gln Asn Lys Lys His
1 5 10

<210> SEQ ID NO 324
<211> LENGTH: 17
<212> TYPE: PRT
<213> ORGANISM: Plasmodium falciparum

<400> SEQUENCE: 324

Lys Asn Asn Ala Glu Glu Met Lys Asn Leu Val Asn Phe Leu Gln Ser
1 5 10 15

His

<210> SEQ ID NO 325
<211> LENGTH: 23
<212> TYPE: PRT
<213> ORGANISM: Plasmodium falciparum

<400> SEQUENCE: 325

Lys Lys Leu Ile Lys Ala Leu Lys Lys Asn Ile Glu Ser Ile Gln Asn
1 5 10 15

Lys Lys Gln Gly His Lys Lys
20

<210> SEQ ID NO 326
<211> LENGTH: 19
<212> TYPE: PRT
<213> ORGANISM: Plasmodium falciparum

<400> SEQUENCE: 326

Lys Lys Asn Asn Ala Glu Glu Met Lys Asn Leu Val Asn Phe Leu Gln
1 5 10 15

Ser His Lys

<210> SEQ ID NO 327
<211> LENGTH: 17
<212> TYPE: PRT
<213> ORGANISM: Plasmodium falciparum

<400> SEQUENCE: 327

Lys Asn Asn Ala Glu Glu Met Lys Asn Leu Val Asn Phe Leu Gln Ser
1 5 10 15

His

<210> SEQ ID NO 328
<211> LENGTH: 22
<212> TYPE: PRT
<213> ORGANISM: Plasmodium falciparum

<400> SEQUENCE: 328

Lys Leu Ile Lys Ala Leu Lys Lys Asn Ile Glu Ser Ile Gln Asn Lys
1 5 10 15

-continued

```
Lys Gln Gly His Lys Lys
            20


<210> SEQ ID NO 329
<211> LENGTH: 28
<212> TYPE: PRT
<213> ORGANISM: Plasmodium falciparum

<400> SEQUENCE: 329

Lys Val Lys Lys Ile Gly Val Thr Leu Lys Lys Phe Glu Pro Leu Lys
1               5                   10                  15

Asn Gly Asn Val Ser Glu Thr Ile Lys Leu Ile His
            20                  25


<210> SEQ ID NO 330
<211> LENGTH: 13
<212> TYPE: PRT
<213> ORGANISM: Plasmodium falciparum

<400> SEQUENCE: 330

Lys Asn Gly Asn Val Ser Glu Thr Ile Lys Leu Ile His
1               5                   10


<210> SEQ ID NO 331
<211> LENGTH: 11
<212> TYPE: PRT
<213> ORGANISM: Plasmodium falciparum

<400> SEQUENCE: 331

Lys Leu Ile His Leu Gly Asn Lys Asp Lys Lys
1               5                   10


<210> SEQ ID NO 332
<211> LENGTH: 28
<212> TYPE: PRT
<213> ORGANISM: Plasmodium falciparum

<400> SEQUENCE: 332

Lys Ser Ala Asn Asn Ser Ala Asn Asn Gly Lys Lys Asn Asn Ala Glu
1               5                   10                  15

Glu Met Lys Asn Leu Val Asn Phe Leu Gln Ser His
            20                  25


<210> SEQ ID NO 333
<211> LENGTH: 18
<212> TYPE: PRT
<213> ORGANISM: Plasmodium falciparum

<400> SEQUENCE: 333

Lys Lys Asn Asn Ala Glu Glu Met Lys Asn Leu Val Asn Phe Leu Gln
1               5                   10                  15

Ser His


<210> SEQ ID NO 334
<211> LENGTH: 19
<212> TYPE: PRT
<213> ORGANISM: Plasmodium falciparum

<400> SEQUENCE: 334

Lys Lys Leu Ile Lys Ala Leu Lys Lys Asn Ile Glu Ser Ile Gln Asn
1               5                   10                  15

Lys Lys His
```

-continued

<210> SEQ ID NO 335
<211> LENGTH: 15
<212> TYPE: PRT
<213> ORGANISM: Plasmodium falciparum

<400> SEQUENCE: 335

Lys Ala Leu Lys Lys Asn Ile Glu Ser Ile Gln Asn Lys Lys His
1               5                   10                  15

<210> SEQ ID NO 336
<211> LENGTH: 12
<212> TYPE: PRT
<213> ORGANISM: Plasmodium falciparum

<400> SEQUENCE: 336

Lys Lys Asn Ile Glu Ser Ile Gln Asn Lys Lys His
1               5                   10

<210> SEQ ID NO 337
<211> LENGTH: 27
<212> TYPE: PRT
<213> ORGANISM: Plasmodium falciparum

<400> SEQUENCE: 337

Lys Glu Leu Met Asn Gln Lys Ala Thr Tyr Ser Phe Val Asn Thr Lys
1               5                   10                  15

Lys Lys Ile Ile Ser Leu Lys Ser Gln Gly His
            20                  25

<210> SEQ ID NO 338
<211> LENGTH: 7
<212> TYPE: PRT
<213> ORGANISM: Plasmodium falciparum

<400> SEQUENCE: 338

Lys Ser Gln Gly His Lys Lys
1               5

<210> SEQ ID NO 339
<211> LENGTH: 12
<212> TYPE: PRT
<213> ORGANISM: Plasmodium falciparum

<400> SEQUENCE: 339

Lys Lys Lys Ile Ile Ser Leu Lys Ser Gln Gly His
1               5                   10

<210> SEQ ID NO 340
<211> LENGTH: 11
<212> TYPE: PRT
<213> ORGANISM: Plasmodium falciparum

<400> SEQUENCE: 340

Lys Lys Ile Ile Ser Leu Lys Ser Gln Gly His
1               5                   10

<210> SEQ ID NO 341
<211> LENGTH: 12
<212> TYPE: PRT
<213> ORGANISM: Plasmodium falciparum

<400> SEQUENCE: 341

Lys Lys Asn Ile Glu Ser Ile Gln Asn Lys Lys His

-continued

```
1               5                   10


<210> SEQ ID NO 342
<211> LENGTH: 11
<212> TYPE: PRT
<213> ORGANISM: Plasmodium falciparum

<400> SEQUENCE: 342

Lys Asn Ile Glu Ser Ile Gln Asn Lys Lys His
1               5                   10


<210> SEQ ID NO 343
<211> LENGTH: 29
<212> TYPE: PRT
<213> ORGANISM: Plasmodium falciparum

<400> SEQUENCE: 343

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys Glu Lys
            20                  25


<210> SEQ ID NO 344
<211> LENGTH: 27
<212> TYPE: PRT
<213> ORGANISM: Plasmodium falciparum

<400> SEQUENCE: 344

His Thr Tyr Val Lys Gly Lys Lys Ala Pro Ser Asp Pro Gln Cys Ala
1               5                   10                  15

Asp Ile Lys Glu Glu Cys Lys Glu Leu Leu Lys
            20                  25


<210> SEQ ID NO 345
<211> LENGTH: 29
<212> TYPE: PRT
<213> ORGANISM: Plasmodium falciparum

<400> SEQUENCE: 345

His Glu Asn Val Leu Ser Ala Ala Leu Glu Asn Thr Gln Ser Glu Glu
1               5                   10                  15

Glu Lys Lys Glu Val Ile Asp Val Ile Glu Glu Val Lys
            20                  25


<210> SEQ ID NO 346
<211> LENGTH: 48
<212> TYPE: PRT
<213> ORGANISM: Plasmodium falciparum

<400> SEQUENCE: 346

Lys Glu Asn Val Val Thr Thr Ile Leu Glu Lys Val Glu Glu Thr Thr
1               5                   10                  15

Ala Glu Ser Val Thr Thr Phe Ser Asn Ile Leu Glu Glu Ile Gln Glu
            20                  25                  30

Asn Thr Ile Thr Asn Asp Thr Ile Glu Glu Lys Leu Glu Glu Leu His
        35                  40                  45


<210> SEQ ID NO 347
<211> LENGTH: 14
<212> TYPE: PRT
<213> ORGANISM: Plasmodium falciparum

<400> SEQUENCE: 347
```

-continued

```
His Tyr Leu Gln Gln Met Lys Glu Lys Phe Ser Lys Glu Lys
1               5                   10


<210> SEQ ID NO 348
<211> LENGTH: 42
<212> TYPE: PRT
<213> ORGANISM: Plasmodium falciparum

<400> SEQUENCE: 348

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys
        35                  40


<210> SEQ ID NO 349
<211> LENGTH: 48
<212> TYPE: PRT
<213> ORGANISM: Plasmodium falciparum

<400> SEQUENCE: 349

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45


<210> SEQ ID NO 350
<211> LENGTH: 57
<212> TYPE: PRT
<213> ORGANISM: Plasmodium falciparum

<400> SEQUENCE: 350

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

Val Pro Lys Lys Arg Arg Thr Gln Lys
    50                  55


<210> SEQ ID NO 351
<211> LENGTH: 59
<212> TYPE: PRT
<213> ORGANISM: Plasmodium falciparum

<400> SEQUENCE: 351

His Tyr Leu Gln Gln Met Lys Glu Lys Phe Ser Lys Glu Lys Asn Asn
1               5                   10                  15

Asn Val Ile Glu Val Thr Asn Lys Ala Glu Lys Lys Gly Asn Val Gln
            20                  25                  30

Val Thr Asn Lys Thr Glu Lys Thr Thr Lys Val Asp Lys Asn Asn Lys
        35                  40                  45

Val Pro Lys Lys Arg Arg Thr Gln Lys Ser Lys
    50                  55
```

-continued

<210> SEQ ID NO 352
<211> LENGTH: 52
<212> TYPE: PRT
<213> ORGANISM: Plasmodium falciparum

<400> SEQUENCE: 352

His Val Asp Glu Val Met Lys Tyr Val Gln Lys Ile Asp Lys Glu Val
1 5 10 15

Asp Lys Glu Val Ser Lys Ala Leu Glu Ser Lys Asn Asp Val Thr Asn
20 25 30

Val Leu Lys Gln Asn Gln Asp Phe Phe Ser Lys Val Lys Asn Phe Val
35 40 45

Lys Lys Tyr Lys
50

<210> SEQ ID NO 353
<211> LENGTH: 50
<212> TYPE: PRT
<213> ORGANISM: Plasmodium falciparum

<400> SEQUENCE: 353

His Val Asp Glu Val Met Lys Tyr Val Gln Lys Ile Asp Lys Glu Val
1 5 10 15

Asp Lys Glu Val Ser Lys Ala Leu Glu Ser Lys Asn Asp Val Thr Asn
20 25 30

Val Leu Lys Gln Asn Gln Asp Phe Phe Ser Lys Val Lys Asn Phe Val
35 40 45

Lys Lys
50

<210> SEQ ID NO 354
<211> LENGTH: 43
<212> TYPE: PRT
<213> ORGANISM: Plasmodium falciparum

<400> SEQUENCE: 354

His Val Asp Glu Val Met Lys Tyr Val Gln Lys Ile Asp Lys Glu Val
1 5 10 15

Asp Lys Glu Val Ser Lys Ala Leu Glu Ser Lys Asn Asp Val Thr Asn
20 25 30

Val Leu Lys Gln Asn Gln Asp Phe Phe Ser Lys
35 40

<210> SEQ ID NO 355
<211> LENGTH: 35
<212> TYPE: PRT
<213> ORGANISM: Plasmodium falciparum

<400> SEQUENCE: 355

His Val Asp Glu Val Met Lys Tyr Val Gln Lys Ile Asp Lys Glu Val
1 5 10 15

Asp Lys Glu Val Ser Lys Ala Leu Glu Ser Lys Asn Asp Val Thr Asn
20 25 30

Val Leu Lys
35

<210> SEQ ID NO 356
<211> LENGTH: 27
<212> TYPE: PRT
<213> ORGANISM: Plasmodium falciparum -continued

<400> SEQUENCE: 356

His Val Asp Glu Val Met Lys Tyr Val Gln Lys Ile Asp Lys Glu Val
1 5 10 15

Asp Lys Glu Val Ser Lys Ala Leu Glu Ser Lys
20 25

<210> SEQ ID NO 357
<211> LENGTH: 22
<212> TYPE: PRT
<213> ORGANISM: Plasmodium falciparum

<400> SEQUENCE: 357

His Val Asp Glu Val Met Lys Tyr Val Gln Lys Ile Asp Lys Glu Val
1 5 10 15

Asp Lys Glu Val Ser Lys
20

<210> SEQ ID NO 358
<211> LENGTH: 18
<212> TYPE: PRT
<213> ORGANISM: Plasmodium falciparum

<400> SEQUENCE: 358

His Val Asp Glu Val Met Lys Tyr Val Gln Lys Ile Asp Lys Glu Val
1 5 10 15

Asp Lys

<210> SEQ ID NO 359
<211> LENGTH: 14
<212> TYPE: PRT
<213> ORGANISM: Plasmodium falciparum

<400> SEQUENCE: 359

His Val Asp Glu Val Met Lys Tyr Val Gln Lys Ile Asp Lys
1 5 10

<210> SEQ ID NO 360
<211> LENGTH: 39
<212> TYPE: PRT
<213> ORGANISM: Plasmodium falciparum

<400> SEQUENCE: 360

Lys Asp Glu Val Ile Asp Leu Ile Val Gln Lys Glu Lys Arg Ile Glu
1 5 10 15

Lys Val Lys Ala Lys Lys Lys Lys Leu Glu Lys Lys Val Glu Glu Gly
20 25 30

Val Ser Gly Leu Lys Lys His
35

<210> SEQ ID NO 361
<211> LENGTH: 23
<212> TYPE: PRT
<213> ORGANISM: Plasmodium falciparum

<400> SEQUENCE: 361

Lys Val Lys Ala Lys Lys Lys Lys Leu Glu Lys Lys Val Glu Glu Gly
1 5 10 15

Val Ser Gly Leu Lys Lys His
20

<210> SEQ ID NO 362

<211> LENGTH: 21
<212> TYPE: PRT
<213> ORGANISM: Plasmodium falciparum

<400> SEQUENCE: 362

Lys Ala Lys Lys Lys Lys Leu Glu Lys Lys Val Glu Glu Gly Val Ser
1 5 10 15

Gly Leu Lys Lys His
20

<210> SEQ ID NO 363
<211> LENGTH: 19
<212> TYPE: PRT
<213> ORGANISM: Plasmodium falciparum

<400> SEQUENCE: 363

Lys Lys Lys Lys Leu Glu Lys Lys Val Glu Glu Gly Val Ser Gly Leu
1 5 10 15

Lys Lys His

<210> SEQ ID NO 364
<211> LENGTH: 18
<212> TYPE: PRT
<213> ORGANISM: Plasmodium falciparum

<400> SEQUENCE: 364

Lys Lys Lys Leu Glu Lys Lys Val Glu Glu Gly Val Ser Gly Leu Lys
1 5 10 15

Lys His

<210> SEQ ID NO 365
<211> LENGTH: 17
<212> TYPE: PRT
<213> ORGANISM: Plasmodium falciparum

<400> SEQUENCE: 365

Lys Lys Leu Glu Lys Lys Val Glu Glu Gly Val Ser Gly Leu Lys Lys
1 5 10 15

His

<210> SEQ ID NO 366
<211> LENGTH: 16
<212> TYPE: PRT
<213> ORGANISM: Plasmodium falciparum

<400> SEQUENCE: 366

Lys Leu Glu Lys Lys Val Glu Glu Gly Val Ser Gly Leu Lys Lys His
1 5 10 15

<210> SEQ ID NO 367
<211> LENGTH: 13
<212> TYPE: PRT
<213> ORGANISM: Plasmodium falciparum

<400> SEQUENCE: 367

Lys Lys Val Glu Glu Gly Val Ser Gly Leu Lys Lys His
1 5 10

<210> SEQ ID NO 368
<211> LENGTH: 12
<212> TYPE: PRT
<213> ORGANISM: Plasmodium falciparum -continued

<400> SEQUENCE: 368

Lys Val Glu Glu Gly Val Ser Gly Leu Lys Lys His
1 5 10

<210> SEQ ID NO 369
<211> LENGTH: 59
<212> TYPE: PRT
<213> ORGANISM: Plasmodium falciparum

<400> SEQUENCE: 369

His Val Glu Gln Asn Val Tyr Val Asp Val Asp Val Pro Ala Met Lys
1 5 10 15

Asp Gln Phe Leu Gly Ile Leu Asn Glu Ala Gly Gly Leu Lys Glu Met
20 25 30

Phe Phe Asn Leu Glu Asp Val Phe Lys Ser Glu Ser Asp Val Ile Thr
35 40 45

Val Glu Glu Ile Lys Asp Glu Pro Val Gln Lys
50 55

<210> SEQ ID NO 370
<211> LENGTH: 53
<212> TYPE: PRT
<213> ORGANISM: Plasmodium falciparum

<400> SEQUENCE: 370

His Ile Lys Gly Leu Glu Glu Asp Asp Leu Glu Glu Val Asp Asp Leu
1 5 10 15

Lys Gly Ser Ile Leu Asp Met Leu Lys Gly Asp Met Glu Leu Gly Asp
20 25 30

Met Asp Lys Glu Ser Leu Glu Asp Val Thr Thr Lys Leu Gly Glu Arg
35 40 45

Val Glu Ser Leu Lys
50

<210> SEQ ID NO 371
<211> LENGTH: 44
<212> TYPE: PRT
<213> ORGANISM: Plasmodium falciparum

<400> SEQUENCE: 371

His Ile Lys Gly Leu Glu Glu Asp Asp Leu Glu Glu Val Asp Asp Leu
1 5 10 15

Lys Gly Ser Ile Leu Asp Met Leu Lys Gly Asp Met Glu Leu Gly Asp
20 25 30

Met Asp Lys Glu Ser Leu Glu Asp Val Thr Thr Lys
35 40

<210> SEQ ID NO 372
<211> LENGTH: 35
<212> TYPE: PRT
<213> ORGANISM: Plasmodium falciparum

<400> SEQUENCE: 372

His Ile Lys Gly Leu Glu Glu Asp Asp Leu Glu Glu Val Asp Asp Leu
1 5 10 15

Lys Gly Ser Ile Leu Asp Met Leu Lys Gly Asp Met Glu Leu Gly Asp
20 25 30

Met Asp Lys
35

-continued

<210> SEQ ID NO 373
<211> LENGTH: 25
<212> TYPE: PRT
<213> ORGANISM: Plasmodium falciparum

<400> SEQUENCE: 373

His Ile Lys Gly Leu Glu Glu Asp Asp Leu Glu Glu Val Asp Asp Leu
1               5                   10                  15

Lys Gly Ser Ile Leu Asp Met Leu Lys
            20                  25

<210> SEQ ID NO 374
<211> LENGTH: 31
<212> TYPE: PRT
<213> ORGANISM: Plasmodium falciparum

<400> SEQUENCE: 374

His Ile Ile Ser Gly Asp Ala Asp Val Leu Ser Ser Ala Leu Gly Met
1               5                   10                  15

Asp Glu Glu Gln Met Lys Thr Arg Lys Lys Ala Gln Arg Pro Lys
            20                  25                  30

<210> SEQ ID NO 375
<211> LENGTH: 23
<212> TYPE: PRT
<213> ORGANISM: Plasmodium falciparum

<400> SEQUENCE: 375

His Asp Ile Thr Thr Thr Leu Asp Glu Val Val Glu Leu Lys Asp Val
1               5                   10                  15

Glu Glu Asp Lys Ile Glu Lys
            20

<210> SEQ ID NO 376
<211> LENGTH: 10
<212> TYPE: PRT
<213> ORGANISM: Plasmodium falciparum

<400> SEQUENCE: 376

Lys Lys Leu Glu Glu Val His Glu Leu Lys
1               5                   10

<210> SEQ ID NO 377
<211> LENGTH: 9
<212> TYPE: PRT
<213> ORGANISM: Plasmodium falciparum

<400> SEQUENCE: 377

Lys Leu Glu Glu Val His Glu Leu Lys
1               5

<210> SEQ ID NO 378
<211> LENGTH: 19
<212> TYPE: PRT
<213> ORGANISM: Plasmodium falciparum

<400> SEQUENCE: 378

Lys Thr Ile Glu Thr Asp Ile Leu Glu Glu Lys Lys Lys Glu Ile Glu
1               5                   10                  15

Lys Asp His

<210> SEQ ID NO 379

-continued

<211> LENGTH: 11
<212> TYPE: PRT
<213> ORGANISM: Plasmodium falciparum

<400> SEQUENCE: 379

Lys Lys Glu Ile Glu Lys Asp His Phe Glu Lys
1 5 10

<210> SEQ ID NO 380
<211> LENGTH: 6
<212> TYPE: PRT
<213> ORGANISM: Plasmodium falciparum

<400> SEQUENCE: 380

Lys Asp His Phe Glu Lys
1 5

<210> SEQ ID NO 381
<211> LENGTH: 11
<212> TYPE: PRT
<213> ORGANISM: Plasmodium falciparum

<400> SEQUENCE: 381

Lys Phe Glu Glu Glu Ala Glu Glu Ile Lys His
1 5 10

<210> SEQ ID NO 382
<211> LENGTH: 47
<212> TYPE: PRT
<213> ORGANISM: Plasmodium falciparum

<400> SEQUENCE: 382

Lys Asp Gly Asp Thr Lys Cys Thr Leu Glu Cys Ala Gln Gly Lys Lys
1 5 10 15

Cys Ile Lys His Lys Ser Asp His Asn His Lys Ser Asp His Asn His
20 25 30

Lys Ser Asp Pro Asn His Lys Lys Lys Asn Asn Asn Asn Asn Lys
35 40 45

<210> SEQ ID NO 383
<211> LENGTH: 40
<212> TYPE: PRT
<213> ORGANISM: Plasmodium falciparum

<400> SEQUENCE: 383

Lys Asp Gly Asp Thr Lys Cys Thr Leu Glu Cys Ala Gln Gly Lys Lys
1 5 10 15

Cys Ile Lys His Lys Ser Asp His Asn His Lys Ser Asp His Asn His
20 25 30

Lys Ser Asp Pro Asn His Lys Lys
35 40

<210> SEQ ID NO 384
<211> LENGTH: 39
<212> TYPE: PRT
<213> ORGANISM: Plasmodium falciparum

<400> SEQUENCE: 384

Lys Asp Gly Asp Thr Lys Cys Thr Leu Glu Cys Ala Gln Gly Lys Lys
1 5 10 15

Cys Ile Lys His Lys Ser Asp His Asn His Lys Ser Asp His Asn His
20 25 30

-continued

```
Lys Ser Asp Pro Asn His Lys
        35


<210> SEQ ID NO 385
<211> LENGTH: 33
<212> TYPE: PRT
<213> ORGANISM: Plasmodium falciparum

<400> SEQUENCE: 385

Lys Asp Gly Asp Thr Lys Cys Thr Leu Glu Cys Ala Gln Gly Lys Lys
1               5                   10                  15

Cys Ile Lys His Lys Ser Asp His Asn His Lys Ser Asp His Asn His
            20                  25                  30

Lys


<210> SEQ ID NO 386
<211> LENGTH: 27
<212> TYPE: PRT
<213> ORGANISM: Plasmodium falciparum

<400> SEQUENCE: 386

Lys Asp Gly Asp Thr Lys Cys Thr Leu Glu Cys Ala Gln Gly Lys Lys
1               5                   10                  15

Cys Ile Lys His Lys Ser Asp His Asn His Lys
            20                  25


<210> SEQ ID NO 387
<211> LENGTH: 21
<212> TYPE: PRT
<213> ORGANISM: Plasmodium falciparum

<400> SEQUENCE: 387

Lys Asp Gly Asp Thr Lys Cys Thr Leu Glu Cys Ala Gln Gly Lys Lys
1               5                   10                  15

Cys Ile Lys His Lys
            20


<210> SEQ ID NO 388
<211> LENGTH: 16
<212> TYPE: PRT
<213> ORGANISM: Plasmodium falciparum

<400> SEQUENCE: 388

Lys Asp Gly Asp Thr Lys Cys Thr Leu Glu Cys Ala Gln Gly Lys Lys
1               5                   10                  15


<210> SEQ ID NO 389
<211> LENGTH: 15
<212> TYPE: PRT
<213> ORGANISM: Plasmodium falciparum

<400> SEQUENCE: 389

Lys Asp Gly Asp Thr Lys Cys Thr Leu Glu Cys Ala Gln Gly Lys
1               5                   10                  15


<210> SEQ ID NO 390
<211> LENGTH: 23
<212> TYPE: PRT
<213> ORGANISM: Plasmodium falciparum

<400> SEQUENCE: 390

Lys Cys Ile Gln Ala Glu Cys Asn Tyr Lys Glu Cys Gly Glu Gln Lys
1               5                   10                  15
```

-continued

Cys Val Trp Asp Gly Ile His
            20

<210> SEQ ID NO 391
<211> LENGTH: 14
<212> TYPE: PRT
<213> ORGANISM: Plasmodium falciparum

<400> SEQUENCE: 391

Lys Glu Cys Gly Glu Gln Lys Cys Val Trp Asp Gly Ile His
1               5                   10

<210> SEQ ID NO 392
<211> LENGTH: 32
<212> TYPE: PRT
<213> ORGANISM: Plasmodium falciparum

<400> SEQUENCE: 392

His Ile Glu Cys Lys Cys Asn Asn Asp Tyr Val Leu Thr Asn Arg Tyr
1               5                   10                  15

Glu Cys Glu Pro Lys Asn Lys Cys Thr Ser Leu Glu Asp Thr Asn Lys
            20                  25                  30

<210> SEQ ID NO 393
<211> LENGTH: 39
<212> TYPE: PRT
<213> ORGANISM: Plasmodium falciparum

<400> SEQUENCE: 393

Lys Ser Asp His Asn His Lys Ser Asp His Asn His Lys Ser Asp His
1               5                   10                  15

Asn His Lys Ser Asp His Asn His Lys Ser Asp Pro Asn His Lys Lys
            20                  25                  30

Lys Asn Asn Asn Asn Asn Lys
        35

<210> SEQ ID NO 394
<211> LENGTH: 33
<212> TYPE: PRT
<213> ORGANISM: Plasmodium falciparum

<400> SEQUENCE: 394

Lys Ser Asp His Asn His Lys Ser Asp His Asn His Lys Ser Asp His
1               5                   10                  15

Asn His Lys Ser Asp Pro Asn His Lys Lys Lys Asn Asn Asn Asn Asn
            20                  25                  30

Lys

<210> SEQ ID NO 395
<211> LENGTH: 27
<212> TYPE: PRT
<213> ORGANISM: Plasmodium falciparum

<400> SEQUENCE: 395

Lys Ser Asp His Asn His Lys Ser Asp His Asn His Lys Ser Asp Pro
1               5                   10                  15

Asn His Lys Lys Lys Asn Asn Asn Asn Asn Lys
            20                  25

<210> SEQ ID NO 396
<211> LENGTH: 21

-continued

<212> TYPE: PRT
<213> ORGANISM: Plasmodium falciparum

<400> SEQUENCE: 396

Lys Ser Asp His Asn His Lys Ser Asp Pro Asn His Lys Lys Lys Asn
1 5 10 15

Asn Asn Asn Asn Lys
20

<210> SEQ ID NO 397
<211> LENGTH: 18
<212> TYPE: PRT
<213> ORGANISM: Plasmodium falciparum

<400> SEQUENCE: 397

Lys Lys Lys Asn Asn Asn Asn Asn Lys Asp Asn Lys Ser Asp Pro Asn
1 5 10 15

His Lys

<210> SEQ ID NO 398
<211> LENGTH: 17
<212> TYPE: PRT
<213> ORGANISM: Plasmodium falciparum

<400> SEQUENCE: 398

Lys Lys Asn Asn Asn Asn Asn Lys Asp Asn Lys Ser Asp Pro Asn His
1 5 10 15

Lys

<210> SEQ ID NO 399
<211> LENGTH: 16
<212> TYPE: PRT
<213> ORGANISM: Plasmodium falciparum

<400> SEQUENCE: 399

Lys Asn Asn Asn Asn Asn Lys Asp Asn Lys Ser Asp Pro Asn His Lys
1 5 10 15

<210> SEQ ID NO 400
<211> LENGTH: 10
<212> TYPE: PRT
<213> ORGANISM: Plasmodium falciparum

<400> SEQUENCE: 400

Lys Asp Asn Lys Ser Asp Pro Asn His Lys
1 5 10

<210> SEQ ID NO 401
<211> LENGTH: 7
<212> TYPE: PRT
<213> ORGANISM: Plasmodium falciparum

<400> SEQUENCE: 401

Lys Ser Asp Pro Asn His Lys
1 5

<210> SEQ ID NO 402
<211> LENGTH: 35
<212> TYPE: PRT
<213> ORGANISM: Plasmodium falciparum

<400> SEQUENCE: 402

His Ser Leu Tyr Ala Leu Gln Gln Asn Glu Glu Tyr Gln Lys Val Lys

-continued

```
1               5                   10                  15

Asn Glu Lys Asp Gln Asn Glu Ile Lys Lys Ile Lys Gln Leu Ile Glu
            20                  25                  30

Lys Asn Lys
        35


<210> SEQ ID NO 403
<211> LENGTH: 28
<212> TYPE: PRT
<213> ORGANISM: Plasmodium falciparum

<400> SEQUENCE: 403

His Ser Leu Tyr Ala Leu Gln Gln Asn Glu Glu Tyr Gln Lys Val Lys
1               5                   10                  15

Asn Glu Lys Asp Gln Asn Glu Ile Lys Lys Ile Lys
            20                  25


<210> SEQ ID NO 404
<211> LENGTH: 26
<212> TYPE: PRT
<213> ORGANISM: Plasmodium falciparum

<400> SEQUENCE: 404

His Ser Leu Tyr Ala Leu Gln Gln Asn Glu Glu Tyr Gln Lys Val Lys
1               5                   10                  15

Asn Glu Lys Asp Gln Asn Glu Ile Lys Lys
            20                  25


<210> SEQ ID NO 405
<211> LENGTH: 25
<212> TYPE: PRT
<213> ORGANISM: Plasmodium falciparum

<400> SEQUENCE: 405

His Ser Leu Tyr Ala Leu Gln Gln Asn Glu Glu Tyr Gln Lys Val Lys
1               5                   10                  15

Asn Glu Lys Asp Gln Asn Glu Ile Lys
            20                  25


<210> SEQ ID NO 406
<211> LENGTH: 11
<212> TYPE: PRT
<213> ORGANISM: Plasmodium falciparum

<400> SEQUENCE: 406

His Lys Leu Glu Asn Leu Glu Glu Met Asp Lys
1               5                   10


<210> SEQ ID NO 407
<211> LENGTH: 11
<212> TYPE: PRT
<213> ORGANISM: Plasmodium falciparum

<400> SEQUENCE: 407

Lys His Phe Asp Asp Asn Thr Asn Glu Gln Lys
1               5                   10


<210> SEQ ID NO 408
<211> LENGTH: 8
<212> TYPE: PRT
<213> ORGANISM: Plasmodium falciparum

<400> SEQUENCE: 408
```

-continued

```
Lys Lys Glu Asp Asp Glu Lys His
1               5


<210> SEQ ID NO 409
<211> LENGTH: 13
<212> TYPE: PRT
<213> ORGANISM: Plasmodium falciparum

<400> SEQUENCE: 409

Lys Glu Glu Asn Asn Lys Lys Glu Asp Asp Glu Lys His
1               5                   10


<210> SEQ ID NO 410
<211> LENGTH: 21
<212> TYPE: PRT
<213> ORGANISM: Plasmodium falciparum

<400> SEQUENCE: 410

Lys Thr Ser Ser Gly Ile Leu Asn Lys Glu Glu Asn Asn Lys Lys Glu
1               5                   10                  15

Asp Asp Glu Lys His
            20


<210> SEQ ID NO 411
<211> LENGTH: 7
<212> TYPE: PRT
<213> ORGANISM: Plasmodium falciparum

<400> SEQUENCE: 411

Lys Asn Ile His Ile Lys Lys
1               5


<210> SEQ ID NO 412
<211> LENGTH: 13
<212> TYPE: PRT
<213> ORGANISM: Plasmodium falciparum

<400> SEQUENCE: 412

His Ile Lys Lys Lys Glu Gly Ile Asp Ile Gly Tyr Lys
1               5                   10


<210> SEQ ID NO 413
<211> LENGTH: 21
<212> TYPE: PRT
<213> ORGANISM: Plasmodium falciparum

<400> SEQUENCE: 413

Lys Lys Met Trp Thr Cys Lys Leu Trp Asp Asn Lys Gly Asn Glu Ile
1               5                   10                  15

Thr Lys Asn Ile His
            20


<210> SEQ ID NO 414
<211> LENGTH: 30
<212> TYPE: PRT
<213> ORGANISM: Plasmodium falciparum

<400> SEQUENCE: 414

Lys Lys Gly Ile Gln Trp Asn Leu Leu Lys Lys Met Trp Thr Cys Lys
1               5                   10                  15

Leu Trp Asp Asn Lys Gly Asn Glu Ile Thr Lys Asn Ile His
            20                  25                  30
```

-continued

<210> SEQ ID NO 415
<211> LENGTH: 50
<212> TYPE: PRT
<213> ORGANISM: Plasmodium falciparum

<400> SEQUENCE: 415

```
Lys Glu Lys Lys Asp Ser Asn Glu Asn Arg Lys Lys Lys Gln Lys Glu
1               5                   10                  15

Asp Lys Lys Asn Pro Asn Lys Leu Lys Lys Ile Glu Tyr Thr Asn Lys
            20                  25                  30

Ile Thr His Phe Phe Lys Ala Lys Asn Asn Lys Gln Gln Asn Asn Val
        35                  40                  45

Thr His
    50
```

<210> SEQ ID NO 416
<211> LENGTH: 48
<212> TYPE: PRT
<213> ORGANISM: Plasmodium falciparum

<400> SEQUENCE: 416

```
Lys Lys Asp Ser Asn Glu Asn Arg Lys Lys Lys Gln Lys Glu Asp Lys
1               5                   10                  15

Lys Asn Pro Asn Lys Leu Lys Lys Ile Glu Tyr Thr Asn Lys Ile Thr
            20                  25                  30

His Phe Phe Lys Ala Lys Asn Asn Lys Gln Gln Asn Asn Val Thr His
        35                  40                  45
```

<210> SEQ ID NO 417
<211> LENGTH: 47
<212> TYPE: PRT
<213> ORGANISM: Plasmodium falciparum

<400> SEQUENCE: 417

```
Lys Asp Ser Asn Glu Asn Arg Lys Lys Lys Gln Lys Glu Asp Lys Lys
1               5                   10                  15

Asn Pro Asn Lys Leu Lys Lys Ile Glu Tyr Thr Asn Lys Ile Thr His
            20                  25                  30

Phe Phe Lys Ala Lys Asn Asn Lys Gln Gln Asn Asn Val Thr His
        35                  40                  45
```

<210> SEQ ID NO 418
<211> LENGTH: 39
<212> TYPE: PRT
<213> ORGANISM: Plasmodium falciparum

<400> SEQUENCE: 418

```
Lys Lys Gln Lys Glu Asp Lys Lys Asn Pro Asn Lys Leu Lys Lys Ile
1               5                   10                  15

Glu Tyr Thr Asn Lys Ile Thr His Phe Phe Lys Ala Lys Asn Asn Lys
            20                  25                  30

Gln Gln Asn Asn Val Thr His
        35
```

<210> SEQ ID NO 419
<211> LENGTH: 38
<212> TYPE: PRT
<213> ORGANISM: Plasmodium falciparum

<400> SEQUENCE: 419

-continued

```
Lys Gln Lys Glu Asp Lys Lys Asn Pro Asn Lys Leu Lys Lys Ile Glu
1               5                   10                  15

Tyr Thr Asn Lys Ile Thr His Phe Phe Lys Ala Lys Asn Asn Lys Gln
            20                  25                  30

Gln Asn Asn Val Thr His
        35


<210> SEQ ID NO 420
<211> LENGTH: 36
<212> TYPE: PRT
<213> ORGANISM: Plasmodium falciparum

<400> SEQUENCE: 420

Lys Glu Asp Lys Lys Asn Pro Asn Lys Leu Lys Lys Ile Glu Tyr Thr
1               5                   10                  15

Asn Lys Ile Thr His Phe Phe Lys Ala Lys Asn Asn Lys Gln Gln Asn
            20                  25                  30

Asn Val Thr His
        35


<210> SEQ ID NO 421
<211> LENGTH: 32
<212> TYPE: PRT
<213> ORGANISM: Plasmodium falciparum

<400> SEQUENCE: 421

Lys Asn Pro Asn Lys Leu Lys Lys Ile Glu Tyr Thr Asn Lys Ile Thr
1               5                   10                  15

His Phe Phe Lys Ala Lys Asn Asn Lys Gln Gln Asn Asn Val Thr His
            20                  25                  30


<210> SEQ ID NO 422
<211> LENGTH: 26
<212> TYPE: PRT
<213> ORGANISM: Plasmodium falciparum

<400> SEQUENCE: 422

Lys Lys Ile Glu Tyr Thr Asn Lys Ile Thr His Phe Phe Lys Ala Lys
1               5                   10                  15

Asn Asn Lys Gln Gln Asn Asn Val Thr His
            20                  25


<210> SEQ ID NO 423
<211> LENGTH: 25
<212> TYPE: PRT
<213> ORGANISM: Plasmodium falciparum

<400> SEQUENCE: 423

Lys Ile Glu Tyr Thr Asn Lys Ile Thr His Phe Phe Lys Ala Lys Asn
1               5                   10                  15

Asn Lys Gln Gln Asn Asn Val Thr His
            20                  25


<210> SEQ ID NO 424
<211> LENGTH: 19
<212> TYPE: PRT
<213> ORGANISM: Plasmodium falciparum

<400> SEQUENCE: 424

Lys Ile Thr His Phe Phe Lys Ala Lys Asn Asn Lys Gln Gln Asn Asn
1               5                   10                  15
```

-continued

Val Thr His

<210> SEQ ID NO 425
<211> LENGTH: 48
<212> TYPE: PRT
<213> ORGANISM: Plasmodium falciparum

<400> SEQUENCE: 425

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys Asp Ile Lys
        35                  40                  45

<210> SEQ ID NO 426
<211> LENGTH: 45
<212> TYPE: PRT
<213> ORGANISM: Plasmodium falciparum

<400> SEQUENCE: 426

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys Asn Asp Asn Ser Lys
        35                  40                  45

<210> SEQ ID NO 427
<211> LENGTH: 40
<212> TYPE: PRT
<213> ORGANISM: Plasmodium falciparum

<400> SEQUENCE: 427

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

Asn Asp Asn Asn Glu Asp Ile Lys
        35                  40

<210> SEQ ID NO 428
<211> LENGTH: 32
<212> TYPE: PRT
<213> ORGANISM: Plasmodium falciparum

<400> SEQUENCE: 428

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys Asp Ile Lys
            20                  25                  30

<210> SEQ ID NO 429
<211> LENGTH: 29
<212> TYPE: PRT
<213> ORGANISM: Plasmodium falciparum

<400> SEQUENCE: 429

His Lys Asn Asn Glu Asp Ile Lys Asn Asp Asn Ser Lys Asp Ile Lys
1               5                   10                  15

Asn Asp Asn Ser Lys Asp Ile Lys Asn Asp Asn Ser Lys

-continued 20 25

<210> SEQ ID NO 430
<211> LENGTH: 24
<212> TYPE: PRT
<213> ORGANISM: Plasmodium falciparum

<400> SEQUENCE: 430

His Lys Asn Asn Glu Asp Ile Lys Asn Asp Asn Ser Lys Asp Ile Lys
1 5 10 15

Asn Asp Asn Ser Lys Asp Ile Lys
20

<210> SEQ ID NO 431
<211> LENGTH: 21
<212> TYPE: PRT
<213> ORGANISM: Plasmodium falciparum

<400> SEQUENCE: 431

His Lys Asn Asn Glu Asp Ile Lys Asn Asp Asn Ser Lys Asp Ile Lys
1 5 10 15

Asn Asp Asn Ser Lys
20

<210> SEQ ID NO 432
<211> LENGTH: 16
<212> TYPE: PRT
<213> ORGANISM: Plasmodium falciparum

<400> SEQUENCE: 432

His Lys Asn Asn Glu Asp Ile Lys Asn Asp Asn Ser Lys Asp Ile Lys
1 5 10 15

<210> SEQ ID NO 433
<211> LENGTH: 8
<212> TYPE: PRT
<213> ORGANISM: Plasmodium falciparum

<400> SEQUENCE: 433

His Lys Asn Asn Glu Asp Ile Lys
1 5

<210> SEQ ID NO 434
<211> LENGTH: 31
<212> TYPE: PRT
<213> ORGANISM: Plasmodium falciparum

<400> SEQUENCE: 434

Lys Lys Tyr Asp Asp Leu Gln Asn Lys Tyr Asn Ile Leu Asn Lys Leu
1 5 10 15

Lys Asn Ser Leu Glu Glu Lys Asn Glu Glu Leu Lys Lys Tyr His
20 25 30

<210> SEQ ID NO 435
<211> LENGTH: 30
<212> TYPE: PRT
<213> ORGANISM: Plasmodium falciparum

<400> SEQUENCE: 435

Lys Tyr Asp Asp Leu Gln Asn Lys Tyr Asn Ile Leu Asn Lys Leu Lys
1 5 10 15

Asn Ser Leu Glu Glu Lys Asn Glu Glu Leu Lys Lys Tyr His
20 25 30

-continued

<210> SEQ ID NO 436
<211> LENGTH: 23
<212> TYPE: PRT
<213> ORGANISM: Plasmodium falciparum

<400> SEQUENCE: 436

Lys Tyr Asn Ile Leu Asn Lys Leu Lys Asn Ser Leu Glu Glu Lys Asn
1 5 10 15

Glu Glu Leu Lys Lys Tyr His
20

<210> SEQ ID NO 437
<211> LENGTH: 17
<212> TYPE: PRT
<213> ORGANISM: Plasmodium falciparum

<400> SEQUENCE: 437

Lys Leu Lys Asn Ser Leu Glu Glu Lys Asn Glu Glu Leu Lys Lys Tyr
1 5 10 15

His

<210> SEQ ID NO 438
<211> LENGTH: 15
<212> TYPE: PRT
<213> ORGANISM: Plasmodium falciparum

<400> SEQUENCE: 438

Lys Asn Ser Leu Glu Glu Lys Asn Glu Glu Leu Lys Lys Tyr His
1 5 10 15

<210> SEQ ID NO 439
<211> LENGTH: 9
<212> TYPE: PRT
<213> ORGANISM: Plasmodium falciparum

<400> SEQUENCE: 439

Lys Asn Glu Glu Leu Lys Lys Tyr His
1 5

<210> SEQ ID NO 440
<211> LENGTH: 35
<212> TYPE: PRT
<213> ORGANISM: Plasmodium falciparum

<400> SEQUENCE: 440

His Met Gly Asn Asn Gln Asp Ile Asn Glu Asn Val Tyr Asn Ile Lys
1 5 10 15

Pro Gln Glu Phe Lys Glu Glu Glu Glu Glu Asp Ile Ser Met Val Asn
20 25 30

Thr Lys Lys
35

<210> SEQ ID NO 441
<211> LENGTH: 17
<212> TYPE: PRT
<213> ORGANISM: Plasmodium falciparum

<400> SEQUENCE: 441

Lys Asn Ser Asn Glu Leu Lys Arg Ile Asn Asp Asn Phe Phe Lys Leu
1 5 10 15

His

-continued

<210> SEQ ID NO 442
<211> LENGTH: 55
<212> TYPE: PRT
<213> ORGANISM: Plasmodium falciparum

<400> SEQUENCE: 442

Lys Pro Cys Leu Tyr Lys Lys Cys Lys Ile Ser Gln Cys Leu Tyr Lys
1               5                   10                  15

Lys Cys Lys Ile Ser Gln Val Trp Trp Cys Met Pro Val Lys Asp Thr
            20                  25                  30

Phe Asn Thr Tyr Glu Arg Asn Asn Val Leu Asn Ser Lys Ile Glu Asn
        35                  40                  45

Asn Ile Glu Lys Ile Pro His
    50                  55

<210> SEQ ID NO 443
<211> LENGTH: 40
<212> TYPE: PRT
<213> ORGANISM: Plasmodium falciparum

<400> SEQUENCE: 443

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Asn Ile Lys Asp Tyr
            20                  25                  30

Ile Asn Ser Met Asn Phe Lys Lys
        35                  40

<210> SEQ ID NO 444
<211> LENGTH: 39
<212> TYPE: PRT
<213> ORGANISM: Plasmodium falciparum

<400> SEQUENCE: 444

His Ile Asn Asn Glu Tyr Thr Asn Lys Asn Pro Lys Asn Cys Leu Leu
1               5                   10                  15

Tyr Lys Asn Glu Glu Arg Asn Tyr Asn Asp Asn Asn Ile Lys Asp Tyr
            20                  25                  30

Ile Asn Ser Met Asn Phe Lys
        35

<210> SEQ ID NO 445
<211> LENGTH: 18
<212> TYPE: PRT
<213> ORGANISM: Plasmodium falciparum

<400> SEQUENCE: 445

His Ile Asn Asn Glu Tyr Thr Asn Lys Asn Pro Lys Asn Cys Leu Leu
1               5                   10                  15

Tyr Lys

<210> SEQ ID NO 446
<211> LENGTH: 23
<212> TYPE: PRT
<213> ORGANISM: Plasmodium falciparum

<400> SEQUENCE: 446

Lys Asn Lys Thr Asn Gln Ser Lys Gly Val Lys Gly Glu Tyr Glu Lys
1               5                   10                  15

-continued

```
Lys Lys Glu Thr Asn Gly His
            20


<210> SEQ ID NO 447
<211> LENGTH: 21
<212> TYPE: PRT
<213> ORGANISM: Plasmodium falciparum

<400> SEQUENCE: 447

Lys Thr Asn Gln Ser Lys Gly Val Lys Gly Glu Tyr Glu Lys Lys Lys
1               5                   10                  15

Glu Thr Asn Gly His
            20


<210> SEQ ID NO 448
<211> LENGTH: 16
<212> TYPE: PRT
<213> ORGANISM: Plasmodium falciparum

<400> SEQUENCE: 448

Lys Gly Val Lys Gly Glu Tyr Glu Lys Lys Lys Glu Thr Asn Gly His
1               5                   10                  15


<210> SEQ ID NO 449
<211> LENGTH: 13
<212> TYPE: PRT
<213> ORGANISM: Plasmodium falciparum

<400> SEQUENCE: 449

Lys Gly Glu Tyr Glu Lys Lys Lys Glu Thr Asn Gly His
1               5                   10


<210> SEQ ID NO 450
<211> LENGTH: 28
<212> TYPE: PRT
<213> ORGANISM: Plasmodium falciparum

<400> SEQUENCE: 450

Lys Ser Gly Met Tyr Thr Asn Glu Gly Asn Lys Ser Cys Glu Cys Ser
1               5                   10                  15

Tyr Lys Lys Lys Ser Ser Ser Ser Asn Lys Val His
            20                  25


<210> SEQ ID NO 451
<211> LENGTH: 18
<212> TYPE: PRT
<213> ORGANISM: Plasmodium falciparum

<400> SEQUENCE: 451

Lys Ser Cys Glu Cys Ser Tyr Lys Lys Lys Ser Ser Ser Ser Asn Lys
1               5                   10                  15

Val His


<210> SEQ ID NO 452
<211> LENGTH: 11
<212> TYPE: PRT
<213> ORGANISM: Plasmodium falciparum

<400> SEQUENCE: 452

Lys Lys Lys Ser Ser Ser Ser Asn Lys Val His
1               5                   10


<210> SEQ ID NO 453
```

-continued

<211> LENGTH: 10
<212> TYPE: PRT
<213> ORGANISM: Plasmodium falciparum

<400> SEQUENCE: 453

```
Lys Lys Ser Ser Ser Ser Asn Lys Val His
1               5                   10
```

<210> SEQ ID NO 454
<211> LENGTH: 9
<212> TYPE: PRT
<213> ORGANISM: Plasmodium falciparum

<400> SEQUENCE: 454

```
Lys Ser Ser Ser Ser Asn Lys Val His
1               5
```

<210> SEQ ID NO 455
<211> LENGTH: 30
<212> TYPE: PRT
<213> ORGANISM: Plasmodium falciparum

<400> SEQUENCE: 455

```
His Ile Met Leu Lys Ser Gly Met Tyr Thr Asn Glu Gly Asn Lys Ser
1               5                   10                  15

Cys Glu Cys Ser Tyr Lys Lys Lys Ser Ser Ser Ser Asn Lys
            20                  25                  30
```

<210> SEQ ID NO 456
<211> LENGTH: 24
<212> TYPE: PRT
<213> ORGANISM: Plasmodium falciparum

<400> SEQUENCE: 456

```
His Ile Met Leu Lys Ser Gly Met Tyr Thr Asn Glu Gly Asn Lys Ser
1               5                   10                  15

Cys Glu Cys Ser Tyr Lys Lys Lys
            20
```

<210> SEQ ID NO 457
<211> LENGTH: 23
<212> TYPE: PRT
<213> ORGANISM: Plasmodium falciparum

<400> SEQUENCE: 457

```
His Ile Met Leu Lys Ser Gly Met Tyr Thr Asn Glu Gly Asn Lys Ser
1               5                   10                  15

Cys Glu Cys Ser Tyr Lys Lys
            20
```

<210> SEQ ID NO 458
<211> LENGTH: 22
<212> TYPE: PRT
<213> ORGANISM: Plasmodium falciparum

<400> SEQUENCE: 458

```
His Ile Met Leu Lys Ser Gly Met Tyr Thr Asn Glu Gly Asn Lys Ser
1               5                   10                  15

Cys Glu Cys Ser Tyr Lys
            20
```

<210> SEQ ID NO 459
<211> LENGTH: 50

-continued

<212> TYPE: PRT
<213> ORGANISM: Plasmodium falciparum

<400> SEQUENCE: 459

Lys Pro Leu Ala Lys Leu Arg Lys Arg Glu Lys Thr Gln Ile Asn Lys
1 5 10 15

Thr Lys Tyr Glu Arg Gly Asp Val Ile Ile Asp Asn Thr Glu Ile Gln
20 25 30

Lys Ile Ile Ile Arg Asp Tyr His Glu Thr Leu Asn Val His Lys Leu
35 40 45

Asp His
50

<210> SEQ ID NO 460
<211> LENGTH: 43
<212> TYPE: PRT
<213> ORGANISM: Plasmodium falciparum

<400> SEQUENCE: 460

Lys Arg Glu Lys Thr Gln Ile Asn Lys Thr Lys Tyr Glu Arg Gly Asp
1 5 10 15

Val Ile Ile Asp Asn Thr Glu Ile Gln Lys Ile Ile Ile Arg Asp Tyr
20 25 30

His Glu Thr Leu Asn Val His Lys Leu Asp His
35 40

<210> SEQ ID NO 461
<211> LENGTH: 40
<212> TYPE: PRT
<213> ORGANISM: Plasmodium falciparum

<400> SEQUENCE: 461

Lys Thr Gln Ile Asn Lys Thr Lys Tyr Glu Arg Gly Asp Val Ile Ile
1 5 10 15

Asp Asn Thr Glu Ile Gln Lys Ile Ile Ile Arg Asp Tyr His Glu Thr
20 25 30

Leu Asn Val His Lys Leu Asp His
35 40

<210> SEQ ID NO 462
<211> LENGTH: 46
<212> TYPE: PRT
<213> ORGANISM: Plasmodium falciparum

<400> SEQUENCE: 462

Lys Pro Leu Ala Lys Leu Arg Lys Arg Glu Lys Thr Gln Ile Asn Lys
1 5 10 15

Thr Lys Tyr Glu Arg Gly Asp Val Ile Ile Asp Asn Thr Glu Ile Gln
20 25 30

Lys Ile Ile Ile Arg Asp Tyr His Glu Thr Leu Asn Val His
35 40 45

<210> SEQ ID NO 463
<211> LENGTH: 40
<212> TYPE: PRT
<213> ORGANISM: Plasmodium falciparum

<400> SEQUENCE: 463

Lys Pro Leu Ala Lys Leu Arg Lys Arg Glu Lys Thr Gln Ile Asn Lys
1 5 10 15

-continued

```
Thr Lys Tyr Glu Arg Gly Asp Val Ile Ile Asp Asn Thr Glu Ile Gln
            20                  25                  30

Lys Ile Ile Ile Arg Asp Tyr His
        35                  40


<210> SEQ ID NO 464
<211> LENGTH: 36
<212> TYPE: PRT
<213> ORGANISM: Plasmodium falciparum

<400> SEQUENCE: 464

Lys Leu Arg Lys Arg Glu Lys Thr Gln Ile Asn Lys Thr Lys Tyr Glu
1               5                   10                  15

Arg Gly Asp Val Ile Ile Asp Asn Thr Glu Ile Gln Lys Ile Ile Ile
            20                  25                  30

Arg Asp Tyr His
        35


<210> SEQ ID NO 465
<211> LENGTH: 33
<212> TYPE: PRT
<213> ORGANISM: Plasmodium falciparum

<400> SEQUENCE: 465

Lys Arg Glu Lys Thr Gln Ile Asn Lys Thr Lys Tyr Glu Arg Gly Asp
1               5                   10                  15

Val Ile Ile Asp Asn Thr Glu Ile Gln Lys Ile Ile Ile Arg Asp Tyr
            20                  25                  30

His


<210> SEQ ID NO 466
<211> LENGTH: 30
<212> TYPE: PRT
<213> ORGANISM: Plasmodium falciparum

<400> SEQUENCE: 466

Lys Thr Gln Ile Asn Lys Thr Lys Tyr Glu Arg Gly Asp Val Ile Ile
1               5                   10                  15

Asp Asn Thr Glu Ile Gln Lys Ile Ile Ile Arg Asp Tyr His
            20                  25                  30


<210> SEQ ID NO 467
<211> LENGTH: 41
<212> TYPE: PRT
<213> ORGANISM: Plasmodium falciparum

<400> SEQUENCE: 467

Lys Lys Asp Lys Glu Lys Lys Lys Asp Ser Asn Glu Asn Arg Lys Lys
1               5                   10                  15

Lys Gln Lys Glu Asp Lys Lys Asn Pro Asn Asp Asn Lys Leu Lys Lys
            20                  25                  30

Ile Glu Tyr Thr Asn Lys Ile Thr His
        35                  40


<210> SEQ ID NO 468
<211> LENGTH: 40
<212> TYPE: PRT
<213> ORGANISM: Plasmodium falciparum

<400> SEQUENCE: 468

Lys Asp Lys Glu Lys Lys Lys Asp Ser Asn Glu Asn Arg Lys Lys Lys
```

-continued

```
1               5                   10                  15

Gln Lys Glu Asp Lys Lys Asn Pro Asn Asp Asn Lys Leu Lys Lys Ile
            20                  25                  30

Glu Tyr Thr Asn Lys Ile Thr His
        35                  40


<210> SEQ ID NO 469
<211> LENGTH: 38
<212> TYPE: PRT
<213> ORGANISM: Plasmodium falciparum

<400> SEQUENCE: 469

Lys Glu Lys Lys Lys Asp Ser Asn Glu Asn Arg Lys Lys Lys Gln Lys
1               5                   10                  15

Glu Asp Lys Lys Asn Pro Asn Asp Asn Lys Leu Lys Lys Ile Glu Tyr
            20                  25                  30

Thr Asn Lys Ile Thr His
        35


<210> SEQ ID NO 470
<211> LENGTH: 36
<212> TYPE: PRT
<213> ORGANISM: Plasmodium falciparum

<400> SEQUENCE: 470

Lys Lys Lys Asp Ser Asn Glu Asn Arg Lys Lys Lys Gln Lys Glu Asp
1               5                   10                  15

Lys Lys Asn Pro Asn Asp Asn Lys Leu Lys Lys Ile Glu Tyr Thr Asn
            20                  25                  30

Lys Ile Thr His
        35


<210> SEQ ID NO 471
<211> LENGTH: 35
<212> TYPE: PRT
<213> ORGANISM: Plasmodium falciparum

<400> SEQUENCE: 471

Lys Lys Asp Ser Asn Glu Asn Arg Lys Lys Lys Gln Lys Glu Asp Lys
1               5                   10                  15

Lys Asn Pro Asn Asp Asn Lys Leu Lys Lys Ile Glu Tyr Thr Asn Lys
            20                  25                  30

Ile Thr His
        35


<210> SEQ ID NO 472
<211> LENGTH: 34
<212> TYPE: PRT
<213> ORGANISM: Plasmodium falciparum

<400> SEQUENCE: 472

Lys Asp Ser Asn Glu Asn Arg Lys Lys Lys Gln Lys Glu Asp Lys Lys
1               5                   10                  15

Asn Pro Asn Asp Asn Lys Leu Lys Lys Ile Glu Tyr Thr Asn Lys Ile
            20                  25                  30

Thr His


<210> SEQ ID NO 473
<211> LENGTH: 27
<212> TYPE: PRT
```

-continued

<213> ORGANISM: Plasmodium falciparum

<400> SEQUENCE: 473

Lys Lys Lys Gln Lys Glu Asp Lys Lys Asn Pro Asn Asp Asn Lys Leu
1 5 10 15

Lys Lys Ile Glu Tyr Thr Asn Lys Ile Thr His
20 25

<210> SEQ ID NO 474
<211> LENGTH: 26
<212> TYPE: PRT
<213> ORGANISM: Plasmodium falciparum

<400> SEQUENCE: 474

Lys Lys Gln Lys Glu Asp Lys Lys Asn Pro Asn Asp Asn Lys Leu Lys
1 5 10 15

Lys Ile Glu Tyr Thr Asn Lys Ile Thr His
20 25

<210> SEQ ID NO 475
<211> LENGTH: 25
<212> TYPE: PRT
<213> ORGANISM: Plasmodium falciparum

<400> SEQUENCE: 475

Lys Gln Lys Glu Asp Lys Lys Asn Pro Asn Asp Asn Lys Leu Lys Lys
1 5 10 15

Ile Glu Tyr Thr Asn Lys Ile Thr His
20 25

<210> SEQ ID NO 476
<211> LENGTH: 23
<212> TYPE: PRT
<213> ORGANISM: Plasmodium falciparum

<400> SEQUENCE: 476

Lys Glu Asp Lys Lys Asn Pro Asn Asp Asn Lys Leu Lys Lys Ile Glu
1 5 10 15

Tyr Thr Asn Lys Ile Thr His
20

<210> SEQ ID NO 477
<211> LENGTH: 20
<212> TYPE: PRT
<213> ORGANISM: Plasmodium falciparum

<400> SEQUENCE: 477

Lys Lys Asn Pro Asn Asp Asn Lys Leu Lys Lys Ile Glu Tyr Thr Asn
1 5 10 15

Lys Ile Thr His
20

<210> SEQ ID NO 478
<211> LENGTH: 19
<212> TYPE: PRT
<213> ORGANISM: Plasmodium falciparum

<400> SEQUENCE: 478

Lys Asn Pro Asn Asp Asn Lys Leu Lys Lys Ile Glu Tyr Thr Asn Lys
1 5 10 15

Ile Thr His

-continued

<210> SEQ ID NO 479
<211> LENGTH: 13
<212> TYPE: PRT
<213> ORGANISM: Plasmodium falciparum

<400> SEQUENCE: 479

Lys Leu Lys Lys Ile Glu Tyr Thr Asn Lys Ile Thr His
1 5 10

<210> SEQ ID NO 480
<211> LENGTH: 11
<212> TYPE: PRT
<213> ORGANISM: Plasmodium falciparum

<400> SEQUENCE: 480

Lys Lys Ile Glu Tyr Thr Asn Lys Ile Thr His
1 5 10

<210> SEQ ID NO 481
<211> LENGTH: 10
<212> TYPE: PRT
<213> ORGANISM: Plasmodium falciparum

<400> SEQUENCE: 481

Lys Ile Glu Tyr Thr Asn Lys Ile Thr His
1 5 10

<210> SEQ ID NO 482
<211> LENGTH: 44
<212> TYPE: PRT
<213> ORGANISM: Plasmodium falciparum

<400> SEQUENCE: 482

His Gly Gln Ile Lys Ile Glu Asp Val Asn Asn Glu Asn Phe Asn Asn
1 5 10 15

Glu Gln Met Lys Asn Lys Tyr Asn Asp Glu Glu Lys Met Asp Ile Ser
20 25 30

Lys Ser Lys Ser Leu Lys Ser Asp Phe Leu Glu Lys
35 40

<210> SEQ ID NO 483
<211> LENGTH: 38
<212> TYPE: PRT
<213> ORGANISM: Plasmodium falciparum

<400> SEQUENCE: 483

His Gly Gln Ile Lys Ile Glu Asp Val Asn Asn Glu Asn Phe Asn Asn
1 5 10 15

Glu Gln Met Lys Asn Lys Tyr Asn Asp Glu Glu Lys Met Asp Ile Ser
20 25 30

Lys Ser Lys Ser Leu Lys
35

<210> SEQ ID NO 484
<211> LENGTH: 35
<212> TYPE: PRT
<213> ORGANISM: Plasmodium falciparum

<400> SEQUENCE: 484

His Gly Gln Ile Lys Ile Glu Asp Val Asn Asn Glu Asn Phe Asn Asn
1 5 10 15

Glu Gln Met Lys Asn Lys Tyr Asn Asp Glu Glu Lys Met Asp Ile Ser

-continued

```
            20                  25                  30

Lys Ser Lys
        35


<210> SEQ ID NO 485
<211> LENGTH: 33
<212> TYPE: PRT
<213> ORGANISM: Plasmodium falciparum

<400> SEQUENCE: 485

His Gly Gln Ile Lys Ile Glu Asp Val Asn Asn Glu Asn Phe Asn Asn
1               5                   10                  15

Glu Gln Met Lys Asn Lys Tyr Asn Asp Glu Glu Lys Met Asp Ile Ser
            20                  25                  30

Lys


<210> SEQ ID NO 486
<211> LENGTH: 31
<212> TYPE: PRT
<213> ORGANISM: Plasmodium falciparum

<400> SEQUENCE: 486

Lys Lys Tyr Asp Asp Leu Gln Asn Lys Tyr Asn Ile Leu Asn Lys Leu
1               5                   10                  15

Lys Asn Ser Leu Glu Glu Lys Asn Glu Glu Leu Lys Lys Tyr His
            20                  25                  30


<210> SEQ ID NO 487
<211> LENGTH: 30
<212> TYPE: PRT
<213> ORGANISM: Plasmodium falciparum

<400> SEQUENCE: 487

Lys Tyr Asp Asp Leu Gln Asn Lys Tyr Asn Ile Leu Asn Lys Leu Lys
1               5                   10                  15

Asn Ser Leu Glu Glu Lys Asn Glu Glu Leu Lys Lys Tyr His
            20                  25                  30


<210> SEQ ID NO 488
<211> LENGTH: 23
<212> TYPE: PRT
<213> ORGANISM: Plasmodium falciparum

<400> SEQUENCE: 488

Lys Tyr Asn Ile Leu Asn Lys Leu Lys Asn Ser Leu Glu Glu Lys Asn
1               5                   10                  15

Glu Glu Leu Lys Lys Tyr His
            20


<210> SEQ ID NO 489
<211> LENGTH: 17
<212> TYPE: PRT
<213> ORGANISM: Plasmodium falciparum

<400> SEQUENCE: 489

Lys Leu Lys Asn Ser Leu Glu Glu Lys Asn Glu Glu Leu Lys Lys Tyr
1               5                   10                  15

His


<210> SEQ ID NO 490
<211> LENGTH: 15
```

-continued

```
<212> TYPE: PRT
<213> ORGANISM: Plasmodium falciparum

<400> SEQUENCE: 490

Lys Asn Ser Leu Glu Glu Lys Asn Glu Glu Leu Lys Lys Tyr His
1               5                   10                  15


<210> SEQ ID NO 491
<211> LENGTH: 9
<212> TYPE: PRT
<213> ORGANISM: Plasmodium falciparum

<400> SEQUENCE: 491

Lys Asn Glu Glu Leu Lys Lys Tyr His
1               5


<210> SEQ ID NO 492
<211> LENGTH: 44
<212> TYPE: PRT
<213> ORGANISM: Plasmodium falciparum

<400> SEQUENCE: 492

His Met Gly Asn Asn Gln Asp Ile Asn Glu Asn Val Tyr Asn Ile Lys
1               5                   10                  15

Pro Gln Glu Phe Lys Glu Glu Glu Glu Glu Asp Ile Ser Met Val Asn
            20                  25                  30

Thr Lys Lys Cys Asp Asp Ile Gln Glu Asn Ile Lys
        35                  40


<210> SEQ ID NO 493
<211> LENGTH: 50
<212> TYPE: PRT
<213> ORGANISM: Plasmodium falciparum

<400> SEQUENCE: 493

Lys Thr Asn Leu Tyr Asn Ile Tyr Asn Asn Lys Asn Asp Asp Lys Asp
1               5                   10                  15

Asn Ile Leu Asp Asn Glu Asn Arg Glu Gly Leu Tyr Leu Cys Asp Val
            20                  25                  30

Met Lys Asn Ser Asn Glu Leu Lys Arg Ile Asn Asp Asn Phe Phe Lys
        35                  40                  45

Leu His
    50


<210> SEQ ID NO 494
<211> LENGTH: 17
<212> TYPE: PRT
<213> ORGANISM: Plasmodium falciparum

<400> SEQUENCE: 494

Lys Asn Ser Asn Glu Leu Lys Arg Ile Asn Asp Asn Phe Phe Lys Leu
1               5                   10                  15

His


<210> SEQ ID NO 495
<211> LENGTH: 11
<212> TYPE: PRT
<213> ORGANISM: Plasmodium falciparum

<400> SEQUENCE: 495

Lys Arg Ile Asn Asp Asn Phe Phe Lys Leu His
1               5                   10
```

-continued

<210> SEQ ID NO 496
<211> LENGTH: 40
<212> TYPE: PRT
<213> ORGANISM: Plasmodium falciparum

<400> SEQUENCE: 496

His Ile Asn Asn Glu Tyr Thr Asn Lys Asn Pro Lys Asn Cys Leu Leu
1 5 10 15

Tyr Lys Asn Glu Glu Arg Asn Tyr Asn Asp Asn Asn Ile Lys Asp Tyr
20 25 30

Ile Asn Ser Met Asn Phe Lys Lys
35 40

<210> SEQ ID NO 497
<211> LENGTH: 39
<212> TYPE: PRT
<213> ORGANISM: Plasmodium falciparum

<400> SEQUENCE: 497

His Ile Asn Asn Glu Tyr Thr Asn Lys Asn Pro Lys Asn Cys Leu Leu
1 5 10 15

Tyr Lys Asn Glu Glu Arg Asn Tyr Asn Asp Asn Asn Ile Lys Asp Tyr
20 25 30

Ile Asn Ser Met Asn Phe Lys
35

<210> SEQ ID NO 498
<211> LENGTH: 18
<212> TYPE: PRT
<213> ORGANISM: Plasmodium falciparum

<400> SEQUENCE: 498

His Ile Asn Asn Glu Tyr Thr Asn Lys Asn Pro Lys Asn Cys Leu Leu
1 5 10 15

Tyr Lys

<210> SEQ ID NO 499
<211> LENGTH: 45
<212> TYPE: PRT
<213> ORGANISM: Plasmodium falciparum

<400> SEQUENCE: 499

Lys Pro Cys Leu Tyr Lys Lys Cys Lys Ile Ser Gln Val Trp Trp Cys
1 5 10 15

Met Pro Val Lys Asp Thr Phe Asn Thr Tyr Glu Arg Asn Asn Val Leu
20 25 30

Asn Ser Lys Ile Glu Asn Asn Ile Glu Lys Ile Pro His
35 40 45

<210> SEQ ID NO 500
<211> LENGTH: 39
<212> TYPE: PRT
<213> ORGANISM: Plasmodium falciparum

<400> SEQUENCE: 500

Lys Cys Lys Ile Ser Gln Val Trp Trp Cys Met Pro Val Lys Asp Thr
1 5 10 15

Phe Asn Thr Tyr Glu Arg Asn Asn Val Leu Asn Ser Lys Ile Glu Asn
20 25 30

-continued

```
Asn Ile Glu Lys Ile Pro His
        35


<210> SEQ ID NO 501
<211> LENGTH: 11
<212> TYPE: PRT
<213> ORGANISM: Plasmodium falciparum

<400> SEQUENCE: 501

Lys Ile Glu Asn Asn Ile Glu Lys Ile Pro His
1               5                   10


<210> SEQ ID NO 502
<211> LENGTH: 23
<212> TYPE: PRT
<213> ORGANISM: Plasmodium falciparum

<400> SEQUENCE: 502

Lys Asn Lys Thr Asn Gly Ser Lys Gly Val Lys Gly Glu Tyr Glu Lys
1               5                   10                  15

Lys Lys Glu Thr Asn Gly His
            20


<210> SEQ ID NO 503
<211> LENGTH: 21
<212> TYPE: PRT
<213> ORGANISM: Plasmodium falciparum

<400> SEQUENCE: 503

Lys Thr Asn Gly Ser Lys Gly Val Lys Gly Glu Tyr Glu Lys Lys Lys
1               5                   10                  15

Glu Thr Asn Gly His
            20


<210> SEQ ID NO 504
<211> LENGTH: 16
<212> TYPE: PRT
<213> ORGANISM: Plasmodium falciparum

<400> SEQUENCE: 504

Lys Gly Val Lys Gly Glu Tyr Glu Lys Lys Lys Glu Thr Asn Gly His
1               5                   10                  15


<210> SEQ ID NO 505
<211> LENGTH: 13
<212> TYPE: PRT
<213> ORGANISM: Plasmodium falciparum

<400> SEQUENCE: 505

Lys Gly Glu Tyr Glu Lys Lys Lys Glu Thr Asn Gly His
1               5                   10


<210> SEQ ID NO 506
<211> LENGTH: 60
<212> TYPE: PRT
<213> ORGANISM: Plasmodium falciparum

<400> SEQUENCE: 506

Lys Thr Ile Glu Lys Ile Asn Lys Ser Lys Ser Trp Phe Phe Glu Glu
1               5                   10                  15

Leu Asp Glu Ile Asp Lys Pro Leu Ala Lys Leu Arg Lys Arg Glu Lys
            20                  25                  30

Thr Gln Ile Asn Lys Thr Lys Tyr Glu Arg Gly Asp Val Ile Ile Asp
```

-continued

```
        35                  40                  45

Asn Thr Glu Ile Gln Lys Ile Ile Arg Asp Tyr His
    50                  55                  60
```

```
<210> SEQ ID NO 507
<211> LENGTH: 56
<212> TYPE: PRT
<213> ORGANISM: Plasmodium falciparum

<400> SEQUENCE: 507

Lys Ile Asn Lys Ser Lys Ser Trp Phe Phe Glu Glu Leu Asp Glu Ile
1               5                   10                  15

Asp Lys Pro Leu Ala Lys Leu Arg Lys Arg Glu Lys Thr Gln Ile Asn
            20                  25                  30

Lys Thr Lys Tyr Glu Arg Gly Asp Val Ile Ile Asp Asn Thr Glu Ile
        35                  40                  45

Gln Lys Ile Ile Arg Asp Tyr His
    50                  55
```

```
<210> SEQ ID NO 508
<211> LENGTH: 39
<212> TYPE: PRT
<213> ORGANISM: Plasmodium falciparum

<400> SEQUENCE: 508

Lys Pro Leu Ala Lys Leu Arg Lys Arg Glu Lys Thr Gln Ile Asn Lys
1               5                   10                  15

Thr Lys Tyr Glu Arg Gly Asp Val Ile Ile Asp Asn Thr Glu Ile Gln
            20                  25                  30

Lys Ile Ile Arg Asp Tyr His
        35
```

```
<210> SEQ ID NO 509
<211> LENGTH: 32
<212> TYPE: PRT
<213> ORGANISM: Plasmodium falciparum

<400> SEQUENCE: 509

His Ile Met Leu Lys Ser Gln Met Tyr Thr Asn Glu Gly Asn Lys Ser
1               5                   10                  15

Cys Glu Cys Ser Tyr Lys Lys Lys Ser Ser Ser Ser Asn Lys Val His
            20                  25                  30
```

```
<210> SEQ ID NO 510
<211> LENGTH: 35
<212> TYPE: PRT
<213> ORGANISM: Plasmodium falciparum

<400> SEQUENCE: 510

Lys Leu Arg Lys Arg Glu Lys Thr Gln Ile Asn Lys Thr Lys Tyr Glu
1               5                   10                  15

Arg Gly Asp Val Ile Ile Asp Asn Thr Glu Ile Gln Lys Ile Ile Arg
            20                  25                  30

Asp Tyr His
        35
```

```
<210> SEQ ID NO 511
<211> LENGTH: 32
<212> TYPE: PRT
<213> ORGANISM: Plasmodium falciparum
```

-continued

<400> SEQUENCE: 511

Lys Arg Glu Lys Thr Gln Ile Asn Lys Thr Lys Tyr Glu Arg Gly Asp
1 5 10 15

Val Ile Ile Asp Asn Thr Glu Ile Gln Lys Ile Ile Arg Asp Tyr His
20 25 30

<210> SEQ ID NO 512
<211> LENGTH: 29
<212> TYPE: PRT
<213> ORGANISM: Plasmodium falciparum

<400> SEQUENCE: 512

Lys Thr Gln Ile Asn Lys Thr Lys Tyr Glu Arg Gly Asp Val Ile Ile
1 5 10 15

Asp Asn Thr Glu Ile Gln Lys Ile Ile Arg Asp Tyr His
20 25

<210> SEQ ID NO 513
<211> LENGTH: 48
<212> TYPE: PRT
<213> ORGANISM: Plasmodium falciparum

<400> SEQUENCE: 513

Lys Pro Leu Ala Lys Leu Arg Lys Arg Glu Lys Thr Gln Ile Asn Lys
1 5 10 15

Thr Lys Tyr Glu Arg Gly Asp Val Ile Ile Asp Asn Thr Glu Ile Gln
20 25 30

Lys Ile Ile Arg Asp Tyr His Thr Leu Asn Val His Lys Leu Asp His
35 40 45

<210> SEQ ID NO 514
<211> LENGTH: 44
<212> TYPE: PRT
<213> ORGANISM: Plasmodium falciparum

<400> SEQUENCE: 514

Lys Leu Arg Lys Arg Glu Lys Thr Gln Ile Asn Lys Thr Lys Tyr Glu
1 5 10 15

Arg Gly Asp Val Ile Ile Asp Asn Thr Glu Ile Gln Lys Ile Ile Arg
20 25 30

Asp Tyr His Thr Leu Asn Val His Lys Leu Asp His
35 40

<210> SEQ ID NO 515
<211> LENGTH: 41
<212> TYPE: PRT
<213> ORGANISM: Plasmodium falciparum

<400> SEQUENCE: 515

Lys Arg Glu Lys Thr Gln Ile Asn Lys Thr Lys Tyr Glu Arg Gly Asp
1 5 10 15

Val Ile Ile Asp Asn Thr Glu Ile Gln Lys Ile Ile Arg Asp Tyr His
20 25 30

Thr Leu Asn Val His Lys Leu Asp His
35 40

<210> SEQ ID NO 516
<211> LENGTH: 38
<212> TYPE: PRT
<213> ORGANISM: Plasmodium falciparum -continued

<400> SEQUENCE: 516

Lys Thr Gln Ile Asn Lys Thr Lys Tyr Glu Arg Gly Asp Val Ile Ile
1 5 10 15

Asp Asn Thr Glu Ile Gln Lys Ile Ile Arg Asp Tyr His Thr Leu Asn
20 25 30

Val His Lys Leu Asp His
35

<210> SEQ ID NO 517
<211> LENGTH: 44
<212> TYPE: PRT
<213> ORGANISM: Plasmodium falciparum

<400> SEQUENCE: 517

Lys Pro Leu Ala Lys Leu Arg Lys Arg Glu Lys Thr Gln Ile Asn Lys
1 5 10 15

Thr Lys Tyr Glu Arg Gly Asp Val Ile Ile Asp Asn Thr Glu Ile Gln
20 25 30

Lys Ile Ile Arg Asp Tyr His Thr Leu Asn Val His
35 40

<210> SEQ ID NO 518
<211> LENGTH: 40
<212> TYPE: PRT
<213> ORGANISM: Plasmodium falciparum

<400> SEQUENCE: 518

Lys Leu Arg Lys Arg Glu Lys Thr Gln Ile Asn Lys Thr Lys Tyr Glu
1 5 10 15

Arg Gly Asp Val Ile Ile Asp Asn Thr Glu Ile Gln Lys Ile Ile Arg
20 25 30

Asp Tyr His Thr Leu Asn Val His
35 40

<210> SEQ ID NO 519
<211> LENGTH: 37
<212> TYPE: PRT
<213> ORGANISM: Plasmodium falciparum

<400> SEQUENCE: 519

Lys Arg Glu Lys Thr Gln Ile Asn Lys Thr Lys Tyr Glu Arg Gly Asp
1 5 10 15

Val Ile Ile Asp Asn Thr Glu Ile Gln Lys Ile Ile Arg Asp Tyr His
20 25 30

Thr Leu Asn Val His
35

<210> SEQ ID NO 520
<211> LENGTH: 34
<212> TYPE: PRT
<213> ORGANISM: Plasmodium falciparum

<400> SEQUENCE: 520

Lys Thr Gln Ile Asn Lys Thr Lys Tyr Glu Arg Gly Asp Val Ile Ile
1 5 10 15

Asp Asn Thr Glu Ile Gln Lys Ile Ile Arg Asp Tyr His Thr Leu Asn
20 25 30

Val His

-continued

<210> SEQ ID NO 521
<211> LENGTH: 32
<212> TYPE: PRT
<213> ORGANISM: Plasmodium falciparum

<400> SEQUENCE: 521

His Ile Met Leu Lys Ser Gln Met Tyr Thr Asn Glu Gly Asn Lys Ser
1 5 10 15

Cys Glu Cys Ser Tyr Lys Lys Lys Ser Ser Ser Ser Asn Lys Val His
20 25 30

<210> SEQ ID NO 522
<211> LENGTH: 28
<212> TYPE: PRT
<213> ORGANISM: Plasmodium falciparum

<400> SEQUENCE: 522

Lys Ser Gln Met Tyr Thr Asn Glu Gly Asn Lys Ser Cys Glu Cys Ser
1 5 10 15

Tyr Lys Lys Lys Ser Ser Ser Ser Asn Lys Val His
20 25

<210> SEQ ID NO 523
<211> LENGTH: 18
<212> TYPE: PRT
<213> ORGANISM: Plasmodium falciparum

<400> SEQUENCE: 523

Lys Ser Cys Glu Cys Ser Tyr Lys Lys Lys Ser Ser Ser Ser Asn Lys
1 5 10 15

Val His

<210> SEQ ID NO 524
<211> LENGTH: 11
<212> TYPE: PRT
<213> ORGANISM: Plasmodium falciparum

<400> SEQUENCE: 524

Lys Lys Lys Ser Ser Ser Ser Asn Lys Val His
1 5 10

<210> SEQ ID NO 525
<211> LENGTH: 10
<212> TYPE: PRT
<213> ORGANISM: Plasmodium falciparum

<400> SEQUENCE: 525

Lys Lys Ser Ser Ser Ser Asn Lys Val His
1 5 10

<210> SEQ ID NO 526
<211> LENGTH: 9
<212> TYPE: PRT
<213> ORGANISM: Plasmodium falciparum

<400> SEQUENCE: 526

Lys Ser Ser Ser Ser Asn Lys Val His
1 5

<210> SEQ ID NO 527
<211> LENGTH: 30
<212> TYPE: PRT
<213> ORGANISM: Plasmodium falciparum -continued

<400> SEQUENCE: 527

His Ile Met Leu Lys Ser Gln Met Tyr Thr Asn Glu Gly Asn Lys Ser
1 5 10 15

Cys Glu Cys Ser Tyr Lys Lys Lys Ser Ser Ser Ser Asn Lys
20 25 30

<210> SEQ ID NO 528
<211> LENGTH: 24
<212> TYPE: PRT
<213> ORGANISM: Plasmodium falciparum

<400> SEQUENCE: 528

His Ile Met Leu Lys Ser Gln Met Tyr Thr Asn Glu Gly Asn Lys Ser
1 5 10 15

Cys Glu Cys Ser Tyr Lys Lys Lys
20

<210> SEQ ID NO 529
<211> LENGTH: 23
<212> TYPE: PRT
<213> ORGANISM: Plasmodium falciparum

<400> SEQUENCE: 529

His Ile Met Leu Lys Ser Gln Met Tyr Thr Asn Glu Gly Asn Lys Ser
1 5 10 15

Cys Glu Cys Ser Tyr Lys Lys
20

<210> SEQ ID NO 530
<211> LENGTH: 22
<212> TYPE: PRT
<213> ORGANISM: Plasmodium falciparum

<400> SEQUENCE: 530

His Ile Met Leu Lys Ser Gln Met Tyr Thr Asn Glu Gly Asn Lys Ser
1 5 10 15

Cys Glu Cys Ser Tyr Lys
20

<210> SEQ ID NO 531
<211> LENGTH: 36
<212> TYPE: PRT
<213> ORGANISM: Plasmodium falciparum

<400> SEQUENCE: 531

His Asn Asn His Asn Ile Gln Ile Tyr Lys Asp Lys Arg Ile Asn Phe
1 5 10 15

Met Asn Pro His Lys Val Met Tyr His Asp Asn Met Ser Lys Asn Glu
20 25 30

Arg Thr Glu Lys
35

<210> SEQ ID NO 532
<211> LENGTH: 30
<212> TYPE: PRT
<213> ORGANISM: Plasmodium falciparum

<400> SEQUENCE: 532

His Asn Asn His Asn Ile Gln Ile Tyr Lys Asp Lys Arg Ile Asn Phe
1 5 10 15

Met Asn Pro His Lys Val Met Tyr His Asp Asn Met Ser Lys

-continued

```
            20                  25                  30


<210> SEQ ID NO 533
<211> LENGTH: 21
<212> TYPE: PRT
<213> ORGANISM: Plasmodium falciparum

<400> SEQUENCE: 533

His Asn Asn His Asn Ile Gln Ile Tyr Lys Asp Lys Arg Ile Asn Phe
1               5                   10                  15

Met Asn Pro His Lys
            20


<210> SEQ ID NO 534
<211> LENGTH: 17
<212> TYPE: PRT
<213> ORGANISM: Plasmodium falciparum

<400> SEQUENCE: 534

His Lys Val Met Tyr His Asp Asn Met Ser Lys Asn Glu Arg Thr Glu
1               5                   10                  15

Lys


<210> SEQ ID NO 535
<211> LENGTH: 11
<212> TYPE: PRT
<213> ORGANISM: Plasmodium falciparum

<400> SEQUENCE: 535

His Lys Val Met Tyr His Asp Asn Met Ser Lys
1               5                   10


<210> SEQ ID NO 536
<211> LENGTH: 40
<212> TYPE: PRT
<213> ORGANISM: Homo sapiens

<400> SEQUENCE: 536

His Arg Glu Ile Cys Thr Ile Gln Ser Ser Gly Gly Ile Met Leu Leu
1               5                   10                  15

Lys Asp Gln Val Leu Arg Cys Ser Lys Ile Ala Gly Val Lys Val Ala
            20                  25                  30

Glu Ile Thr Glu Leu Ile Leu Lys
        35                  40


<210> SEQ ID NO 537
<211> LENGTH: 25
<212> TYPE: PRT
<213> ORGANISM: Homo sapiens

<400> SEQUENCE: 537

His Arg Glu Ile Cys Thr Ile Gln Ser Ser Gly Gly Ile Met Leu Leu
1               5                   10                  15

Lys Asp Gln Val Leu Arg Glu Ser Lys
            20                  25


<210> SEQ ID NO 538
<211> LENGTH: 48
<212> TYPE: PRT
<213> ORGANISM: Homo sapiens

<400> SEQUENCE: 538
```

-continued

```
His Arg Glu Ile Cys Thr Ile Gln Ser Ser Gly Gly Ile Met Leu Leu
1               5                   10                  15

Lys Asp Gln Val Leu Arg Cys Ser Lys Ile Ala Gly Val Lys Val Ala
            20                  25                  30

Glu Ile Thr Glu Leu Ile Lys Leu Lys Ala Leu Glu Asn Asp Gln Lys
        35                  40                  45


<210> SEQ ID NO 539
<211> LENGTH: 40
<212> TYPE: PRT
<213> ORGANISM: Homo sapiens

<400> SEQUENCE: 539

His Arg Glu Ile Cys Thr Ile Gln Ser Ser Gly Gly Ile Met Leu Leu
1               5                   10                  15

Lys Asp Gln Val Leu Arg Cys Ser Lys Ile Ala Gly Val Lys Val Ala
            20                  25                  30

Glu Ile Thr Glu Leu Ile Leu Lys
        35                  40


<210> SEQ ID NO 540
<211> LENGTH: 23
<212> TYPE: PRT
<213> ORGANISM: Homo sapiens

<400> SEQUENCE: 540

Lys Lys Met Gln Gln Glu Asn Met Lys Gln Pro Glu Gln Leu Thr Leu
1               5                   10                  15

Glu Pro Tyr Glu Arg Asp His
            20


<210> SEQ ID NO 541
<211> LENGTH: 22
<212> TYPE: PRT
<213> ORGANISM: Homo sapiens

<400> SEQUENCE: 541

Lys Met Gln Gln Glu Asn Met Lys Pro Gln Glu Gln Leu Thr Leu Glu
1               5                   10                  15

Pro Tyr Glu Arg Asp His
            20


<210> SEQ ID NO 542
<211> LENGTH: 38
<212> TYPE: PRT
<213> ORGANISM: Homo sapiens

<400> SEQUENCE: 542

His Glu Met Glu Glu Ser Lys Lys Asn Arg Val Glu Ile Asn Asp Val
1               5                   10                  15

Glu Pro Glu Val Phe Lys Glu Met Met Cys Phe Ile Tyr Thr Gly Lys
            20                  25                  30

Ala Pro Asn Leu Asp Lys
        35


<210> SEQ ID NO 543
<211> LENGTH: 32
<212> TYPE: PRT
<213> ORGANISM: Homo sapiens

<400> SEQUENCE: 543
```

-continued

His Glu Met Glu Glu Ser Lys Lys Asn Arg Val Glu Ile Asn Asp Val
1               5                   10                  15

Glu Pro Glu Val Phe Lys Glu Met Met Cys Phe Ile Tyr Thr Gly Lys
            20                  25                  30

<210> SEQ ID NO 544
<211> LENGTH: 9
<212> TYPE: PRT
<213> ORGANISM: Homo sapiens

<400> SEQUENCE: 544

Lys His Gly Glu Leu Lys Val Tyr Lys
1               5

<210> SEQ ID NO 545
<211> LENGTH: 14
<212> TYPE: PRT
<213> ORGANISM: Homo sapiens

<400> SEQUENCE: 545

Lys Leu Ile Leu Gly Pro Gln Glu Glu Lys Gly Lys Gln His
1               5                   10

<210> SEQ ID NO 546
<211> LENGTH: 7
<212> TYPE: PRT
<213> ORGANISM: Homo sapiens

<400> SEQUENCE: 546

His Asn Arg Ile His His Lys
1               5

<210> SEQ ID NO 547
<211> LENGTH: 17
<212> TYPE: PRT
<213> ORGANISM: Homo sapiens

<400> SEQUENCE: 547

His His Asn Ser Ser Arg Lys Ser Thr Lys Lys Thr Asn Gln Ser Ser
1               5                   10                  15

Lys

<210> SEQ ID NO 548
<211> LENGTH: 16
<212> TYPE: PRT
<213> ORGANISM: Homo sapiens

<400> SEQUENCE: 548

His Asn Ser Ser Arg Lys Ser Thr Lys Lys Thr Asn Gln Ser Ser Lys
1               5                   10                  15

<210> SEQ ID NO 549
<211> LENGTH: 20
<212> TYPE: PRT
<213> ORGANISM: Homo sapiens

<400> SEQUENCE: 549

Lys His His Asn Ile Leu Pro Lys Thr Leu Ala Asn Asp Lys His Ser
1               5                   10                  15

His Lys Pro His
            20

<210> SEQ ID NO 550

-continued

<211> LENGTH: 17
<212> TYPE: PRT
<213> ORGANISM: Homo sapiens

<400> SEQUENCE: 550

His His Asn Ile Leu Pro Lys Thr Leu Ala Asn Asp Lys His Ser His
1 5 10 15

Lys

<210> SEQ ID NO 551
<211> LENGTH: 16
<212> TYPE: PRT
<213> ORGANISM: Homo sapiens

<400> SEQUENCE: 551

His Asn Ile Leu Pro Lys Thr Leu Ala Asn Asp Lys His Ser His Lys
1 5 10 15

<210> SEQ ID NO 552
<211> LENGTH: 12
<212> TYPE: PRT
<213> ORGANISM: Homo sapiens

<400> SEQUENCE: 552

His Asn Ile Leu Pro Lys Thr Leu Ala Asn Asp Lys
1 5 10

<210> SEQ ID NO 553
<211> LENGTH: 18
<212> TYPE: PRT
<213> ORGANISM: Homo sapiens

<400> SEQUENCE: 553

Lys Asn Thr Pro Asp Ser Lys Lys Ile Ser Ser Arg Asn Ile Asn Asp
1 5 10 15

His His

<210> SEQ ID NO 554
<211> LENGTH: 17
<212> TYPE: PRT
<213> ORGANISM: Homo sapiens

<400> SEQUENCE: 554

Lys Asn Thr Pro Asp Ser Lys Lys Ile Ser Ser Arg Asn Ile Asn Asp
1 5 10 15

His

<210> SEQ ID NO 555
<211> LENGTH: 27
<212> TYPE: PRT
<213> ORGANISM: Homo sapiens

<400> SEQUENCE: 555

Lys Asp Thr Cys Ile Gln Ser Pro Ser Lys Glu Cys Gln Lys Ser His
1 5 10 15

Pro Lys Ser Val Pro Val Ser Ser Lys Lys Lys
20 25

<210> SEQ ID NO 556
<211> LENGTH: 26
<212> TYPE: PRT
<213> ORGANISM: Homo sapiens -continued

<400> SEQUENCE: 556

Lys Asp Thr Cys Ile Gln Ser Pro Ser Lys Glu Cys Gln Lys Ser His
1 5 10 15

Pro Lys Ser Val Pro Val Ser Ser Lys Lys
20 25

<210> SEQ ID NO 557
<211> LENGTH: 12
<212> TYPE: PRT
<213> ORGANISM: Homo sapiens

<400> SEQUENCE: 557

His Pro Lys Ser Val Pro Val Ser Ser Lys Lys Lys
1 5 10

<210> SEQ ID NO 558
<211> LENGTH: 11
<212> TYPE: PRT
<213> ORGANISM: Homo sapiens

<400> SEQUENCE: 558

His Pro Lys Ser Val Pro Val Ser Ser Lys Lys
1 5 10

<210> SEQ ID NO 559
<211> LENGTH: 10
<212> TYPE: PRT
<213> ORGANISM: Homo sapiens

<400> SEQUENCE: 559

His Pro Lys Ser Val Pro Val Ser Ser Lys
1 5 10

<210> SEQ ID NO 560
<211> LENGTH: 14
<212> TYPE: PRT
<213> ORGANISM: Homo sapiens

<400> SEQUENCE: 560

Lys Ala Leu Gln Glu Lys Val Glu Ile Lys Gln Leu Asn His
1 5 10

<210> SEQ ID NO 561
<211> LENGTH: 41
<212> TYPE: PRT
<213> ORGANISM: Homo sapiens

<400> SEQUENCE: 561

Lys Thr Leu Phe Pro Leu Ile Glu Ala Lys Lys Asp Gln Val Thr Ala
1 5 10 15

Gly Glu Ile Phe Gly Asp Asn His Glu Asp Gly Pro Thr Ala Lys Lys
20 25 30

Leu Lys Thr Glu Gly Gly Gly Ala His
35 40

<210> SEQ ID NO 562
<211> LENGTH: 25
<212> TYPE: PRT
<213> ORGANISM: Homo sapiens

<400> SEQUENCE: 562

Lys Thr Leu Phe Pro Leu Ile Glu Ala Lys Lys Lys Asp Gln Val Thr
1 5 10 15

-continued

Ala Gly Glu Ile Phe Gln Asp Asn Asx
20 25

<210> SEQ ID NO 563
<211> LENGTH: 14
<212> TYPE: PRT
<213> ORGANISM: Homo sapiens

<400> SEQUENCE: 563

Lys Leu Cys Val Phe Lys Lys Ile Glu Arg His Ser Ile His
1 5 10

<210> SEQ ID NO 564
<211> LENGTH: 11
<212> TYPE: PRT
<213> ORGANISM: Homo sapiens

<400> SEQUENCE: 564

Lys Leu Cys Val Phe Lys Lys Ile Glu Arg His
1 5 10

<210> SEQ ID NO 565
<211> LENGTH: 22
<212> TYPE: PRT
<213> ORGANISM: Homo sapiens

<400> SEQUENCE: 565

Lys Gly Pro Ser Phe Pro Leu Lys Gly Ile Thr Glu Gln Gln Lys Glu
1 5 10 15

Gly Leu Glu Ile Val Lys
20

<210> SEQ ID NO 566
<211> LENGTH: 15
<212> TYPE: PRT
<213> ORGANISM: Homo sapiens

<400> SEQUENCE: 566

His Gly Pro Ser Phe Pro Leu Lys Gly Ile Thr Glu Gln Gln Lys
1 5 10 15

<210> SEQ ID NO 567
<211> LENGTH: 13
<212> TYPE: PRT
<213> ORGANISM: Homo sapiens

<400> SEQUENCE: 567

His Thr Leu Leu Lys Ile Leu Ser Thr Phe Leu Phe Lys
1 5 10

<210> SEQ ID NO 568
<211> LENGTH: 14
<212> TYPE: PRT
<213> ORGANISM: Homo sapiens

<400> SEQUENCE: 568

His Leu Leu Gly Asn Asn Asp Lys Asn Leu Leu Pro Ser Lys
1 5 10

<210> SEQ ID NO 569
<211> LENGTH: 19
<212> TYPE: PRT
<213> ORGANISM: Homo sapiens -continued

<400> SEQUENCE: 569

His Arg His Glu Gly Val Phe Ile Cys Arg Gly Lys Glu Asp Ala Leu
1 5 10 15

Val Thr Lys

<210> SEQ ID NO 570
<211> LENGTH: 17
<212> TYPE: PRT
<213> ORGANISM: Homo sapiens

<400> SEQUENCE: 570

His Glu Gly Val Phe Ile Cys Arg Gly Lys Glu Asp Ala Leu Val Thr
1 5 10 15

Lys

<210> SEQ ID NO 571
<211> LENGTH: 20
<212> TYPE: PRT
<213> ORGANISM: Homo sapiens

<400> SEQUENCE: 571

His Ser Gly Gly Asn Arg Gly Arg Gly Arg Gly Gly Lys Arg Gly His
1 5 10 15

Gln Ser Gly Lys
20

<210> SEQ ID NO 572
<211> LENGTH: 15
<212> TYPE: PRT
<213> ORGANISM: Homo sapiens

<400> SEQUENCE: 572

Lys Arg Gly Asn Gln Ser Gly Lys Asn Val Met Val Glu Pro His
1 5 10 15

<210> SEQ ID NO 573
<211> LENGTH: 17
<212> TYPE: PRT
<213> ORGANISM: Homo sapiens

<400> SEQUENCE: 573

Lys Arg Gly Asn Gln Ser Gly Lys Asn Val Met Val Glu Pro His Arg
1 5 10 15

His

<210> SEQ ID NO 574
<211> LENGTH: 23
<212> TYPE: PRT
<213> ORGANISM: Homo sapiens

<400> SEQUENCE: 574

Lys Lys Met Gln Gln Glu Asn Met Lys Pro Gln Glu Gln Leu Thr Leu
1 5 10 15

Glu Pro Tyr Glu Arg Asp His
20

<210> SEQ ID NO 575
<211> LENGTH: 22
<212> TYPE: PRT
<213> ORGANISM: Homo sapiens

<400> SEQUENCE: 575

-continued

Lys Met Gln Gln Glu Asn Met Lys Pro Gln Glu Gln Leu Thr Leu Glu
1               5                   10                  15

Pro Tyr Glu Arg Asp His
            20

<210> SEQ ID NO 576
<211> LENGTH: 16
<212> TYPE: PRT
<213> ORGANISM: Homo sapiens

<400> SEQUENCE: 576

His Ala Tyr Pro Glu Asp Ala Glu Asn Lys Glu Lys Glu Thr Ala Lys
1               5                   10                  15

<210> SEQ ID NO 577
<211> LENGTH: 22
<212> TYPE: PRT
<213> ORGANISM: Homo sapiens

<400> SEQUENCE: 577

Lys Glu Ala Asn Val Lys Cys Pro Gln Ile Val Ile Ala Phe Tyr Glu
1               5                   10                  15

Glu Arg Leu Thr Trp His
            20

<210> SEQ ID NO 578
<211> LENGTH: 25
<212> TYPE: PRT
<213> ORGANISM: Homo sapiens

<400> SEQUENCE: 578

Lys Val Leu Asp Arg Arg Val Val Lys Gly Gln Val Glu Tyr Leu Leu
1               5                   10                  15

Lys Trp Lys Gly Phe Ser Glu Glu His
            20                  25

<210> SEQ ID NO 579
<211> LENGTH: 17
<212> TYPE: PRT
<213> ORGANISM: Homo sapiens

<400> SEQUENCE: 579

Lys Gly Gln Val Glu Tyr Leu Leu Lys Trp Lys Gly Phe Ser Glu Glu
1               5                   10                  15

His

<210> SEQ ID NO 580
<211> LENGTH: 31
<212> TYPE: PRT
<213> ORGANISM: Homo sapiens

<400> SEQUENCE: 580

Lys Ser Glu Val Ala Ala Gly Val Lys Lys Ser Gly Leu Pro Ser Ala
1               5                   10                  15

Glu Arg Leu Glu Asn Val Leu Phe Gly Pro His Asp Cys Ser His
            20                  25                  30

<210> SEQ ID NO 581
<211> LENGTH: 28
<212> TYPE: PRT
<213> ORGANISM: Homo sapiens -continued

<400> SEQUENCE: 581

Lys Ser Glu Val Ala Ala Gly Val Lys Lys Ser Gly Pro Leu Pro Ser
1               5                   10                  15

Ala Glu Arg Leu Glu Asn Val Leu Phe Gly Pro His
            20                  25

<210> SEQ ID NO 582
<211> LENGTH: 28
<212> TYPE: PRT
<213> ORGANISM: Homo sapiens

<400> SEQUENCE: 582

Lys Ala Ala Glu Tyr Gly Lys Lys Ala Lys Ser Glu Thr Phe Arg Leu
1               5                   10                  15

Leu His Ala Lys Asn Ile Ile Arg Pro Gln Leu Lys
            20                  25

<210> SEQ ID NO 583
<211> LENGTH: 20
<212> TYPE: PRT
<213> ORGANISM: Homo sapiens

<400> SEQUENCE: 583

Lys Ala Ala Glu Tyr Gly Lys Lys Ala Lys Ser Glu Thr Phe Arg Leu
1               5                   10                  15

Leu His Ala Lys
            20

<210> SEQ ID NO 584
<211> LENGTH: 11
<212> TYPE: PRT
<213> ORGANISM: Homo sapiens

<400> SEQUENCE: 584

Lys Ser Glu Thr Phe Arg Leu Leu His Ala Lys
1               5                   10

<210> SEQ ID NO 585
<211> LENGTH: 11
<212> TYPE: PRT
<213> ORGANISM: Homo sapiens

<400> SEQUENCE: 585

His Ala Lys Asn Ile Ile Arg Pro Gln Leu Lys
1               5                   10

<210> SEQ ID NO 586
<211> LENGTH: 12
<212> TYPE: PRT
<213> ORGANISM: Homo sapiens

<400> SEQUENCE: 586

His Met Asn Leu Lys Ile Ala Glu Glu Leu Pro Lys
1               5                   10

<210> SEQ ID NO 587
<211> LENGTH: 17
<212> TYPE: PRT
<213> ORGANISM: Homo sapiens

<400> SEQUENCE: 587

His Ser Leu Asp His Leu Leu Lys Leu Tyr Cys Asn Val Asp Ser Asn
1               5                   10                  15

-continued

```
Lys

<210> SEQ ID NO 588
<211> LENGTH: 13
<212> TYPE: PRT
<213> ORGANISM: Homo sapiens

<400> SEQUENCE: 588

His Leu Leu Lys Leu Tyr Cys Asn Val Asp Ser Asn Lys
1               5                   10

<210> SEQ ID NO 589
<211> LENGTH: 10
<212> TYPE: PRT
<213> ORGANISM: Homo sapiens

<400> SEQUENCE: 589

Lys Ala Lys Glu Arg Leu Glu Ala Lys His
1               5                   10

<210> SEQ ID NO 590
<211> LENGTH: 8
<212> TYPE: PRT
<213> ORGANISM: Homo sapiens

<400> SEQUENCE: 590

Lys Asp Arg Gln His Thr Leu Lys
1               5

<210> SEQ ID NO 591
<211> LENGTH: 9
<212> TYPE: PRT
<213> ORGANISM: Homo sapiens

<400> SEQUENCE: 591

Lys Asp Arg Gln His Thr Leu Lys His
1               5

<210> SEQ ID NO 592
<211> LENGTH: 12
<212> TYPE: PRT
<213> ORGANISM: Homo sapiens

<400> SEQUENCE: 592

Lys Glu Thr Cys Ser Glu Lys Ser Thr Asn Leu His
1               5                   10

<210> SEQ ID NO 593
<211> LENGTH: 16
<212> TYPE: PRT
<213> ORGANISM: Homo sapiens

<400> SEQUENCE: 593

Lys Thr Glu Glu Ile Ser Glu Val Lys Met Asp Ala Glu Phe Gly His
1               5                   10                  15

<210> SEQ ID NO 594
<211> LENGTH: 24
<212> TYPE: PRT
<213> ORGANISM: Homo sapiens

<400> SEQUENCE: 594

Lys Thr Glu Glu Ile Ser Glu Val Lys Met Asp Ala Glu Phe Gly His
1               5                   10                  15
```

```
Asp Ser Gly Phe Glu Val Arg His
            20


<210> SEQ ID NO 595
<211> LENGTH: 17
<212> TYPE: PRT
<213> ORGANISM: Homo sapiens

<400> SEQUENCE: 595

Lys Lys Tyr Val Arg Ala Glu Gln Lys Asp Arg Gln His Thr Leu Lys
1               5                   10                  15

His


<210> SEQ ID NO 596
<211> LENGTH: 16
<212> TYPE: PRT
<213> ORGANISM: Homo sapiens

<400> SEQUENCE: 596

Lys Tyr Val Arg Ala Glu Gln Lys Asp Arg Gln His Thr Leu Lys His
1               5                   10                  15


<210> SEQ ID NO 597
<211> LENGTH: 13
<212> TYPE: PRT
<213> ORGANISM: Homo sapiens

<400> SEQUENCE: 597

Lys Lys Tyr Val Arg Ala Glu Gln Lys Asp Arg Gln His
1               5                   10


<210> SEQ ID NO 598
<211> LENGTH: 13
<212> TYPE: PRT
<213> ORGANISM: Homo sapiens

<400> SEQUENCE: 598

Lys Tyr Val Arg Ala Glu Gln Lys Asp Arg Gln His Thr
1               5                   10


<210> SEQ ID NO 599
<211> LENGTH: 16
<212> TYPE: PRT
<213> ORGANISM: Homo sapiens

<400> SEQUENCE: 599

His His Val Phe Asn Met Leu Lys Lys Tyr Val Arg Ala Glu Gln Lys
1               5                   10                  15


<210> SEQ ID NO 600
<211> LENGTH: 15
<212> TYPE: PRT
<213> ORGANISM: Homo sapiens

<400> SEQUENCE: 600

His Val Phe Asn Met Leu Lys Lys Tyr Val Arg Ala Glu Gln Lys
1               5                   10                  15


<210> SEQ ID NO 601
<211> LENGTH: 24
<212> TYPE: PRT
<213> ORGANISM: Homo sapiens

<400> SEQUENCE: 601
```

-continued

His His Val Phe Asn Met Leu Lys Lys Tyr Val Arg Ala Glu Gln Lys
1 5 10 15

Asp Arg Gln His Thr Leu Lys His
20

<210> SEQ ID NO 602
<211> LENGTH: 23
<212> TYPE: PRT
<213> ORGANISM: Homo sapiens

<400> SEQUENCE: 602

His Val Phe Asn Met Leu Lys Lys Tyr Val Arg Ala Glu Gln Lys Asp
1 5 10 15

Arg Gln His Thr Leu Lys His
20

<210> SEQ ID NO 603
<211> LENGTH: 15
<212> TYPE: PRT
<213> ORGANISM: Homo sapiens

<400> SEQUENCE: 603

His Ala His Phe Gln Lys Ala Lys Glu Arg Leu Glu Ala Lys His
1 5 10 15

<210> SEQ ID NO 604
<211> LENGTH: 14
<212> TYPE: PRT
<213> ORGANISM: Homo sapiens

<400> SEQUENCE: 604

His Ala His Phe Gln Lys Ala Lys Glu Arg Leu Glu Ala Lys
1 5 10

<210> SEQ ID NO 605
<211> LENGTH: 12
<212> TYPE: PRT
<213> ORGANISM: Homo sapiens

<400> SEQUENCE: 605

His Phe Gln Lys Ala Lys Glu Arg Leu Glu Ala Lys
1 5 10

<210> SEQ ID NO 606
<211> LENGTH: 30
<212> TYPE: PRT
<213> ORGANISM: Homo sapiens

<400> SEQUENCE: 606

His Gln Glu Arg Met Asp Val Cys Glu Thr His Leu His Trp His Thr
1 5 10 15

Val Ala Lys Glu Thr Cys Ser Glu Lys Ser Thr Asn Leu His
20 25 30

<210> SEQ ID NO 607
<211> LENGTH: 25
<212> TYPE: PRT
<213> ORGANISM: Homo sapiens

<400> SEQUENCE: 607

His Gln Glu Arg Met Asp Val Cys Glu Thr His Leu His Trp His Thr
1 5 10 15

-continued

```
Val Ala Lys Glu Thr Cys Ser Glu Lys
            20                  25


<210> SEQ ID NO 608
<211> LENGTH: 13
<212> TYPE: PRT
<213> ORGANISM: Homo sapiens

<400> SEQUENCE: 608

His Trp His Thr Val Ala Lys Glu Thr Cys Ser Glu Lys
1               5                   10


<210> SEQ ID NO 609
<211> LENGTH: 11
<212> TYPE: PRT
<213> ORGANISM: Homo sapiens

<400> SEQUENCE: 609

His Thr Val Ala Lys Glu Thr Cys Ser Glu Lys
1               5                   10


<210> SEQ ID NO 610
<211> LENGTH: 15
<212> TYPE: PRT
<213> ORGANISM: Homo sapiens

<400> SEQUENCE: 610

His Leu His Trp His Thr Val Ala Lys Glu Thr Cys Ser Glu Lys
1               5                   10                  15


<210> SEQ ID NO 611
<211> LENGTH: 23
<212> TYPE: PRT
<213> ORGANISM: Homo sapiens

<400> SEQUENCE: 611

His Met Asn Val Gln Asn Gly Lys Trp Glu Ser Asp Pro Ser Gly Thr
1               5                   10                  15

Lys Thr Cys Ile Gly Thr Lys
            20


<210> SEQ ID NO 612
<211> LENGTH: 17
<212> TYPE: PRT
<213> ORGANISM: Homo sapiens

<400> SEQUENCE: 612

His Met Asn Val Gln Asn Gly Lys Trp Glu Ser Asp Pro Ser Gly Thr
1               5                   10                  15

Lys


<210> SEQ ID NO 613
<211> LENGTH: 16
<212> TYPE: PRT
<213> ORGANISM: Human immunodeficiency virus

<400> SEQUENCE: 613

His Leu Val Cys Gly Lys Lys Gly Leu Gly Leu Ser Gly Arg Lys Lys
1               5                   10                  15


<210> SEQ ID NO 614
<211> LENGTH: 27
<212> TYPE: PRT
<213> ORGANISM: Triticum aestivum
```

-continued

<400> SEQUENCE: 614

His Lys Asp Arg Leu Thr Lys Lys Val Val Asp Ile Ala Arg Glu Val
1 5 10 15

Ala Lys Val Asp Val Pro Glu Tyr Arg Arg His
20 25

<210> SEQ ID NO 615
<211> LENGTH: 27
<212> TYPE: PRT
<213> ORGANISM: Triticum aestivum

<400> SEQUENCE: 615

His Lys Glu Arg Leu Asp Arg Lys Val Val Asp Val Ala Arg Glu Val
1 5 10 15

Ala Lys Val Glu Val Pro Ser Tyr Arg Arg His
20 25

<210> SEQ ID NO 616
<211> LENGTH: 27
<212> TYPE: PRT
<213> ORGANISM: Triticum aestivum

<400> SEQUENCE: 616

His Lys Glu Arg Leu Asp Arg Lys Val Val Asp Val Ala Arg Glu Val
1 5 10 15

Ala Lys Met Glu Val Pro Ser Tyr Arg Arg His
20 25

<210> SEQ ID NO 617
<211> LENGTH: 23
<212> TYPE: PRT
<213> ORGANISM: Triticum aestivum

<400> SEQUENCE: 617

His Leu Gln Pro Lys Trp Lys Pro Ser Leu Ser Trp Phe Lys Asn Ala
1 5 10 15

Glu Ser Arg Leu Asn His His
20

<210> SEQ ID NO 618
<211> LENGTH: 14
<212> TYPE: PRT
<213> ORGANISM: Triticum aestivum

<400> SEQUENCE: 618

His Leu Gln Pro Lys Trp Lys Pro Ser Leu Ser Trp Phe Lys
1 5 10

<210> SEQ ID NO 619
<211> LENGTH: 19
<212> TYPE: PRT
<213> ORGANISM: Triticum aestivum

<400> SEQUENCE: 619

Lys Trp Lys Pro Ser Leu Ser Trp Phe Lys Asn Ala Glu Ser Arg Leu
1 5 10 15

Asn His His

<210> SEQ ID NO 620
<211> LENGTH: 18
<212> TYPE: PRT

-continued

<213> ORGANISM: Triticum aestivum

<400> SEQUENCE: 620

Lys Trp Lys Pro Ser Leu Ser Trp Phe Lys Asn Ala Glu Ser Arg Leu
1 5 10 15

Asn His

<210> SEQ ID NO 621
<211> LENGTH: 17
<212> TYPE: PRT
<213> ORGANISM: Triticum aestivum

<400> SEQUENCE: 621

Lys Pro Ser Leu Ser Trp Phe Lys Asn Ala Glu Ser Arg Leu Asn His
1 5 10 15

His

<210> SEQ ID NO 622
<211> LENGTH: 16
<212> TYPE: PRT
<213> ORGANISM: Triticum aestivum

<400> SEQUENCE: 622

Lys Pro Ser Leu Ser Trp Phe Lys Asn Ala Glu Ser Arg Leu Asn His
1 5 10 15

<210> SEQ ID NO 623
<211> LENGTH: 32
<212> TYPE: PRT
<213> ORGANISM: Triticum aestivum

<400> SEQUENCE: 623

His His Ala Ile Ala Leu Gly Leu His Thr Thr Thr Leu Ile Leu Val
1 5 10 15

Lys Gly Ala Leu Asp Ala Arg Gly Ser Lys Leu Met Pro Asp Lys Lys
20 25 30

<210> SEQ ID NO 624
<211> LENGTH: 31
<212> TYPE: PRT
<213> ORGANISM: Triticum aestivum

<400> SEQUENCE: 624

His Ala Ile Ala Leu Gly Leu His Thr Thr Thr Leu Ile Leu Val Lys
1 5 10 15

Gly Ala Leu Asp Ala Arg Gly Ser Lys Leu Met Pro Asp Lys Lys
20 25 30

<210> SEQ ID NO 625
<211> LENGTH: 26
<212> TYPE: PRT
<213> ORGANISM: Triticum aestivum

<400> SEQUENCE: 625

His His Ala Ile Ala Leu Gly Leu His Thr Thr Thr Leu Ile Leu Val
1 5 10 15

Lys Gly Ala Leu Asp Ala Arg Gly Ser Lys
20 25

<210> SEQ ID NO 626
<211> LENGTH: 25
<212> TYPE: PRT

-continued

<213> ORGANISM: Triticum aestivum

<400> SEQUENCE: 626

His Ala Ile Ala Leu Gly Leu His Thr Thr Thr Leu Ile Leu Val Lys
1 5 10 15

Gly Ala Leu Asp Ala Arg Gly Ser Lys
20 25

<210> SEQ ID NO 627
<211> LENGTH: 24
<212> TYPE: PRT
<213> ORGANISM: Triticum aestivum

<400> SEQUENCE: 627

His Thr Thr Thr Leu Ile Leu Val Lys Gly Ala Leu Asp Ala Arg Gly
1 5 10 15

Ser Lys Leu Met Pro Asp Lys Lys
20

<210> SEQ ID NO 628
<211> LENGTH: 23
<212> TYPE: PRT
<213> ORGANISM: Triticum aestivum

<400> SEQUENCE: 628

His Thr Thr Thr Leu Ile Leu Val Lys Gly Ala Leu Asp Ala Arg Gly
1 5 10 15

Ser Lys Leu Met Pro Asp Lys
20

<210> SEQ ID NO 629
<211> LENGTH: 18
<212> TYPE: PRT
<213> ORGANISM: Triticum aestivum

<400> SEQUENCE: 629

His Thr Thr Thr Leu Ile Leu Val Lys Gly Ala Leu Asp Ala Arg Gly
1 5 10 15

Ser Lys

<210> SEQ ID NO 630
<211> LENGTH: 44
<212> TYPE: PRT
<213> ORGANISM: Triticum aestivum

<400> SEQUENCE: 630

His His His Leu Ala Ile Ala Ile Leu Phe Leu Ile Ala Gly His Met
1 5 10 15

Tyr Arg Thr Asn Trp Gly Ile Gly His Gly Leu Lys Asp Ile Leu Glu
20 25 30

Ala His Lys Gly Pro Phe Thr Gly Gln Gly His Lys
35 40

<210> SEQ ID NO 631
<211> LENGTH: 43
<212> TYPE: PRT
<213> ORGANISM: Triticum aestivum

<400> SEQUENCE: 631

His His Leu Ala Ile Ala Ile Leu Phe Leu Ile Ala Gly His Met Tyr
1 5 10 15

-continued

```
Arg Thr Asn Trp Gly Ile Gly His Gly Leu Lys Asp Ile Leu Glu Ala
            20                  25                  30

His Lys Gly Pro Phe Thr Gly Gln Gly His Lys
        35                  40
```

```
<210> SEQ ID NO 632
<211> LENGTH: 42
<212> TYPE: PRT
<213> ORGANISM: Triticum aestivum

<400> SEQUENCE: 632

His Leu Ala Ile Ala Ile Leu Phe Leu Ile Ala Gly His Met Tyr Arg
1               5                   10                  15

Thr Asn Trp Gly Ile Gly His Gly Leu Lys Asp Ile Leu Glu Ala His
            20                  25                  30

Lys Gly Pro Phe Thr Gly Gln Gly His Lys
        35                  40
```

```
<210> SEQ ID NO 633
<211> LENGTH: 30
<212> TYPE: PRT
<213> ORGANISM: Triticum aestivum

<400> SEQUENCE: 633

His Met Tyr Arg Thr Asn Trp Gly Ile Gly His Gly Leu Lys Asp Ile
1               5                   10                  15

Leu Glu Ala His Lys Gly Pro Phe Thr Gly Gln Gly His Lys
            20                  25                  30
```

```
<210> SEQ ID NO 634
<211> LENGTH: 20
<212> TYPE: PRT
<213> ORGANISM: Triticum aestivum

<400> SEQUENCE: 634

His Gly Leu Lys Asp Ile Leu Glu Ala His Lys Gly Pro Phe Thr Gly
1               5                   10                  15

Gln Gly His Lys
            20
```

```
<210> SEQ ID NO 635
<211> LENGTH: 17
<212> TYPE: PRT
<213> ORGANISM: Triticum aestivum

<400> SEQUENCE: 635

His Asp Ile Leu Glu Ala His Lys Gly Pro Phe Thr Gly Gln Gly His
1               5                   10                  15

Lys
```

```
<210> SEQ ID NO 636
<211> LENGTH: 11
<212> TYPE: PRT
<213> ORGANISM: Triticum aestivum

<400> SEQUENCE: 636

His Lys Gly Pro Phe Thr Gly Gln Gly His Lys
1               5                   10
```

```
<210> SEQ ID NO 637
<211> LENGTH: 10
<212> TYPE: PRT
```

-continued

<213> ORGANISM: Triticum aestivum

<400> SEQUENCE: 637

Lys Gly Pro Phe Thr Gly Gln Gly His Lys
1 5 10

<210> SEQ ID NO 638
<211> LENGTH: 16
<212> TYPE: PRT
<213> ORGANISM: Oryza sativa

<400> SEQUENCE: 638

Lys Phe Pro Asp Val Ile His Ala Phe Lys Pro Asn Pro Arg Ser His
1 5 10 15

<210> SEQ ID NO 639
<211> LENGTH: 10
<212> TYPE: PRT
<213> ORGANISM: Oryza sativa

<400> SEQUENCE: 639

Lys Phe Pro Asp Val Ile His Ala Phe Lys
1 5 10

<210> SEQ ID NO 640
<211> LENGTH: 10
<212> TYPE: PRT
<213> ORGANISM: Oryza sativa

<400> SEQUENCE: 640

Lys Ala Arg Tyr Val Lys Phe His Trp Lys
1 5 10

<210> SEQ ID NO 641
<211> LENGTH: 33
<212> TYPE: PRT
<213> ORGANISM: Oryza sativa

<400> SEQUENCE: 641

His Pro Lys Val Ser Pro Glu Leu Arg Ala Ile Trp Val Asn Tyr Leu
1 5 10 15

Ser Gln Glu Asp Glu Ser Leu Gly Val Lys Ile Ala Asn Leu Asn Val
20 25 30

Lys

<210> SEQ ID NO 642
<211> LENGTH: 11
<212> TYPE: PRT
<213> ORGANISM: Oryza sativa

<400> SEQUENCE: 642

Lys Ala Thr Ile His Lys Gln Asn Asp Phe Lys
1 5 10

<210> SEQ ID NO 643
<211> LENGTH: 28
<212> TYPE: PRT
<213> ORGANISM: Oryza sativa

<400> SEQUENCE: 643

His Ala Pro Pro Thr Pro Ile Thr Pro Arg Pro Val Val Gly Arg Arg
1 5 10 15

Gln Lys Ala Thr Ile His Lys Gln Asn Asp Phe Lys 20 25

<210> SEQ ID NO 644
<211> LENGTH: 49
<212> TYPE: PRT
<213> ORGANISM: Oryza sativa

<400> SEQUENCE: 644

Lys Phe Arg Pro Ser Ser Ser Phe Asp Thr Lys Thr Thr Thr Thr Asn
1 5 10 15

Ala Gly Ala Pro Val Trp Asn Asp Asn Glu Ala Leu Thr Val Gly Pro
20 25 30

Arg Gly Pro Ile Leu Leu Glu Asp Tyr His Leu Ile Glu Lys Val Ala
35 40 45

His

<210> SEQ ID NO 645
<211> LENGTH: 42
<212> TYPE: PRT
<213> ORGANISM: Oryza sativa

<400> SEQUENCE: 645

Lys Phe Arg Pro Ser Ser Ser Phe Asp Thr Lys Thr Thr Thr Thr Asn
1 5 10 15

Ala Gly Ala Pro Val Trp Asn Asp Asn Glu Ala Leu Thr Val Gly Pro
20 25 30

Arg Gly Pro Ile Leu Leu Glu Asp Tyr Asn
35 40

<210> SEQ ID NO 646

<400> SEQUENCE: 646

000

<210> SEQ ID NO 647
<211> LENGTH: 9
<212> TYPE: PRT
<213> ORGANISM: Oryza sativa

<400> SEQUENCE: 647

Lys Val Lys Ala His Phe Gln Lys His
1 5

<210> SEQ ID NO 648
<211> LENGTH: 8
<212> TYPE: PRT
<213> ORGANISM: Oryza sativa

<400> SEQUENCE: 648

Lys Val Lys Ala His Phe Gln Lys
1 5

<210> SEQ ID NO 649
<211> LENGTH: 12
<212> TYPE: PRT
<213> ORGANISM: Oryza sativa

<400> SEQUENCE: 649

Lys Asp Tyr Glu Ile Asp Lys Asp Asp Leu Ile His
1 5 10

```
<210> SEQ ID NO 650
<211> LENGTH: 14
<212> TYPE: PRT
<213> ORGANISM: Oryza sativa

<400> SEQUENCE: 650

His Met Lys Gln Cys Phe Ala Phe Cys Ala Val Phe Pro Lys
1               5                   10


<210> SEQ ID NO 651
<211> LENGTH: 49
<212> TYPE: PRT
<213> ORGANISM: Oryza sativa

<400> SEQUENCE: 651

His Val Phe Trp Glu Leu Val Trp Arg Ser Phe Phe Gln Asn Val Lys
1               5                   10                  15

Gln Ile Gly Ser Ile Phe Gln Arg Lys Val Tyr Arg Tyr Gly Gln Ser
            20                  25                  30

Asp Val Thr Thr Ser Lys Ile His Asp Leu Met His Asp Leu Ala Val
        35                  40                  45

His


<210> SEQ ID NO 652
<211> LENGTH: 33
<212> TYPE: PRT
<213> ORGANISM: Oryza sativa

<400> SEQUENCE: 652

Lys Gln Ile Gly Ser Ile Phe Gln Arg Lys Val Arg Tyr Gly Pro Ser
1               5                   10                  15

Asp Val Thr Thr Ser Lys Ile His Asp Leu Met His Asp Leu Ala Val
            20                  25                  30

His


<210> SEQ ID NO 653
<211> LENGTH: 29
<212> TYPE: PRT
<213> ORGANISM: Oryza sativa

<400> SEQUENCE: 653

Lys Gln Ile Gly Ser Ile Phe Gln Arg Lys Val Tyr Arg Tyr Gly Pro
1               5                   10                  15

Ser Asp Val Thr Thr Ser Lys Ile His Asp Leu Met His
            20                  25


<210> SEQ ID NO 654
<211> LENGTH: 25
<212> TYPE: PRT
<213> ORGANISM: Oryza sativa

<400> SEQUENCE: 654

Lys Gln Ile Gly Ser Ile Phe Gln Arg Lys Val Tyr Arg Tyr Gly Gln
1               5                   10                  15

Ser Asp Val Thr Thr Ser Lys Ile His
            20                  25


<210> SEQ ID NO 655
<211> LENGTH: 9
<212> TYPE: PRT
<213> ORGANISM: Oryza sativa
```

-continued

<400> SEQUENCE: 655

Lys His Gly Val Ser Ala Gly Ile Lys
1 5

<210> SEQ ID NO 656

<400> SEQUENCE: 656

000

<210> SEQ ID NO 657
<211> LENGTH: 15
<212> TYPE: PRT
<213> ORGANISM: Oryza sativa

<400> SEQUENCE: 657

His Thr Val Phe Asp Tyr Gly Lys Met Arg Val Gly Phe Ala Lys
1 5 10 15

<210> SEQ ID NO 658
<211> LENGTH: 17
<212> TYPE: PRT
<213> ORGANISM: Oryza sativa

<400> SEQUENCE: 658

His Ser Arg Tyr Lys Ser Gly Gln Ser Ser Thr Tyr Gln Lys Asn Gly
1 5 10 15

Lys

<210> SEQ ID NO 659
<211> LENGTH: 29
<212> TYPE: PRT
<213> ORGANISM: Oryza sativa

<400> SEQUENCE: 659

Lys Gln Glu Ala Met Val Leu Lys Gln Glu Ile Asn Leu Leu Gln Lys
1 5 10 15

Gly Leu Arg Tyr Ile Tyr Gly Asn Arg Ala Asn Glu His
20 25

<210> SEQ ID NO 660
<211> LENGTH: 22
<212> TYPE: PRT
<213> ORGANISM: Oryza sativa

<400> SEQUENCE: 660

Lys Gln Glu Ile Asn Leu Leu Gln Lys Gly Leu Arg Tyr Ile Tyr Gly
1 5 10 15

Asn Arg Ala Asn Glu His
20

<210> SEQ ID NO 661
<211> LENGTH: 38
<212> TYPE: PRT
<213> ORGANISM: Oryza sativa

<400> SEQUENCE: 661

Lys Ser Lys Glu Gly Met Leu Lys Ala Ala Asn Glu Ile Leu Gln Glu
1 5 10 15

Lys Ile Val Glu Gln Asn Gly Leu Ile Asp Val Gly Met Met Val Ala
20 25 30

Asp Gln Gln Asn Gly His

-continued

35

<210> SEQ ID NO 662
<211> LENGTH: 31
<212> TYPE: PRT
<213> ORGANISM: Oryza sativa

<400> SEQUENCE: 662

Lys Ala Ala Asn Glu Ile Leu Gln Glu Lys Ile Val Glu Gln Asn Gly
1 5 10 15

Leu Ile Asp Val Gly Met Met Val Ala Asp Gln Gln Asn Gly His
20 25 30

<210> SEQ ID NO 663
<211> LENGTH: 11
<212> TYPE: PRT
<213> ORGANISM: Zea mays

<400> SEQUENCE: 663

Lys Val Leu Ala Ala His Arg Tyr Gly Ile Lys
1 5 10

<210> SEQ ID NO 664
<211> LENGTH: 17
<212> TYPE: PRT
<213> ORGANISM: Zea mays

<400> SEQUENCE: 664

Lys Leu Lys Ile Ala Met Lys His Leu Ile Pro Arg Val Leu Glu Gln
1 5 10 15

His

<210> SEQ ID NO 665
<211> LENGTH: 8
<212> TYPE: PRT
<213> ORGANISM: Zea mays

<400> SEQUENCE: 665

Lys Leu Lys Ile Ala Met Lys His
1 5

<210> SEQ ID NO 666
<211> LENGTH: 33
<212> TYPE: PRT
<213> ORGANISM: Zea mays

<400> SEQUENCE: 666

Lys Thr Ser Leu Ala Ser Ser Ile Ala Lys Ala Leu Asn Arg Lys Phe
1 5 10 15

Ile Arg Ile Ser Leu Gly Gly Val Lys Asp Glu Ala Asp Ile Arg Gly
20 25 30

His

<210> SEQ ID NO 667
<211> LENGTH: 24
<212> TYPE: PRT
<213> ORGANISM: Zea mays

<400> SEQUENCE: 667

Lys Ala Leu Asn Arg Lys Phe Ile Arg Ile Ser Leu Gly Gly Val Lys
1 5 10 15

Asp Glu Ala Asp Ile Arg Gly His

20

<210> SEQ ID NO 668
<211> LENGTH: 19
<212> TYPE: PRT
<213> ORGANISM: Zea mays

<400> SEQUENCE: 668

Lys Phe Ile Arg Ile Ser Leu Gly Gly Val Lys Asp Glu Ala Asp Ile
1               5                   10                  15

Arg Gly His

<210> SEQ ID NO 669
<211> LENGTH: 37
<212> TYPE: PRT
<213> ORGANISM: Zea mays

<400> SEQUENCE: 669

Lys Val Arg Leu Ser Lys Ala Thr Glu Leu Val Asp Arg His Leu Gln
1               5                   10                  15

Ser Ile Leu Val Ala Glu Lys Ile Thr Gln Lys Val Glu Gly Gln Leu
            20                  25                  30

Ser Lys Ser Gln Lys
        35

<210> SEQ ID NO 670
<211> LENGTH: 24
<212> TYPE: PRT
<213> ORGANISM: Zea mays

<400> SEQUENCE: 670

His Leu Gln Ser Ile Leu Val Ala Glu Lys Ile Thr Gln Lys Val Glu
1               5                   10                  15

Gly Gly Leu Ser Lys Ser Gln Lys
            20

<210> SEQ ID NO 671
<211> LENGTH: 14
<212> TYPE: PRT
<213> ORGANISM: Zea mays

<400> SEQUENCE: 671

Lys Val Arg Leu Ser Lys Ala Thr Glu Leu Val Asp Arg His
1               5                   10

<210> SEQ ID NO 672
<211> LENGTH: 34
<212> TYPE: PRT
<213> ORGANISM: Zea mays

<400> SEQUENCE: 672

Lys Val Gly Gly Ser Ala Val Glu Ser Ser Lys Gln Asp Thr Lys Asn
1               5                   10                  15

Gly Lys Glu Pro Ile His Trp His Ser Lys Gly Val Ala Ala Arg Ala
            20                  25                  30

Leu His

<210> SEQ ID NO 673
<211> LENGTH: 24
<212> TYPE: PRT
<213> ORGANISM: Zea mays

-continued

<400> SEQUENCE: 673

Lys Val Gly Gly Ser Ala Val Glu Ser Ser Lys Gln Asp Thr Lys Asn
1 5 10 15

Gly Lys Glu Pro Ile His Trp His
20

<210> SEQ ID NO 674
<211> LENGTH: 22
<212> TYPE: PRT
<213> ORGANISM: Zea mays

<400> SEQUENCE: 674

Lys Val Gly Gly Ser Ala Val Glu Ser Ser Lys Gln Asp Thr Lys Asn
1 5 10 15

Gly Lys Glu Pro Ile His
20

<210> SEQ ID NO 675
<211> LENGTH: 24
<212> TYPE: PRT
<213> ORGANISM: Zea mays

<400> SEQUENCE: 675

Lys Gln Asp Thr Lys Asn Gly Lys Glu Pro Ile His Trp His Ser Lys
1 5 10 15

Gly Val Ala Ala Arg Ala Leu His
20

<210> SEQ ID NO 676
<211> LENGTH: 12
<212> TYPE: PRT
<213> ORGANISM: Zea mays

<400> SEQUENCE: 676

Lys Gln Asp Thr Lys Asn Gly Lys Glu Pro Ile His
1 5 10

<210> SEQ ID NO 677
<211> LENGTH: 33
<212> TYPE: PRT
<213> ORGANISM: Zea mays

<400> SEQUENCE: 677

His Arg Asp Leu Arg Arg Ala Arg Ala Ala Ala Leu Asn Ile Val Pro
1 5 10 15

Thr Ser Thr Gly Ala Ala Lys Ala Val Ser Leu Val Leu Pro Asn Leu
20 25 30

Lys

<210> SEQ ID NO 678
<211> LENGTH: 19
<212> TYPE: PRT
<213> ORGANISM: Zea mays

<400> SEQUENCE: 678

Lys Val Leu Asp Asp Gln Lys Phe Gly Ile Ile Lys Gly Thr Met Thr
1 5 10 15

Thr Thr His

<210> SEQ ID NO 679
<211> LENGTH: 16

-continued

<212> TYPE: PRT
<213> ORGANISM: Zea mays

<400> SEQUENCE: 679

His Ile Gln Ala Gly Ala Lys Lys Val Leu Ile Thr Ala Pro Gly Lys
1 5 10 15

<210> SEQ ID NO 680
<211> LENGTH: 28
<212> TYPE: PRT
<213> ORGANISM: Zea mays

<400> SEQUENCE: 680

His Gly Arg Gly Asp Ala Ser Pro Leu Asp Val Ile Ala Ile Asn Asp
1 5 10 15

Thr Gly Gly Val Lys Gln Ala Ser His Leu Leu Lys
20 25

<210> SEQ ID NO 681
<211> LENGTH: 51
<212> TYPE: PRT
<213> ORGANISM: Zea mays

<400> SEQUENCE: 681

Lys Val Arg Arg Val Leu Ser Lys Asp Tyr Ser Ser Leu Lys Gln Leu
1 5 10 15

Met Thr Leu Met Met Asp Asp Asp Ile Ser Lys His Leu Gln Ile Ile
20 25 30

Glu Ser Gly Leu Glu Glu Arg Glu Asp Lys Val Trp Met Lys Glu Asn
35 40 45

Ile Ile Lys
50

<210> SEQ ID NO 682
<211> LENGTH: 28
<212> TYPE: PRT
<213> ORGANISM: Zea mays

<400> SEQUENCE: 682

Lys Val Arg Arg Val Leu Ser Lys Asp Tyr Ser Ser Leu Lys Gln Leu
1 5 10 15

Met Thr Leu Met Met Asp Asp Asp Ile Ser Lys His
20 25

<210> SEQ ID NO 683
<211> LENGTH: 24
<212> TYPE: PRT
<213> ORGANISM: Zea mays

<400> SEQUENCE: 683

His Leu Gln Ile Ile Glu Ser Gly Leu Glu Glu Arg Glu Asp Lys Val
1 5 10 15

Trp Met Lys Glu Asn Ile Ile Lys
20

<210> SEQ ID NO 684
<211> LENGTH: 17
<212> TYPE: PRT
<213> ORGANISM: Zea mays

<400> SEQUENCE: 684

His Asp Leu Arg Glu Asn Ile Ile Met Lys Ala Asp Asp Leu Ala Ser

-continued

```
1               5                   10                  15

Lys


<210> SEQ ID NO 685
<211> LENGTH: 18
<212> TYPE: PRT
<213> ORGANISM: Zea mays

<400> SEQUENCE: 685

His Val Gln Asn Leu Glu Asn Val Ile Gly Lys Asp Glu Ala Leu Ala
1               5                   10                  15

Ser Lys


<210> SEQ ID NO 686
<211> LENGTH: 21
<212> TYPE: PRT
<213> ORGANISM: Zea mays

<400> SEQUENCE: 686

Lys Lys Gln Gly Tyr Glu Leu Arg Gln Leu Lys Asp Leu Asn Glu Leu
1               5                   10                  15

Gly Gly Ser Leu His
            20


<210> SEQ ID NO 687
<211> LENGTH: 20
<212> TYPE: PRT
<213> ORGANISM: Zea mays

<400> SEQUENCE: 687

Lys Gln Gly Tyr Glu Leu Arg Gln Leu Lys Asp Leu Asn Glu Leu Gly
1               5                   10                  15

Gly Ser Leu His
            20


<210> SEQ ID NO 688
<211> LENGTH: 28
<212> TYPE: PRT
<213> ORGANISM: Zea mays

<400> SEQUENCE: 688

Lys Leu Tyr Leu Lys Ser Arg Leu Lys Glu Leu Ile Leu Glu Trp Ser
1               5                   10                  15

Ser Glu Asn Gly Met Asp Ala Met Asn Ile Leu His
            20                  25


<210> SEQ ID NO 689
<211> LENGTH: 39
<212> TYPE: PRT
<213> ORGANISM: Zea mays

<400> SEQUENCE: 689

His Leu Gln Leu Leu Gln Leu Asn Gly Met Val Glu Arg Leu Pro Asn
1               5                   10                  15

Lys Val Cys Asn Leu Ser Lys Leu Arg Tyr Leu Arg Gly Tyr Lys Asp
            20                  25                  30

Gln Ile Pro Asn Ile Gly Lys
        35


<210> SEQ ID NO 690
<211> LENGTH: 30
```

-continued

<212> TYPE: PRT
<213> ORGANISM: Zea mays

<400> SEQUENCE: 690

His Leu Gln Leu Leu Gln Leu Asn Gly Met Val Glu Arg Leu Pro Asn
1               5                   10                  15

Lys Val Cys Asn Leu Ser Lys Arg Tyr Leu Arg Gly Tyr Lys
            20                  25                  30

<210> SEQ ID NO 691
<211> LENGTH: 23
<212> TYPE: PRT
<213> ORGANISM: Zea mays

<400> SEQUENCE: 691

His Leu Gln Leu Leu Gln Leu Asn Gly Met Val Glu Arg Leu Pro Asn
1               5                   10                  15

Lys Val Cys Asn Leu Ser Lys
            20

<210> SEQ ID NO 692
<211> LENGTH: 14
<212> TYPE: PRT
<213> ORGANISM: Zea mays

<400> SEQUENCE: 692

His Asn Ser Asn Lys Leu Pro Lys Ser Val Gly Glu Leu Lys
1               5                   10

<210> SEQ ID NO 693
<211> LENGTH: 10
<212> TYPE: PRT
<213> ORGANISM: Zea mays

<400> SEQUENCE: 693

Lys Leu Pro Lys Val Gly Glu Leu Lys His
1               5                   10

<210> SEQ ID NO 694
<211> LENGTH: 18
<212> TYPE: PRT
<213> ORGANISM: Zea mays

<400> SEQUENCE: 694

His Leu Ser Val Arg Val Glu Ser Met Gln Lys His Lys Glu Ile Ile
1               5                   10                  15

Tyr Lys

<210> SEQ ID NO 695
<211> LENGTH: 8
<212> TYPE: PRT
<213> ORGANISM: Zea mays

<400> SEQUENCE: 695

Lys His Lys Glu Ile Ile Tyr Lys
1               5

<210> SEQ ID NO 696
<211> LENGTH: 23
<212> TYPE: PRT
<213> ORGANISM: Zea mays

<400> SEQUENCE: 696

-continued

Lys Leu Arg Asp Ile Leu Gln Glu Ser Gln Lys Phe Leu Leu Val Leu
1               5                   10                  15

Asp Leu Ala Leu Phe Lys His
            20

<210> SEQ ID NO 697
<211> LENGTH: 46
<212> TYPE: PRT
<213> ORGANISM: Zea mays

<400> SEQUENCE: 697

His Ala Phe Ser Gly Ala Glu Ile Lys Asp Gln Leu Leu Arg Met Lys
1               5                   10                  15

Leu Gln Asp Thr Ala Glu Glu Ile Ala Lys Arg Leu Gly Gln Cys Pro
            20                  25                  30

Leu Ala Ala Lys Val Leu Gly Ser Arg Met Cys Arg Arg Lys
        35                  40                  45

<210> SEQ ID NO 698
<211> LENGTH: 16
<212> TYPE: PRT
<213> ORGANISM: Zea mays

<400> SEQUENCE: 698

His Ala Phe Ser Gly Ala Glu Ile Lys Asp Gln Leu Leu Arg Met Lys
1               5                   10                  15

<210> SEQ ID NO 699
<211> LENGTH: 46
<212> TYPE: PRT
<213> ORGANISM: Zea mays

<400> SEQUENCE: 699

Lys Leu Gln Asp Thr Ala Glu Glu Ile Ala Lys Arg Leu Gly Gln Cys
1               5                   10                  15

Leu Ala Ala Lys Val Leu Gly Ser Arg Met Cys Arg Arg Lys Asp Ile
            20                  25                  30

Ala Glu Trp Lys Ala Ala Asp Val Trp Phe Glu Lys Ser His
        35                  40                  45

<210> SEQ ID NO 700
<211> LENGTH: 27
<212> TYPE: PRT
<213> ORGANISM: Zea mays

<400> SEQUENCE: 700

Lys Val Leu Gly Ser Arg Met Cys Arg Arg Lys Asp Ile Ala Glu Trp
1               5                   10                  15

Lys Ala Ala Asp Val Trp Phe Glu Lys Ser His
            20                  25

<210> SEQ ID NO 701
<211> LENGTH: 17
<212> TYPE: PRT
<213> ORGANISM: Zea mays

<400> SEQUENCE: 701

Lys Asp Ile Ala Glu Trp Lys Ala Ala Asp Val Trp Phe Glu Lys Ser
1               5                   10                  15

His

-continued

<210> SEQ ID NO 702
<211> LENGTH: 11
<212> TYPE: PRT
<213> ORGANISM: Zea mays

<400> SEQUENCE: 702

Lys Ala Ala Asp Val Trp Phe Glu Lys Ser His
1 5 10

<210> SEQ ID NO 703
<211> LENGTH: 40
<212> TYPE: PRT
<213> ORGANISM: Zea mays

<400> SEQUENCE: 703

His Val Pro Thr Thr Thr Ser Leu Pro Thr Ser Lys Val Phe Gly Arg
1 5 10 15

Asn Ser Asp Arg Asp Arg Ile Val Lys Phe Leu Leu Gly Lys Thr Thr
20 25 30

Thr Ala Glu Ala Ser Ser Thr Lys
35 40

<210> SEQ ID NO 704
<211> LENGTH: 18
<212> TYPE: PRT
<213> ORGANISM: Zea mays

<400> SEQUENCE: 704

Lys Ala Ile Leu Thr Glu Ala Lys Gln Leu Arg Asp Leu Leu Gly Leu
1 5 10 15

Pro His

<210> SEQ ID NO 705
<211> LENGTH: 29
<212> TYPE: PRT
<213> ORGANISM: Zea mays

<400> SEQUENCE: 705

Lys Ala Lys Ala Lys Ser Gly Lys Gly Pro Leu Leu Arg Glu Asp Glu
1 5 10 15

Ser Ser Ser Thr Ala Thr Thr Val Met Lys Pro Phe His
20 25

<210> SEQ ID NO 706
<211> LENGTH: 29
<212> TYPE: PRT
<213> ORGANISM: Zea mays

<400> SEQUENCE: 706

Lys Ser Pro His Arg Gly Lys Leu Glu Ser Trp Leu Arg Arg Leu Lys
1 5 10 15

Glu Ala Phe Tyr Asp Ala Glu Asp Leu Leu Asp Glu His
20 25

<210> SEQ ID NO 707
<211> LENGTH: 16
<212> TYPE: PRT
<213> ORGANISM: Zea mays

<400> SEQUENCE: 707

Lys Ser Pro His Arg Gly Lys Leu Glu Ser Trp Leu Arg Arg Leu Lys
1 5 10 15

-continued

<210> SEQ ID NO 708
<211> LENGTH: 13
<212> TYPE: PRT
<213> ORGANISM: Zea mays

<400> SEQUENCE: 708

His Arg Gly Lys Leu Glu Ser Trp Leu Arg Arg Leu Lys
1 5 10

<210> SEQ ID NO 709
<211> LENGTH: 7
<212> TYPE: PRT
<213> ORGANISM: Zea mays

<400> SEQUENCE: 709

Lys Ser Pro His Arg Gly Lys
1 5

<210> SEQ ID NO 710
<211> LENGTH: 8
<212> TYPE: PRT
<213> ORGANISM: Zea mays

<400> SEQUENCE: 710

Lys Gln Ala Ser His Leu Leu Lys
1 5

<210> SEQ ID NO 711

<400> SEQUENCE: 711

000

<210> SEQ ID NO 712
<211> LENGTH: 21
<212> TYPE: PRT
<213> ORGANISM: Human SARS virus

<400> SEQUENCE: 712

Lys His Leu Asp Ala Tyr Lys Thr Phe Pro Pro Thr Glu Pro Lys Lys
1 5 10 15

Asp Lys Lys Lys Lys
20

<210> SEQ ID NO 713

<400> SEQUENCE: 713

000

<210> SEQ ID NO 714

<400> SEQUENCE: 714

000

<210> SEQ ID NO 715
<211> LENGTH: 27
<212> TYPE: PRT
<213> ORGANISM: Avian bronchitis coronavirus

<400> SEQUENCE: 715

Lys Lys Ile Asn Ser Pro Gln Pro Lys Phe Glu Gly Ser Gly Val Pro
1 5 10 15

-continued

```
Asp Asn Glu Asn Leu Lys Thr Ser Gln Gln His
            20                  25


<210> SEQ ID NO 716
<211> LENGTH: 23
<212> TYPE: PRT
<213> ORGANISM: Porcine epidemic diarrhea coronavirus

<400> SEQUENCE: 716

Lys Thr Gly Asn Ala Lys Leu Gln Arg Lys Lys Glu Lys Lys Asn Lys
1               5                   10                  15

Arg Glu Thr Thr Leu Gln His
            20


<210> SEQ ID NO 717
<211> LENGTH: 18
<212> TYPE: PRT
<213> ORGANISM: Human SARS virus

<400> SEQUENCE: 717

Lys His Arg Glu Phe Val Phe Lys Asn Lys Asp Gly Phe Leu Tyr Val
1               5                   10                  15

Tyr Lys


<210> SEQ ID NO 718
<211> LENGTH: 11
<212> TYPE: PRT
<213> ORGANISM: Human SARS virus

<400> SEQUENCE: 718

Lys Glu Glu Leu Asp Lys Tyr Phe Lys Asn His
1               5                   10


<210> SEQ ID NO 719
<211> LENGTH: 9
<212> TYPE: PRT
<213> ORGANISM: Human SARS virus

<400> SEQUENCE: 719

Lys Tyr Arg Tyr Leu Arg His Gly Lys
1               5


<210> SEQ ID NO 720
<211> LENGTH: 9
<212> TYPE: PRT
<213> ORGANISM: Human SARS virus

<400> SEQUENCE: 720

Lys Lys Gly Ala Lys Leu Leu His Lys
1               5


<210> SEQ ID NO 721
<211> LENGTH: 19
<212> TYPE: PRT
<213> ORGANISM: Monkeypox virus

<400> SEQUENCE: 721

Lys Lys Ile Thr Asn Ile Thr Thr Lys Phe Glu Gln Leu Glu Lys Cys
1               5                   10                  15

Cys Lys His


<210> SEQ ID NO 722
<211> LENGTH: 17
```

-continued

<212> TYPE: PRT
<213> ORGANISM: African swine fever virus

<400> SEQUENCE: 722

Lys Lys Leu Lys Lys Ser Leu Lys Leu Leu Ser Phe Tyr His Pro Lys
1 5 10 15

Lys

<210> SEQ ID NO 723
<211> LENGTH: 16
<212> TYPE: PRT
<213> ORGANISM: West Nile virus

<400> SEQUENCE: 723

Lys Asn Arg Ile Glu Arg Leu Lys Lys Glu Tyr Ser Ser Thr Trp His
1 5 10 15

<210> SEQ ID NO 724
<211> LENGTH: 11
<212> TYPE: PRT
<213> ORGANISM: Nipah virus

<400> SEQUENCE: 724

Lys Ser Arg Gly Ile Pro Ile Lys Lys Gly His
1 5 10

<210> SEQ ID NO 725
<211> LENGTH: 11
<212> TYPE: PRT
<213> ORGANISM: Hendra virus

<400> SEQUENCE: 725

Lys Ser Arg Ile Met Pro Ile Lys Lys Gly His
1 5 10

<210> SEQ ID NO 726
<211> LENGTH: 10
<212> TYPE: PRT
<213> ORGANISM: Sindbis virus

<400> SEQUENCE: 726

Lys Lys Phe Leu Asn Gln Phe Lys His His
1 5 10

<210> SEQ ID NO 727
<211> LENGTH: 9
<212> TYPE: PRT
<213> ORGANISM: Smallpox virus

<400> SEQUENCE: 727

Lys Ile His Leu Ile Ser Val Lys Lys
1 5

<210> SEQ ID NO 728
<211> LENGTH: 8
<212> TYPE: PRT
<213> ORGANISM: Smallpox virus

<400> SEQUENCE: 728

Lys Leu Ile Ser Ile His Glu Lys
1 5

<210> SEQ ID NO 729
<211> LENGTH: 8

-continued

<212> TYPE: PRT
<213> ORGANISM: Bacillus anthracis

<400> SEQUENCE: 729

Lys Leu Arg Glu Glu His Glu Lys
1 5

<210> SEQ ID NO 730
<211> LENGTH: 8
<212> TYPE: PRT
<213> ORGANISM: Ebola virus

<400> SEQUENCE: 730

Lys Lys His Ala Thr Val Leu Lys
1 5

<210> SEQ ID NO 731
<211> LENGTH: 8
<212> TYPE: PRT
<213> ORGANISM: Homo sapiens

<400> SEQUENCE: 731

Lys His Lys Glu Lys Met Ser Lys
1 5

<210> SEQ ID NO 732
<211> LENGTH: 6
<212> TYPE: PRT
<213> ORGANISM: Artificial Sequence
<220> FEATURE:
<223> OTHER INFORMATION: Synthetic replikin peptide sequence

<400> SEQUENCE: 732

Lys Lys Lys Lys His Lys
1 5

<210> SEQ ID NO 733
<211> LENGTH: 6
<212> TYPE: PRT
<213> ORGANISM: Artificial Sequence
<220> FEATURE:
<223> OTHER INFORMATION: Synthetic replikin peptide sequence

<400> SEQUENCE: 733

Lys Lys Lys His Lys Lys
1 5

<210> SEQ ID NO 734
<211> LENGTH: 6
<212> TYPE: PRT
<213> ORGANISM: Artificial Sequence
<220> FEATURE:
<223> OTHER INFORMATION: Synthetic replikin peptide sequence

<400> SEQUENCE: 734

Lys Lys His Lys Lys Lys
1 5

<210> SEQ ID NO 735
<211> LENGTH: 6
<212> TYPE: PRT
<213> ORGANISM: Artificial Sequence
<220> FEATURE:
<223> OTHER INFORMATION: Synthetic replikin peptide sequence

<400> SEQUENCE: 735

-continued

```
Lys His Lys Lys Lys Lys
1               5


<210> SEQ ID NO 736
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 736

Lys Lys Lys Lys Lys Lys His
1               5


<210> SEQ ID NO 737
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 737

Lys Lys Lys Lys Lys His Lys
1               5


<210> SEQ ID NO 738
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 738

Lys Lys Lys Lys His Lys Lys
1               5


<210> SEQ ID NO 739
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 739

Lys Lys Lys His Lys Lys Lys
1               5


<210> SEQ ID NO 740
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 740

Lys Lys His Lys Lys Lys Lys
1               5


<210> SEQ ID NO 741
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 741

Lys His Lys Lys Lys Lys Lys
```

-continued

```
1               5


<210> SEQ ID NO 742
<211> LENGTH: 7
<212> TYPE: PRT
<213> ORGANISM: Artificial Sequence
<220> FEATURE:
<223> OTHER INFORMATION: Synthetic replikin peptide sequence

<400> SEQUENCE: 742

His Lys Lys Lys Lys Lys Lys
1               5


<210> SEQ ID NO 743
<211> LENGTH: 7
<212> TYPE: PRT
<213> ORGANISM: Artificial Sequence
<220> FEATURE:
<223> OTHER INFORMATION: Replikin peptide sequence

<400> SEQUENCE: 743

Lys His Leu Asp Ala Tyr Lys
1               5


<210> SEQ ID NO 744
<211> LENGTH: 29
<212> TYPE: PRT
<213> ORGANISM: Influenza virus

<400> SEQUENCE: 744

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25


<210> SEQ ID NO 745
<211> LENGTH: 29
<212> TYPE: PRT
<213> ORGANISM: Influenza Virus

<400> SEQUENCE: 745

Leu Lys Glu Asp Leu Tyr Pro Lys Leu Arg Lys Ser Val Val His Asn
1               5                   10                  15

Lys Lys Lys Glu Val Leu Val Ile Trp Gly Ile His His
            20                  25


<210> SEQ ID NO 746
<211> LENGTH: 29
<212> TYPE: PRT
<213> ORGANISM: Influenza virus

<400> SEQUENCE: 746

Leu Lys Glu Asn Ser Tyr Pro Lys Leu Arg Lys Ser Ile Ile Ile Asn
1               5                   10                  15

Lys Lys Lys Glu Val Leu Val Ile Trp Gly Ile His His
            20                  25


<210> SEQ ID NO 747
<211> LENGTH: 29
<212> TYPE: PRT
<213> ORGANISM: Influenza virus

<400> SEQUENCE: 747

Lys Lys Gly Thr Ser Tyr Pro Lys Leu Ser Lys Ser Tyr Thr Asn Asn
```

-continued

```
1               5                   10                  15

Lys Lys Lys Glu Val Leu Val Leu Trp Gly Val His His
            20                  25


<210> SEQ ID NO 748
<211> LENGTH: 29
<212> TYPE: PRT
<213> ORGANISM: Influenza virus

<400> SEQUENCE: 748

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 749
<211> LENGTH: 28
<212> TYPE: PRT
<213> ORGANISM: Influenza virus

<400> SEQUENCE: 749

Lys Asn Gly Leu Tyr Pro Asn Leu Ser Lys Ser Tyr Ala Asn Asn Lys
1               5                   10                  15

Glu Lys Glu Val Leu Ile Leu Trp Gly Val His His
            20                  25


<210> SEQ ID NO 750
<211> LENGTH: 8
<212> TYPE: PRT
<213> ORGANISM: Plasmodium falciparum

<400> SEQUENCE: 750

Lys His Lys Lys Gln Ile Val Lys
1               5


<210> SEQ ID NO 751
<211> LENGTH: 29
<212> TYPE: PRT
<213> ORGANISM: Influenza virus

<400> SEQUENCE: 751

Lys Lys Glu Asn Ser Tyr Pro Lys Leu Arg Lys Ser Ile Ile Ile Asn
1               5                   10                  15

Lys Lys Lys Glu Val Leu Val Ile Trp Gly Ile His His
            20                  25


<210> SEQ ID NO 752
<211> LENGTH: 29
<212> TYPE: PRT
<213> ORGANISM: Fujian Influenza virus

<400> SEQUENCE: 752

Lys Leu Glu Tyr Lys Tyr Pro Ala Leu Asn Val Thr Met Pro Asn Asn
1               5                   10                  15

Asp Lys Phe Asp Lys Leu Tyr Ile Trp Gly Val His His
            20                  25


<210> SEQ ID NO 753
<211> LENGTH: 27
<212> TYPE: PRT
<213> ORGANISM: Fujian Influenza virus

<400> SEQUENCE: 753
```

-continued

```
Lys Tyr Lys Tyr Pro Ala Leu Asn Val Thr Met Pro Asn Asn Glu Lys
1               5                   10                  15

Phe Asp Lys Leu Tyr Ile Trp Gly Val His His
            20                  25


<210> SEQ ID NO 754
<211> LENGTH: 27
<212> TYPE: PRT
<213> ORGANISM: Shrimp white spot syndrome virus

<400> SEQUENCE: 754

Lys Lys Asn Val Lys Ser Ala Lys Gln Leu Pro His Leu Lys Val Leu
1               5                   10                  15

Leu Asp Val Arg Gly Ala Lys Gln Leu Pro His
            20                  25


<210> SEQ ID NO 755
<211> LENGTH: 20
<212> TYPE: PRT
<213> ORGANISM: Human SARS virus

<400> SEQUENCE: 755

Lys His Leu Arg Glu Phe Val Phe Lys Asn Lys Asp Gly Phe Leu Tyr
1               5                   10                  15

Val Tyr Lys Lys
            20


<210> SEQ ID NO 756
<211> LENGTH: 14
<212> TYPE: PRT
<213> ORGANISM: Human SARS virus

<400> SEQUENCE: 756

Lys Lys Gly Ala Lys Leu Leu His Lys Pro Ile Val Trp His
1               5                   10


<210> SEQ ID NO 757
<211> LENGTH: 15
<212> TYPE: PRT
<213> ORGANISM: Tomato yellow leaf curl virus

<400> SEQUENCE: 757

His Cys Ser Gln Val Ser Ile Lys Val Gln His Lys Ile Ala Lys
1               5                   10                  15


<210> SEQ ID NO 758
<211> LENGTH: 16
<212> TYPE: PRT
<213> ORGANISM: Tomato yellow leaf curl virus

<400> SEQUENCE: 758

His Cys Ser Gln Val Ser Ile Lys Val Gln His Lys Ile Ala Lys Lys
1               5                   10                  15


<210> SEQ ID NO 759
<211> LENGTH: 17
<212> TYPE: PRT
<213> ORGANISM: Tomato yellow leaf curl virus

<400> SEQUENCE: 759

His Cys Ser Gln Val Ser Ile Lys Val Gln His Lys Ile Ala Lys Lys
1               5                   10                  15
```

-continued

Lys

<210> SEQ ID NO 760
<211> LENGTH: 22
<212> TYPE: PRT
<213> ORGANISM: Tomato yellow leaf curl virus

<400> SEQUENCE: 760

His Cys Ser Gln Val Ser Ile Lys Val Gln His Lys Ile Ala Lys Lys
1               5                   10                  15

Lys Pro Ile Arg Arg Lys
            20

<210> SEQ ID NO 761
<211> LENGTH: 34
<212> TYPE: PRT
<213> ORGANISM: Tomato yellow leaf curl virus

<400> SEQUENCE: 761

Lys Val Gln His Lys Ile Ala Lys Lys Lys Pro Ile Arg Arg Lys Arg
1               5                   10                  15

Val Asn Leu Asp Cys Gly Cys Ser Tyr Tyr Leu His Leu Asn Cys Asn
            20                  25                  30

Asn His

<210> SEQ ID NO 762
<211> LENGTH: 57
<212> TYPE: PRT
<213> ORGANISM: Tomato yellow leaf curl virus

<400> SEQUENCE: 762

Lys Ala Ser Ala Leu Asn Ile Leu Arg Glu Lys Ala Pro Lys Asp Phe
1               5                   10                  15

Val Leu Gln Phe His Gln His Lys Ile Ala Lys Lys Lys Pro Ile Arg
            20                  25                  30

Arg Lys Arg Val Asn Leu Asp Cys Gly Cys Ser Tyr Tyr Leu His Leu
        35                  40                  45

Asn Cys Asn Asn His Gly Phe Thr His
    50                  55

<210> SEQ ID NO 763
<211> LENGTH: 42
<212> TYPE: PRT
<213> ORGANISM: Tomato yellow leaf curl virus

<400> SEQUENCE: 763

Lys Val Gln His Lys Ile Ala Lys Lys Lys Pro Ile Arg Arg Lys Arg
1               5                   10                  15

Val Asn Leu Asp Cys Gly Cys Ser Tyr Tyr Leu His Leu Asn Cys Asn
            20                  25                  30

Asn His Gly Phe Thr His Arg Gly Thr His
        35                  40

<210> SEQ ID NO 764
<211> LENGTH: 8
<212> TYPE: PRT
<213> ORGANISM: Tomato yellow leaf curl virus

<400> SEQUENCE: 764

Lys Val Gln His Lys Ile Ala Lys
1               5

-continued

<210> SEQ ID NO 765
<211> LENGTH: 43
<212> TYPE: PRT
<213> ORGANISM: Tomato yellow leaf curl virus

<400> SEQUENCE: 765

Lys Val Gln His Lys Ile Ala Lys Lys Lys Pro Ile Arg Arg Lys Arg
1 5 10 15

Val Asn Leu Asp Cys Gly Cys Ser Tyr Tyr Leu His Leu Asn Cys Asn
20 25 30

Asn His Gly Phe Thr His Arg Gly Thr His His
35 40

<210> SEQ ID NO 766
<211> LENGTH: 9
<212> TYPE: PRT
<213> ORGANISM: Tomato yellow leaf curl virus

<400> SEQUENCE: 766

Lys Val Gln His Lys Ile Ala Lys Lys
1 5

<210> SEQ ID NO 767
<211> LENGTH: 28
<212> TYPE: PRT
<213> ORGANISM: Tomato yellow leaf curl virus

<400> SEQUENCE: 767

Lys Val Gln His Lys Ile Ala Lys Lys Lys Pro Ile Arg Arg Lys Arg
1 5 10 15

Val Asn Leu Asp Cys Gly Cys Ser Tyr Tyr Leu His
20 25

<210> SEQ ID NO 768
<211> LENGTH: 10
<212> TYPE: PRT
<213> ORGANISM: Tomato yellow leaf curl virus

<400> SEQUENCE: 768

Lys Val Gln His Lys Ile Ala Lys Lys Lys
1 5 10

<210> SEQ ID NO 769
<211> LENGTH: 12
<212> TYPE: PRT
<213> ORGANISM: Tomato yellow leaf curl virus

<400> SEQUENCE: 769

His Lys Ile Ala Lys Lys Lys Pro Ile Arg Arg Lys
1 5 10

<210> SEQ ID NO 770
<211> LENGTH: 34
<212> TYPE: PRT
<213> ORGANISM: Tomato yellow leaf curl virus

<400> SEQUENCE: 770

Lys Ile Ala Lys Lys Lys Pro Ile Arg Arg Lys Arg Val Asn Leu Asp
1 5 10 15

Cys Gly Cys Ser Tyr Tyr Leu His Leu Asn Cys Asn Asn His Gly Phe
20 25 30

-continued

Thr His

<210> SEQ ID NO 771
<211> LENGTH: 38
<212> TYPE: PRT
<213> ORGANISM: Tomato yellow leaf curl virus

<400> SEQUENCE: 771

Lys Ile Ala Lys Lys Lys Pro Ile Arg Arg Lys Arg Val Asn Leu Asp
1 5 10 15

Cys Gly Cys Ser Tyr Tyr Leu His Leu Asn Cys Asn Asn His Gly Phe
20 25 30

Thr His Arg Gly Thr His
35

<210> SEQ ID NO 772
<211> LENGTH: 39
<212> TYPE: PRT
<213> ORGANISM: Tomato yellow leaf curl virus

<400> SEQUENCE: 772

Lys Ile Ala Lys Lys Lys Pro Ile Arg Arg Lys Arg Val Asn Leu Asp
1 5 10 15

Cys Gly Cys Ser Tyr Tyr Leu His Leu Asn Cys Asn Asn His Gly Phe
20 25 30

Thr His Arg Gly Thr His His
35

<210> SEQ ID NO 773
<211> LENGTH: 24
<212> TYPE: PRT
<213> ORGANISM: Tomato yellow leaf curl virus

<400> SEQUENCE: 773

Lys Ile Ala Lys Lys Lys Pro Ile Arg Arg Lys Arg Val Asn Leu Asp
1 5 10 15

Cys Gly Cys Ser Tyr Tyr Leu His
20

<210> SEQ ID NO 774
<211> LENGTH: 30
<212> TYPE: PRT
<213> ORGANISM: Tomato yellow leaf curl virus

<400> SEQUENCE: 774

Lys Ile Ala Lys Lys Lys Pro Ile Arg Arg Lys Arg Val Asn Leu Asp
1 5 10 15

Cys Gly Cys Ser Tyr Tyr Leu His Leu Asn Cys Asn Asn His
20 25 30

<210> SEQ ID NO 775
<211> LENGTH: 35
<212> TYPE: PRT
<213> ORGANISM: Tomato yellow leaf curl virus

<400> SEQUENCE: 775

Lys Lys Lys Pro Ile Arg Arg Lys Arg Val Asn Leu Asp Cys Gly Cys
1 5 10 15

Ser Tyr Tyr Leu His Leu Asn Cys Asn Asn His Gly Phe Thr His Arg
20 25 30

Gly Thr His

35

<210> SEQ ID NO 776
<211> LENGTH: 36
<212> TYPE: PRT
<213> ORGANISM: Tomato yellow leaf curl virus

<400> SEQUENCE: 776

```
Lys Lys Lys Pro Ile Arg Arg Lys Arg Val Asn Leu Asp Cys Gly Cys
1               5                   10                  15

Ser Tyr Tyr Leu His Leu Asn Cys Asn Asn His Gly Phe Thr His Arg
            20                  25                  30

Gly Thr His His
        35
```

<210> SEQ ID NO 777
<211> LENGTH: 21
<212> TYPE: PRT
<213> ORGANISM: Tomato yellow leaf curl virus

<400> SEQUENCE: 777

```
Lys Lys Lys Pro Ile Arg Arg Lys Arg Val Asn Leu Asp Cys Gly Cys
1               5                   10                  15

Ser Tyr Tyr Leu His
            20
```

<210> SEQ ID NO 778
<211> LENGTH: 27
<212> TYPE: PRT
<213> ORGANISM: Tomato yellow leaf curl virus

<400> SEQUENCE: 778

```
Lys Lys Lys Pro Ile Arg Arg Lys Arg Val Asn Leu Asp Cys Gly Cys
1               5                   10                  15

Ser Tyr Tyr Leu His Leu Asn Cys Asn Asn His
            20                  25
```

<210> SEQ ID NO 779
<211> LENGTH: 31
<212> TYPE: PRT
<213> ORGANISM: Tomato yellow leaf curl virus

<400> SEQUENCE: 779

```
Lys Lys Lys Pro Ile Arg Arg Lys Arg Val Asn Leu Asp Cys Gly Cys
1               5                   10                  15

Ser Tyr Tyr Leu His Leu Asn Cys Asn Asn His Gly Phe Thr His
            20                  25                  30
```

<210> SEQ ID NO 780
<211> LENGTH: 26
<212> TYPE: PRT
<213> ORGANISM: Tomato yellow leaf curl virus

<400> SEQUENCE: 780

```
Lys Lys Pro Ile Arg Arg Lys Arg Val Asn Leu Asp Cys Gly Cys Ser
1               5                   10                  15

Tyr Tyr Leu His Leu Asn Cys Asn Asn His
            20                  25
```

<210> SEQ ID NO 781
<211> LENGTH: 30
<212> TYPE: PRT

-continued

<213> ORGANISM: Tomato yellow leaf curl virus

<400> SEQUENCE: 781

Lys Lys Pro Ile Arg Arg Lys Arg Val Asn Leu Asp Cys Gly Cys Ser
1 5 10 15

Tyr Tyr Leu His Leu Asn Cys Asn Asn His Gly Phe Thr His
20 25 30

<210> SEQ ID NO 782
<211> LENGTH: 35
<212> TYPE: PRT
<213> ORGANISM: Tomato yellow leaf curl virus

<400> SEQUENCE: 782

Lys Lys Pro Ile Arg Arg Lys Arg Val Asn Leu Asp Cys Gly Cys Ser
1 5 10 15

Tyr Tyr Leu His Leu Asn Cys Asn Asn His Gly Phe Thr His Arg Gly
20 25 30

Thr His His
35

<210> SEQ ID NO 783
<211> LENGTH: 34
<212> TYPE: PRT
<213> ORGANISM: Tomato yellow leaf curl virus

<400> SEQUENCE: 783

Lys Lys Pro Ile Arg Arg Lys Arg Val Asn Leu Asp Cys Gly Cys Ser
1 5 10 15

Tyr Tyr Leu His Leu Asn Cys Asn Asn His Gly Phe Thr His Arg Gly
20 25 30

Thr His

<210> SEQ ID NO 784
<211> LENGTH: 20
<212> TYPE: PRT
<213> ORGANISM: Tomato yellow leaf curl virus

<400> SEQUENCE: 784

Lys Lys Pro Ile Arg Arg Lys Arg Val Asn Leu Asp Cys Gly Cys Ser
1 5 10 15

Tyr Tyr Leu His
20

<210> SEQ ID NO 785
<211> LENGTH: 7
<212> TYPE: PRT
<213> ORGANISM: Plasmodium falciparum

<400> SEQUENCE: 785

Lys Ser Asp Ser Asn His Lys
1 5

<210> SEQ ID NO 786
<211> LENGTH: 7
<212> TYPE: PRT
<213> ORGANISM: Plasmodium falciparum

<400> SEQUENCE: 786

Lys Ser Gly Ser Asn His Lys
1 5

<210> SEQ ID NO 787
<211> LENGTH: 7
<212> TYPE: PRT
<213> ORGANISM: Plasmodium falciparum

<400> SEQUENCE: 787

Lys Ser Asp Cys Asn His Lys
1 5

<210> SEQ ID NO 788
<211> LENGTH: 7
<212> TYPE: PRT
<213> ORGANISM: Plasmodium falciparum

<400> SEQUENCE: 788

Lys Ser Asp Asn Asn His Lys
1 5

<210> SEQ ID NO 789
<211> LENGTH: 7
<212> TYPE: PRT
<213> ORGANISM: Plasmodium falciparum

<400> SEQUENCE: 789

Lys Ser Asp Ser Ser His Lys
1 5

<210> SEQ ID NO 790
<211> LENGTH: 7
<212> TYPE: PRT
<213> ORGANISM: Plasmodium falciparum

<400> SEQUENCE: 790

Lys Ser Asp His Asn His Lys
1 5

<210> SEQ ID NO 791
<211> LENGTH: 7
<212> TYPE: PRT
<213> ORGANISM: Plasmodium falciparum

<400> SEQUENCE: 791

Lys Asn Glu Ser Asn His Lys
1 5

<210> SEQ ID NO 792
<211> LENGTH: 7
<212> TYPE: PRT
<213> ORGANISM: Plasmodium falciparum

<400> SEQUENCE: 792

Lys Asn Asp Ser Asn His Lys
1 5

<210> SEQ ID NO 793
<211> LENGTH: 7
<212> TYPE: PRT
<213> ORGANISM: Plasmodium falciparum

<400> SEQUENCE: 793

Lys Ser Asp Asn Asn His Lys
1 5

<210> SEQ ID NO 794

-continued

<211> LENGTH: 40
<212> TYPE: PRT
<213> ORGANISM: Human coronavirus

<400> SEQUENCE: 794

```
Lys Lys Ser Ala Lys Thr Gly Thr Pro Lys Pro Ser Arg Asn Gln Ser
1               5                   10                  15

Pro Ala Ser Ser Gln Thr Ser Ala Lys Ser Leu Ala Arg Ser Gln Ser
            20                  25                  30

Ser Glu Thr Lys Glu Gln Lys His
        35                  40
```

<210> SEQ ID NO 795
<211> LENGTH: 37
<212> TYPE: PRT
<213> ORGANISM: Canine coronavirus

<400> SEQUENCE: 795

```
Lys Lys Leu Gly Val Asp Thr Glu Lys Gln Gln Gln Arg Ser Arg Ser
1               5                   10                  15

Lys Ser Lys Glu Arg Ser Asn Ser Lys Thr Arg Asp Thr Thr Pro Lys
            20                  25                  30

Asn Glu Asn Lys His
        35
```

<210> SEQ ID NO 796
<211> LENGTH: 7
<212> TYPE: PRT
<213> ORGANISM: Human SARS virus

<400> SEQUENCE: 796

```
Lys His Leu Asp Ala Tyr Lys
1               5
```

<210> SEQ ID NO 797
<211> LENGTH: 8
<212> TYPE: PRT
<213> ORGANISM: Mycobacterium leprae

<400> SEQUENCE: 797

```
Lys Val Met Arg Thr Asp Lys His
1               5
```

<210> SEQ ID NO 798
<211> LENGTH: 17
<212> TYPE: PRT
<213> ORGANISM: Mycobacterium tuberculosis

<400> SEQUENCE: 798

```
His Pro Arg Pro Lys Val Ala Ala Ala Leu Lys Asp Ser Tyr Arg Leu
1               5                   10                  15

Lys
```

<210> SEQ ID NO 799
<211> LENGTH: 11
<212> TYPE: PRT
<213> ORGANISM: Mycobacterium tuberculosis

<400> SEQUENCE: 799

```
His Pro Arg Pro Lys Val Ala Ala Ala Leu Lys
1               5                   10
```

<210> SEQ ID NO 800
<211> LENGTH: 19
<212> TYPE: PRT
<213> ORGANISM: Mycobacterium tuberculosis

<400> SEQUENCE: 800

Lys Ser Ala Gln Lys Trp Pro Asp Lys Phe Leu Ala Gly Ala Ala Gln
1 5 10 15

Val Ala His

<210> SEQ ID NO 801
<211> LENGTH: 15
<212> TYPE: PRT
<213> ORGANISM: Escherichia coli

<400> SEQUENCE: 801

His Ala Trp Gln His Gln Gly Lys Thr Leu Phe Ile Ser Arg Lys
1 5 10 15

<210> SEQ ID NO 802
<211> LENGTH: 11
<212> TYPE: PRT
<213> ORGANISM: Escherichia coli

<400> SEQUENCE: 802

His Gln Gly Lys Thr Leu Phe Ile Ser Arg Lys
1 5 10

<210> SEQ ID NO 803
<211> LENGTH: 19
<212> TYPE: PRT
<213> ORGANISM: Agrobacterium tumefaciens

<400> SEQUENCE: 803

His Ser Asp Gln Gln Leu Ala Val Met Ile Ala Ala Lys Arg Leu Asp
1 5 10 15

Asp Tyr Lys

<210> SEQ ID NO 804
<211> LENGTH: 33
<212> TYPE: PRT
<213> ORGANISM: Agrobacterium tumefaciens

<400> SEQUENCE: 804

His Leu Leu Asp His Pro Ala Ser Val Gly Gln Leu Asp Leu Arg Ala
1 5 10 15

Met Leu Ala Val Glu Glu Val Lys Ile Asp Asn Pro Val Tyr Met Glu
20 25 30

Lys

<210> SEQ ID NO 805
<211> LENGTH: 29
<212> TYPE: PRT
<213> ORGANISM: Agrobacterium tumefaciens

<400> SEQUENCE: 805

His Pro Ala Ser Val Gly Gln Leu Asp Leu Arg Ala Met Leu Ala Val
1 5 10 15

Glu Glu Val Lys Ile Asp Asn Pro Val Tyr Met Glu Lys
20 25

<210> SEQ ID NO 806

-continued

<211> LENGTH: 39
<212> TYPE: PRT
<213> ORGANISM: Agrobacterium tumefaciens

<400> SEQUENCE: 806

Lys Cys Val Met Ala Lys Asn Cys Asn Ile Lys Cys Pro Ala Gly Leu
1 5 10 15

Thr Thr Asn Gln Glu Ala Phe Asn Gly Asp Pro Arg Ala Leu Ala Gln
20 25 30

Tyr Leu Met Asn Ile Ala His
35

<210> SEQ ID NO 807
<211> LENGTH: 34
<212> TYPE: PRT
<213> ORGANISM: Agrobacterium tumefaciens

<400> SEQUENCE: 807

Lys Asn Cys Asn Ile Lys Cys Pro Ala Gly Leu Thr Thr Asn Gln Glu
1 5 10 15

Ala Phe Asn Gly Asp Pro Arg Ala Leu Ala Gln Tyr Leu Met Asn Ile
20 25 30

Ala His

<210> SEQ ID NO 808
<211> LENGTH: 27
<212> TYPE: PRT
<213> ORGANISM: Agrobacterium tumefaciens

<400> SEQUENCE: 808

His His Asp Thr Tyr Ser Ile Glu Asp Leu Ala Gln Leu Ile His Asp
1 5 10 15

Ala Lys Ala Ala Arg Val Arg Val Ile Val Lys
20 25

<210> SEQ ID NO 809
<211> LENGTH: 26
<212> TYPE: PRT
<213> ORGANISM: Agrobacterium tumefaciens

<400> SEQUENCE: 809

His Asp Thr Tyr Ser Ile Glu Asp Leu Ala Gln Leu Ile His Asp Ala
1 5 10 15

Lys Ala Ala Arg Val Arg Val Ile Val Lys
20 25

<210> SEQ ID NO 810
<211> LENGTH: 13
<212> TYPE: PRT
<213> ORGANISM: Agrobacterium tumefaciens

<400> SEQUENCE: 810

His Asp Ala Lys Ala Ala Arg Val Arg Val Ile Val Lys
1 5 10

<210> SEQ ID NO 811
<211> LENGTH: 42
<212> TYPE: PRT
<213> ORGANISM: Agrobacterium tumefaciens

<400> SEQUENCE: 811

Lys Ile Gly Gln Gly Ala Lys Pro Gly Glu Gly Gly Gln Leu Pro Ser

-continued

```
1               5                   10                  15

Pro Lys Val Thr Val Glu Ile Ala Ala Ala Arg Gly Gly Thr Pro Gly
            20                  25                  30

Val Glu Leu Val Ser Pro Pro Pro His His
        35                  40


<210> SEQ ID NO 812
<211> LENGTH: 41
<212> TYPE: PRT
<213> ORGANISM: Agrobacterium tumefaciens

<400> SEQUENCE: 812

Lys Ile Gly Gln Gly Ala Lys Pro Gly Glu Gly Gly Gln Leu Pro Ser
1               5                   10                  15

Pro Lys Val Thr Val Glu Ile Ala Ala Ala Arg Gly Gly Thr Pro Gly
            20                  25                  30

Val Glu Leu Val Ser Pro Pro Pro His
        35                  40


<210> SEQ ID NO 813
<211> LENGTH: 46
<212> TYPE: PRT
<213> ORGANISM: Agrobacterium tumefaciens

<400> SEQUENCE: 813

Lys Ala Ser Glu Ile Thr Lys Thr Leu Ala Ser Gly Ala Met Ser His
1               5                   10                  15

Gly Ala Leu Val Ala Ala Ala His Glu Ala Val Ala His Gly Thr Asn
            20                  25                  30

Met Val Gly Gly Met Ser Asn Ser Gly Glu Gly Gly Glu His
        35                  40                  45


<210> SEQ ID NO 814
<211> LENGTH: 29
<212> TYPE: PRT
<213> ORGANISM: Agrobacterium tumefaciens

<400> SEQUENCE: 814

Lys Ala Ser Glu Ile Thr Lys Thr Leu Ala Ser Gly Ala Met Ser His
1               5                   10                  15

Gly Ala Leu Val Ala Ala Ala His Glu Ala Val Ala His
            20                  25


<210> SEQ ID NO 815
<211> LENGTH: 24
<212> TYPE: PRT
<213> ORGANISM: Agrobacterium tumefaciens

<400> SEQUENCE: 815

Lys Ala Ser Glu Ile Thr Lys Thr Leu Ala Ser Gly Ala Met Ser His
1               5                   10                  15

Gly Ala Leu Val Ala Ala Ala His
            20


<210> SEQ ID NO 816
<211> LENGTH: 16
<212> TYPE: PRT
<213> ORGANISM: Agrobacterium tumefaciens

<400> SEQUENCE: 816

Lys Ala Ser Glu Ile Thr Lys Thr Leu Ala Ser Gly Ala Met Ser His
```

-continued 1 5 10 15

<210> SEQ ID NO 817
<211> LENGTH: 27
<212> TYPE: PRT
<213> ORGANISM: Agrobacterium tumefaciens

<400> SEQUENCE: 817

Lys Arg Tyr Phe Pro Asn Val Lys Thr Pro Val Gly Gly Val Thr Phe
1 5 10 15

Ala Val Ile Ala Gln Ala Val Ala Asp Trp His
20 25

<210> SEQ ID NO 818
<211> LENGTH: 48
<212> TYPE: PRT
<213> ORGANISM: Agrobacterium tumefaciens

<400> SEQUENCE: 818

His His Ile Ala Ala Gly Leu Gly Phe Gly Ala Ser Ala Val Tyr Pro
1 5 10 15

Leu Gly Val Gln Phe Arg Ala Glu Glu Lys Phe Gly Ala Asp Ala Asp
20 25 30

Lys Ala Phe Lys Arg Phe Ala Lys Ala Ala Glu Lys Ser Leu Met Lys
35 40 45

<210> SEQ ID NO 819
<211> LENGTH: 48
<212> TYPE: PRT
<213> ORGANISM: Agrobacterium tumefaciens

<400> SEQUENCE: 819

His His Ile Ala Ala Gly Leu Gly Phe Gly Ala Ser Ala Val Tyr Pro
1 5 10 15

Leu Gly Val Gln Phe Arg Ala Glu Glu Lys Phe Gly Ala Asp Ala Asp
20 25 30

Lys Ala Phe Lys Arg Phe Ala Lys Ala Ala Glu Lys Ser Leu Met Lys
35 40 45

<210> SEQ ID NO 820
<211> LENGTH: 44
<212> TYPE: PRT
<213> ORGANISM: Agrobacterium tumefaciens

<400> SEQUENCE: 820

His His Ile Ala Ala Gly Leu Gly Phe Gly Ala Ser Ala Val Tyr Pro
1 5 10 15

Leu Gly Val Gln Phe Arg Ala Glu Glu Lys Phe Gly Ala Asp Ala Asp
20 25 30

Lys Ala Phe Lys Arg Phe Ala Lys Ala Ala Glu Lys
35 40

<210> SEQ ID NO 821
<211> LENGTH: 40
<212> TYPE: PRT
<213> ORGANISM: Agrobacterium tumefaciens

<400> SEQUENCE: 821

His His Ile Ala Ala Gly Leu Gly Phe Gly Ala Ser Ala Val Tyr Pro
1 5 10 15

Leu Gly Val Gln Phe Arg Ala Glu Glu Lys Phe Gly Ala Asp Ala Asp

-continued

```
            20                  25                  30

Lys Ala Phe Lys Arg Phe Ala Lys
        35                  40


<210> SEQ ID NO 822
<211> LENGTH: 33
<212> TYPE: PRT
<213> ORGANISM: Agrobacterium tumefaciens

<400> SEQUENCE: 822

His His Ile Ala Ala Gly Leu Gly Phe Gly Ala Ser Ala Val Tyr Pro
1               5                   10                  15

Leu Gly Val Gln Phe Arg Ala Glu Glu Lys Phe Gly Ala Asp Ala Asp
            20                  25                  30

Lys


<210> SEQ ID NO 823
<211> LENGTH: 47
<212> TYPE: PRT
<213> ORGANISM: Agrobacterium tumefaciens

<400> SEQUENCE: 823

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys Ala Ala Glu Lys Ser Leu Met Lys
        35                  40                  45


<210> SEQ ID NO 824
<211> LENGTH: 43
<212> TYPE: PRT
<213> ORGANISM: Agrobacterium tumefaciens

<400> SEQUENCE: 824

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys Ala Ala Glu Lys
        35                  40


<210> SEQ ID NO 825
<211> LENGTH: 39
<212> TYPE: PRT
<213> ORGANISM: Agrobacterium tumefaciens

<400> SEQUENCE: 825

His Ile Ala Ala Gly Leu Gly Phe Gly Ala Ser Ala Val Tyr Pro Leu
1               5                   10                  15

Gly Val Gln Phe Arg Ala Glu Glu Lys Phe Gly Ala Asp Ala Asp Lys
            20                  25                  30

Ala Phe Lys Arg Phe Ala Lys
        35


<210> SEQ ID NO 826
<211> LENGTH: 32
<212> TYPE: PRT
<213> ORGANISM: Agrobacterium tumefaciens

<400> SEQUENCE: 826
```

His Ile Ala Ala Gly Leu Gly Phe Gly Ala Ser Ala Val Tyr Pro Leu
1 5 10 15

Gly Val Gln Phe Arg Ala Glu Glu Lys Phe Gly Ala Asp Ala Asp Lys
20 25 30

<210> SEQ ID NO 827
<211> LENGTH: 28
<212> TYPE: PRT
<213> ORGANISM: Agrobacterium tumefaciens

<400> SEQUENCE: 827

Lys Phe Gly Leu Tyr Asp Ala Ala Phe Glu Lys Ser Ser Cys Gly Val
1 5 10 15

Gly Phe Ile Thr Arg Lys Asp Gly Val Gln Thr His
20 25

<210> SEQ ID NO 828
<211> LENGTH: 9
<212> TYPE: PRT
<213> ORGANISM: Unknown Organism
<220> FEATURE:
<223> OTHER INFORMATION: Replikin peptide sequence

<400> SEQUENCE: 828

Lys Ala Gly Val Ala Phe His Lys Lys
1 5

<210> SEQ ID NO 829
<211> LENGTH: 9
<212> TYPE: PRT
<213> ORGANISM: Unknown Organism
<220> FEATURE:
<223> OTHER INFORMATION: Replikin peptide sequence

<400> SEQUENCE: 829

Lys Ala Gly Val Ala Thr His Lys Lys
1 5

<210> SEQ ID NO 830
<211> LENGTH: 29
<212> TYPE: PRT
<213> ORGANISM: Influenza virus H1N1
<220> FEATURE:
<221> NAME/KEY: misc_feature
<222> LOCATION: (4)..(4)
<223> OTHER INFORMATION: Xaa can be Thr or Ser
<220> FEATURE:
<221> NAME/KEY: misc_feature
<222> LOCATION: (14)..(14)
<223> OTHER INFORMATION: Xaa can be Thr or Val

<400> SEQUENCE: 830

Lys Lys Gly Xaa Ser Tyr Pro Lys Leu Ser Lys Ser Tyr Xaa Asn Asn
1 5 10 15

Lys Gly Lys Glu Val Leu Val Leu Trp Gly Val His His
20 25

<210> SEQ ID NO 831
<211> LENGTH: 29
<212> TYPE: PRT
<213> ORGANISM: Influenza virus H1N

<400> SEQUENCE: 831

Lys Lys Gly Thr Ser Tyr Pro Lys Leu Ser Lys Ser Tyr Thr Asn Asn
1 5 10 15

```
Lys Gly Lys Glu Val Leu Val Leu Trp Gly Val His His
            20                  25


<210> SEQ ID NO 832
<211> LENGTH: 29
<212> TYPE: PRT
<213> ORGANISM: Influenza virus H1N1

<400> SEQUENCE: 832

Lys Lys Gly Ser Ser Tyr Pro Lys Leu Ser Lys Ser Tyr Val Asn Asn
1               5                   10                  15

Lys Gly Lys Glu Val Leu Val Leu Trp Gly Val His His
            20                  25


<210> SEQ ID NO 833
<211> LENGTH: 29
<212> TYPE: PRT
<213> ORGANISM: Influenza virus H1N

<400> SEQUENCE: 833

Lys Lys Gly Thr Ser Tyr Pro Lys Leu Ser Lys Ser Tyr Thr Asn Asn
1               5                   10                  15

Lys Gly Lys Glu Val Leu Val Leu Trp Gly Val His His
            20                  25


<210> SEQ ID NO 834
<211> LENGTH: 29
<212> TYPE: PRT
<213> ORGANISM: Influenza virus H5N1

<400> SEQUENCE: 834

Lys Lys Asn Ser Ala Tyr Pro Thr Ile Lys Arg Ser Tyr Asn Asn Thr
1               5                   10                  15

Asn Gln Glu Asp Leu Leu Val Leu Trp Gly Ile His His
            20                  25


<210> SEQ ID NO 835
<211> LENGTH: 29
<212> TYPE: PRT
<213> ORGANISM: Influenza virus H1N2

<400> SEQUENCE: 835

Lys Lys Gly Thr Ser Tyr Pro Lys Leu Ser Lys Ser Tyr Thr Asn Asn
1               5                   10                  15

Lys Lys Lys Glu Val Leu Val Leu Trp Gly Val His His
            20                  25


<210> SEQ ID NO 836
<211> LENGTH: 28
<212> TYPE: PRT
<213> ORGANISM: Influenza virus H1N2

<400> SEQUENCE: 836

Lys Asn Gly Leu Tyr Pro Asn Leu Ser Lys Ser Tyr Ala Asn Asn Lys
1               5                   10                  15

Glu Lys Glu Val Leu Ile Leu Trp Gly Val His His
            20                  25


<210> SEQ ID NO 837
<211> LENGTH: 21
<212> TYPE: PRT
<213> ORGANISM: Human SARS virus
```

<400> SEQUENCE: 837

Lys His Leu Asp Ala Tyr Lys Thr Phe Pro Pro Thr Glu Pro Lys Lys
1 5 10 15

Asp Lys Lys Lys Lys
20

<210> SEQ ID NO 838
<211> LENGTH: 24
<212> TYPE: PRT
<213> ORGANISM: Porcine epidemic diarrhea coronavirus

<400> SEQUENCE: 838

Lys Thr Gly Asn Ala Lys Leu Gln Arg Lys Lys Glu Lys Lys Asn Lys
1 5 10 15

Arg Glu Thr Thr Leu Gln Gln His
20

<210> SEQ ID NO 839
<211> LENGTH: 27
<212> TYPE: PRT
<213> ORGANISM: Avian bronchitis coronavirus

<400> SEQUENCE: 839

Lys Lys Ile Asn Ser Pro Gly Pro Lys Phe Glu Gly Ser Gly Val Pro
1 5 10 15

Asp Asn Glu Asn Leu Lys Thr Ser Gln Gln His
20 25

<210> SEQ ID NO 840
<211> LENGTH: 27
<212> TYPE: PRT
<213> ORGANISM: Avian bronchitis coronavirus

<400> SEQUENCE: 840

Lys Lys Ile Asn Ser Pro Gly Pro Lys Phe Glu Gly Ser Gly Val Pro
1 5 10 15

Asp Asn Glu Asn Leu Lys Thr Ser Gln Gln His
20 25

<210> SEQ ID NO 841
<211> LENGTH: 20
<212> TYPE: PRT
<213> ORGANISM: Human SARS virus

<400> SEQUENCE: 841

Lys His Leu Arg Glu Phe Val Phe Lys Asn Lys Asp Gly Phe Leu Tyr
1 5 10 15

Val Tyr Lys Lys
20

<210> SEQ ID NO 842
<211> LENGTH: 14
<212> TYPE: PRT
<213> ORGANISM: Human SARS virus

<400> SEQUENCE: 842

Lys Lys Gly Ala Lys Leu Leu His Lys Pro Ile Val Trp His
1 5 10

<210> SEQ ID NO 843
<211> LENGTH: 11

-continued

<212> TYPE: PRT
<213> ORGANISM: Human SARS virus

<400> SEQUENCE: 843

Lys Glu Glu Leu Asp Lys Tyr Phe Lys Asn His
1 5 10

<210> SEQ ID NO 844
<211> LENGTH: 9
<212> TYPE: PRT
<213> ORGANISM: Human SARS virus

<400> SEQUENCE: 844

Lys Lys Gly Ala Lys Leu Leu His Lys
1 5

<210> SEQ ID NO 845
<211> LENGTH: 9
<212> TYPE: PRT
<213> ORGANISM: Human SARS virus

<400> SEQUENCE: 845

Lys Tyr Arg Tyr Leu Arg His Gly Lys
1 5

<210> SEQ ID NO 846
<211> LENGTH: 7
<212> TYPE: PRT
<213> ORGANISM: Human SARS virus

<400> SEQUENCE: 846

Lys His Leu Asp Ala Tyr Lys
1 5

<210> SEQ ID NO 847
<211> LENGTH: 11
<212> TYPE: PRT
<213> ORGANISM: Nipah virus

<400> SEQUENCE: 847

Lys Ser Arg Gly Ile Pro Ile Lys Lys Gly His
1 5 10

<210> SEQ ID NO 848
<211> LENGTH: 11
<212> TYPE: PRT
<213> ORGANISM: Hendra virus

<400> SEQUENCE: 848

Lys Ser Arg Ile Met Pro Ile Lys Lys Gly His
1 5 10

<210> SEQ ID NO 849
<211> LENGTH: 10
<212> TYPE: PRT
<213> ORGANISM: Sindbis virus

<400> SEQUENCE: 849

Lys Lys Phe Leu Asn Gln Phe Lys His His
1 5 10

<210> SEQ ID NO 850
<211> LENGTH: 10
<212> TYPE: PRT
<213> ORGANISM: Homo sapiens

<400> SEQUENCE: 850

Lys Lys Lys Ser Lys Lys His Lys Asp Lys
1               5                   10

<210> SEQ ID NO 851
<211> LENGTH: 10
<212> TYPE: PRT
<213> ORGANISM: Homo sapiens

<400> SEQUENCE: 851

Lys His His Pro Lys Asp Asn Leu Ile Lys
1               5                   10

<210> SEQ ID NO 852
<211> LENGTH: 10
<212> TYPE: PRT
<213> ORGANISM: Homo sapiens

<400> SEQUENCE: 852

Lys His Lys Arg Lys Lys Phe Arg Gln Lys
1               5                   10

<210> SEQ ID NO 853
<211> LENGTH: 10
<212> TYPE: PRT
<213> ORGANISM: Unknown Organism
<220> FEATURE:
<223> OTHER INFORMATION: Glioma replikin peptide sequence

<400> SEQUENCE: 853

Lys Ala Gly Val Ala Phe Leu His Lys Lys
1               5                   10

<210> SEQ ID NO 854
<211> LENGTH: 9
<212> TYPE: PRT
<213> ORGANISM: Smallpox virus

<400> SEQUENCE: 854

Lys Ile His Leu Ile Ser Val Lys Lys
1               5

<210> SEQ ID NO 855
<211> LENGTH: 9
<212> TYPE: PRT
<213> ORGANISM: Human immunodeficiency virus

<400> SEQUENCE: 855

Lys Arg Phe Ile Leu His Ala Lys Lys
1               5

<210> SEQ ID NO 856
<211> LENGTH: 8
<212> TYPE: PRT
<213> ORGANISM: Smallpox virus

<400> SEQUENCE: 856

Lys Leu Ile Ser Ile His Glu Lys
1               5

<210> SEQ ID NO 857
<211> LENGTH: 8
<212> TYPE: PRT
<213> ORGANISM: Bacillus anthracis

<400> SEQUENCE: 857

Lys Leu Arg Glu Glu His Cys Lys
1 5

<210> SEQ ID NO 858
<211> LENGTH: 8
<212> TYPE: PRT
<213> ORGANISM: Ebola virus

<400> SEQUENCE: 858

Lys Lys His Ala Thr Val Leu Lys
1 5

<210> SEQ ID NO 859
<211> LENGTH: 10
<212> TYPE: PRT
<213> ORGANISM: Influenza virus H1N2
<220> FEATURE:
<221> NAME/KEY: misc_feature
<222> LOCATION: (5)..(5)
<223> OTHER INFORMATION: Xaa can be Ile or Val
<220> FEATURE:
<221> NAME/KEY: misc_feature
<222> LOCATION: (8)..(8)
<223> OTHER INFORMATION: Xaa can be Val or Ile

<400> SEQUENCE: 859

Lys Glu Val Leu Xaa Trp Gly Xaa His His
1 5 10

<210> SEQ ID NO 860
<211> LENGTH: 23
<212> TYPE: PRT
<213> ORGANISM: Human immunodeficiency virus

<400> SEQUENCE: 860

Lys Cys Ser Tyr His Cys Leu Val Cys Phe Gln Lys Lys Gly Leu Gly
1 5 10 15

Ile Ser Tyr Gly Arg Lys Lys
20

<210> SEQ ID NO 861
<211> LENGTH: 23
<212> TYPE: PRT
<213> ORGANISM: Human immunodeficiency virus
<220> FEATURE:
<223> OTHER INFORMATION: formula peptide
<220> FEATURE:
<221> NAME/KEY: misc_feature
<222> LOCATION: (1)..(1)
<223> OTHER INFORMATION: Xaa can be Lys, His, Arg, Tyr, Ile, Ser, Val, Ala, Phe, Pro or Gln
<220> FEATURE:
<221> NAME/KEY: misc_feature
<222> LOCATION: (3)..(3)
<223> OTHER INFORMATION: Xaa can be Ser, Cys or Trp
<220> FEATURE:
<221> NAME/KEY: misc_feature
<222> LOCATION: (4)..(4)
<223> OTHER INFORMATION: Xaa can be Tyr, Phe, Pro or Ser
<220> FEATURE:
<221> NAME/KEY: misc_feature
<222> LOCATION: (7)..(7)
<223> OTHER INFORMATION: Xaa can be Gln or Leu
<220> FEATURE:
<221> NAME/KEY: misc_feature
<222> LOCATION: (8)..(8)
<223> OTHER INFORMATION: Xaa can be Val, Ile, Leu, Ser or Arg
<220> FEATURE:

-continued

<221> NAME/KEY: misc_feature
<222> LOCATION: (10)..(10)
<223> OTHER INFORMATION: Xaa can be Phe or Leu
<220> FEATURE:
<221> NAME/KEY: misc_feature
<222> LOCATION: (11)..(11)
<223> OTHER INFORMATION: Xaa can be Gln, His, Ile, Leu, Met or Asn
<220> FEATURE:
<221> NAME/KEY: misc_feature
<222> LOCATION: (12)..(12)
<223> OTHER INFORMATION: Xaa can be Lys, Thr, His, Met or Ser
<220> FEATURE:
<221> NAME/KEY: misc_feature
<222> LOCATION: (14)..(14)
<223> OTHER INFORMATION: Xaa can be Gly, Ala, Gln or Arg
<220> FEATURE:
<221> NAME/KEY: misc_feature
<222> LOCATION: (16)..(16)
<223> OTHER INFORMATION: Xaa can be Gly, Ala, Val or Ser
<220> FEATURE:
<221> NAME/KEY: misc_feature
<222> LOCATION: (17)..(17)
<223> OTHER INFORMATION: Xaa can be Ile or Leu
<220> FEATURE:
<221> NAME/KEY: misc_feature
<222> LOCATION: (18)..(18)
<223> OTHER INFORMATION: Xaa can be Ser or Tyr
<220> FEATURE:
<221> NAME/KEY: misc_feature
<222> LOCATION: (19)..(19)
<223> OTHER INFORMATION: Xaa can be Tyr or His
<220> FEATURE:
<221> NAME/KEY: misc_feature
<222> LOCATION: (20)..(20)
<223> OTHER INFORMATION: Xaa can be Gly or Gln

<400> SEQUENCE: 861

```
Xaa Cys Xaa Xaa His Cys Xaa Xaa Cys Xaa Xaa Xaa Lys Xaa Leu Xaa
1               5                   10                  15

Xaa Xaa Xaa Xaa Arg Lys Lys
            20
```

<210> SEQ ID NO 862
<211> LENGTH: 135
<212> TYPE: PRT
<213> ORGANISM: Tomato yellow leaf curl virus

<400> SEQUENCE: 862

```
Met Gln Pro Ser Ser Pro Ser Thr Ser His Cys Ser Gln Val Ser Ile
1               5                   10                  15

Lys Val Gln His Lys Ile Ala Lys Lys Lys Pro Ile Arg Arg Lys Arg
            20                  25                  30

Val Asn Leu Asp Cys Gly Cys Ser Tyr Tyr Leu His Leu Asn Cys Asn
        35                  40                  45

Asn His Gly Phe Thr His Arg Gly Thr His His Cys Ser Ser Ser Arg
    50                  55                  60

Glu Trp Arg Phe Tyr Leu Gly Asp Lys Gln Ser Pro Leu Phe Gln Asp
65                  70                  75                  80

Asn Arg Thr Gln Pro Glu Ala Ile Ser Asn Glu Pro Arg His His Phe
                85                  90                  95

His Ser Asp Lys Ile Gln Pro Gln His Gln Glu Gly Thr Gly Asp Ser
            100                 105                 110

Gln Met Phe Ser Gln Leu Pro Asn Leu Asp Asp Ile Thr Ala Ser Asp
        115                 120                 125

Trp Ser Phe Leu Lys Ser Ile
    130                 135
```

<210> SEQ ID NO 863
<211> LENGTH: 420
<212> TYPE: PRT
<213> ORGANISM: Plasmodium falciparum

<400> SEQUENCE: 863

```
Lys Ser Asp Ser Asn His Lys Lys Ser Asp Ser Asn His Lys Lys Ser
1               5                   10                  15

Asp Ser Asn His Lys Lys Ser Gly Ser Asn His Lys Lys Ser Asp Cys
            20                  25                  30

Asn His Lys Lys Ser Gly Ser Asn His Lys Lys Ser Asp Asn Asn His
        35                  40                  45

Lys Lys Ser Asp Ser Ser His Lys Lys Ser Asp Ser Ser His Lys Lys
    50                  55                  60

Ser Gly Ser Asn His Lys Lys Ser Asp Asn Asn His Lys Lys Ser Asp
65                  70                  75                  80

Ser Ser His Lys Lys Ser Gly Ser Asn His Lys Lys Ser Asp His Asn
                85                  90                  95

His Lys Lys Ser Asp Ser Asn His Lys Lys Ser Asp Ser Asn His Lys
            100                 105                 110

Lys Asn Glu Ser Asn His Lys Lys Asn Glu Ser Asn His Lys Lys Asn
        115                 120                 125

Glu Ser Asn His Lys Lys Asn Glu Ser Asn His Lys Lys Asn Glu Ser
    130                 135                 140

Asn His Lys Lys Asn Asp Ser Asn His Lys Lys Ser Asp Asn Asn His
145                 150                 155                 160

Lys Lys Ser Asp Asn Asn His Lys Lys Ser Asp Asn Asn His Lys Lys
                165                 170                 175

Ser Asp Asn Asn His Lys Lys Ser Asp Asn Asn His Lys Lys Ser Asp
            180                 185                 190

Asn Asn His Lys Lys Ser Asp His Asn His Lys Lys Ser Asp His Asn
        195                 200                 205

His Lys Lys Ser Asp His Asn His Lys Lys Ser Asp Asn Asn His Lys
    210                 215                 220

Lys Ser Asp Ser Asn His Lys Lys Ser Asp Ser Asn His Lys Lys Ser
225                 230                 235                 240

Asp His Asn His Lys Lys Ser Asp His Asn His Lys Lys Ser Asp Asn
                245                 250                 255

Asn His Lys Lys Ser Asp Ser Asn His Lys Lys Ser Asp Ser Asn His
            260                 265                 270

Lys Lys Ser Asp His Asn His Lys Lys Ser Asp His Asn His Lys Lys
        275                 280                 285

Ser Asp Asn Asn His Lys Lys Ser Asp Ser Asn His Lys Lys Ser Asp
    290                 295                 300

Ser Asn His Lys Lys Ser Asp Ser Asn His Lys Lys Ser Asp His Asn
305                 310                 315                 320

His Lys Lys Ser Asp Asn Asn His Lys Lys Ser Asp His Asn His Lys
                325                 330                 335

Lys Ser Asp Asn Asn His Lys Lys Ser Asp His Asn His Lys Lys Ser
            340                 345                 350

Asp Ser Asn His Lys Lys Ser Asp Ser Asn His Lys Lys Ser Asp Ser
        355                 360                 365

Asn His Lys Lys Ser Asp Ser Asn His Lys Lys Ser Asp Asn Asn His
    370                 375                 380
```

Lys Lys Ser Asp His Asn His Lys Lys Ser Asp His Asn His Lys Lys
385 390 395 400

Ser Asp Asn Asn His Lys Lys Ser Asp Asn Asn His Lys Lys Ser Asp
405 410 415

His Asn His Lys
420

<210> SEQ ID NO 864
<211> LENGTH: 21
<212> TYPE: PRT
<213> ORGANISM: Human SARS virus

<400> SEQUENCE: 864

Lys His Leu Asp Ala Tyr Lys Thr Phe Pro Pro Thr Glu Pro Lys Lys
1 5 10 15

Asp Lys Lys Lys Lys
20

<210> SEQ ID NO 865
<211> LENGTH: 6
<212> TYPE: PRT
<213> ORGANISM: Artificial Sequence
<220> FEATURE:
<223> OTHER INFORMATION: Replikin peptide sequence

<400> SEQUENCE: 865

Lys Lys Lys Lys His Lys
1 5

<210> SEQ ID NO 866
<211> LENGTH: 17
<212> TYPE: PRT
<213> ORGANISM: Artificial Sequence
<220> FEATURE:
<223> OTHER INFORMATION: Replikin peptide sequence

<400> SEQUENCE: 866

Tyr Lys Ala Gly Val Ala Phe Leu His Lys Lys Asn Asp Ile Ile Asp
1 5 10 15

Glu

<210> SEQ ID NO 867
<211> LENGTH: 29
<212> TYPE: PRT
<213> ORGANISM: Influenza virus

<400> SEQUENCE: 867

Lys Lys Gly Pro Asn Tyr Pro Val Ala Lys Gly Ser Tyr Asn Asn Thr
1 5 10 15

Ser Gly Glu Gln Met Leu Ile Ile Trp Gly Val His His
20 25

<210> SEQ ID NO 868
<211> LENGTH: 29
<212> TYPE: PRT
<213> ORGANISM: Influenza virus

<400> SEQUENCE: 868

Lys Lys Gly Asp Ser Tyr Pro Lys Leu Ser Lys Ser Tyr Thr Asn Asn
1 5 10 15

Lys Gly Lys Glu Val Leu Val Ile Trp Gly Val His His
20 25

-continued

<210> SEQ ID NO 869
<211> LENGTH: 29
<212> TYPE: PRT
<213> ORGANISM: Influenza virus

<400> SEQUENCE: 869

Lys Lys Gly Ser Ser Tyr Pro Lys Leu Ser Lys Ser Tyr Val Asn Asn
1 5 10 15

Lys Gly Lys Glu Val Leu Val Leu Trp Gly Val His His
20 25

<210> SEQ ID NO 870
<211> LENGTH: 29
<212> TYPE: PRT
<213> ORGANISM: Influenza virus

<400> SEQUENCE: 870

Lys Lys Gly Asn Ser Tyr Pro Lys Ile Ser Lys Ser Tyr Ile Asn Asn
1 5 10 15

Lys Glu Lys Glu Val Leu Val Leu Trp Gly Ile His His
20 25

<210> SEQ ID NO 871
<211> LENGTH: 29
<212> TYPE: PRT
<213> ORGANISM: Influenza virus

<400> SEQUENCE: 871

Lys Lys Gly Asn Ser Tyr Pro Lys Leu Ser Lys Ser Tyr Ile Asn Asn
1 5 10 15

Lys Lys Lys Glu Val Leu Val Ile Trp Gly Ile His His
20 25

<210> SEQ ID NO 872
<211> LENGTH: 29
<212> TYPE: PRT
<213> ORGANISM: Influenza virus

<400> SEQUENCE: 872

Lys Lys Gly Asn Ser Tyr Pro Lys Leu Ser Lys Ser Tyr Ile Asn Asn
1 5 10 15

Lys Gly Lys Lys Val Leu Val Leu Trp Gly Ile His His
20 25

<210> SEQ ID NO 873
<211> LENGTH: 40
<212> TYPE: PRT
<213> ORGANISM: Human coronavirus 229E

<400> SEQUENCE: 873

Lys Lys Ser Ala Lys Thr Gly Thr Pro Lys Pro Ser Arg Asn Gln Ser
1 5 10 15

Pro Ala Ser Ser Gln Thr Ser Ala Lys Ser Leu Ala Arg Ser Gln Ser
20 25 30

Ser Glu Thr Lys Glu Gln Lys His
35 40

<210> SEQ ID NO 874
<211> LENGTH: 37
<212> TYPE: PRT
<213> ORGANISM: Canine coronavirus 2003

-continued

```
<400> SEQUENCE: 874

Lys Lys Leu Gly Val Asp Thr Glu Lys Gln Gln Gln Arg Ser Arg Ser
1               5                   10                  15

Lys Ser Lys Glu Arg Ser Asn Ser Lys Thr Arg Asp Thr Thr Pro Lys
            20                  25                  30

Asn Glu Asn Lys His
        35


<210> SEQ ID NO 875
<211> LENGTH: 29
<212> TYPE: PRT
<213> ORGANISM: Influenza virus

<400> SEQUENCE: 875

Lys Lys Gly Ser Asn Tyr Pro Val Ala Lys Gly Ser Tyr Asn Asn Thr
1               5                   10                  15

Ser Gly Glu Gln Met Leu Ile Ile Trp Gly Val His His
            20                  25
```

REPLIKIN PEPTIDES AND USES THEREOF

This application claims priority to Provisional Applications Ser. Nos. 60/531,686 filed Dec. 23, 2003, 60/504,958 filed Sep. 23, 2003, and 60/476,186 filed Jun. 6, 2003.

SEQUENCE LISTING

The instant application contains a "lengthy" Sequence Listing which has been submitted via CD-R in lieu of a printed paper copy, and is hereby incorporated by reference in its entirety. Said CD-R, recorded on Dec. 12, 2004, are labeled "Copy 1" and "Copy 2", respectively, and each contains only one identical 244 Kb file (94254697.APP).

Replikins are a newly discovered class of peptides that share structural characteristics. Replikins have been found in viruses, bacteria, fungus, cancer associated proteins, plants and unicellular parasites and their use as targets in the development of methods of treating or preventing diseases. Replikins are useful in the detection of these diseases. Also this invention relates to the use of Replikins to stimulate growth of plants used for food.

Rapid replication is characteristic of virulence in certain bacteria, viruses and malignancies, but no chemistry common to rapid replication in different organisms has been described previously. This application describes a new class of protein structures related to rapid replication which the applicants have discovered. This new family of conserved small proteins related to rapid replication, named Replikins, can be used to predict and control rapid replication in multiple organisms and diseases and to induce rapid replication in plant and animal life.

We constructed an algorithm to search for Replikins. In applying the algorithm not only was the function of the epitope revealed—rapid replication, but an entire family of homologues whose function is related to rapid replication was discovered, which we named Replikins.

The algorithm is based on the following: 1) Evidence that the immune system looks to parts rather than a whole protein in recognition. Protein chains are first hydrolyzed by the immune system into smaller pieces, frequently six (6) to ten (10) amino acids long, as part of the immune systems' process of recognition of foreign structures against which it may mount an immune defense. By way of example, the immune system recognizes the presence of disease by chopping up proteins of the disease agent into smaller peptide sequences and reading them. This principle is used as a basis for the algorithm with which to search for homologues of the malignin cancer epitope, once the structure of the epitope was known; 2) The specific structure of the malignin epitope, in which two of the three lysines (K's) are eight residues apart is in accordance with the apparent 'rules' used by the immune system for recognition referred to above (6-10 amino acids long); 3) The fact that the malignin cancer epitope was shown to be a very strong antigen, that is—a generator of a strong immune response; that there are three lysines (K's) in the 10-mer peptide glioma Replikin and that K's are known to bind frequently to DNA and RNA, potential targets for the entry of viruses; and 4) One histidine (H) is included in the sequence of the malignin epitope, between the two K's which are eight (8) residues apart, suggesting a connection to the metals of redox systems which are required to provide the energy for replication.

Engineered enzymes and catalytic antibodies, possessing tailored binding pockets with appropriately positioned functional groups have been successful in catalyzing a number of chemical transformations, sometimes with impressive efficiencies. Just as two or more separate proteins with specific and quite different functions are now often recognized to be synthesized together by organisms, and then separately cleaved to 'go about their separate functions', so the Replikin structure is a unique protein with a unique function that appears to be recognized separately by the immune system and may be now rationally engineered—e.g. synthesized to produce a functional unit.

From a proteomic point of view, this template based on the newly determined glioma peptide sequence has led to the discovery of a wide class of proteins with related conserved structures and a particular function, in this case replication. Examples of the increase in Replikin concentration with virulence of a disease appear in diseases including, influenza, HIV, cancer and tomato leaf curl virus. This class of structures is related to the phenomenon of rapid replication in organisms as diverse as yeast, algae, plants, the gemini curl leaf tomato virus, HIV and cancer.

In addition to detecting the presence of Replikins in rapidly replicating organisms, we found that 1) Replikin concentration (number of Replikins per 100 amino acids) and 2) Replikin compositions in specific functional states dependant on rapid replication, provide the basis for the finding that Replikins are related quantitatively as well as qualitatively to the rate of replication of the organism in which they reside. Examples of these functional proofs include the relationship found between rapid replication and virulence in glioblastoma cells, between Replikins in influenza virus and the prediction of influenza pandemics and epidemics, and the relationship between Replikin concentration and rapid replication in HIV.

The first functional basis for Replikins' role in rapid replication was found in the properties of the glioma Replikin, a 10 KD peptide called Malignin in brain glioblastoma multiforme (glioma)—a 250 KD cell protein. Antimalignin antibody increased in concentration in serum (AMAS), measured by an early stage diagnostic test for cancer now used for most or all cell types. Malignin was so named because in tissue culture the expression of this peptide and its concentration per milligram membrane protein extractable increased with increased rate of cell division per unit time. Not only is there an increase in the amount of malignin in proportion to the cell number increase but the amount of malignin is enriched, that is—increased ten fold whereas the cell number increased only five fold.

The structure of malignin protein was determined through hydrolysis and mass spectrometry which revealed what proved to be a novel 16 mer peptide sequence. We searched for the 16 mer peptide sequence which we have named a Glioma Replikin protein in databases for the healthy human genome and found that it was not present in these databases.

As such, the fixed requirement algorithm was used to search in other organisms for the Glioma Replikin protein or homologues thereof. Over 4,000 protein sequences in the "Pub Med" database were searched and homologues were found in viruses and plant forms specifically associated with rapid replication. Homologues of such Replikin proteins occurred frequently in proteins called 'replicating proteins' by their investigators.

Homologues of the Replikin sequence were found in all tumor viruses (that is viruses that cause cancer), and in 'replicating proteins' of algae, plants, fungi, viruses and bacteria.

That malignin is enriched ten-fold compared to the five-fold increase in cell number and membrane protein concentration in rapid replication of glioma cells suggests an integral relationship of the Replikins to replication. When the glioma replikin was synthesized in vitro and administered as a synthetic vaccine to rabbits, abundant antimalignin antibody was produced establishing rigourously the antigenic basis of the antimalignin antibody in serum (AMAS) test, and providing the first potential synthetic cancer vaccine and the prototype for Replikin vaccines in other organisms.

The demonstration of the relationship of the Replikins to replication and the natural immune response to cancer Replikins (overriding cell type) based upon the shared specificity of cancer Replikins, permits passive augmentation of immunity with antimalignin antibody and active augmentation with synthetic Replikin vaccines.

A study of 8,090 serum specimens from cancer patients and controls has demonstrated that the concentration of antimalignin antibody increases with age in healthy individuals, as the incidence of cancer in the population increases, and increases further two to three-fold in early malignancy, regardless of cell type. In vitro this antibody is cytotoxic to cancer cells at picograms (femtomoles) per cancer cell, and in vivo the concentration of antimalignin antibody relates quantitatively to the survival of cancer patients. As shown in glioma cells, the stage in cancer at which cells only have been transformed to the immortal malignant state but remain quiescent or dormant, now can be distinguished from the more active life-threatening replicating state which is characterized by the increased concentration of Replikins. In addition, clues to the viral pathogenesis of cancer may be found in the fact that glioma glycoprotein 10B has a 50% reduction in carbohydrate residues when compared to the normal 10B. This reduction is associated with virus entry in other instances and so may be evidence of the attachment of virus for the delivery of virus Replikins to the 10B of glial cells as a step in the transformation to the malignant state.

The sharing of immunological specificity by diverse members of the class, as demonstrated with antimalignin antibody for the glioma and related cancer Replikins, suggests that B cells and their product antibodies may recognize Replikins by means of a similar recognition ‘language’. With the discovery of the Replikins, this shared immunological specificity may explain what was previously difficult to understand: why the antimalignin antibody is elevated in all cancers, and is cytotoxic to cancer cells and related to survival of cancer patients in most or all cell types. Thus antimalignin antibody is produced against cancer Replikins, which share immunological specificity and which are related to the phenomenon of rapid replication, not to cell type.

The recognition of the cancer Replikins, whether those in viruses known to cause cancer, or those in transforming proteins, or those isolated in cancer cell proteins (see Table 2, sections on cancer Replikins) is sufficiently general that the antimalignin antibody in serum test (AMAS Test) is an effective general cancer test. Yet there is sufficient individuality and difference in the fine structure (primary amino acid sequence) of each of the cancer replikins that they can be assayed specifically in tissues and in fluids by diagnostic methods common in the art, such as mass spectrometry. Once the particular Replikin is identified in the sequences of the cancer proteins by the methods discovered and described here, the Replikin is synthesized and acts as a standard for assays of tissues and fluids for the same structure. For example, the definitive and highly specific mass spectrometry analysis for one such cancer protein, the first defined cancer cell Replikin, the Glioma Replikin ‘kagvaflhkk’ (SEQ ID NO: 1), is shown in Table 2. This specific measurement of the cancer Replikins permits the diagnostic specification of the tissue or organ type affected by the cancer and its specifc treatment. Thus, for example, the Glioma Replikin occurs only in glioblastoma multiforme, a malignant brain tumor, one of the most malignant of all tumors with a mortality of over 90%, for which no effective treatment is available. If its Glioma Replikin is measured in serum, the presence of brain malignancy is detected. It is also now possible to target the Glioma Replikin specifically with chemical, radiological and other treatments. The same novel diagnostic and therapeutic methods are now available for ovarian cancer Replikin and the other cancer Replikins as listed, by example, only in Table 2.

A second functional basis for the Replikins’ role in rapid replication is the study of data from the past 100 years on influenza virus hemagglutinin protein sequences and epidemiology of influenza epidemics and pandemics. To date, only serological hemagglutinin and antibody classification, but no strain-specific conserved peptide sequences have previously been described in influenza, and no changes in concentration and composition of any strain-specific peptide sequences have been described previously which correlate with epidemiologically documented epidemics or rapid replication.

A four to ten-fold increase in the concentration of strain-specific influenza Replikins in one of each of the four major strains, influenza B, (A)H1N1, (A)H2N2 and (A)H3N2 was found, and that such increase of Replikin concentration was related to influenza epidemics caused specifically by each strain from 1902 to 2001. These increases in concentration were then shown to be due to the reappearance of at least one specific Replikin composition from 1 to up to 64 years after its disappearance, plus the emergence of new strain-specific Replikin compositions. Previously, no strain-specific chemical structures were known with which to predict which strains would predominate in coming influenza seasons, nor to devise annual mixtures of whole-virus strains for vaccines. The recent sharp increase in H3N2 Replikin concentration (1997 to 2000), the largest in H3N2’s history, and the reappearance of specific Replikin compositions which were last seen in the high mortality H3N2 pandemic of 1968 and in the two high mortality epidemics of 1975 and 1977, but were absent for 20-25 years, together may be a warning of coming epidemics.

Synthetic Replikins are new vaccines. This high degree of conservation of Replikin structures observed whereby the identical structure can persist for 100 years, or reappear after an absence of from one to 64 years reappears indicates that what was previously thought to be change in virulence due to random substitution of amino acids in influenza proteins is more likely to be change due to an organized process of conservation of Replikins. In fact, if random substitutions of each amino acid occurred, the chance against an average length influenza Replikin sequence being conserved for one year (let alone 84) is calculated to be in the order of 2 to the $27^{th}$ power to 1.

The significant conservation of Replikins is not unique to influenza virus, for example, it is also present in foot and mouth disease virus type O and in HIV, as well as in wheat. More recently, significant conservation of Replikins is present in coronavirus nucleocapsid proteins.

A third functional basis for Replikins’ role in rapid replication is the increase in Replikin concentration shown to be related to rapid replication in HIV. The Replikin concentration in the slow-growing low-titre strain of HIV (NS1, “Bru”), prevalent in early stage infection, was found to be one-sixth of the Replikin concentration in the rapidly-growing high-titre strain of HIV (SI, “Lai”), prevalent in late stage HIV infection.

Other examples are given of the relation of Replikins to rapid replication. For example, in tomato curl leaf gemini virus, which devastates tomato crops, the first 161 amino acids of the 'replicating protein', which have been shown to bind to DNA, contain five Replikins.

In malaria, legendary for rapid replication, trypanosomes are released from the liver in tens of thousands from one trypanosome. Multiple, novel, almost 'flamboyant' Replikin structures with concentrations of up to 111 overlapping Replikins per 100 amino acids are found therein.

The increase in Replikin concentration in influenza epidemics is functionally comparable to the glioma Replikin's increase in concentration during rapid replication of malignant glioma cells and comparable to rapid replication in HIV and in a diverse range of other organisms. Replikins thus are associated with and appear to be part of the structural bases of rapid replication in different organisms.

Replikin concentration and composition therefore provide new methods to detect and to control the process of replication, which is central to the survival and dominance of each biological population. The discovery of these new proteins related to rapid replication provides new opportunities 1) for detection of pathogens by qualitative and quantitative determinations of Replikins, 2) for the control of a broad range of diseases in which rapid replication is a key factor by targeting native Replikins and by using synthetic Replikins as vaccines, and 3) for the use of Replikins to foster growth of algal and plant foods.

There is a significant number of diseases and pathogens which have proved difficult to detect and treat and for which there is no effective vaccine. Thus, for each disorder there is a need for developing a target that will provide effective methods of detecting, treating or preventing these diseases and pathogens.

SUMMARY OF THE INVENTION

The present invention provides a method for identifying nucleotide or amino acid sequences that include a Replikin sequence. The method is referred to herein as a 3-point-recognition method. By use of the "3-point recognition" method, namely, peptides comprising from 7 to about 50 amino acids including (1) at least one lysine residue located six to ten amino acid residues from a second lysine residue; (2) at least one histidine residue; and (3) at least 6% lysine residues (Replikin)—constituting a new class of peptides was revealed in algae, yeast, fungi, amoebae, bacteria, plant and virus proteins having replication, transformation, or redox functions.

In one aspect of the invention there are provided isolated or synthesized peptides containing a Replikin sequence. The peptides comprise from 7 to about 50 amino acids including (1) at least one lysine residue located six to ten amino acid residues from a second lysine residues; (2) at least one histidine residue; and (3) at least 6% lysine residues.

The present invention also provides methods for detecting the presence of a contaminating organism in a body sample or environmental sample comprising:

(1) isolating nucleic acids from the body sample or environmental sample;

(2) screening the nucleic acids for the presence of a Replikin structure; and (3) correlating the presence of a Replikin structure with the presence of the contaminating organism.

In another aspect of the invention there is provided a process for stimulating the immune system of a subject to produce antibodies that bind specifically to a Replikin sequence, said process comprising administering to the subject an effective amount of a dosage of a composition comprising at least one Replikin peptide. One embodiment comprises at least one peptide that is present in an emerging strain of the organism if such new strain emerges.

The present invention also provides antibodies that bind specifically to a Replikin, as defined herein, as well as antibody cocktails containing a plurality of antibodies that specifically bind to Replikins. In one embodiment of the invention, there are provided compositions comprising an antibody or antibodies that specifically bind to a Replikin and a pharmaceutically acceptable carrier.

In one aspect of the invention there are provided isolated, or separated from other proteins, recombinant, or synthesized peptides or other methods containing a viral Replikin sequence. The viral Replikin peptides comprise from 7 to about 50 amino acids including (1) at least one lysine residue located six to ten amino acid residues from a second lysine residue; (2) at least one histidine residue; and (3) at least 6% lysine residues. (viral Replikin).

The present application also provides isolated, or separated from nucleocapsid proteins, amongst others, recombinant, or synthesized peptides or other methods containing a viral Replikin sequence. The viral nucleocapsid Replikin peptides comprise from 7 to about 50 amino acids including (1) at least one lysine residue located six to ten amino acid residues from a second lysine residue; (2) at least one histidine residue; and (3) at least 6% lysine residues.

The present invention also provides methods for detecting the presence of a contaminating virus in a body sample or environmental sample comprising:

(1) isolating nucleic acids from the body sample or environmental sample;

(2) screening the nucleic acids for the presence of a viral Replikin structure; and (3) correlating the presence of viral Replikin structures, their concentration and composition, with the presence of the contaminating virus.

In another aspect of the invention there is provided a process for stimulating the immune system of a subject to produce antibodies that bind specifically to a viral Replikin sequence, said process comprising administering to the subject an effective amount of a dosage of a composition comprising at least one Replikin peptide. One embodiment comprises at least one peptide that is present in an emerging strain of the virus if such new strain emerges.

The present invention also provides antibodies that bind specifically to a viral Replikin, as defined herein, as well as antibody cocktails containing a plurality of antibodies that specifically bind to viral Replikins. In one embodiment of the invention, there are provided compositions comprising an antibody or antibodies that specifically bind to a viral Replikin and a pharmaceutically acceptable carrier.

The present invention also provides therapeutic compositions comprising one or more of isolated virus peptides having from 7 to about 50 amino acids comprising: (1) at least one lysine residue located six to ten residues from a second lysine residue; (2) at least one histidine residue; and (3) at least 6% lysine residues, and a pharmaceutically acceptable carrier.

In another aspect of the invention there is provided an antisense nucleic acid molecule complementary to a virus Replikin mRNA sequence, said Replikin mRNA sequence denoting from 7 to about 50 amino acids comprising:

(1) at least one lysine residue located six to ten residues from a second lysine residue;

(2) at least one histidine residue; and (3) at least 6% lysine residues.

In yet another aspect of the invention there is provided a method of simulating the immune system of a subject to produce antibodies to viruses, said method comprising: administering an effective amount of at least one virus Replikin peptide having from 7 to about 50 amino acids comprising (1) at least one lysine residue located six to ten amino acid residues from a second lysine residue; (2) at least one histidine residue; (3) and at least 6% lysine residues.

In another aspect, there is provided a method of selecting a virus peptide for inclusion in a preventive or therapeutic virus vaccine comprising:

(1) obtaining at least one isolate of each strain of a plurality of strains of said virus;

(2) analyzing the amino acid sequence of the at least one isolate of each strain of the plurality of strains of the virus for the presence and concentration of Replikin sequences;

(3) comparing the concentration of Replikin sequences in the amino acid sequence of the at least one isolate of each strain of the plurality of strains of the virus to the concentration of Replikin sequences observed in the amino acid sequence of each of the strains at least one earlier time period to provide the concentration of Replikins for at least two time periods, said at least one earlier time period being within about six months to about three years prior to step (1);

(4) indentifying the strain of the virus having the highest increase in concentration of Replikin sequences during the at least two time periods; and (5) selecting at least one Replikin sequence present in the strain of the virus peptide identified in step (4) as a peptide for inclusion in the virus vaccine.

The present invention also provides a method of making a preventive or therapeutic virus vaccine comprising:

(1) identifying a strain of a virus as an emerging strain, (2) selecting at least one Replikin sequence present in the emerging strain as a peptide template for the virus vaccine manufacture, (3) synthesizing peptides having the amino acid sequence of the at least one Replikin sequence selected in step (2), and (4) combining a therapeutically effective amount of the peptides of step (3) with a pharmaceutically acceptable carrier and/or adjuvant.

In another aspect, the invention is directed to a method of identifying an emerging strain of a virus for diagnostic, preventive or therapeutic purposes comprising:

(1) obtaining at least one isolate of each strain of a plurality of strains of the virus;

(2) analyzing the amino acid sequence of the at least one isolate of each strain of the plurality of strains of the virus for the presence and concentration of Replikin sequences;

(3) comparing the concentration of Replikin sequences in the amino acid sequence of the at least one isolate of each strain of the plurality of strains of the virus to the concentration of Replikin sequences observed in the amino acid sequence of each of the strains at least one earlier time period to provide the concentration of Replikins for at least two time periods, said at least one earlier time period being within about six months to about three years prior to step (1); and (4) identifying the strain of the virus having the highest increase in concentration of Replikin sequences during the at least two time periods.

In yet another aspect of the invention, there is provided a preventive or therapeutic virus vaccine comprising at least one isolated Replikin present in a protein of an emerging strain of the virus and a pharmaceutically acceptable carrier and/or adjuvant.

Also provided by the present invention is a method of preventing or treating a virus infection comprising administering to a patient in need thereof a preventive or therapeutic virus vaccine comprising at least one isolated Replikin present in a protein of an emerging strain of the virus and a pharmaceutically acceptable carrier and/or adjuvant.

Influenza

Influenza is an acute respiratory illness of global importance. Despite international attempts to control influenza virus outbreaks through vaccination, influenza infections remain an important cause of morbidity and mortality. Worldwide influenza epidemics and pandemics have occurred at irregular and previously unpredictable intervals throughout history and it is expected that they will continue to occur in the future. The impact of both pandemic and epidemic influenza is substantial in terms of morbidity, mortality and economic cost.

Influenza vaccines remain the most effective defense against influenza virus, but because of the ability of the virus to mutate and the availability of non-human host reservoirs, it is expected that influenza will remain an emergent or reemergent infection. Global influenza surveillance indicates that influenza viruses may vary within a country and between countries and continents during an influenza season. Virological surveillance is of importance in monitoring antigenic shift and drift. Disease surveillance is also important in assessing the impact of epidemics. Both types of information have provided the basis of the vaccine composition and the correct use of antivirals. However, to date there has been only annual post hoc hematological classification of the increasing number of emerging influenza virus strains, and no specific chemical structure of the viruses has been identified as an indicator of approaching influenza epidemics or pandemics. Currently, the only basis for annual classification of influenza virus as active, inactive or prevalent in a given year is the activities of the virus hemagglutinin and neuraminidase proteins. No influenza viral chemical structure has been identified prior to this application that can be used for quantitative warning of epidemics or pandemics or to design more effective and safer vaccines.

Because of the annual administration of influenza vaccines and the short period of time when a vaccine can be administered, strategies directed at improving vaccine coverage are of critical importance.

In one aspect of the invention there are provided isolated or synthesized influenza virus peptides containing a Replikin sequence. The influenza Replikin virus peptides comprise from 7 to about 50 amino acids including (1) at least one lysine residue located six to ten amino acid residues from a second lysine residue; (2) at least one histidine residue; and (3) at least 6% lysine residues. (Influenza Replikin).

In another aspect of the invention, there is provided a process for stimulating the immune system of a subject to produce antibodies that bind specifically to an influenza virus Replikin sequence, said process comprising administering to the subject an effective amount of dosage of a composition comprising at least one influenza virus Replikin peptide. In a preferred embodiment the composition comprises at least on peptide that is present in an emerging strain of influenza virus.

The present invention also provides antibodies that bind specifically to an influenza virus Replikin, as defined herein, as well as antibody cocktails containing a plurality of antibodies that specifically bind to influenza virus Replikins. In one embodiment of the invention, there are provided compositions comprising an antibody or antibodies that specifically bind to an influenza Replikin and a pharmaceutically acceptable carrier.

The present invention also provides therapeutic compositions comprising one or more of isolated influenza virus peptides having from 7 to about 50 amino acids comprising:

(1) at least one lysine residue located six to ten residues form a second lysine residue;

(2) at least one histidine residue; and (3) at least 6% lysine residues, and a pharmaceutical acceptable carrier.

In another aspect of the invention there is provided an antisense nucleic acid molecule complementary to an influenza virus hemagglutinin Replikin mRNA sequence, said Replikin mRNA sequence denoting from 7 to about 50 amino acids comprising:

(1) at least one lysine residue located six to ten residues from a second lysine residue;

(2) at least one histidine residue; and (3) at least 6% lysine residues.

In yet another aspect of the invention there is provided a method of simulating the immune system of a subject to produce antibodies to influenza virus comprising administering an effective amount of at least one influenza virus Replikin peptide having from 7 to about 50 amino acids comprising:

(1) at least one lysine residue located six to ten amino acid residues from a second lysine residue;

(2) at least one histidine residue; and (3) at least 6% lysine residues.

In another aspect, there is provided a method of selecting an influenza virus peptide for inclusion in a preventive or therapeutic influenza virus vaccine comprising:

(1) obtaining at least one isolate of each strain of a plurality of strains of influenza virus;

(2) analyzing the hemagglutinin amino acid sequence of the at least one isolate of each strain of the plurality of strains of influenza virus for the presence and concentration of Replikin sequences;

(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1);

(4) identifying the strain of influenza virus having the highest increase in concentration of Replikin sequences during the at least two time periods;

(5) selecting at least one Replikin sequence present in the strain of influenza virus peptide identified in step (4) as a peptide for inclusion in an influenza virus vaccine.

The present invention also provides a method of making a preventive or therapeutic influenza virus vaccine comprising:

(1) identifying a strain of influenza virus as an emerging strain;

(2) selecting at least one Replikin sequence present in the emerging strain as a peptide template for influenza virus vaccine manufacture, (3) synthesizing peptides having the amino acid sequence of the at least one Replikin sequence selected in step (2), and (4) combining a therapeutically effective amount of the peptides of step (3) with a pharmaceutically acceptable carrier and/or adjuvant.

In another aspect, the invention is directed to a method of identifying an emerging strain of influenza virus for diagnostic, preventive or therapeutic purposes comprising:

(1) obtaining at least one isolate of each strain of a plurality of strains of influenza virus;

(2) analyzing the hemagglutinin amino acid sequence of the at least one isolate of each strain of the plurality of strains of influenza virus for the presence and concentration of Replikin sequences;

(3) comparing the concentration of Replikin sequences in the hemagglutinin amino acid sequence of the at least one isolate of each strain of the plurality of strains of influenza virus to the concentration of Replikin sequences observed in the hemagglutinin amino acid sequence of each of the strains at least one earlier time period to provide the concentration of Replikins for at least two time periods, said at least one earlier time period being within about six months to about three years prior to step (1); and (4) identifying the strain of influenza virus having the highest increase in concentration of Replikin sequences during the at least two time periods.

In yet another aspect of the invention, there is provided a preventive or therapeutic influenza virus vaccine comprising at least one isolated Replikin present in the hemagglutinin protein of an emerging strain of influenza virus and a pharmaceutically acceptable carrier and/or adjuvant.

Also provided by the present invention is a method of preventing or treating influenza virus infection comprising administering to a patient in need thereof a preventive or therapeutic vaccine comprising at least one isolated Replikin present in the hemagglutinin protein of an emerging strain of influenza virus and a pharmaceutically acceptable carrier and/or adjuvant.

Trypanosomes

In one aspect of the invention there are provided isolated or synthesized trypanosome peptides containing a Replikin sequence. The trypanosome Replikin peptides comprise from 7 to about 50 amino acids including (1) at least one lysine residue located six to ten amino acid residues from a second lysine residue; (2) at least one histidine residue; and (3) at least 6% lysine residues. (Trypanosome Replikins).

Malaria

One trypanosome disorder which has proved difficult to treat and for which there is no effective vaccine is malaria. Malaria causes much death, and physical and economic hardship in tropical regions. Malaria is caused mainly by *Plasmodium falciparum,* which has proved to be extremely resistant to treatment and to date, a vaccine for malaria has remained elusive. Thus there is a need for effective malaria vaccines and methods of treating or preventing the disease. This application provides the basis for such vaccines and methods of treatment and prevention. All of the methods described above for production of and treatment with Replikin virus vaccines and Replikin influenza virus vaccines are applicable to the production of and treatment with Replikin malaria vaccines.

In the present invention, there are provided vaccines and methods for preventing or treating malaria. The malaria vaccines comprise at least one isolated *Plasmodium falciparum* Replikin. The present invention also provides methods for treating or preventing malaria comprising administering to a patient an effective amount of preventive or therapeutic vaccine comprising at least one isolated *Plasmodium falciparum* Replikin.

Also provided by the present invention are antibodies, antibody cocktails and compositions that comprise antibodies that specifically bind to a Replikin or Replikins present in a malaria antigen of *Plasmodium falciparum.*

Another example of a trypanosome which may be treated under the present invention as is the case for malaria, the Replikins of *Treponema Pallidum* (syphilis), can be used for detection, prevention, treatment of syphilis. BACTERIA In one aspect of the invention there are provided isolated or synthesized bacterial peptides containing a Replikin sequence (bacterial Replikins). The bacterial peptides comprise from 7 to about 50 amino acids including (1) at least one lysine residue located six to ten amino acid residues from a second lysine residue; (2) at least one histidine residue; and (3) at least 6% lysine residues. (bacterial Replikins). U.S. application Ser. No. 10/105,232 filed Mar. 26, 2002 is incorporated by reference in its entirety, including but not limited to the bacterial sequence listing and information.

The present invention also provides methods for detecting the presence of a contaminating bacterial organism in a body sample or environmental sample comprising:

(1) isolating nucleic acids from the body sample or environmental sample;

(2) screening the nucleic acids for the presence of a Replikin structure; and (3) correlating the presence of a Replikin structure with the presence of the contaminating organism.

In another aspect of the invention there is provided a process for stimulating the immune system of a subject to produce antibodies that bind specifically to a bacterial Replikin sequence, said process comprising administering to the subject an effective amount of a dosage of a composition comprising at least one bacterial Replikin peptide. One embodiment comprises at least one bacterial peptide that is present in an emerging strain of the bacterial organism if such new strain emerges.

The present invention also provides antibodies that bind specifically to a bacterial Replikin, as defined herein, as well as antibody cocktails containing a plurality of antibodies that specifically bind to bacterial Replikins. In one embodiment of the invention, there are provided compositions comprising an antibody or antibodies that specifically bind to a bacterial Replikin and a pharmaceutically acceptable carrier.

The present invention also provides therapeutic compositions comprising one or more of isolated bacterial peptides having from 7 to about 50 amino acids comprising:

(1) at least one lysine residue located six to ten residues from a second lysine residue;

(2) at least one histidine residue;

(3) at least 6% lysine residues; and (4) a pharmaceutically acceptable carrier.

In another aspect of the invention there is provided an antisense nucleic acid molecule complementary to a bacterial Replikin mRNA sequence, said Replikin mRNA sequence denoting from 7 to about 50 amino acids comprising:

(1) at least one lysine residue located six to ten residues from a second lysine residue;

(2) at least one histidine residue; and (3) at least 6% lysine residues.

In yet another aspect of the invention there is provided a method of simulating the immune system of a subject to produce antibodies to bacteria comprising administering an effective amount of at least one bacterial Replikin peptide having from 7 to about 50 amino acids comprising:

(1) at least one lysine residue located six to ten amino acid residues from a second lysine residue;

(2) at least one histidine residue; and (3) at least 6% lysine residues.

In another aspect, there is provided a method of selecting a bacterial Replikin peptide for inclusion in a preventive or therapeutic bacterial vaccine comprising:

(1) obtaining at least one isolate of each strain of a plurality of strains of the bacteria;

(2) analyzing the amino acid sequence of the at least one isolate of each strain of the plurality of strains of the bacteria for the presence and concentration of bacterial Replikin sequences;

(3) comparing the concentration of bacterial Replikin sequences in the amino acid sequence of the at least one isolate of each strain of the plurality of strains of the bacteria to the concentration of bacterial Replikin sequences observed in the amino acid sequence of each of the strains at least one earlier time period to provide the concentration of bacterial Replikins for at least two time periods, said at least one earlier time period being within about six months to about three years prior to step (1), or earlier in rapidly mutating bacteria;

(4) indentifying the strain of the bacteria having the highest increase in concentration of bacterial Replikin sequences during the at least two time periods; and (5) selecting at least one bacterial Replikin sequence present in the strain of the bacterial peptide identified in step (4) as a peptide for inclusion in the bacterial vaccine.

The present invention also provides a method of making a preventive or therapeutic bacterial vaccine comprising:

(1) identifying a strain of a bacteria as an emerging strain;

(2) selecting at least one bacterial Replikin sequence present in the emerging strain as a peptide template for the bacterial vaccine manufacture;

(3) synthesizing peptides having the amino acid sequence of the at least one bacterial Replikin sequence selected in step (2); and (4) combining a therapeutically effective amount of the peptides of step (3) with a pharmaceutically acceptable carrier and/or adjuvant.

In another aspect, the invention is directed to a method of identifying an emerging strain of bacteria for diagnostic, preventive or therapeutic purposes comprising:

(1) obtaining at least one isolate of each strain of a plurality of strains of the bacteria;

(2) analyzing the amino acid sequence of the at least one isolate of each strain of the plurality of strains of the bacteria for the presence and concentration of bacterial Replikin sequences;

(3) comparing the concentration of bacterial Replikin sequences in the amino acid sequence of the at least one isolate of each strain of the plurality of strains of the bacteria to the concentration of bacterial Replikin sequences observed in the amino acid sequence of each of the strains at least one earlier time period to provide the concentration of bacterial Replikins for at least two time periods, said at least one earlier time period being within about six months to about three years prior to step (1); and (4) identifying the strain of the bacteria having the highest increase in concentration of bacterial Replikin sequences during the at least two time periods.

In yet another aspect of the invention, there is provided a preventive or therapeutic bacterial vaccine comprising at least one isolated bacterial Replikin present in a protein of an emerging strain of the bacteria and a pharmaceutically acceptable carrier and/or adjuvant.

Replikins in the ATPase of *Mycobacterium tuberculosis* are:

hprpkvaaalkdsyrlk (SEQ ID NO: 798)
hprpkvaaalk (SEQ ID NO: 799)
ksaqkwpdkflagaaqvah (SEQ ID NO: 800)

Replikins in the B-D-galactosidase of *E. coli*:

hawqhqgktlfisrk (SEQ ID NO: 801)
hqgktlfisrk (SEQ ID NO: 802)

-continued

Replikins in
*Agrobacterium tumefaciens*:

```
hsdqqlavmiaakrlddyk (SEQ ID NO: 803)
hlldhpasvgqldlramlaveevkidnpvymek (SEQ ID NO: 804)
hpasvgqldlramlaveevkidnpvymek (SEQ ID NO: 805)
kcvmakncnikcpaglttnqeafngdpralaqylmniah
(SEQ ID NO: 806)
kncnikcpaglttnqeafNgdpralaqylmniah
(SEQ ID NO: 807)
hhdtysiedlaqlihdakaarvrvivk (SEQ ID NO: 808)
hdtysiedlaqlihdakaarvrvivk (SEQ ID NO: 809)
hdakaarvrvivk (SEQ ID NO: 810)
kigqgakpgeggqlpspkvtveiaaarggtpgvelvsppphh
(SEQ ID NO: 811)
kigqgakpgeggqlpspkvtveiaaarggtpgvelvsppph
(SEQ ID NO: 812)
kaseitktlasgamshgalvaaaheavahgtnmvggmsnsgeggeh
(SEQ ID NO: 813)
kaseitktlasgamshgalvaaaheavah (SEQ ID NO: 814)
kaseitktlasgamshgalvaaah (SEQ ID NO: 815)
kaseitktlasgamsh (SEQ ID NO: 816)
kryfpnvktpvggvtfaviaqavadwh (SEQ ID NO: 817)
hhiaaglgfgasavyplgvqfraeekfgadadkafkrfakaaekslmk
(SEQ ID NO: 818)
hhiaaglgfgasavyplgvqfraeekfgadadkafkrfakaaekslmk
(SEQ ID NO: 819)
hhiaaglgfgasavyplgvqfraeekfgadadkafkrfakaaek
(SEQ ID NO: 820)
hhiaaglgfgasavyplgvqfraeekfgadadkafkrfak
(SEQ ID NO: 821)
hhiaaglgfgasavyplgvqfraeekfgadadk (SEQ ID NO: 822)
hiaaglgfgasavyplgvqfraeekfgadadkafkrfakaaekslmk
(SEQ ID NO: 823)
hiaaglgfgasavyplgvqfraeekfgadadkafkrfakaaek
(SEQ ID NO: 824)
hiaaglgfgasavyplgvqfraeekfgadadkafkrfak
(SEQ ID NO: 825)
hiaaglgfgasavyplgvqfraeekfgadadk (SEQ ID NO: 826)
kfglydaafeksscgvgfitrkdgvqth (SEQ ID NO: 827)
```

Also provided by the present invention is a method of preventing or treating a bacterial infection comprising administering to a patient in need thereof a preventive or therapeutic vaccine comprising at least one isolated bacterial Replikin present in a protein of an emerging strain of the bacteria and a pharmaceutically acceptable carrier and/or adjuvant.

Fungus

In one aspect of the invention there are provided isolated or synthesized fungal peptides containing a Replikin sequence. The fungal Replikin peptides comprise from 7 to about 50 amino acids including (1) at least one lysine residue located six to ten amino acid residues from a second lysine residue; (2) at least one histidine residue; and (3) at least 6% lysine residues (fungal Replikins).

All of the methods described above for production of and treatment with bacterial Replikin vaccines are applicable to the production of and treatment with fungal Replikin vaccines.

In another aspect of the invention there is provided a process for stimulating the immune system of a subject to produce antibodies that bindspecifically to a fungal Replikin sequence, said process comprising administering to the subject an effective amount of a dosage of a composition comprising at least one fungal Replikin peptide.

The present invention also provides antibodies that bind specifically to a fungal Replikin, as defined herein, as well as antibody cocktails containing a plurality of antibodies that specifically bind to viral Replikins. In one embodiment of the invention, there are provided compositions comprising an antibody or antibodies that specifically bind to a fungal Replikin and a pharmaceutically acceptable carrier.

The present invention also provides therapeutic compositions comprising one or more of isolated fungal peptides having from 7 to about 50 amino acids comprising:

(1) at least one lysine residue located six to ten residues from a second lysine residue;

(2) at least one histidine residue;

(3) at least 6% lysine residues; and (4) a pharmaceutically acceptable carrier.

In another aspect of the invention there is provided an antisense nucleic acid molecule complementary to an fungal Replikin mRNA sequence, said Replikin mRNA sequence having from 7 to about 50 amino acids comprising:

(1) at least one lysine residue located six to ten residues from a second lysine residue;

(2) at least one histidine residue; and (3) at least 6% lysine residues.

In another aspect of the invention there is provided a process for stimulating the immune system of a subject to produce antibodies that bind specifically to a fungal Replikin sequence, said process comprising administering to the subject an effective amount of a dosage of a composition comprising at least one Replikin peptide.

Increasing Replication

In yet another aspect of the invention there is provided a method for increasing the replication rate of an organism comprising transforming a gene encoding an enzyme or other protein having a replication function in the organism with at least one Replikin structure.

Definitions

As used herein, the term "peptide" or "protein" refers to a compound of two or more amino acids in which the carboxyl group of one is united with an amino group of another, forming a peptide bond. The term peptide is also used to denote the amino acid sequence encoding such a compound. As used herein, "isolated" or "synthesized" peptide or biologically active portion thereof refers to a peptide that is substantially free of cellular material or other contaminating peptides from the cell or tissue source from which the peptide is derived, or substantially free from chemical precursors or other chemicals when chemically synthesized by any method, or substantially free from contaminating peptides when synthesized by recombinant gene techniques.

As used herein, a Replikin peptide or Replikin protein is an amino acid sequence having 7 to about 50 amino acids comprising:

(1) at least one lysine residue located six to ten amino acid residues from a second lysine residue;

(2) at least one histidine residue;

(3) at least 6% lysine residues.

Similarly, a Replikin sequence is the amino acid sequence encoding such a peptide or protein.

As used herein, "emerging strain" as used herein refers to a strain of a virus, bacterium, fungus, or other organisms identified as having an increased increasing concentration of Replikin sequences in one or more of its protein sequences relative to the concentration of Replikins in other strains of such organism. The increase or increasing concentration of Replikins occurs over a period of at least about six months, and preferably over a period of at least about one year, most preferably over a period of at least about three years or more, for example, in influenza virus, but may be a much shorter period of time for bacteria and other organisms.

As used herein, "mutation" refers to change in this structure and properties of an organism caused by substitution of amino acids. In contrast, the term "conservation" as used herein, refers to conservation of particular amino acids due to lack of substitution.

BRIEF DESCRIPTION OF THE DRAWINGS

FIG. 10 is a chart depicting the mean Replikin count per year for nucleocapsid coronavirus isolates.

DETAILED DESCRIPTION OF THE INVENTION

Figure 1:
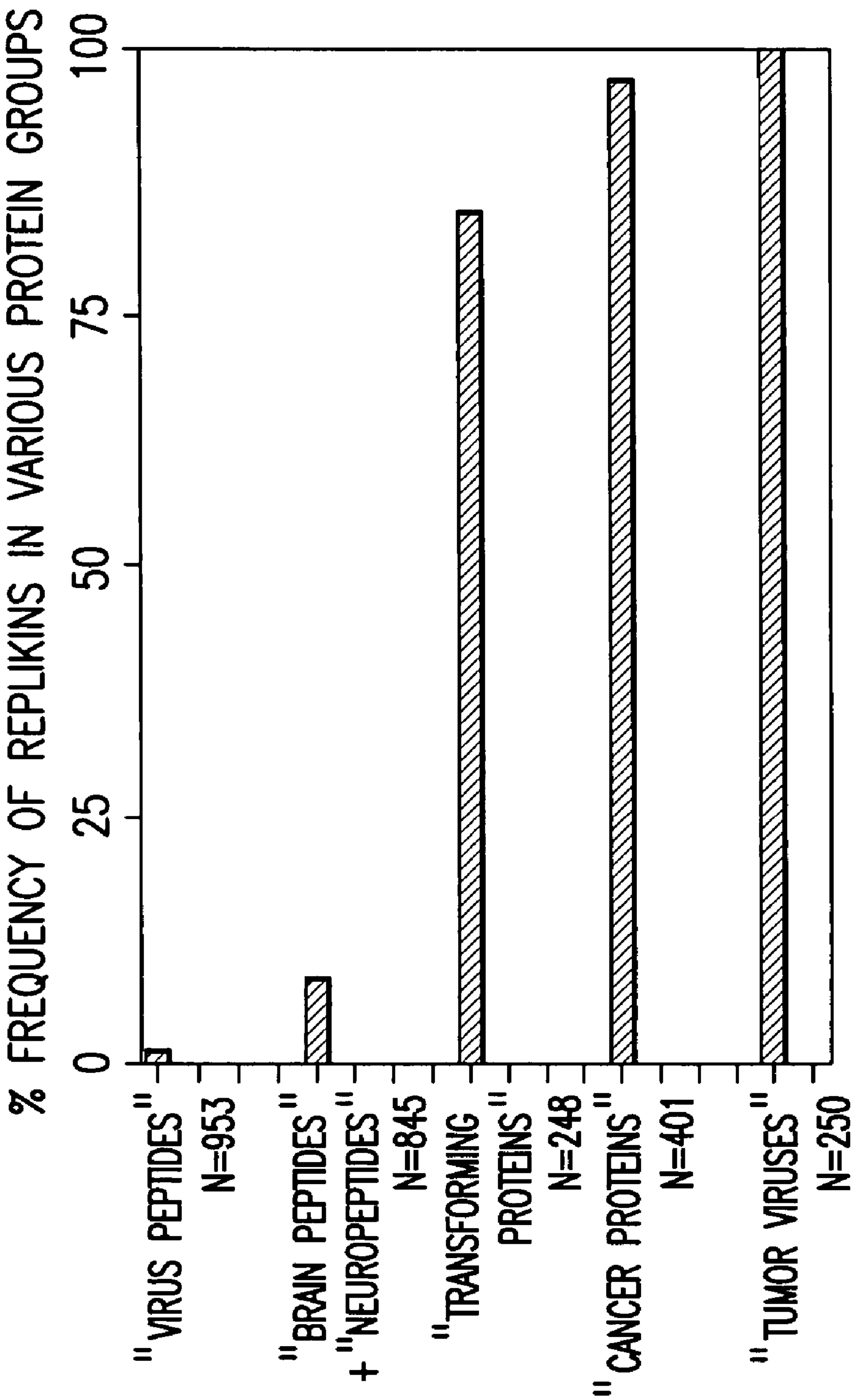
FIG. 1 is a bar graph depicting the frequency of occurrence of Replikins in various organisms.

The identification of a new family of small peptides related to the phenomenon of rapid replication, referred to herein as Replikins, provides targets for detection of pathogens in a sample and developing therapies, including vaccine development. In general, knowledge of and identification of this family of peptides enables development of effective therapies and vaccines for any organism that harbors Replikins. Identification of this family of peptides also provides for the detection of viruses and virus vaccine development.

For example, identification of this family of peptides provides for the detection of influenza virus and provides new targets for influenza treatment. Identification of this family of peptides also provides for example, for the detection of malaria and provides new targets for malaria vaccine development. Further examples provided by the identification of this family of peptides include the detection of infectious disease Replikins, cancer immune Replikins and structural protein Replikins.

Rapid replication is characteristic of virulence in certain bacteria, viruses and malignancies, but no chemistry common to rapid replication in different organisms has been described. We have found a family of conserved small protein sequences related to rapid replication, which we have named Replikins. Such Replikins offer new targets for developing effective detection methods and therapies. The first Replikin found was the glioma Replikin, which was identified in brain glioblastoma multiforme (glioma) cell protein called malignin.

Hydrolysis and mass spectrometry of malignin revealed the novel 16 mer peptide sequence which contains the glioma Replikin. This Replikin was not found in databases for the normal healthy human genome and therefore appeared to be derived from some source outside the body.

We have devised an algorithm to search for the glioma Replikin or homologue thereof. Homologues were not common in over 4,000 protein sequences, but were found, surprisingly, in all tumor viruses, and in the replicating proteins of algae, plants, fungi, viruses and bacteria.

We have identified that both 1) Replikin concentration (number of Replikins per 100 amino acids) and 2) Replikin composition correlate with the functional phenomenon of rapid replication. These relationships provide functional basis for the determination that Replikins are related quantitatively as well as qualitatively to the rate of replication.

The first functional basis for Replikins role to rapid replication is seen in glioma replication. The fact that glioma malignin is enriched ten-fold compared to the five-fold increase in cell number and membrane protein concentration in rapid replication of glioma cells suggests an integral relationship of the Replikins to replication. When the glioma Replikin was synthesized in vitro and administered as a synthetic vaccine to rabbits, abundant antimalignin antibody was produced. This establishes the antigenic basis of the antimalignin antibody in serum (AMAS) test, and provides the first potential synthetic cancer vaccine and the prototype for Replikin vaccines in other organisms. With the demonstration of this natural immune relationship of the Replikins to replication and this natural immune response to cancer Replikins, which overrides cell type, based upon the shared specificity of cancer Replikins and rapid replication, both passive augmentation of this immunity with antimalignin antibody and active augmentation with synthetic Replikin vaccines now is possible.

The relationship between the presence of antimalignin antibody and survival in patients was shown in a study of 8,090 serum specimens from cancer patients. The study showed that the concentration of antimalignin antibody increases with age, as the incidence of cancer in the population increases, and increases further two to three-fold in early malignancy, regardless of cell type. In vitro, the antimalignin antibody is cytotoxic to cancer cells at picograms (femtomoles) per cancer cell, and in vivo the concentration of antimalignin antibody relates quantitatively to the survival of cancer patients. As shown in glioma cells, the stage in cancer at which cells have only been transformed to the immortal malignant state but remain quiescent or dormant, now can be distinguished from the more active life-threatening replicating state, which is characterized by the increased concentration of Replikins. In addition, clues to the viral pathogenesis of cancer may be found in the fact that glioma glycoprotein 10B has a 50% reduction in carbohydrate residues when compared to the normal 10B. This reduction is associated with virus entry in other instances, and so may be evidence of the attachment of virus for the delivery of virus Replikins to the 10B of glial cells as a step in the transformation to the malignant state.

Our study concerning influenza virus hemagglutinin protein sequences and influenza epidemiology over the past 100 years, has provided a second functional basis for the relations of Replikins to rapid replication. Only serological hemagglutinin and antibody classification, but no strain-specific conserved peptide sequences have previously been described in influenza. Further, no changes in concentration and composition of any strain-specific peptide sequences have been described previously that correlate with epidemiologically documented epidemics or rapid replication. In this study, a four to ten-fold increase in the concentration of strain-specific influenza Replikins in one of each of the four major strains, influenza B, (A)H1N1, (A)H2N2 and, (A)H3N2 is shown to relate to influenza epidemics caused by each strain from 1902 to 2001.

We then showed that these increases in concentration are due to the reappearance of at least one specific Replikin composition from 1 to up to 64 years after its disappearance, plus the emergence of new strain-specific Replikin compositions. Previously, no strain-specific chemical structures were known with which to predict the strains that would predominate in coming influenza seasons, nor to devise annual mixtures of whole-virus strains for vaccines. The recent sharp increase in H3N2 Replikin concentration (1997 to 2000), the largest in H3N2's history, and the reappearance of specific Replikin compositions that were last seen in the high mortality H3N2 pandemic of 1968, and in the two high mortality epidemics of 1975 and 1977, but were absent for 20-25 years, together may be a warning of coming epidemics. This high degree of conservation of Replikin structures observed, whereby the identical structure can persist for 100 years, or reappear after an absence of from one to 64 years, indicate that what was previously thought to be change due to random substitution of amino acids in influenza proteins is more likely to be change due to an organized process of conservation of Replikins.

The conservation of Replikins is not unique to influenza virus but was also observed in other sources, for example in foot and mouth disease virus, type 0, HIV tat, and wheat.

A third functional basis for Replikins' role in rapid replication is seen in the increase in rapid replication in HIV. Replikin concentration was shown to be related to rapid replication in HIV. We found the Replikin concentration in the slow growing low-titre strain of HIV (NS1, "Bru"), which is prevalent in early stage infection, to be one-sixth of the Replikin concentration in the rapidly-growing high-titre strain of HIV (SI, "Lai")(prevalent in late stage HIV infection).

Further examples demonstrate the relationship of Replikins to rapid replication. In the "replicating protein," of tomato curl leaf gemini virus, which devastates tomato crops, the first 161 amino acids, the sequence that has been shown to bind to DNA, was shown to contain five Replikins. In malaria, legendary for rapid replication when trypanosomes are released from the liver in the tens of thousands from one trypanosome, multiple, novel, almost 'flamboyant' Replikin structures have been found with concentrations of up to 36 overlapping Replikins per 100 amino acids.

The conservation of any structure is critical to whether that structure provides a stable invariant target to attack and destroy or to stimulate. When a structure is tied in some way to a basic survival mechanism of the organism, the structures tend to be conserved. A varying structure provides an inconstant target, which is a good strategy for avoiding attackers, such as antibodies that have been generated specifically against the prior structure and thus are ineffective against the modified form. This strategy is used by influenza virus, for example, so that a previous vaccine may be quite ineffective against the current virulent virus.

Replikins as Stable Targets for Treatment

Both bacteria and HIV have both Replikin and non-Replikin amino acids. In HIV, for example, there has been a recent increase in drug-resistance from 9% to 13% due to mutation, that is substitution of non-Replikin amino acids. (See detailed analysis of TAT protein of HIV discussed herein). In bacteria, the development of 'resistant strains' is due to a similar mechanism. However, we have found that Replikin structures do not mutate or change to the same degree as non Replikin amino acids (see also discussion of foot and mouth disease virus conservation of Replikins discussed herein; further see discussion of conservation of coronavirus Replikins discussed herein). The Replikin structures, as opposed to the non-Replikin structures are conserved and thus provide new constant targets for treatment.

Certain structures too closely related to survival functions apparently cannot change constantly. Because an essential component of the Replikin structure is histidine (h), which is know for its frequent binding to metal groups in redox enzymes and probable source of energy needed for replication, and since this histidine structure remains constant, this structure remains all the more attractive a target for destruction or stimulation.

From a proteomic point of view, inventors construction of a template based on the newly determined glioma peptide sequence led them to the discovery of a wide class of proteins with related conserved structures and a particular function, in this case replication. Examples of the increase in Replikin concentration with virulence of a disease include, influenza, HIV, cancer and tomato leaf curl virus. This newly recognized class of structures is related to the phenomenon of rapid replication in organisms as diverse as yeast, algae, plants, the gemini curl leaf tomato virus, HIV and cancer.

Replikin concentration and composition provide new quantitative methods to detect and control the process of replication, which is central to the survival and dominance of each biological population. The sharing of immunological specificity by diverse members of the class, as demonstrated with antimalignin antibody for the glioma and related cancer Replikins, suggests that B cells and their product antibodies may recognize Replikins by means of a similar recognition language.

Examples of peptide sequences of cancer Replikins or as containing a Replikin, i.e., a homologue of the glioma peptide, kagvaflhkk, may be found in such cancers of, but not limited to, the lung, brain, liver, soft-tissue, salivary gland, nasopharynx, esophagus, stomach, colon, rectum, gallbladder, breast, prostate, uterus, cervix, bladder, eye, forms of melanoma, lymphoma, leukemia, and kidney.

Replikins provide for: 1) detection of pathogens by qualitative and quantitative determinations of Replikins; 2) treatment and control of a broad range of diseases in which rapid replication is a key factor by targeting native Replikins and by using synthetic Replikins as vaccines; and 3) fostering increased growth rates of algal and plant foods.

The first Replikin sequence to be identified was the cancer cell Replikin found in a brain cancer protein, malignin, which was demonstrated to be enriched ten-fold during rapid anaerobic replication of glioblastoma multiforme (glioma) cells. (FIG. 2) Malignin is a 10 KDa portion of the 250 KDa glycoprotein 10B, which was isolated in vivo and in vitro from membranes of glioblastoma multiforme (glioma) cells. Hydrolysis and mass spectroscopy of malignin revealed a 16-mer peptide sequence, ykagvaflhkkndide (SEQ ID NO.: 4), which is referred to herein as the glioma Replikin and which includes the shorter peptide, kagvaflhkk (SEQ ID NO.: 1), both of which apparently are absent in the normal human genome.

TABLE 1

16-mer peptide sequence ykagvaflhkkndide (SEQ ID NO: 4) obtained from malignin by hydrolysis and mass spectrometry

| | | | | Method By Which Fragment Obtained | | | |
|---|---|---|---|---|---|---|---|
| Seq ID NO. | Fragment Identified | MH+ (mass) | Sequence | Auto-hydrolysis of malignin free in solution | Auto-hydrolysis of malignin immobilized on bromoacetyl cellulose | Micro-waved 5 seconds | Micro-waved 30 seconds |
| 19 | 1-3 | 381.21 | ( )yka(g) | | | | + |
| 20 | 1-5 | 537.30 | ( )ykagv(a) | | + | | |
| 21 | 2-6 | 445.28 | (y)kagva(f) | | + | | |
| 22 | 2-7 | 592.35 | (y)kagvaf(1) | | | + | |
| 23 | 4-11 | 899.55 | (a)gvaf1hkk(n) | | | | + |
| 24 | 5-7 | 336.19 | (g)vaf(1) | | | | + |
| 25 | 6-7 | 237.12 | (v)af(1) | + | | | |
| 26 | 6-10 | 615.36 | (v)aflhk(k) | | | | + |
| 27 | 6-10 | 615.36 | (v)aflhk(k) | + | | | |
| 28 | 6-12 | 857.50 | (v)aflhkkn(d) | | + | | |
| 29 | 6-12 | 857.50 | (v)afhkkn(d) | + | | | |
| 30 | 7-8 | 279.17 | (a)fl(h) | | | + | |
| 31 | 10-16 | 861.43 | (h)kkndide( ) | | + | | |
| 32 | 11-14 | 489.27 | (k)kndi(d) | | + | | |
| 33 | 12-15 | 476.2– | (k)ndid(e) | + | | | |

When the 16-mer glioma Replikin was synthesized and injected as a synthetic vaccine into rabbits, abundant antimalignin antibody was produced. (Bogoch et al., Cancer Detection and Prevention, 26 (Suppl. 1): 402 (2002)). The concentration of antimalignin antibody in serum in vivo has been shown to relate quantitatively to the survival of cancer patients. (Bogoch et al., Protides of Biological Fluids, 31:739-747 (1984). In vitro antimalignin antibodies have been shown to be cytotoxic to cancer cells at a concentration of picograms (femtomolar) per cancer cell. (Bogoch et al., Cancer Detection and Prevention, 26 (Suppl. 1): 402 (2002).

Studies carried out by the inventors showed that the glioma Replikin is not represented in the normal healthy human genome. Consequently, a search for the origin and possible homologues of the Replikin sequence was undertaken by analysis of published sequences of various organisms.

By using the 16-mer glioma Replikin sequence as a template and constructing a recognition proteomic system to visually scan the amino acid sequences of proteins of several different organisms, a new class of peptides, the Replikins, was identified. The present invention provides a method for identifying nucleotide or amino acid sequences that include a Replikin sequence. The method is referred to herein as a 3-point-recognition method. The three point recognition method comprises: a peptide from 7 to about 50 amino acids including (1) at least one lysine residue located six to ten amino acid residues from a second lysine residue; (2) at least one histidine residue; and (3) at least 6% lysine residues. (Replikin). These peptides or proteins constitute a new class of peptides in species including algae, yeast, fungi, amoebae, bacteria, plant, virus and cancer proteins having replication, transformation, or redox functions. Replikin peptides have been found to be concentrated in larger 'replicating' and 'transforming' proteins (so designated by their investigators, See Table 2) and cancer cell proteins. No sequences were found to be identical to the malignin 16-mer peptide.

TABLE 2

Examples of Replikins in various organisms - prototype: Glioma Replikin* kagvaflhkk (SEQ ID No.: 1)

| | SEQ ID NO. | | |
|---|---|---|---|
| Algae: | 34 | Caldophera prolifera | kaskftkh |
| | 35 | Isolepisprolifera | kagaetgeikgh |
| Yeast: | 36 | Schizosaccharomyces pombe | ksfkypkkhk |
| | 37 | Oryza sativa | kkaygnelhk |
| | 2 | *Sacch. cerevisiae* replication binding protein | hsikrelgiifdk |
| Fungi: | 38 | Isocitrate lyase ICI 1, Penicillium marneffei | kvdivthqk |
| | 39 | DNA-dependent RNA polymerase 11, Diseula dcstructiva | kleedaayhrkk |
| | 40 | Ophiostoma novo-ulm 1, RNA in Dutch elm disease fungus | kvilplrgnikgiffkh |

TABLE 2-continued

| | SEQ ID NO. | Examples of Replikins in various organisms - prototype: Glioma Replikin* kagvaflhkk (SEQ ID No.: 1) | |
|---|---|---|---|
| Amoeba: | 41 | Entamoeba invadens, histone H2B | klilkgdlnkh |
| Bacteria: | 42 | Pribosomal protein replication factor, *Helicobacter pylori* Replication-associated protein *Staph. aureus* | ksvhaflk |
| | 10 | Mycoplasma pulmonic, chromosome replication | kkektthnk |
| | 43 | Macrophage infectivity potentiator, *L. legionella* | kvhffqlkk |
| | 90 | *Bacillus anthracis* | kihlisvkk |
| | 91 | *Bacillus anthracis* | hvkkekeknk |
| | 92 | *Bacillus anthracis* | khivkievk |
| | 93 | *Bacillus anthracis* | kkkkikdiygkdallh |
| | 94 | *Bacillus anthracis* | kwekikqh |
| | 95 | *Bacillus anthracis* | kklqipppiepkkddiih |
| | 96 | *Bacillus anthracis* | hnryasnivesayllilnew-knniqsdlikk |
| | 97 | *Bacillus anthracis* | havddyagylldknqsdlv-tnskk |
| | 98 | *Bacillus anthracis* | haerlkvgknapk |
| Plants: | 44 | Arabidopsis thaliana, prolifera | kdhdfdgdk |
| | 45 | Arabidopsis thaliana, cytoplasmic ribosomal | kmkglkqkkah |
| | 46 | Arabidopsis thaliana, DNA binding protein | kelssttgeksh |
| Viruses: | 9 | Replication associated protein A [Maize streak virus] | kekkpskdeimrdiish |
| | 11 | Bovine herpes virus 4, DNA replication protein | hkinitngqk |
| | 12 | Meleagrid herpesvirus 1, replication binding protein | hkdlyrllmk |
| | 47 | Feline immunodeficiency | hlkdyklvk |
| | 3 | Foot and Mouth Disease (O) | hkqkivapvk |
| | 5 | HIV Type 1 | kcfncgkegh |
| | 7 | HIV Type 2 | kcwncgkegh |
| | 99 | Small Pox Virus (Variola) | khynnitwyk |
| | 100 | Small Pox Virus (Variola) | kysqtgkeliih |
| | 101 | Small Pox Virus (Variola) | hyddvnikndivvsrck |
| | 102 | Small Pox Virus (Variola) | hrfklildski |
| | 103 | Small Pox Virus (Variola) | kerghnyyfek |
| Tumor Viruses: | 48 | Rous sarcoma virus tyrosine-protein kinase | kklrhek |
| | 49 | v-yes, avian sarcoma | kklrhdk |
| | 50 | c-yes, colon cancer, malignant melanoma | kklrhdk |
| | 51 | v-srcC, avian sarcoma | kklrhek |
| | 52 | c-src, colon, mammary, panrcreatic cancer | kklrhek |
| | 53 | Neuroblastoma RAS viral (v-ras) oncogene | kqahelak |
| | 54 | VPI (major capsid protein) [*Polyamavirus* sp.] | kthrfskh |
| | 55 | Sindbis | knlhekik |
| | 56 | E1 [Human papilloamavirus type 71] | khrpllqlk |
| | 57 | v-erbB from AEV and c-erb | kspnhvk |
| | 58 | v-fms (feline sarcoma) | knihlekk |
| | 59 | c-fms (acute and chronic myelomonocytic tumors) | knihlekk |
| | 60 | large t-antigen I [*Polyomavirus* sp.1 | kphlaqslek |
| | 61 | middle t-antigen [Polyomavirus sp, 1- | kqhrelkdk |
| | 62 | small t-antigen [Polyomavirus spJ, | kqhrelkdk |
| | 63 | v-abl, murine acute leukemia | kvpvlisptlkh |
| | 64 | Human T-cell lymphotropic virus typo 2 | kslllevdkdish |

TABLE 2-continued

| | SEQ ID NO. | Examples of Replikins in various organisms - prototype: Glioma Replikin* kagvaflhkk (SEQ ID No.: 1) | |
|---|---|---|---|
| | 65 | c-kit, GI tumors, small cell lung carcinoma | kagitimvkreyh |
| | 18 | Hepatitis C | hyppkpgcivpak |
| Trans-Forming Proteins: | 66 | Transforming protein myb | ksgkhlgk |
| | 67 | Transforming protein myc, Burkitt lymphoma | krreqlkhk |
| | 68 | Ras-related GTP-binding protein | ksfevikvih |
| | 69 | Transforming protein ras (teratocarcinoma) | kkkhtvkk |
| | 70 | TRAF-associated NF·kB activator TANK | kaqkdhlsk |
| | 71 | RFP transforming protein | hlkrvkdlkk |
| | 72 | Transforming protein D (S.C.) | kygspkhrlik |
| | 73 | Papilloma virus type 11, transforming protein | klkhilgkarfik |
| | 74 | Protein tryosine kinasc (EC 2.7.1.112slk | kgdhvkhykirk |
| | 75 | Transforming protein (axl(-)) | keklrdvmvdrhk |
| | 76 | Transforming protein (N-myc) | klqarqqqllkkieh |
| | 77 | Fibroblast growth factor 4 (Kaposi sarcoma) | kkgnrvsptmkvth |
| Cancer Cell Proteins: | 78 | Matrix metaloproteinase 7 (uterine) | keiplhfrk |
| | 79 | Transcription factor 7-like | kkkphikk |
| | 80 | Breast cancer antigen NY-BR-87 | ktrhdplak |
| | 81 | BRCA-1-Associated Ring Domain Protein (breast) | khhpkdnlik |
| | 82 | 'Autoantigen from a breast tumor' | khkrkkfrqk |
| | 83 | Glioma Replikin (this study) | kagvaflhkk |
| | 84 | Ovarian cancer antigen | khkrkkfrqk |
| | 85 | EE L leukemia | kkkskkhkdk |
| | 86 | Proto-oncogene tyrosine-protein kinase C-ABLE | hksekpalprk |
| | 87 | Adenomatosis polyposis coli | kkkkpsrlkgdnek |
| | 88 | Gastric cancer transforming protein | ktkkgnrvsptmkvth |
| | 89 | Transforming protein (K-RAS 2B),lung | khkekmskdgkkkkkksk |

Identification of an amino acid sequence as a Replikin or as containing a Replikin, i.e., a homologue of the glioma peptide, kagvaflhkk (SEQ ID NO: 1), requires that the three following requirements be met. According to the three point recognition system the sequences have three elements: (1) at least one lysine residue located six to ten residues from another lysine residue; (2) at least one histidine residue; and (3) a composition of at least 6% lysine within an amino acid sequence of 7 to about 50 residues.

Databases were searched using the National Library of Medicine keyword "PubMed" descriptor for protein sequences containing Replikin sequences. Over 4,000 protein sequences were visually examined for homologues. Sequences of all individual proteins within each group of PubMed-classified proteins were visually scanned for peptides meeting the three above-listed requirements. An infrequent occurrence of homologues was observed in "virus peptides" as a whole (1.5%) (N=953), and in other peptides not designated as associated with malignant transformation or replication such as "brain peptides" and "neuropeptides" (together 8.5%) (N=845). However, surprisingly, homologues were significantly more frequently identified in large "replicating proteins," which were identified as having an established function in replication in bacteria, algae, and viruses. Even more surprising was the finding that Replikin homologues occurred in 100% of "tumor viruses" (N=250), in 97% of "cancer proteins" (N=401), and in 85% of "transforming viruses" (N=248). These results suggest that there are shared properties of cancer pathogenesis regardless of cell type and suggest a role of viruses in carcinogenesis, i.e., conversion of cells from a transformed albeit dormant state to a more virulent actively replicating state.

Homologues of the following amino acid sequence, kagvaflhkk (SEQ ID NO: 1), as defined by the three point recognition method, were found in such viruses, or viral peptides, as, but not limited to, adenovirus, lentivirus, a-virus, retrovirus, andeno-associated virus, human immunodeficiency virus, hepatitis virus, influenza virus, maize streak virus, herpes virus, bovine herpes virus, feline immunodeficiency virus, foot and mouth disease virus, small pox virus, rous sarcoma virus, neuroblastoma RAS viral oncogene, polyamavirus, sindbis, human papilloma virus, myelomonocytic tumor virus, murine acute leukemia, T-cell lymphotropic virus, and tomato leaf curl virus.

Furthermore, homologues of the amino acid sequence kagvafhkk (SEQ ID NO: 828) are present in known classes of coronavirus, which are members of a family of enveloped viruses that replicate in the cytoplasm of host cells. Additionally, the homologue of the amino acid sequence kagvatlhkk (SEQ ID NO: 829) are present in the recently identified class of coronavirus responsible for severe acute respiratory syndrome, or SARS. The replikin is located in the nucleocapsid whole protein sequence of the SARS coronovirus. In addition, the location of the replikins is present in other members of the coronavirus class and, more specifically, are also present in the nucleocapsid protein sequences from these coronaviruses. members of the coronavirus class and, more specifically, are also present in the nucleocapsid protein sequences from these coronaviruses.

Replikins are present in such bacteria as, but not limited to, *Acetobacter, Achromobacter, Actinomyces, Aerobacter, Alcaligenes, Arthrobacter, Azotobacter, Bacillus, Brevibacterium, Chainia, Clostridium, Corynebacterium, Erwinia, Escheria, Lebsiella, Lactobacillus, Haemophilus, Flavobacterium, Methylomonas, Micrococcus, Mycobacterium, Micronomspora, Mycoplasma, Neisseria, Nocardia, Proteus, Pseudomonas, Rhizobium, Salmonella, Serratia, Staphylococcus, Streptocossus, Streptomyces, Streptosporangium, Strepto-virticillium, Vibrio* peptide, and *Xanthomas.*

Replikins are present in such fungi as, but not limited to, *Penicillium, Diseula, Ophiostoma novo-ulim, Mycophycophta, Phytophthora infestans, Absidia, Aspergillus, Candida, Cephalosporium, Fusarium, Hansenula, Mucor, Paecilomyces, Pichia, Rhizopus, Torulopsis, Trichoderma,* and *Erysiphe.*

Replikins are present in such yeast as, but not limited to, *Saccharomyces, Cryptococcus,* including *Cryptococcusneoformas, Schizo-saccharomyces,* and *Oryza.*

Replikins are present in algae such as, but not limited to, *Caldophera, Isolepisprolifera, Chondrus, Gracilaria, Gelidium, Caulerpa, Laurencia, Cladophexa, Sargassum, Penicillos, Halimeda, Laminaria, Fucus, Ascophyllum, Undari, Rhodymenia, Macrocystis, Eucheuma, Ahnfeltia,* and *Pteroclasia.*

Replikins are present in amoeba such as, but not limited to, *Entamoeba* (including *Entamoeba invadens*), *Amoebidae, Acanthamoeba* and *Naegleria.*

Replikins are present in plants such as, but not limited to, *Arabidopsis,* wheat, rice, and maize.

Auxiliary Specifications

To permit classification of subtypes of Replikins, additional or "auxiliary specifications" to the basic "3-point-recognition" requirements may be added: (a) on a structural basis, such as the common occurrence of adjacent di- and polylysines in cancer cell proteins (e.g., transforming protein P21B(K-RAS 2B), lung, Table 2, SEQ ID NO.: 89), and other adjacent di-amino acids in TOLL-like receptors, or b) on a functional basis, such as exhibiting ATPase, tyrosine kinase or redox activity as seen in Table 2.

Functional Derivatives

"Functional derivatives" of the Replikins as described herein are fragments, variants, analogs, or chemical derivatives of the Replikins, which retain at least a portion of the immunological cross reactivity with an antibody specific for the Replikin. A fragment of the Replikin peptide refers to any subset of the molecule. Variant peptides may be made by direct chemical synthesis, for example, using methods well known in the art. An analog of a Replikin to a non-natural protein substantially similar to either the entire protein or a fragment thereof. Chemical derivatives of a Replikin contain additional chemical moieties not normally a part of the peptide or peptide fragment.

Figure 2:
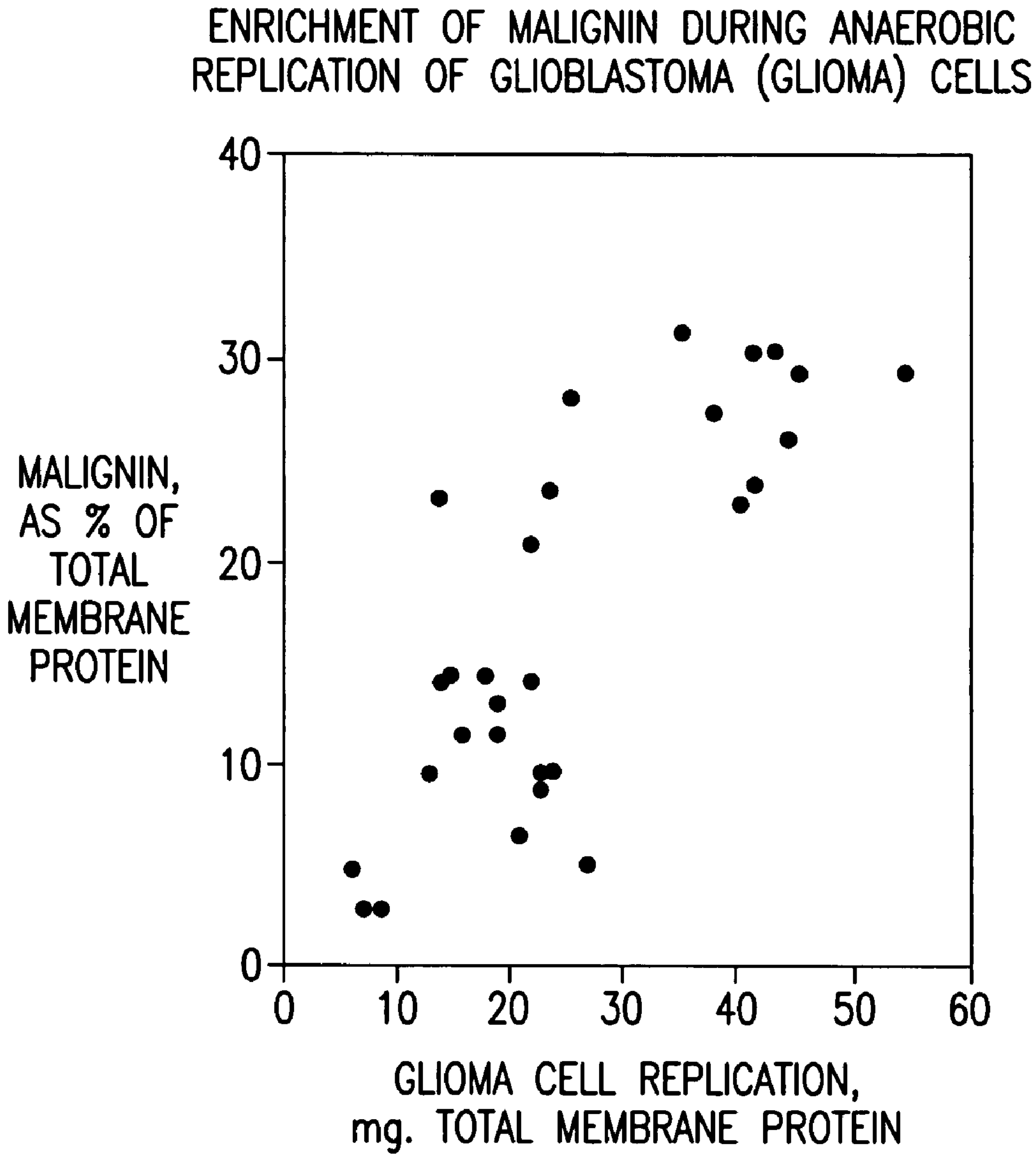
FIG. 2 is a graph depicting the percentage of malignin per milligram total membrane protein during anaerobic replication of glioblastoma cells.

As seen in FIG. 2, during anaerobic respiration when the rate of cell replication is increased, malignin is enriched. That is, malignin is found to increase not simply in proportion to the increase in cell number and total membrane proteins, but is enriched as much as ten-fold in concentration, starting with 3% at rest and reaching 30% of total membrane protein. This clear demonstration of a marked increase in Replikin concentration with glioma cell replication points to, and is consistent with, the presence of Replikins identified with the 3-point recognition method in various organisms. For example, Replikins were identified in such proteins as "*Saccharomyces cerevisiae* replication binding protein" (SEQ ID NO.: 2) (hsikrelgiifdk); the "replication associated protein A of maize streak virus" (SEQ ID NO.: 8) (kyivcareahk) and (SEQ ID NO.: 9) (kekkpskdeimrdiish); the "replication-associated protein of *Staphylococcus aureus*" (SEQ ID NO.: 10) (kkektthnk); the "DNA replication protein of bovine herpes virus 4" (SEQ ID NO.: 11) (hkinitngqk); and the "Mealigrid herpes virus 1 replication binding protein" (SEQ ID NO.: 12) (hkdlyrllmk). Previous studies of tomato leaf curl gemini virus show that the regulation of virus accumulation appears to involve binding of amino acids 1-160 of the "replicating protein" of that virus to leaf DNA and to other replication protein molecules during virus replication. Analysis of this sequence showed that amino acids 1-135 of this "replicating protein" contain a replikin count (concentration) as high as 20.7 (see section on tomato leaf curl Gemini virus.)

Table 2 shows that Replikin-containing proteins also are associated frequently with redox functions, and protein synthesis or elongation, as well as with cell replication. The association with metal-based redox functions, the enrichment of the Replikin-containing glioma malignin concentration during anaerobic replication, and the cytotoxicity of antimalignin at low concentrations (picograms/cell) (FIG. 4*c-f*), all suggest that the Replikins are related to central respiratory survival functions, have been found less often subjected to the mutations characteristic of non-Replikin amino acids.

Of particular interest, it was observed that at least one Replikin per 100 amino acids was found to be present in the hemagglutinin proteins of almost all of the individual strains of influenza viruses examined. The Replikin sequences that were observed to occur in the hemagglutinin proteins of isolates of each of the four prevalent strains of influenza virus, influenza B, H1N1, H2N2, and H3N2, for each year that amino acid sequence data are available (1902-2001), are shown in Tables 3, 4, 5 and 6.

TABLE 3

Replikin Sequences present in hemagglutinins of Influenza B viruses in each year for which amino acid sequences were available (1940-2001).

Figure 7:
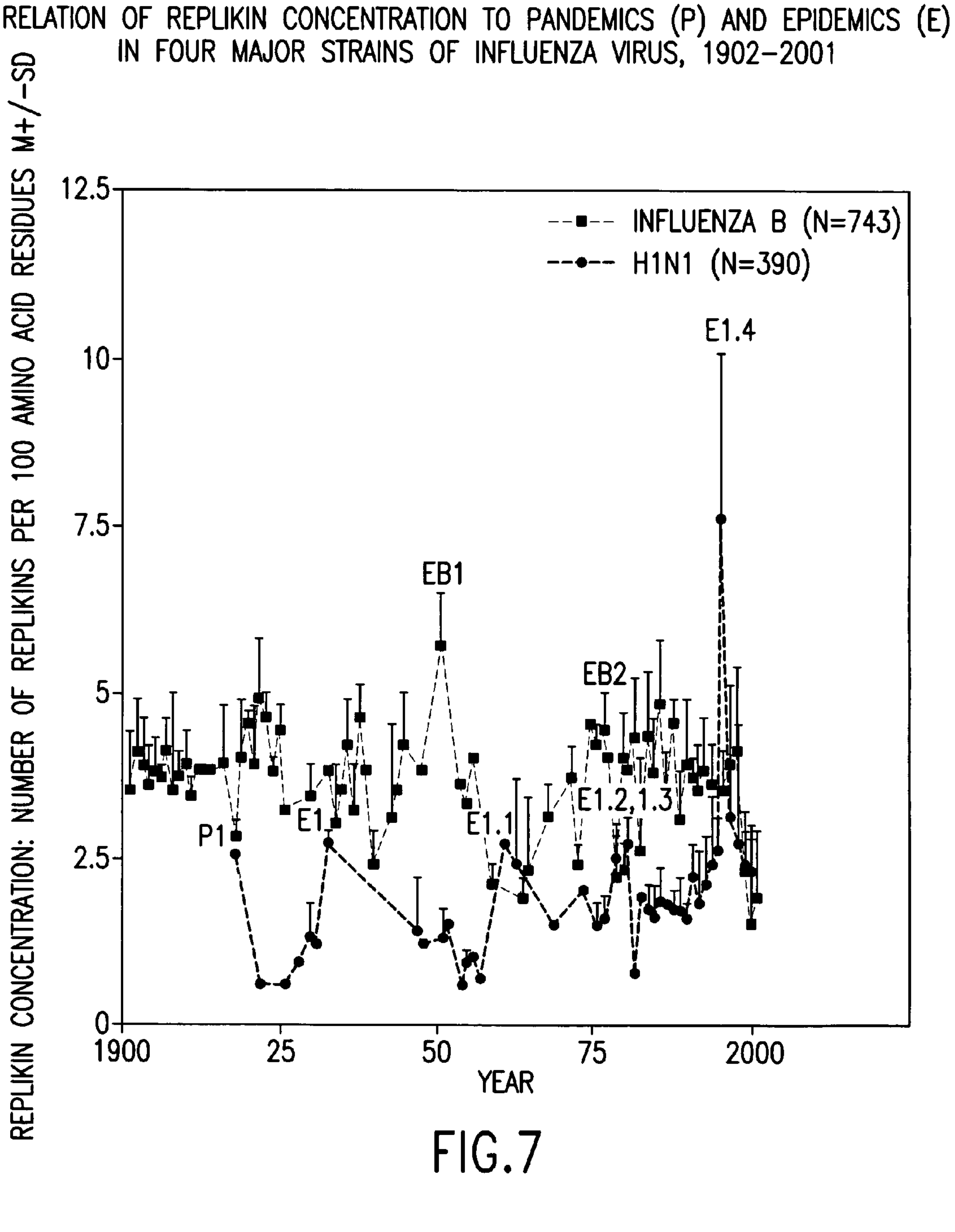
FIG. 7 is a graph showing the concentration of Replikins observed in hemagglutinin of influenza B and influenza A strain, H1N1, on a year by year basis from 1940 through 2001.

| Influenza B Replikins | Year Detected in Influenza B strain Peak in FIG. 7: E |
|---|---|
| **kshfanlk**(SEQ ID NO. 104) | 1940,43,51,59,75,76,77,89,90,93,97,98,99,00,01 |

TABLE 3-continued

| Replikin Sequences present in hemagglutinins of Influenza B viruses in each year for which amino acid sequences were available (1940-2001). Influenza B Replikins Year Detected in Influenza B strain Peak in FIG. 7: E | |
|---|---|
| kshfanlkgtk(SEQ ID NO. 105) | 1940,43,51,59,75,76,77,89,90,93,97,98,99,00,01 |
| kshfanlkgtktrgklcpk(SEQ ID NO. 106) | 1940,43,51,59,75,76,77,89,90,93,97,98,99,00,01 |
| hekyggink(SEQ ID NO. 107) | 1940,43,51,59,75,76,77,89,90,93,97,98,99,00,01 |
| hekygglnksk(SEQ ID NO. 108) | 1940,43,51,59,75,76,77,89,90,93,97,98,99,00,01 |
| hekygglnkskpyytgehak(SEQ ID NO. 109) | 1940,43,51,59,75,76,77,89,90,93,97,98,99,00,01 |
| hakaigncpiwvk(SEQ ID NO. 110) | 1940,43,51,59,75,76,77,89,90,93,97,98,99,00,01 |
| hakaigncpiwvktplklangtk(SEQ ID NO. 111) | 1940,43,51,59,75,76,77,89,90,93,97,98,99,00,01 |
| hakaigncpiwvktplklangtkyrppak(SEQ ID NO. 112) | 1940,43,51,59,75,76,77,89,90,93,97,98,99,00,01 |
| hakaigncpiwvktplklangtkyrppakllk(SEQ ID NO. 113) | 1940,43,51,59,75,76,77,89,90,93,97,98,99,00,01 |
| k(a/v)silhevk(SEQ ID NO. 119) | 1940, 59, 90,93 |
| kvwcasgrskvikgslpligeadclh(SEQ ID NO. 123) | 1940,43, 59,75,76,77,89,90, 98,99,00 |
| kpyytgehak(SEQ ID NO. 124) | 1940, 59, 89,90,93,97,98, 01 |
| hgvavaadlkstqeaink(SEQ ID NO. 128) | 1940, 59, 00 |
| hgvavaadlkstqeainkdtistqeaink(SEQ ID NO. 129) | 1940 |
| hsdneiqmvklygdsk(SEQ ID NO. 116) | |
| hsdneiqdkmvklygdskpqk(SEQ ID NO. 117) | |
| kygglnkskpyytgeh(SEQ ID NO. 122) | |
| kcmgtipsakasilhevk(SEQ ID NO. 125) | 1943, 75,76,77 93 |
| klygdskpqkflssangvtth(SEQ ID NO. 130) | 1943, 75,76,77 93,97, 00 |
| hsdnetqmaklygdskpqk(SEQ ID NO. 131) | 1943, 75,76,77 93 |
| hfanlkgtqtrgk(SEQ ID NO. 132) | 1959 |
| hfanlkgtktrgk(SEQ ID NO. 114) | 1976, 89,90, 99,00,01 |
| hfanlkgtktrgklcpk(SEQ ID NO. 115) | 1976, 90 00,01 |
| kprsalkckgfh (SEQ ID NO. 133) | 1988 |
| kctgtipsakasilhevk (SEQ ID NO. 121) | 1993 |
| hnvinaekapggpyk(SEQ ID NO. 126) | 1993,97, 00 |
| hsdnetqmaklygdsk(SEQ ID NO. 127) | 1993,97, 00 |
| hsdneiqmvklygdskpqk(SEQ ID NO. 118) | 1997,98, 00 |
| kctgtipsakasilh(SEQ ID NO. 120) | 2000 |
| kskpyytgehakai(g/a)ncpiwvk(SEQ ID NO. 134) | 2000 |

1. Influenza B has not been responsible for any human pandemic.
2. Abbreviation for years: e.g., "43" = 1943, "01" = 2001.
3. The first year that a given Replikin appears is indicated at the beginning of the series of years in which that Replikin has been found.
4. Overlapping Replikin sequences are listed separately.
5. Return of replikins, absent for several years, in the two years before the epidemic of 1977, underlined, correlates with increased total Replikin concentration (Replikin Count = number of Replikins per 100 amino acid residues). See FIG. 7.

TABLE 4

HINI Replikin Sequences present in H1N1 hemagglutinins of Influenza viruses in each year for which amino acid sequences were available (1918-2000)
H1N1 Replikin Year Detected in Influenza H1N1 Strain

| Peak in FIG. 7: P1 | E1    E1.1, 1.2, 1.3    E1.4 ) |
|---|---|
| hp(v/i)tigecpkyv(r/k)(s/t)(t/a)k (SEQ ID NO. 135) | 1918,25,28,30,31,35,47,48,51,52,55,56,57,59,63,77,79,80,81,85,87,88,89 91,92,95,96,97,98,99,00 |
| hdsnvknly(e/g)kv(k/r)(n/s)ql(k/r)nnak (SEQ ID NO. 136) | 1918, 28,30,31 77,79,80, 88, 91, 95, 98 |
| hdsnvknly(e/g)kv(k/r)(n/s)qlk (SEQ ID NO. 137) | 1918, 28,30,31 77,79,80, 88, 91, 95, 98 |
| hkc(nn/dd)(a/t/e)cmesv(r/k)ngtydypkyseesklnre(e/k)idgvk (SEQ ID NO. 138) | 1918, 30, 35, 77, 80, 98 |
| hkc(nn/dd)(a/t/e)cmesv(r/k)ngtydypkyseesk (SEQ ID NO. 139) | 1918, 30, 35, 77, 80, 98 |
| hqn(e/g)qgsgyaadqkstqnai(d/n) gitnkvnsviekmntqftavgkefnklek (SEQ ID NO. 140) | 1918, 28,30,31,35, 59, 79, 95 |
| hqn(e/g)qgsgyaadqkstqnai(d/n)gitnkvnsviek (SEQ ID NO. 141) | 1918, 28,30,31,35, 59, 79, 95 |
| hqn(e/g)qgsgyaadqkstqnai(d/n)gitnk (SEQ ID NO. 142) | 1918, 28,30,31,35, 59, 79, 95 |
| kfeifpktsswpnh (SEQ ID NO. 143) | 1918, 77 |
| kg(n/s/t)sypkl(n/s)ksy(v/t)nnkgkevlvlwgvh (SEQ ID NO. 144) | 1918, 35, 77, 96 |
| ksy(v/t)nnkgkevlvlwgvh (SEQ ID NO. 145) | 1918, 35, 77, 96 |
| hkcnnecmesvkngtydypkyseesklnrekidgvk (SEQ ID NO. 146) | 1928, 31, 95 |
| hkcnnecmesvkngtydypkyseesk (SEQ ID NO. 147) | 1928, 31, 95 |
| hkcnnecmesvkngtydypk (SEQ ID NO. 148) | 1928, 31, 95 |
| hkcnnecmesvk (SEQ ID NO. 149) | 1928, 31, 95 |
| hngkssfy(k/r)nllwlt(e/g)knglypnlsksyvnnkek (SEQ ID NO. 150) | 1928, 95, 00 |
| hngkssfy(k/r)nllwlt(e/g)knglypnlsksyvnnk (SEQ ID NO. 151) | 1928, 31, 95, 00 |
| hngkssfy(k/r)nllwlt(e/g)knglypnlsk (SEQ ID NO. 152) | 1928, 31, 95, 00 |

TABLE 4-continued

HINI Replikin Sequences present in H1N1 hemagglutinins of Influenza viruses in each year for which amino acid sequences were available (1918-2000)

| H1N1 Replikin | Year Detected in Influenza H1N1 Strain |
| --- | --- |
| Peak in FIG. 7: P1 | E1    E1.1, 1.2, 1.3    E1.4 ) |
| **h**ng**k**ssfy(**k**/r)nllwlt(e/g)**k** (SEQ ID NO. 153) | 1928, 31, 95, 00 |
| **k**ssfy**k**nllwlte**k**nglypnls**k**syvnn**k**e**k**evlvlwgv**h** (SEQ ID NO. 154) | 1928, 31, 95 |
| **k**nllwlte**k**nglypnls**k**syvnn**k**e**k**evlvlwgv**h** (SEQ ID NO. 155) | 1928, 31, 95 |
| **k**nglypnls**k**syvnn**k**e**k**evlvlwgv**h** (SEQ ID NO. 156) | 1928, 31, 95, 96, 00 |
| **k**sy(v/a)nn**k**e**k**ev(l/-)(v/-)lwgv**h** (SEQ ID NO. 157) | 1928, 31, 51, 95, 96, 98, 00 |
| **k**esswpn**h**tvt**k** (SEQ ID NO. 158) | 1928, 31, 95 |
| **h**et(t/n)**k**gvtaacpyagassfyrnllwlv**kk**ensyp**k**ls**k**syvnn**k** (SEQ ID NO. 159) | 1930, 35 |
| **h**et(t/n)**k**gvtaacpyagassfyrnllwlv**kk**ensyp**k**ls**k** (SEQ ID NO. 160) | 1930, 35 |
| **k**feifp**k**tsswpnevlvlwgv**h** (SEQ ID NO. 161) | 1930 |
| **k**erswp**kh** (SEQ ID NO. 162) | 1947, 51,52,55,56, 79, 82 |
| **k**ls**k**syvnn**k**e**k**evlvlwqv**h** (SEQ ID NO. 163) | 1947, 51 |
| **k**nn**k**e**k**evlvlwqv**h** (SEQ ID NO. 164) | 1947 |
| **h**(**k**/n)(g/q)**k**ssfy(r/**k**)nllwlte**k**ng(l/s) yp(n/t)ls**k**syann**k**e**k** (SEQ ID NO. 165) | 1948, 79, 89, 96 |
| **h**(**k**/n)(g/q)**k**ssfy(r/**k**)nllwlte**k** (SEQ ID NO. 166) | 1948, 79, 89, 96 |
| **h**a**kk**ssfy**k** (SEQ ID NO. 167) | 1951, 57,59 |
| **h**ng**k**lcrl**k**g**k** (SEQ ID NO. 168) | 1951,52,55,56,57,59, 79, |
| **h**y**k**lnn(q/g)**kk** (SEQ ID NO. 169) | 1956, 00 |
| **h**diyrdeainnrfqiqgv**k**ltqgy**k** (SEQ ID NO. 170) | 1956 |
| **k**gngcfeif**hk** (SEQ ID NO. 171) | 1956 |
| **k**lnrlie**k**tnd**k**y**h**qie**k** (SEQ ID NO. 172) | 1956 |

TABLE 4-continued

HINI Replikin Sequences present in H1N1 hemagglutinins of Influenza viruses in each year for which amino acid sequences were available (1918-2000)

| H1N1 Replikin | Year Detected in Influenza H1N1 Strain |
| --- | --- |
| Peak in FIG. 7: P1 | E1 E1.1, 1.2, 1.3 E1.4 ) |
| klnrliektndkyh (SEQ ID NO. 173) | 1956 |
| kchtdkgslsttk (SEQ ID NO. 174) | 1956 |
| kinngdyaklyiwgvh (SEQ ID NO. 175) | 1956 |
| hngklcrkgiaplqlgk (SEQ ID NO. 176) | 1959, 82 |
| hetnrqvtaacpyagansffmliwlvkkessypklsk (SEQ ID NO. 177) | 1963, 81 |
| hetnrqvtaacpyagansffrnliwlvkkessypk (SEQ ID NO. 178) | 1963, 81 |
| hpptstdqqslyqnadayifvgsskynrkfk (SEQ ID NO. 179) | 1963, 81 |
| hpptstdqqslyqnadayifvgsskynrkfkpeia (SEQ ID NO. 180) | 1963, 81 |
| hdiyrdeainnrfqiqgvkitqgyk (SEQ ID NO. 181) | 1977,79, 91 |
| hqneqgsgyaadqkstqnaidgitnkvnsviekmntqflavgk (SEQ ID NO. 182) | 1977 |
| hqneqgsgyaadqkstqnaidgitnkvnsviek (SEQ ID NO. 183) | 1977 |
| hqneqgsgyaadqkstqnaingitnkvnsviekmntqftavgkefnklek (SEQ ID NO. 184) | 1979, 91 |
| hngklcrlkgiaplqlgk (SEQ ID NO. 185) | 1979 |
| hkcnnecmesvk (SEQ ID NO. 186) | 1979 |
| kfeifpkasswpnh (SEQ ID NO. 187) | 1981 |
| hdsnvknlyekvrsqlrnnak (SEQ ID NO. 188) | 1981 |
| kvnsvikkmntqfaavgkefnh (SEQ ID NO. 189) | 1981 |
| khngklck (SEQ ID NO. 190) | 1981 |
| kkgtsypklsksythnkgkevlvlwgvh (SEQ ID NO. 191) | 1981 |
| kgtsypklsksythnkgkevlvlwgvh (SEQ ID NO. 192) | 1981 |
| klsksythnkgkevlvlwgvh (SEQ ID NO. 193) | 1981 |

TABLE 4-continued

H1NI Replikin Sequences present in H1N1 hemagglutinins of Influenza viruses in each year for which amino acid sequences were available (1918-2000)

| H1N1 Replikin | Year Detected in Influenza H1N1 Strain |
|---|---|
| Peak in FIG. 7: P1 | E1  E1.1, 1.2, 1.3  E1.4 ) |
| ksythnkgkevlvlwgvh (SEQ ID NO. 194) | 1981 |
| kgvtascshk (SEQ ID NO. 195) | 1985,87 |
| kgvtascshkgrssfyrnllwlteknglypnlsk (SEQ ID NO. 196) | 1985,87 |
| kgnsypklsksyvnnkekevlvlwgih (SEQ ID NO. 197) | 1988 |
| kefnhlek (SEQ ID NO. 198) | 1988 |
| hpptstdqqslyqnadayvfvgsskynkkfkpeiatrpk (SEQ ID NO. 199) | 1988 |
| hpptstdqqslyqnadayvfvgsskynkkfk (SEQ ID NO. 200) | 1988 |
| hegkssfyrnllwltekegsypklknsyvnk (SEQ ID NO. 201) | 1991 |
| hegkssfyrnllwltekegsypk (SEQ ID NO. 202) | 1991 |
| hkcdnecmesvrngtydypkyseesk (SEQ ID NO. 203) | 1991 |
| kesswpnhtvtk (SEQ ID NO. 204) | 1991,92 |
| knllwlteknglypnlsksyvnnkekeilvlwgvh (SEQ ID NO. 205) | 1991,92, 96 |
| hngkssfy(k/m)(n/-)llwlt(e/g)(-/k)knglypnlsk (SEQ ID NO. 206) | 1991,92, 96, 00 |
| hngkssfyknhlwltek (SEQ ID NO. 207) | 1991,92, 96 |
| htvtkgvtascshngkssfyknllwlteknglypnlsksyvnn kekevlvlwgvh (SEQ ID NO. 208) | 1995 |
| htvt(k/g)gv(t/s)ascshngkssfy(k/m)(n/-)llwlt(e/g)k(-n/k)glypnlsk (SEQ ID NO. 209) | 1995, 00 |
| htvtkgvtascshngkssfyknllwltek (SEQ ID NO. 210) | 1995 |
| kyvrstklrmvtglrnipsiqsrglfgaiagfieggwtgmidgwygyh (SEQ ID NO. 211) | 1995 |
| hqneqgsgyaadqkstqnaingitnkvnsiiekmntqftavgk (SEQ ID NO. 212) | 1995 |
| hqneqgsgyaadqkstqnaingitnkvnsiiek (SEQ ID NO. 213) | 1995 |

TABLE 4-continued

| HINI Replikin Sequences present in H1N1 hemagglutinins of Influenza viruses in each year for which amino acid sequences were available (1918-2000) H1N1 Replikin Year Detected in Influenza H1N1 Strain | | | | |
|---|---|---|---|---|
| Peak in FIG. 7: | P1 | E1 | E1.1, 1.2, 1.3 | E1.4 ) |
| hqneqgsgyaadqkstqnaingitnk (SEQ ID NO. 214) | | | | 1995 |
| hsgarsfyrnllwivkkgnsypk (SEQ ID NO. 215) | | | | 1996 |
| hsgarsfyrnllwivkkgnsypklnk (SEQ ID NO. 216) | | | | 1996 |
| hsgarsfyrnllwivkkgnsypklnksytndk (SEQ ID NO. 217) | | | | 1996 |
| hsgarsfyrnhlwivkkgnsypklnksytndkgk (SEQ ID NO. 218) | | | | 1996 |
| htvskgvttscshngk (SEQ ID NO. 219) | | | | 1996 |
| katswpnbettk (SEQ ID NO. 220) | | | | 1996 |
| kqvttscshnqk (SEQ ID NO. 221) | | | | 1996 |
| kgnsypklnksytndkgkevlviwgvh (SEQ ID NO. 222) | | | | 1996 |
| klnksytndkgkevlviwgvh (SEQ ID NO. 223) | | | | 1996 |
| ksytndkgkevlviwgvh (SEQ ID NO. 224) | | | | 1996 |
| hnqkssfyrnllwlt(e/q)knglypnlsksy(v/a)annkek (SEQ ID NO. 225) | | | | 1997,98,99 |
| hpitigecpkyvrsak (SEQ ID NO. 226) | | | | 1997 |
| hqneqgsgyaadqkstqnaingitnkvnsviekmntqflavgk (SEQ ID NO. 227) | | | | 1998 |
| hqneqgsgyaadqkstqnaingitnkvnsviek (SEQ ID NO. 228) | | | | 1998 |
| hngkssfyrnllwlteknglypnlsksyvnnkek (SEQ ID NO. 229) | | | | 1998 |

1. Influenza H1N1 was responsible for the human pandemic (global distribution) of 1918.
2. Abbreviation for years: eg. "96" = 1996.
3. The first year that a given Replikin appears is indicated at the beginning of the series of years in which that Replikin has been found in this work.
4. Overlapping Replikin sequences are listed separately.
5. Increase in number of new Replikin structures occurs in years of epidemics (underlined): eg. 1918 and 1977 and correlates with increased total Replikin concentration (number of Replikins per 100 amino acid residues). See FIG. 7.

TABLE 5

Replikin Sequences present in hemagglutinins of Influenza H2N2 viruses in years 1957-2000

Figure 8:
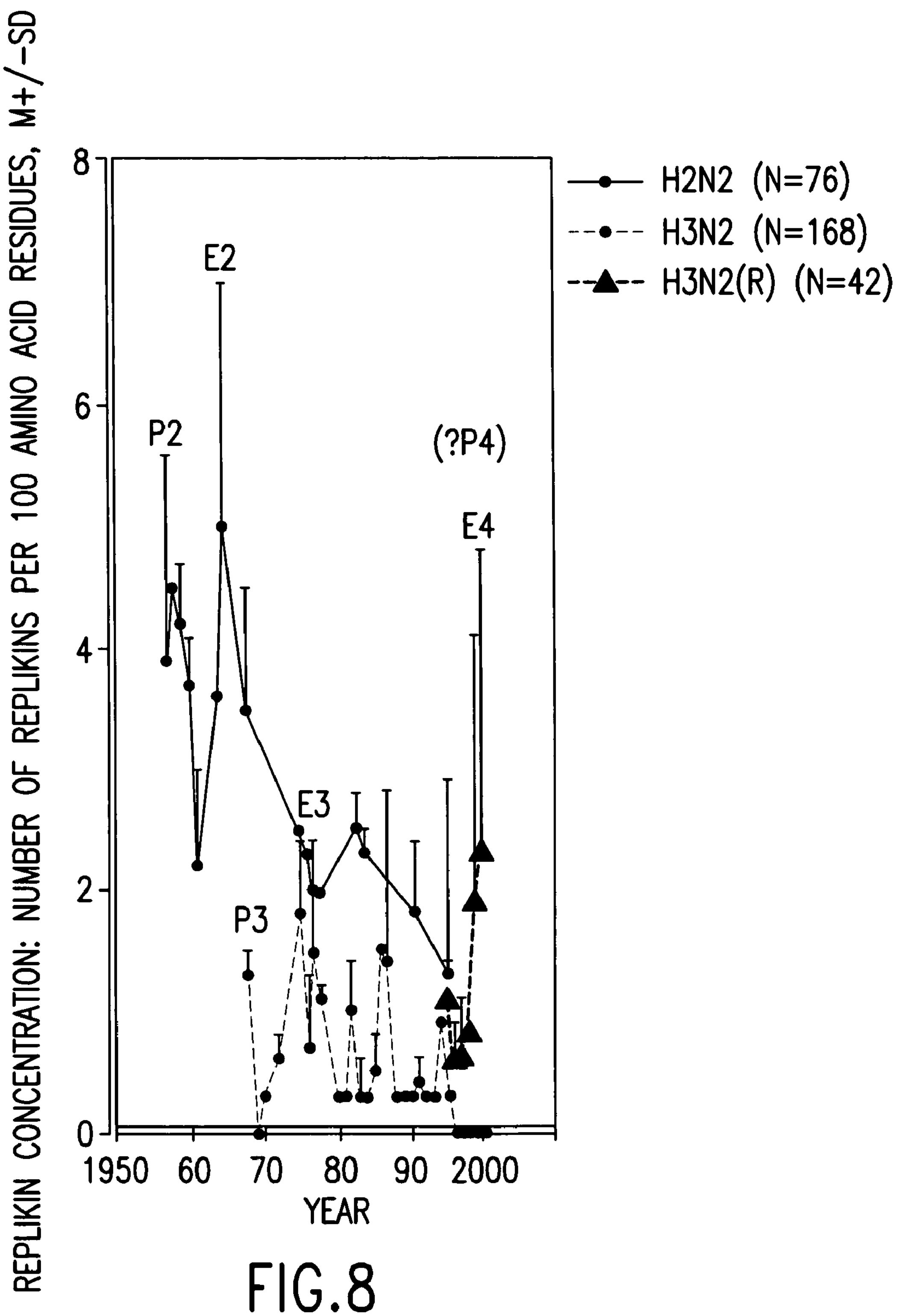
FIG. 8 is a graph of the Replikin concentration observed in hemagglutinin of influenza A strains, H2N2 and H3N2, as well as an emerging strain defined by its constituent Replikins, designated H3N2(R), on a year by year basis from 1950 to 2001.

| Influenza H2N2 Replikins | Year Detected in Influenza H2N2 strain (Peak in FIG. 8: P2 E2 ) |
|---|---|
| khfekvkilpk(SEQ ID NO. 230) | 1957,58,59,60,61,64,65,68, 78,83,84,91 |
| khllssvkhfekvk(SEQ ID NO. 231) | 1957,58,59,60,61, 83,84,91 |
| ha(k/q/m)(d/n)ilekthngk(SEQ ID NO. 232) | 1957,58,59,60,61,64,65,68, 78,83,84,91, 95 |
| ha(k/q/m)(d/n)ilekthngklc(k/r) (SEQ ID NO. 233) | 1957,58,59,60,61,64,65,68, 78,83,84,91, 95 |
| hnvhpltigecpkyvksek(SEQ ID NO. 234) | 1957,58,59, 65,68 |
| hpltigecpkyvksek(SEQ ID NO. 235) | 1957,58,59, 65,68,64,65,68,78,83,84,91 |
| khllssvkhfekvkilpk(SEQ ID NO. 236) | 1957,58,59,60,61,64,65,68, 78 |
| krqssgimktegtlencetkcqtplgainttlpfhnvh(SEQ ID NO. 237) | 1957, 59, 83 |
| kgsnyp(v/i)ak(g/r)synntsgeqmliiwq(v/i)h (SEQ ID NO. 238) | 1957,58,59, 61, 83, 91, 95 |
| httlgqsracavsgnpsffmmvwltekgsnypvak(SEQ ID NO. 239) | 1957 |
| khfekvk(SEQ ID NO. 240) | 1957, 59, 65 |
| kiskrgssgimktegtlencetkcqtplgainttlpfh(SEQ ID NO. 241) | 1957, 59, 65, 91 |
| krgssgimktegtlencetkcqtplgainttlpfh(SEQ ID NO. 242) | 1957, 59, 65, 91 |
| ktegtlencetkcqtplgainttlpfh (SEQ ID NO. 243) | 1957, 59, 65, 91 |
| kiskrgssgimktegtlencetkcqtplgainttlpfh (SEQ ID NO. 244) | 1957, 59, 65, 91 |
| ktegtlencetkcqtplgainttlpfhn(v/i)h(SEQ ID NO. 245) | 1957, 59, 65, 91 |
| kiskrgssgimktegtlencetkcqtplgainttlpfh(SEQ ID NO. 246) | 1957, 59, 65, 91 |
| k(e/g)snypvakgsynntsgeqmliiwgvh(SEQ ID NO. 247) | 1957, 60, 65 |
| hpltigecpkyvksek(SEQ ID NO. 248) | 1957, 60, 65 |
| kcqtplgaikttlpfh(SEQ ID NO. 249) | 1957, 65 |
| hhsndqgsgyaadkestqka(f/i)dgitnkvnsviek- -mntqfeavgklf(n/s)nleklenlnkk(SEQ ID NO. 250) | 1961, 65,68, 83,84 |
| hsndqgsgyaadkestqka(f/i)dgitnkvnsviek- -mntqfeavgklf(n/s)nleklenlnkk(SEQ ID NO. 251) | 1961, 65,68, 83,84 |
| hsndqgsgyaadkestqka(f/i)dgitnk(SEQ ID NO. 252) | 1961, 65,68, 83,84 |
| hdsnvrnlydkvrmqlrdnak(SEQ ID NO. 253) | 1964, 68,76, 84,91 |
| hkcddecmnsvkngtydypklnrneikgvk(SEQ ID NO. 254) | 1964,65,68,76, 83,84,91 |
| hkcddecmnsvkngtydypklnrneik(SEQ ID NO. 255) | 1964,65,68,76, 83,84,91 |
| hkcddecmnsvkngtydypk(SEQ ID NO. 256) | 1964,65,68,76, 83,84,91 |
| hkcddecmnsvk(SEQ ID NO. 257) | 1964,65,68,76, 83,84,91 |
| kgsnypvakgsynntngeqiliiwgvh(SEQ ID NO. 258) | 1976,78 |
| hsndqgsgyaadkestqkavdgitnkvnsviekmntqfeavgk (SEQ ID NO. 259) | 1976, 91 |

TABLE 5-continued

| Replikin Sequences present in hemagglutinins of Influenza H2N2 viruses in years 1957-2000<br>Influenza H2N2 Replikins Year Detected in Influenza H2N2 strain<br>(Peak in FIG. 8: P2 E2 ) | | |
|---|---|---|
| **k**rgssgim**k**tegtlencet**k**cqtplgainttlpf**h** (SEQ ID NO. 260) | 1976,78, | 83,84 |
| **h**pltigecp**k**yv**k**se**k**(SEQ ID NO. 261) | 1976 | |
| **h**a**k**dile**k**thng**k**lc**k**(SEQ ID NO. 262) | 1976 | |

1. Influenza H2N2 was responsible for the human pandemic (global distribution) of 1957.
2. Abbreviation for years: eg. "58" = 1958.
3. The first year that a given Replikin appears is indicated at the beginning of the series of years in which that Replikin has been found in this work.
4. Overlapping Replikin sequences are listed separately.
5. Increase in number of new Replikin structures occurs in years of epidemics (underlined): eg. 1957 and 1965 and correlates with increased total Replikin concentration (number of Replikins per 100 amino acid residues). See FIG. 8.

TABLE 6

| H3N2 Replikin Sequences present in H3N2 hemagglutinins of Influenza viruses in each year for which amino acid sequences were available (1968-2000) Influenza H3N2 Replikins | Year Detected in Influenza H3N2 strain Influenza Replikins (Peak in FIG. 8: P3 E3 E4) |
|---|---|
| **h**dvyrdealnnrfqi**k**gvelksgy**k**(SEQ ID NO. 263) | 1968,72, 75 96,97,98 |
| **h**tidltdsemn**k**lfertr**k**(SEQ ID NO. 264) | 1968 |
| **k**f**h**qie**k**(SEQ ID NO. 265) | 1968,72, 75, 77 96,97,98 |
| **k**tne**k**f**h**(g/q)ie**k**(SEQ ID NO. 266) | 1968 86 98 |
| **k**lnr(v/l)ie**k**tne**k**f**h** (SEQ ID NO. 267) | 1968,72, 75, 77 97,98 |
| **h**qie**k**efsevegriqdle**k**yvedt**k**(SEQ ID NO. 268) | 1968,72, 98 |
| **k**icnnp**hk**(SEQ ID NO. 269) | 1975 |
| **k**lnrvi**kk**tne**k**f**h** (SEQ ID NO. 270) | 1975 |
| **h**d(i/v)yrdealnnrfqi**k**(g/q)ve(r/**k**)s(q/g)y**k** (SEQ ID NO. 271) | 1975,76,77, 86 |
| **h**qie**k**efsevegriqdle**k**yvedt**k**(SEQ ID NO. 272) | 1975 |
| **k**yvedt**k**idlwsynaellvalenq**h**(SEQ ID NO. 273) | 1975 |
| **k**yv**k**qnsl**k**latgmrnvpe**k**qtrglfgaiagfiengwegmidgwygfr**h** (SEQ ID NO. 274) | 1975 |
| **k**efsevegriqdle**k**yvedt**k**idlwsynaellvalenq**h** (SEQ ID NO. 275) | 1975 2000 |
| **h**qn(s/e)(e/q)g(t/s)g(q/y)aad(l/q)**k**- -stq(a/n)a(i/l)d(q/g)I(n/t)(g/n)**k**(l/v)n(r/s)vi(e/c)**k** (SEQ ID NO. 276) | 1975 2000 |
| **h**cd(g/q)f(q,r)ne**k**wdlf(v,/i)er(s/t)**k** (SEQ ID NO. 277) | 1975,76,77,78,80,81,82,83,84,85,86,88,89,90,91,92,93,94,95,96,97,98 |
| **h**tidltdsemn**kk**lfertr**k**(SEQ ID NO. 278) | 1977, |
| **k**sgstypvl**k**vtmpnndnfd**k**lyiwgv**h** (SEQ ID NO. 279) | 1977 |
| **k**lnwlt**k**sgntypvlnvtmpnndnfd**k**lviwgv**h** (SEQ ID NO. 280) | 1982 |
| **h**tidltdsemn**k**lfe**k**tr**k**(SEQ ID NO. 281) | 1986 |

TABLE 6-continued

H3N2 Replikin Sequences present in H3N2 hemagglutinins of Influenza viruses in each year for which amino acid sequences were available (1968-2000)

| Influenza H3N2 Replikins | Year Detected in Influenza H3N2 strain Influenza Replikins (Peak in FIG. 8: P3 E3 E4) |
|---|---|
| klnrliektnekfhqtek(SEQ ID NO. 282) | 1987 |
| htgkssvmrsdapidfcnsecitpnqsipndkpfqnvnkitygacpk (SEQ ID NO. 283) | 1994 |
| htgkssvmrsdapidfcnsecitpnqsipndkpfqnvnk (SEQ ID NO. 284) | 1994 |
| hpstdsdqtslyvrasgrvtvstkrsqqtvipk(SEQ ID NO. 285) | 1994 |
| kyvedtkidlwsynaellvalenqh(SEQ ID NO. 286) | 1997,98 |
| klfertrkqlrenaedmgngcfkiyh(SEQ ID NO. 287) | 1998 |
| krrsiksffsrlnwlh(SEQ ID NO. 288) | 1998 |
| hpvtigecpky(v/r)kstk(SEQ ID NO. 289) | 2000 |
| kgnsypklsklsksyiinkkkevlviwgih (SEQ ID NO. 290) | 2000 |
| klsklsks(v/y)iinkkkevlviwgih (SEQ ID NO. 291) | 2000 |
| klsks(v/y)iinkkkevlviwgih (SEQ ID NO. 292) | 2000 |

1. Influenza H3N2 was responsible for the human pandemic (global distribution) of 1968.
2. Abbreviation for years: eg. "77" = 1977.
3. The first year that a given Replikin appears is indicated at the beginning of the series of years in which that Replikin has been found.
4. Overlapping Replikin sequences are listed separately.
5. Increase in number of new Replikin structures occurs in years of epidemics (underlined): eg. 1975 and correlates with increased total Replikin concentration (number of Replikins per 100 amino acid residues). See FIG 8.

Both the concentration and type, i.e., composition of Replikins observed, were found to relate to the occurrence of influenza pandemics and epidemics. The concentration of Replikins in influenza viruses was examined by visually scanning the hemagglutinin amino acid sequences published in the National Library of Medicine "PubMed" data base for influenza strains isolated world wide from human and animal reservoirs year by year over the past century, i.e., 1900 to 2001. These Replikin concentrations (number of Replikins per 100 amino acids, mean ±SD) were then plotted for each strain.

The concentration of Replikins was found to directly relate to the occurrence of influenza pandemics and epidemics. The concentration of Replikins found in influenza B hemagglutinin and influenza A strain, H1N1, is shown in FIG. 7, and the concentration of Replikins found in the two other common influenza virus A strains, H2N2 and H3N2 is shown in FIG. 8 (H2N2, H3N2). The data in FIG. 8 also demonstrate an emerging new strain of influenza virus as defined by its constituent Replikins (H3N2(R)).

Each influenza A strain has been responsible for one pandemic: in 1918, 1957, and 1968, respectively. The data in FIGS. 7 and 8 show that at least one Replikin per 100 amino acids is present in each of the influenza hemagglutinin proteins of all isolates of the four common influenza viruses examined, suggesting a function for Replikins in the maintenance of survival levels of replication. In the 1990s, during the decline of the H3N2 strain, there were no Replikins in many isolates of H3N2, but a high concentration of new Replikins appeared in H3N2 isolates, which define the emergence of the H3N2(R) strain.

Several properties of Replikin concentration are seen in FIG. 7 and FIG. 8 to be common to all four influenza virus strains. First, the concentration is cyclic over the years, with a single cycle of rise and fall occurring over a period of two to thirty years. This rise and fall is consistent with the known waxing and waning of individual influenza virus strain predominance by hemagglutinin and neuraminidase classification. Second, peak Replikin concentrations of each influenza virus strain previously shown to be responsible for a pandemic were observed to relate specifically and individually to each of the three years of the pandemics. For example, for the pandemic of 1918, where the influenza virus strain, H1N1, was shown to be responsible, a peak concentration of the Replikins in H1N1 independently occurred (P1); for the pandemic of 1957, where H2N2 emerged and was shown to be responsible, a peak concentration of the Replikins in H2N2 occurred (P2); and for the pandemic of 1968, where H3N2 emerged and was shown to be the cause of the pandemic, a peak concentration of the Replikins in H3N2 occurred (P3). Third, in the years immediately following each of the above three pandemics, the specific Replikin concentration decreased markedly, perhaps reflecting the broadly distributed immunity generated in each case. Thus, this post-pandemic decline is specific for H1N1 immediately following the pandemic (P1) for which it was responsible, and is not a general property of all strains at the time. An increase of Replikin concentration in influenza B repeatedly occurred simultaneously with the decrease in Replikin concentration in H1N1, e.g., EB1 in 1951 and EB2 in 1976, both associated with influenza B epidemics having the highest mortality. (Stuart-Harris, et al., Edward Arnold Ltd. (1985). Fourth, a secondary peak concentration, which exceeded the primary peak increase in concentration, occurred 15 years after each of the three pandemics, and this secondary peak was accompanied by an epidemic: 15 years after the 1918 pandemic in an H1N1 'epidemic' year (E1); eight years after the 1957 pandemic in an H2N2 'epidemic' year (E2); and occurred seven years after the 1968 pandemic in an H3N2 'epidemic' year (E3). These secondary peak concentrations of specific Replikins may reflect recovery of the strain. Fifth, peaks of each strain's specific Replikin concentration frequently appear to be associated with declines in Replikin concentration of one or both other strains, suggesting competition between strains for host sites. Sixth, there is an apparent overall tendency for the Replikin concentration of each strain to decline over a period of 35 years (H2N2) to 60 years (influenza B). This decline cannot be ascribed to the influence of vaccines because it was evident in the case of influenza B from 1940 to 1964, prior to common use of influenza vaccines. In the case of influenza B, Replikin recovery from the decline is seen to occur after 1965, but Replikin concentration declined again between 1997 and 2000 (FIG. 7). This correlates with the low occurrence of influenza B in recent case isolates. H1N1 Replikin concentration peaked in 1978-1979 (FIG. 7) together with the reappearance and prevalence of the H1N1 strain, and then peaked in 1996 coincident with an H1N1 epidemic. (FIG. 7). H1N1 Replikin concentration also declined between 1997 and 2000, and the presence of H1N1 strains decreased in isolates obtained during these years. For H2N2 Replikins, recovery from a 35 year decline has not occurred (FIG. 8), and this correlates with the absence of H2N2 from recent isolates. For H3N2, the Replikin concentration of many isolates fell to zero during the period from 1996 to 2000, but other H3N2 isolates showed a significant, sharp increase in Replikin concentration. This indicates the emergence of a substrain of H3N2, which is designated herein as H3N2(R).

FIGS. 7 and 8 demonstrate that frequently, a one to three year stepwise increase is observed before Replikin concentration reaches a peak. This stepwise increase proceeds the occurrence of an epidemic, which occurs concurrently with the Replikin peak. Thus, the stepwise increase in concentration of a particular strain is a signal that particular strain is the most likely candidate to cause an epidemic or pandemic.

Currently, Replikin concentration in the H3N2(R) strain of influenza virus is increasing (FIG. 8, 1997 to 2000). Three similar previous peak increases in H3N2 Replikin concentration are seen to have occurred in the H3N2-based pandemic of 1968 (FIG. 8), when the strain first emerged, and in the H3N2-based epidemics of 1972 and 1975 (FIG. 8). Each of these pandemic and epidemics was associated with excess mortality. (Ailing, et al., Am J. Epidemiol., 113(1):30-43 (1981). The rapid ascent in concentration of the H3N2(R) subspecies of the H3N2 Replikins in 1997-2000, therefore, statistically represents an early warning of an approaching severe epidemic or pandemic. An H3N2 epidemic occurred in Russia in 2000 (FIG. 8, E4); and the CDC report of December 2001 states that currently, H3N2 is the most frequently isolated strain of influenza virus worldwide. (Morbidity and Mortality Weekly Reports (MMWR), Center for Disease Control; 50(48):1084-68 (Dec. 7, 2001).

In each case of influenza virus pandemic or epidemic new Replikins emerge. There has been no observation of two of the same Replikins in a given hemagglutinin in a given isolate. To what degree the emergence of a new Replikin represents mutations versus transfer from another animal or avian pool is unknown. In some cases, each year one or more of the original Replikin structures is conserved, while at the same time, new Replikins emerge. For example, in influenza virus B hemagglutinin, five Replikins were constantly conserved between 1919 and 2001, whereas 26 Replikins came and went during the same period (some recurred after several years absence). The disappearance and re-emergence years later of a particular Replikin structure suggests that the Replikins return from another virus host pool rather than through de novo mutation.

In the case of H1N1 Replikins, the two Replikins present in the P1 peak associated with the 1918 pandemic were not present in the recovery E1 peak of 1933, which contains 12 new Replikins. Constantly conserved Replikins, therefore, are the best choice for vaccines, either alone or in combination. However, even recently appearing Replikins accompanying one year's increase in concentration frequently persist and increase further for an additional one or more years, culminating in a concentration peak and an epidemic, thus providing both an early warning and time to vaccinate with synthetic Replikins (see for example, H1N1 in the early 1990's, FIG. 7; see also, for example, H5N1 1995-2002, FIG. 11, "Replikin Count" (number of Replikins per 100 amino acids) refers to Replikin concentration).

Figure 11:
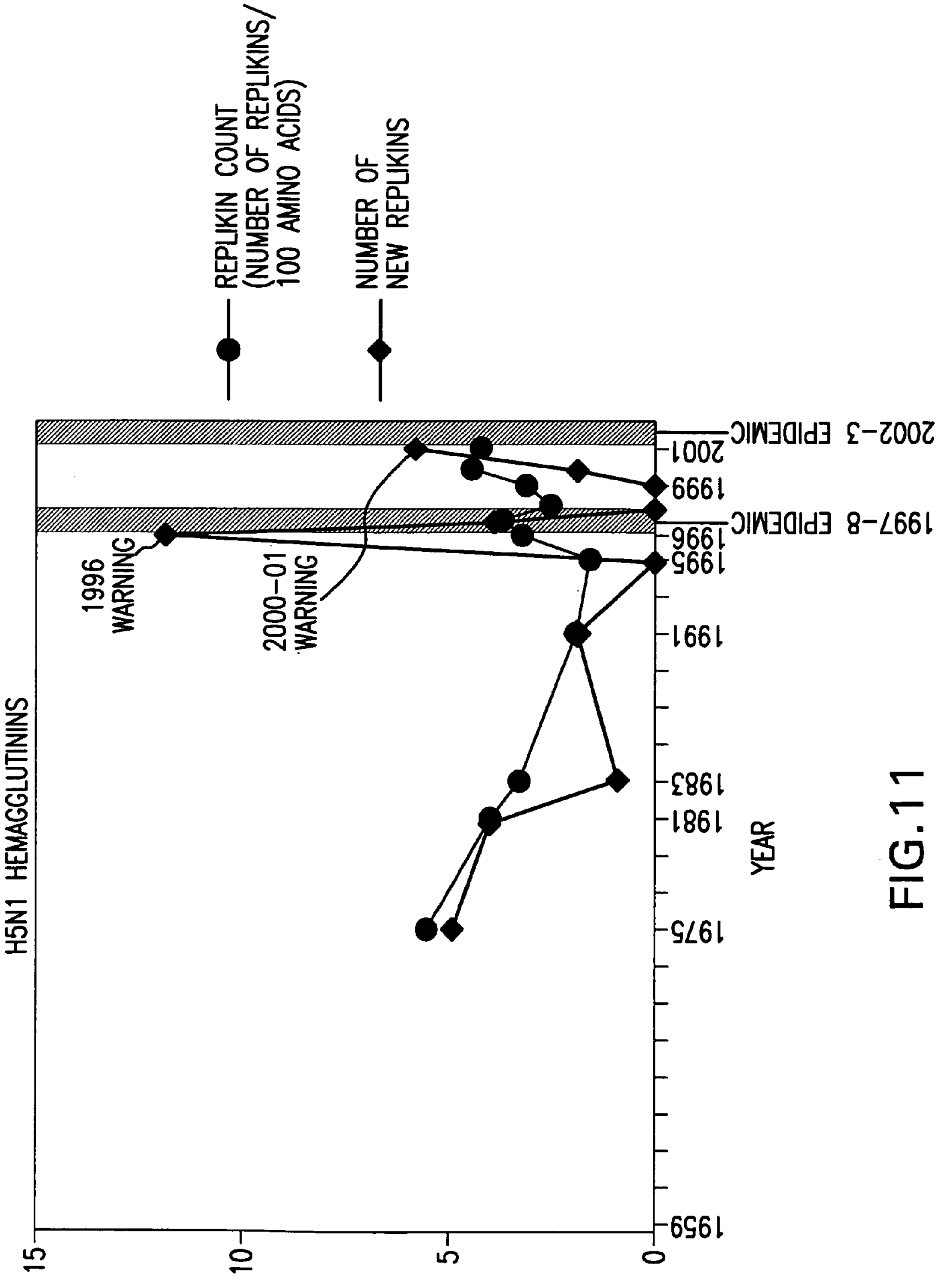
FIG. 11 is a chart depicting the Replikin count per year for H5N1 Hemagglutinins.

The data in FIGS. 7, 8 and 11 demonstrate a direct relationship between the presence and concentration of a particular Replikin in influenza protein sequences and the occurrence of pandemics and epidemics of influenza. Thus, analysis of the influenza virus hemagglutinin protein sequence for the presence and concentration of Replikins provides a predictor of influenza pandemics and/or epidemics, as well as a target for influenza vaccine formulation. It is worth nothing again (see paragraph [0109]) with reference to this data, previously, no strain-specific chemical structures were known with which to predict the strains that would predominate in coming influenza seasons, nor to devise annual mixtures of whole-virus strains for vaccines.

Similar to the findings of strain-specific Replikin Count increases in the influenza group one to three years prior to the occurrence of a strain-specific epidemics, the increase in Replikin Count of the coronavirus nucleocapsid protein has also been identified. Replikin Counts of the coronavirus nucleocapsid protein has increased as follows: 3.1 (±1.8) in 1999; 3.9(±1.2) in 2000; 3.9 (±1.3) in 2001; and 5.1 (±3.6) in 2002. This pre-pandemic increase supports the finding that a coronavirus is responsible for the current (2003) SARS pandemic. (See Table 7)

Thus, monitoring Replikin structure and Replikin Count provides a means for developing synthetic strain-specific preventive vaccination and antibody therapies against the 1917-1918 Goose Replikin and its modified and accompanying Replikins as observed in both influenza and coronavirus strains.

Figure 9:
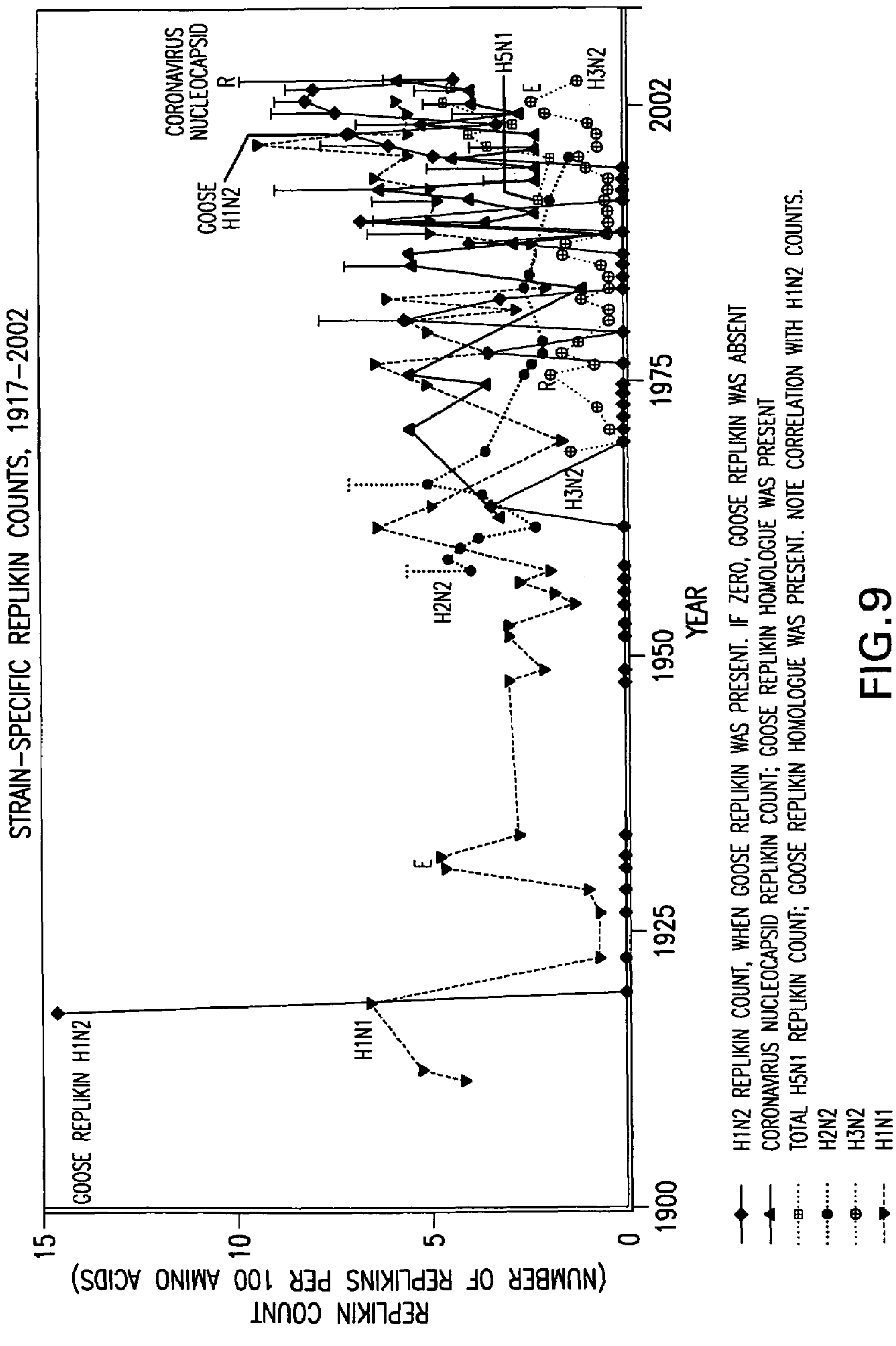
FIG. 9 is a graph depicting the Replikin count per year for specific Replikin strains.

FIG. 10 depicts the automated Replikin analysis of nucleocapsid coronavirus proteins for which the protein sequence is available on isolates collected from 1962 to 2003. Each individual protein is represented by an accession number and is analyzed for the presence of Replikins. The Replikin Count (number of Replikins per 100 amino acid) is automatically calculated as part of the automated Replikin analysis. For each year, the mean (± Standard deviation (S.D.)) Replikin Count per year is automatically calculated for all Replikin Counts that year. This example of early warning of increasing replication, before an epidemic, of a particular protein (the nucleocapsid protein) in a particular virus strain (the coronavirus) is comparable to the increase seen in strains of influenza virus preceding influenza epidemics and pandemics (FIGS. 7, 8 and 11). It may be seen that the Replikin Count rose from 1999 to 2002, consistent with the SARS coronavirus pandemic, which emerged at the end of 2002 and has persisted into 2003. FIG. 9 provides a graph of the Replikin Counts for several virus strains, including the coronavirus nucleocapsid Replikin, from 1917 to 2002.

TABLE 7

| Replikin Sequence | 'Multi-K' Replikins: Length | % Untreated Mortality | ORGANISM |
|---|---|---|---|
| 1 2 3 4 5 6 7 8 9 10 11 12 13 14 15 16 17 18 19 20 21 22 23 24 25 26 27 28 29 | | | Amino Acid position |
| A. INFLUENZA, SARS AND OTHER CORONAVIRUSES | | | |
| **k** **k** g t s y p **k** l s **k** s y t n n **k** g **k** e v l v l w g v **h** **h** | 29 | | 1917-18 Goose Replik in (SEQ ID NO. 743) |
| **k** **k** g t s y p **k** l s **k** s y t n n **k** g **k** e v l v l w g v **h** **h** | 29 | 2.5 | 1918 Human Influenza (SEQ ID NO. 744) |
| l **k** e d l y p **k** l r **k** s v v **h** n **k** **k** **k** e v l v l w g i **h** **h** | 29 | | 1919-2001 H1N1, H1N2 (SEQ ID NO. 745) |
| l **k** e n s y p **k** l r **k** s i i i n **k** **k** **k** e v l v l w g i **h** **h** | | | H3N2 Influenza (SEQ ID NO. 746) |
| **k** **k** g t s y p **k** l s **k** s y t n n **k** **k** **k** e v l v l w g v **h** **h** | 29 | | 2001 H1N2 Influenza (SEQ ID NO. 747) |
| **k** **k** n s a y p t l **k** r s y n n t n q e d l l v l w g i **h** **h** | >37 | | 1996-2001 H5N1 Influenza (SEQ ID NO. 748) |
| **k** **k** s a **k** t g t p **k** p s r n q s p a s s q t s a **k** s l a **h** | >37 | | 2000 Human coronavirus 229E (SEQ ID NO. 794)[1] |
| **k** **k** l g v d t e **k** q q q r s **k** s **k** e r s n s **k** t r d t t p | >37 | | 2003 Cancine coronavirus (SEQ ID NO. 795)[2] |
| **k** n g l y p n l s **k** s y a n n **k** e **k** e v l i l w g v **h** **h** | 28 | | 2002 H1N2 (SEQ ID NO. 749) |
| **k** **k** i n s p q p **k** f e g s g v p d n e n l **k** t s q q **h** | 27 | | Avian bronchitis coronavirus (SEQ ID NO. 715) |

TABLE 7-continued

| Replikin Sequence | 'Multi-K' Replikins: Length | % Untreated Mortality | ORGANISM |
|---|---|---|---|
| **k** t g n a **k** l q r **k k** e **k k** n **k** r e t t l q q **h** | 24 | | Porcine epidemic diarrhea coronavirus (SEQ ID NO. 716) |
| **k h** l d a y **k** t f p p t e p **k k** d **k k k k** | 21 | | 2003 Human SARS nucleocapsid (SEQ ID NO. 712) |
| **k h** r e f v f **k** n **k** d g f l y v y **k** | 19 | | 2003 Human SARS spike protein (SEQ ID NO. 717) |
| **k** e e l d **k** y f **k** n **h** | 11 | | 2003 Human SARS spike protein (SEQ ID NO. 718) |
| **k** y r y l r **h** g **k** | 9 | | 2003 Human SARS spike protein (SEQ ID NO. 719) |
| **k k** g a **k** l l **h k** | 9 | 55 | 2003 SARS envelope protein (SEQ ID NO. 720) |
| **k h** l d a y **k** | 7 | 55 | 2003 Human SARS nucleocapsid protein (SEQ ID NO. 796) |
| B. OTHER VIRUSES, BACTERIA, MALARIA AND CANCER REPLIKINS | | | |
| **h** l v c g **k k** g l g l s g r **k k** | 19 | | HIV-TAT (SEQ ID NO. 613) |
| **k k** i t n i t t **k** f e q l e **k** c c **k h** | 19 | | Monkeypox virus (SEQ ID NO. 721) |
| **k k** l **k k** s l **k** l l s f y **h** p **k k** | 17 | | African swine fever virus (SEQ ID NO. 722) |
| **k** n r i e r l **k k** e y s s t w **h** | 16 | | West Nile Virus (SEQ ID NO. 723) |
| **k** s r g i p i **k k** g **h** | 11 | | Nipah virus, v-protein (SEQ ID NO. 724) |
| **k** s r i m p i **k k** g **h** | 11 | | Hendra virus, V-protein (SEQ ID NO. 725) |
| **k k** f l n q f **k hh** | 10 | | Sindbis virus (SEQ ID NO. 726) |
| **k k k** s **k k hk** d **k** | 10 | | EEL Leukemia (SEQ ID NO. 85) |
| **k h h**p **k** d n l i **k** | 10 | | BRCA-1 Breast cancer (SEQ ID NO. 81) |
| **k h k** r **k k** f r q **k** | 10 | | Ovarian cancer (SEQ ID NO. 84) |
| **k** a g v a f l **h k k** | 10 | >90% | Glioma Replikin (SEQ ID NO. 83) |
| **k** i **h**l i s v **k k** | 9 | | Smallpox virus (SEQ ID NO. 727) |
| **k** l i s i **h** e **k** | 8 | | Smallpox virus (SEQ ID NO. 728) |
| **k** l r e e **h** e **k** | 8 | | *B. anthracis*, HATPase (SEQ ID NO. 729) |
| **k h k k** g i v **k** | 8 | | Plasm. Falciparum ATPase (SEQ ID NO. 750) |
| **k k h**a t v l **k** | 8 | >90% | Ebola virus polymerase (SEQ ID NO. 730 |
| **k k** e d d e **k h** | 8 | | *P. falciparum* blood trophozoites (SEQ ID NO. 408) |
| **k h k** e **k** m s **k** | 8 | >90% | (K-RAS 2B) lung cancer (SEQ ID NO.731) |

TABLE 7-continued

| Replikin Sequence | 'Multi-K' Replikins: Length | % Untreated Mortality | ORGANISM |
|---|---|---|---|
| **k k l r he k** | 7 | | Rous sarcoma virus (SEQ ID NO. 48) |
| **k k l r he k** | 7 | | c-src, colon, breast cancer (SEQ ID NO. 52) |
| **k k l r h d k** | 7 | | c-yes, melanoma, colon cancer (SEQ ID NO. 50) |

[1] Human coronavirus 229E 2000, SEQ ID NO. 873: kksaktgtpkpsrnqspassqtsakslarsqssetkeqkh

[2] Canine coronavirus 2003, SEQ ID NO. 874: kklgvdtekqqqrsrskskersnsktrdttpknenkh SARS and H3N2-Fujian Influenza Virus Replikins Traced Back to a 1918 Pandemic Replikin The origin of the SARS virus is as yet unknown. We report evidence that certain SARS virus peptides can be traced back through homologous peptides in several strains of influenza virus isolates from 2002 to a sequence in the strain of the 1918 influenza pandemic responsible for the deaths of over 20 million people.

By quantitative analysis of primary protein sequences of influenza virus and other microorganisms recorded through the last century we have found a new class of peptide structures rich in lysines and histidine, related to the phenomenon of rapid replication itself and to epidemics, rather than to the type of organism (eg. Table 1) and named them Replikins. We have found a new class of peptide structures with the following obligatory algorithm: at least two lysines 6 to 10 residues apart, lysine concentration 6% or greater, one histidine, in 7 to 50 amino acids. Because these peptides relate to the phenomenon of rapid replication itself and to epidemics, we named them Replikins. We have found a quantitative correlation of strain-specific replikin concentration (replikin count=number of replikins per 100 amino acids) in the hemagglutinin protein with influenza epidemics and pandemics (FIG. 7). No previous correlation of influenza epidemics with strain-specific viral protein chemistry have been reported. Conservation, condensation and concentration of replikin structure also has been found in influenza (eg. in Table 7a), HIV and malaria. The detection of replikins in SARS coronavirus, in addition to tracing its possible evolution, has permitted the synthesis of small SARS antigens for vaccines.

We have found a quantitative correlation of strain-specific replikin concentration (count) in the influenza hemagglutinin proteins with influenza epidemics and with each of the three pandemics of the last century, in 1918, 1957, and 1968. A similar course was observed for each of these three pandemics: after a strain-specific high replikin count, an immediate decline followed, then a 'rebound' increase with an accompanying epidemic occurred. Also, a 1 to 3 year warning increase in count preceded most epidemics.

We found that the replikin in the hemagglutinin of an influenza virus isolated from a goose in 1917 (which we named the Goose Replikin) appeared in the next year in the H1N1 strain of influenza responsible for the 1918 pandemic, with only two substitutions as follows: kkg(t/s)sypklsksy(t/v)nnkgkevlvlwgvhh (SEQ ID NO: 830). Table 7a shows that the influenza 1917 Goose Replikin (GR) then was essentially conserved for 85 years, despite multiple minor substitutions and apparent translocations to other influenza strains. We have found that the 1917 influenza GR demonstrated apparent mobility between several influenza strains, appearing in H1N1 (the pandemic of 1918), in H2N2 (pandemic of 1957-58), in H3N2 (pandemic of 1968, epidemic in China and Russia 2000, Fujian strain epidemic 2003) and in H5N1 (epidemic in China 1997). In 1997 its structure was restored in H1N2 exactly to its 1918 structure kkgssypklsksyvnnkgkevlvlwgvhh (SEQ ID NO: 832).

The SARS coronavirus first appeared in the 2002-2003 influenza season. The dual origin in 2002 of SARS replikins, from influenza GR and coronavirus replikins (or from some unknown shared precursor) is suggested by the following events, all of which occurred in 2002: 1) a condensation for the first time in 85 years is seen in the GR-H1N2 Replikin sequence from 29 to 28 amino acids (Table 7a)(A similar condensation was found in H3N2 Fujian from 29 to 27 amino acids in the current epidemic (Table 7a)); 2) the replikin count of GR-H1N2 showed a marked decline consistent with GR moving out of H1N2; 3) the replikin count of coronavirus nucleocapsid proteins showed a marked increase; and 4) SARS coronavirus appeared in 2002-2003 with replikins containing the following motifs: 'kkg' and 'k-k', previously seen in GR 1918 and GR-H1N2 2001; 'k-kk', 'kk' and 'kl' seen in influenza GR-H1N2 2001; 'kk' seen in the avian bronchitis coronavirus replikin; and 'kk-kk-k', 'k-k', 'kk', 'kl' and 'kt' seen in the replikin of porcine epidemic diarrhea coronavirus (Table 7a) (SARS is believed to have made its first appearance in humans as the epidemic pneumonia which erupted in a crowded apartment house where there was a severe back-up of fecal sewage, which was then airborne by ventilating fans).

TABLE 7a

Goose Replikin (GR) sequences in different influenza strains from 1917 to 2003; SARS and H3N2-Fujian appearance 2002-2003.

| | SEQ. ID NO. | | |
|---|---|---|---|
| kkgtsypklsksytnnkgkevlvlwgvhh | 831 | 29 | 1917 H1N_Influenza Goose Replikin (GR) |
| kkgssypklsksyvnnkgkevlvlwgvhh | 832 | 29 | 1918 GR in H1N1Human Influenza |
| kkgsnypvakgsynntsqeqmliiwgvhh | 875 | 29 | 1958 GR H2N2 Infuenza |
| kkgpnypvakgsynntsqeqmliiwgvhh | 867 | 29 | 1964, 1965, 1968 GR in H2N2 infuenza |
| kkgtsypklsksytnnkgkevlvlwgvhh | 833 | 29 | 1976, '77, '80, '81, '85 GR in H1N1 Influenza |
| kknsayptikrsynntnqedllvlwgihh | 834 | 29 | 1996-2001 GR in H5N1 Influenza |
| kkgdsypklsksytnnkgkevlvlwgvhh | 868 | 29 | 1996 GR in H1N1 Influenza |
| kkgssypklsksyvnnkgkevlvlwgvhh | 869 | 29 | 1997, 1998 GR in H1N1 Influenza |
| kkgnsypklsksyinnkekevlvlwgihh | 870 | 29 | 1999 GR in H1N2 Influenza |
| kkgnsypklsksyinnkkkevlvlwgihh | 871 | 29 | 2000 GR in H1N2 Influenza |
| kkgnsypklsksyinnkgkkvlwgihh | 872 | 29 | 2001 GR in H1N2 Influenza |
| kkgtsypklsksytnnkkkevlvlwgvhh | 835 | 29 | 2001 GR in H1N2 Influenza |
| knglypnlsksyannkekevlilwgvhh | 836 | 28 | 2002 GR in H1N2 Influenza (condensed) |
| khldayktfpptepkkdkkkk | 837 | 21 | 2002-3 Human SARS nucleocapsid protein |
| kkensypklrksiiihkkkevlvlwgihh | 751 | 29 | 1968-2001 GR in H3N2 Influenza (complete) |
| kleykypalnvtmpnndkfdklyiwgvhh | 752 | 29 | 1996 H3N2 Fujian Influenza (incomplete) |
| kykypalnvtmpnnekfdklyiwgvhh | 753 | 27 | 2003 H3N2 Fujian(condensed, incomplete) |
| ktgnaklqrkkekknkrettlqqh | 838 | 24 | Porcine epidemic diarrhea coronavirus |
| kkinspgpkfegsgvpdnenlktsqqh | 839 | 27 | Avian bronchitis coronavirus |
| kknvkksakqlphlkvlldvrgakqlph | 754 | 27 | 2000 shrimp white spot syndrome virus |
| kkinspgpkfegsgvpdnenlktsqqh | 840 | 27 | Avian bronchitis coronavirus |
| khlrefvfknkdgflyvykk | 755 | 20 | 2002-3 Human SARS spike protein |
| kkgakllhkpivwh | 756 | 14 | 2002-3 Human SARS nucleocapsid protein |
| khlrefvfknkdgflyvykk | 841 | 20 | 2002-3 Human SARS spike protein |
| kkgakllhkpivwh | 842 | 14 | 2002-3 Human SARS nucleocapsid protein |
| keeldkyfknh | 843 | 11 | 2002-3 Human SARS spike protein |
| kkgakllhk | 844 | 9 | 2002-3 Human SARS envelope protein |
| kyrylrhgk | 845 | 9 | 2002-3 Human SARS spike protein |
| khldayk | 846 | 7 | 2002-3 Human SARS nucleopcapsid protein |
| kargipikkgh | 847 | 11 | Nipah virus, v-protein |
| ksrimpikkgh | 848 | 11 | Hendra virus, v-protein |
| kkflnqfkhh | 849 | 10 | Sindbis virus |
| kkkskkhkdk | 850 | 10 | EEL leukemia |
| khhpkdnlik | 851 | 10 | BRCA-1 breast cancer |
| khkrkkfkqk | 852 | 10 | Ovarian Cancer |
| kagvaflhkk | 853 | 10 | Glioma Replikin |
| kihlisvkk | 854 | 9 | Smallpox virus |
| krfilhakk | 855 | 9 | HIV TAT protein |
| klisihek | 856 | 8 | Smalpox virus |
| klreehck | 857 | 8 | B.anthracis, HATPase |
| kkhatvlk | 858 | 8 | Ebola virus polymerase |

Replikins related to the Goose Replikin:
Continuous amino acid sequences
Shared motif and/or position–shaded Amino acid substitutions-clear background
'Condensed' indicates condensation of acids)
sequence length in H1N2 and H3N2-Fujian
Replikin Virus or other organism Length containing replikin
(Number (Complete replikins of amino except for Fujian strain)

The recent increasingly high replikin count peaks of the 1917 Goose Replikin (FIG. 7), now in H1N2 (Table 7a), approaching the 1917 replikin count, could be a warning of a coming pandemic which may already have begun since the SARS virus and the H3N2-Fujian virus are the current carriers of the short replikin derivatives of the Goose Replikin seen in Table 7 and 7a to be associated with high mortality.

Since the Goose Replikin has at least an 85 year history involving most or all of the A-strains of influenza and SARS, it and its components are conserved vaccine candidates for pan-strain protection. Condensed short SARS replikins, 7 to 21 amino acids long, enriched in % lysine and histidine compared to the Goose Replikin, occurred in association with the higher mortality rate of SARS (10-55%) when compared to that (2.5%) of the Goose Replikin, 29 amino acids long. Short replikins here mixed with long replikins in SARS may be responsible for high mortality. This is also the case for replikins of other organisms such as the ebola and smallpox viruses and anthrax bacteria (Table 7a). These short SARS replikins showed surprising homology with short replikins of other organisms such as smallpox, anthrax, and ebola which are associated with even higher untreated mortality rates (Table 7a).

Short synthetic vaccines, besides being much more rapidly produced (days rather than months), and far less expensive, should avoid the side effects attendant on the contamination and the immunological interference engendered by multiple epitopes of thousands of undesired proteins in current whole virus vaccines in general. In any case for influenza, current whole virus vaccines are ineffective in more than half of the elderly. But would short replikins be sufficiently immunogenic? The short glioma replikin 'kagvaflhkk' (SEQ ID NO: 1) proved to be a successful basis for a synthetic anti-glioblastoma multiforme and anti-bronchogenic carcinoma vaccine. It produced anti-malignin antibody, which is cytotoxic to cancer cells at picograms/cell and relates quantitatively to the survival of cancer patients. In order to prepare for a recurrent SARS attack, which appears likely because of the surge we found in the coronavirus nucleocapsid replikin count in 2002, We synthesized four SARS short replikins, found in nucleocapsid, spike, and envelope proteins. We found that these synthetic short SARS replikins when injected into rabbits also produced abundant specific antibody. For example, the 21 amino acid SARS nucleocapsid replikin antibody binds at dilutions greater than 1 in 204,800. Because of previous unsuccessful attempts by others to achieve with various small peptides a strong immune response without the unwanted side effects obtained with a whole protein or the thousands of proteins or nucleic acids as in smallpox vaccine, the ability of small synthetic replikin antigens to achieve strong immune responses is significant for the efficacy of these SARS vaccines.

We examined the relationship of Replikin structure in influenza and SARS viruses to increased mortality, with results as shown in Table 7. The relation of high mortality to short or condensed Replikin sequences is seen in the high mortality organisms shown in Section B of Table 7, in viruses other than influenza and SARS, and in bacteria, malaria and cancer. In support of the unifying concept of Replikin structure and of the relation of Replikins to rapid replication rather than any cell type or infectious organism, in addition to the prevalence of the basic Replikin structure in a broad range of viral, bacterial, malarial and cancer organisms in which replication is crucial to propagation and virulence, the following homologous sequences have been observed: note the "k"s in positions 1 and 2, note the alignment of "k"s as they would present to DNA, RNA or other receptor or ligand for incorporation or to stimulate rapid replication, note the frequency of "double k"s and "multiple k"s, note the frequency of "g" in position 3 and the occurrence of the triplets "kkg", "hek", "hdk" and "hkk" in the most condensed shortened Replikins associated with the highest mortality organisms, cancer cells and genes as diverse as the smallpox virus, the anthrax virus, Rous sarcoma virus and glioblastome multiforme (glioma), c-src in colon and breast cancer, and c-yes in melanoma and colon cancer. Note also the almost identical Replikin structure for two recently emerging high mortality viruses in Australia and Southeast Asia, Nipah and Hendrah viruses. These two viruses are reported to have similar or identical antibodies formed against them but no structural basis has been known for this up till now, with our finding of their two almost identical Replikins, for this similar antibody. Table 7 also shows the relationship of five SARS Replikins of 2003 which we have found both to the influenza Goose Replikin of 1917 and to two coronaviruses, the avian bronchitis coronavirus and the porcine epidemic diarrhea virus. The first 2003 human SARS Replikin in Table 7 shows certain sequence homologies to the influenza virus goose 1917 and human 1918 Replikins through an intermediary structure of influenza H1N2 in 2002 (e.g., see Replikin "k" in positions 1, 18 and 19). The 1917 Goose Replikin sequence is seen in Table 7 to have been largely conserved despite many substitutions in amino acids which are not crucial to the definition of Replikins through 1999 (substitutions are show in italics). The original 29 amino acid 1917 Replikin sequence was then found to have been almost exactly restored to its structure of 1917-1918 in the 2001 H1N2 Replikin. However, the 2002 H1N2 influenza Replikin has been shortened from 29 to 28 amino acids and the "shift to the left" of amino acids kevl(i/v)wg (v/i)hh (SEQ ID NO: 859) is clearly evident. In 2003, one Replikin was further shortened (or compacted) to the 21 amino acid Replikin of the first listed 2003 human SARS virus. The % k of the 2003 SARS Replikin is now 38.1% (8/21) in comparison to 20.7% of the Goose Replikin and the 1918 Human Pandemic Replikin. Compared to the influenza 29 amino acid Replikin, three SARS Replikins were found to be further shortened (or compacted) to 19, 11 and 9 amino acid long sequences, respectively. In the SARS 9 amino acid sequences shown, the % k is 44.4% (4/9). With the shortening of the SARS Replikin, the SARS mortality rate in humans rose to 10% in the young and 55.5% in the elderly compared to the 2.5% mortality in the 1918 influenza pandemic.

The amino acid sequences are shown in Table 7 to emphasize the degree of homology and conservation for 85 years (1917-2002) of the influenza Replikin, for which evidence has first been observed in the 1917 Goose Replikin. No such conservation has ever been observed before. Table 7 also illustrates that the Replikins in the 2003 human SARS virus, in addition to having homologies to the influenza Replikins which first appeared as the 1917 Goose Replikin and the 1918 Human Pandemic influenza Replikin, show certain sequence homologies to both the coronavirus avian bronchitis virus Replikin (e.g. "k" in positions 1 and 2, end in "h") and to the coronavirus acute diarrhea virus Replikin (e.g. "k" in positions 1 and 11, "h" at the end of the Replikin). This evidence of relation to both influenza and coronavirus Replikins is of interest because SARS arose in Hong Kong as did several recent influenza epidemics and earlier pandemics, and the SARS virus has been classified as a new coronavirus partly because of its structure, including nucleocapsid, spike, and envelope proteins. Certain epidemiological evidence also is relevant in that SARS made its first appearance in humans as the epidemic pneumonia, which erupted, in a crowded Hong Kong apartment house where there was a severe back-up of fecal sewage, which was airborne by ventilating fans.

Composition of Replikins in Strains of Influenza Virus B: Of a total of 26 Replikins identified in this strain (Table 3), the following ten Replikins are present in every influenza B isolate examined from 1940-2001. Overlapping Replikin sequences are listed separately. Lysines and histidines are in bold type to demonstrate homology consistent with the "3-point recognition."

| | |
|---|---|
| kshfanlk | (SEQ ID NO. 104) |
| kshfanlkgtk | (SEQ ID NO. 105) |
| kshfanlkgtktrgklcpk | (SEQ ID NO. 106) |
| hekygglnk | (SEQ ID NO. 107) |
| hekygglnksk | (SEQ ID NO. 108) |
| hekygglnkskpyytgehak | (SEQ ID NO. 10) |
| hakaigncpiwvk | (SEQ ID NO. 110) |
| hakaigncpiwvvkktplklangtk | (SEQ ID NO. 111) |
| hakaigncpiwvktplklangtkyrppak | (SEQ ID NO. 112) |
| hakaigncpiwvktplklangtkyrppakllk | (SEQ ID NO. 113) |

Tables 3 and 4 indicate that there appears to be much greater stability of the Replikin structures in influenza B hemagglutinins compared with H1N1 Replikins. Influenza B has not been responsible for any pandemic, and it appears not to have an animal or avian reservoirs. (Stuart-Harris et al., Edward Arnold Ltd., London (1985)).

Influenza H1N1 Replikins: Only one Replikin "hp(v/i) tigecpkyv-(r/k)(s/t)(t/a)k" (SEQ ID NO: 135) is present in every H1N1 isolate for which sequences are available from 1918, when the strain first appeared and caused the pandemic of that year, through 2000. (Table 4). ("(v/i)" indicates that the amino acid v or i is present in the same position in different years.) Although H1N1 contains only one persistent Replikin, H1N1 appears to be more prolific than influenza B. There are 95 different Replikin structures in 82 years on H1N1 versus only 31 different Replikins in 62 years of influenza B isolates (Table 4). An increase in the number of new Replikin structures occurs in years of epidemics (Tables 3, 4, 5 and 6) and correlates with increased total Replikin concentration (FIGS. 7 and 8).

Influenza H2N2 Replikins: Influenza H2N2 was responsible for the human pandemic of 1957. Three of the 20 Replikins identified in that strain for 1957 were conserved in each of the H2N2 isolates available for examination on PubMed until 1995 (Table 5).

```
                                    (SEQ ID NO. 232)
ha(k/q/m)(d/n)ilekthngk

                                    (SEQ ID NO. 233)
ha(k/q/m)(d/n)ilekthngklc(k/r)

                                    (SEQ ID No. 238)
kgsnyp(v/i)ak(g/r)synntsgeqmliiwq(v/i)h
```

However, in contrast to H1N1, only 13 additional Replikins have been found in H2N2 beginning in 1961. This paucity of appearance of new Replikins correlates with the decline in the concentration of the H2N2 Replikins and the appearance of H2N2 in isolates over the years. (FIG. 8).

Influenza H3N2 Replikins: Influenza H3N2 was responsible for the human pandemic of 1968. Five Replikins which appeared in 1968 disappeared after 1977, but reappeared in the 1990s (Table 6). The only Replikin structure which persisted for 22 years was hcd(g/q)f(q/r)nekwdlf(v/i)er(s/t)k (SEQ ID NO: 277), which appeared first in 1977 and persisted through 1998. The emergence of twelve new H3N2 Replikins in the mid 1990s (Table 6) correlates with the increase in Replikin concentration at the same time (FIG. 8), and with the prevalence of the H3N2 strain in recent isolates together with the concurrent disappearance of all Replikins from some of these isolates (FIG. 8), this suggests the emergence of the new substrain H3N2(R). The current epidemic in November-December 2003 of a new strain of H3N2 (Fujian) confirms this prediction made first in the Provisional Application U.S. 60/303,396, filed Jul. 9, 2001.

FIGS. 1 and 2 show that influenza epidemics and pandemics correlate with the increased concentration of Replikins in influenza virus, which is due to the reappearance of at least one Replikin from one to 59 years after its disappearance. Also, in the A strain only, there is an emergence of new strain-specific Replikin compositions (Tables 4-6, see also increase in number of new Replikins, pre-epidemic for H5N1 in FIG. 11). Increase in Replikin concentration by repetition of individual Replikins within a single protein appears not to occur in influenza virus, but is seen in other organisms.

It has been believed that changes in the activity of different influenza strains are related to sequence changes in influenza hemagglutinins, which in turn are the products of substitutions effected by one of two poorly understood processes: i) antigenic drift, thought to be due to the accumulation of a series of point mutations in the hemagglutinin molecule, or ii) antigenic shift, in which the changes are so great that genetic reassortment is postulated to occur between the viruses of human and non-human hosts. First, the present data suggests that the change in activity of different influenza strains, rather than being related to non-specific sequence changes, are based upon, or relate to the increased concentration of strain-specific Replikins and strain-specific increases in the replication associated with epidemics. In addition, the data were examined for a possible insight into which sequence changes are due to "drift" or "shift", and which are due to conservation, storage in reservoirs, and reappearance. The data show that the epidemic-related increase in Replikin concentration is not due to the duplication of existing Replikins per hemagglutinin, but is due to the reappearance of at least one Replikin composition from 1 to up to 59 years after its disappearance, plus in the A strains only, the emergence of new strain-specific Replikin compositions (Tables 3-6). Thus the increase in Replikin concentration in the influenza B epidemics of 1951 and 1977 are not associated with the emergence of new Replikin compositions in the year of the epidemic but only with the reappearance of Replikin compositions which had appeared in previous years then disappeared (Table 3). In contrast, for the A strains, in addition to the reappearance of previously disappeared virus Replikins, new compositions appear (e.g. in H1N1 in the year of the epidemic of 1996, in addition to the reappearance of 6 earlier Replikins, 10 new compositions emerged). Since the A strains only, not influenza B, have access to non-human animal and avian reservoirs, totally new compositions probably derive from non-human host reservoirs rather than from mutations of existing human Replikins which appear to bear no resemblance to the new compositions other than the basic requirements of "3-point recognition" (Tables 2-5). The more prolific nature of H1N1 compared with B, and the fact that pandemics have been produced by the three A strains only, but not by the B strain, both may also be a function of the ability of the human A strains to receive new Replikin compositions from non-human viral reservoirs.

Some Replikins have appeared in only one year, disappeared, and not reappeared to date (Tables 3-6). Other Replikins disappear from one to up to 81 years, when the identical Replikin sequence reappears. Key Replikin 'k' and 'h' amino acids, and the spaces between them, are conserved during the constant presence of particular Replikins over many years, as shown in Tables 2 and 3-6 for the following strain-specific Replikins: ten of influenza B, the single Replikin of H1N1, and the single Replikin of H3N2 as well as for the reappearance of identical Replikins after an absence. Despite the marked replacement or substitution activity of other amino acids both inside the Replikin structure and outside it in the rest of the hemagglutinin sequences, influenza Replikin histidine (h) appears never to be, and lysine (k) is rarely replaced. Examples of this conservation are seen in the H1N1 Replikin "hp(v/i)tigecpkyv(r/k)(s/t)(t/a)k," (SEQ ID NO. 135) constant between 1918 and 2000, in the H3N2 Replikin "hcd(g/q)f(q,r)nekwdlf(v/i)er(s/t)k" (SEQ ID NO. 277) constant between 1975 and 1998 and in the H3N2 Replikin "hqn(s/e)(e/q)g(t/s)g(q/y)aad(l/q)kstq(a/n)a(i/l)d(q/g)l(n/t)(g/n)k,(I/v)n(r/s) vi(e/c)k" (SEQ ID NO. 276) which first appeared in 1975, disappeared for 25 years, and then reappeared in 2000. While many amino acids were substituted, the basic Replikin structure of 2 Lysines, 6 to 10 residues apart, one histidine, a minimum of 6% lysine in not more than approximately 50 amino acids, was conserved.

Totally random substitution would not permit the persistence of these H1N1 and H3N2 Replikins, nor from 1902 to 2001 in influenza B the persistence of 10 Replikin structures, nor the reappearance in 1993 of a 1919 18mer Replikin after an absence of 74 years. Rather than a random type of substitution, the constancy suggests an orderly controlled process, or in the least, protection of the key Replikin residues so that they are fixed or bound in some way: lysines, perhaps bound to nucleic acids, and histidines, perhaps bound to respiratory redox enzymes. The mechanisms, which control this conservation, are at present unknown.

Conservation of Replikin Structures

Whether Replikin structures are conserved or are subject to extensive natural mutation also was examined by scanning the protein sequences of various isolates of foot and mouth disease virus (FMDV), where mutations in proteins of these viruses have been well documented worldwide for decades. Protein sequences of FMDV isolates were visually examined for the presence of both the entire Replikin and each of the component Replikin amino acid residues observed in a particular Replikin.

Rather than being subject to extensive substitution over time as occurs in neighboring amino acids, the amino acids which comprise the Replikin structure are substituted little or not at all, that is the Replikin structure is conserved.

For example, in the protein VP1 of FMDV type O, the Replikin (SEQ ID NO.: 3) "hkqkivapvk" was found to be conserved in 78% of the 236 isolates reported in PubMed, and each amino acid was found to be conserved in individual isolates as follows: his, 95.6%; lys, 91.8%; gln 92.3%; lys, 84.1%; ile, 90.7%; val, 91.8%; ala, 97.3%; pro, 96.2%; ala, 75.4%; and lys, 88.4%. The high rate of conservation suggests structural and functional stability of the Replikin structure and provides constant targets for treatment.

Similarly, sequence conservation was found in different isolates of HIV for its Replikins, such as (SEQ ID NO.: 5) "kcfficgkegh" or (SEQ ID NO.: 6) "kvylawvpahk" in HIV Type 1 and (SEQ ID NO.: 7) "kcwncgkegh" in HIV Type 2 (Table 2). Further examples of sequence conservation were found in the HIV tat proteins, such as (SEQ ID NO.: 613) "hclvckqkkglgisygrkk," wherein the key lysine and histidine amino acids are conserved. (See Table 8).

Similarly, sequence conservation was observed in plants, for example in wheat, such as in wheat ubiguitin activating enzyme E (SEQ ID NOs. 614-616). The Replikins in wheat even provided a reliable target for stimulation of plant growth as described within. Other examples of conservation are seen in the constant presence of malignin in successive generations, over ten years of tissue culture of glioma cells, and by the constancy of affinity of the glioma Replikin for antimalignin antibody isolated by immunoadsorption from 8,090 human sera from the U.S., U.K., Europe and Asia (e.g., FIG. 5 and U.S. Pat. No. 6,242,578 B1).

Similarly, conservation was observed in trans-activator (Tat) proteins in isolates of HIV. Tat (trans-activator) proteins are early RNA binding proteins regulating lentiviral transcription. These proteins are necessary components in the life cycle of all known lentivirases, such as the human immunodeficiency viruses (HIV). Tat is a transcriptional regulator protein that acts by binding to the trans-activating response sequence (TAR) RNA element and activates transcription Initiation and/or elongation from the LTR promoter. HIV cannot replicate without tat, but the chemical basis of this has been unknown. In the HIV tat protein sequence from 89 to 102 residues, we have found a Replikin that is associated with rapid replication in other organisms. The amino acid sequence of this Replikin is "hclvckqkkglgisygrkk (SEQ ID NO: 613)." In fact, we found that this Replikin is present in every HIV tat protein. Some tat amino acids are substituted frequently, as shown in Table 9, by alternate amino acids (in small size fonts lined up below the most frequent amino acid (Table 8), the percentage of conservation for the predominant Replikin "hclvcfqkkglgisygrkk (SEQ ID NO: 613)"). These substitutions have appeared for most of the individual amino acids. However, the key lysine and histidine amino acids within the Replikin sequence, which define the Replikin structure, are conserved 100% in the sequence; while substitutions are common elsewhere in other amino acids, both within and outside the Replikin, none occurs on these key histidine amino acids.

As shown in Table 8 it is not the case that lysines are not substituted in the tat protein amino acid sequence. From the left side of the table, the very first lysine in the immediate neighboring sequence, but outside the Replikin sequence, and the second lysine (k) in the sequence inside the Replikin, but "extra" in that it is not essential for the Replikin formation, are both substituted frequently. However, the 3rd, 4th and 5th lysines, and the one histidine, in parentheses, which together set up the Replikin structure, are never substituted. Thus, these key amino acid sequences are 100% conserved. As observed in the case of the influenza virus Replikins, random substitution would not permit this selective substitution and selective non-substitution to occur due to chance.

TABLE 8

```
% Replikin CONSERVATION of each constituent amino acid in the first 117
different isolates of HIV tat protein as reported in PubMed:

38 (100) 57 86 (100) (100)  66 76 (100) 99 57 49 (100) 94  (100) 97 98 85 97 99    (100)(100)(100)%
Neighboring
Amino acids                      tat Replikin
k (c) s y [(h) (c) l v (c) f q k (k) g  (l) g i s y g (r) (k) (k)] (SEQ ID NO: 860)

below are the amino acid substitutions observed for each amino acid above:
h   c f         q i      l h   t        a        a  l y  h q (SEQ ID NO: 861)
r   w p         l l        i   h        q        v
y     s           s        l   m        r        s
i                 s        m   s
s                 r        n
v
a
f
p
q
```

The conservation of the Replikin structure suggests that the Replikin structure has a specific survival function for the HIV virus which must be preserved and conserved, and cannot be sacrificed to the virus 'defense' maneuver of amino acid substitution created to avoid antibody and other 'attack.' These 'defense' functions, although also essential, cannot 'compete' with the virus survival function of HIV replication.

Further conservation was observed in different isolates of HIV for its Replikins such as "kcfficgkegh" (SEQ ID NO. 5) or "kvylawvpahk" (SEQ ID NO. 6) in HIV Type 1 and "kcwncgkegh" (SEQ ID NO. 7) in HIV Type 2.

The high rate of conservation observed in FMVD and HIV Replikins suggests that conservation also observed in the Replikins of influenza Replikins is a general property of viral Replikins. This conservation makes them a constant and reliable targeted for either destruction, for example by using specific Replikins such as for influenza, FMVD or HIV vaccines as illustrated for the glioma Replikin, or stimulation.

Similarly, as provided in examples found in viruses including influenza viruses, FMDV, and HIV, where high rates of conservation in Replikins suggest that conservation is a general property of viral Replikins and thus making Replikins a constant and reliable target for destruction or stimulation, conservation of Replikin structures occurs in plants. For example, in wheat plants, Replikins are conserved and provide a reliable target for stimulation. Examples of conserved Replikins in wheat plants ubiquitin activating enzyme E include:

E3 hkdrltkkvvdiarevakvdvpeyrrh (SEQ ID NO. 614)

E2 hkerldrkvvdvarevakvevpsyrrh (SEQ ID NO. 615)

E1 hkerldrkvvdvarevakmevpsyrrh (SEQ ID NO. 616)

```
      *  *        *  **  *
```

Similarly to conservation found in the HIV tat protein, the Replikin in the wheat ubiquitin activating enzyme E is conserved. As with the HIV tat protein, substitutions of amino acids (designated with an '*') adjacent to the Replikin variant forms in wheat ubiquitin activating enzyme E are common. The key k and h amino acids that form the Replikin structure, however, do not vary whereas the 'unessential' k that is only 5 amino acids (from the first k on the left) is substituted.

Anti-Replikin Antibodies

Figure 3:
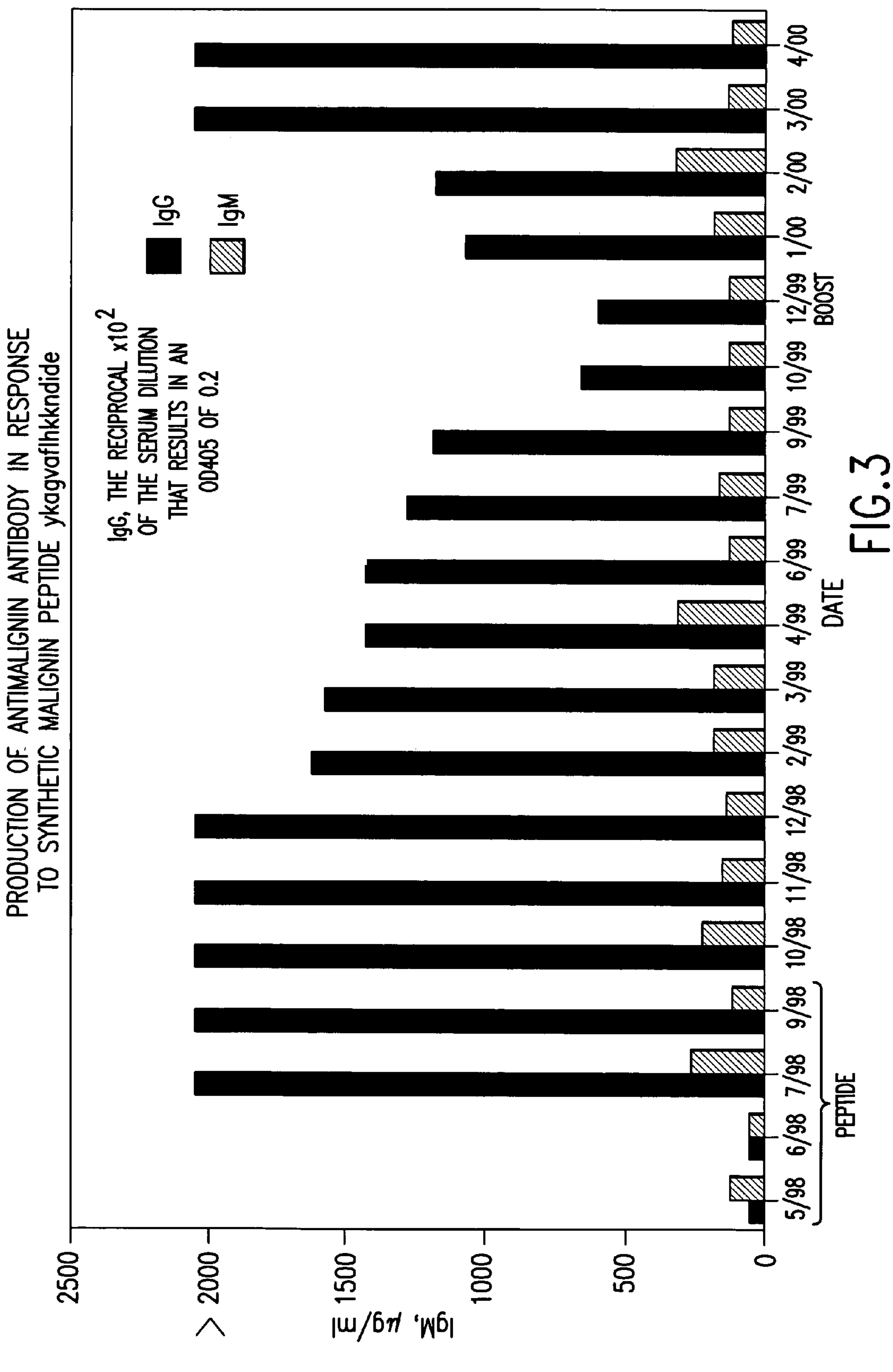
FIG. 3 is a bar graph showing amount of antimalignin antibody produced in response to exposure to the recognin 16-mer.

An anti-Replikin antibody is an antibody against a Replikin. Data on anti-Replikin antibodies also support Replikin class unity. An anti-Replikin antibody response has been quantified by immunoadsorption of serum antimalignin antibody to immobilized malignin (see Methods in U.S. Pat. No. 5,866,690). The abundant production of antimalignin antibody by administration to rabbits of the synthetic version of the 16-mer peptide whose sequence was derived from malignin, absent carbohydrate or other groups, has established rigorously that this peptide alone is an epitope, that is, provides a sufficient basis for this immune response (FIG. 3). The 16-mer peptide produced both IgM and IgG forms of the antibody. Antimalignin antibody was found to be increased in concentration in serum in 37% of 79 cases in the U.S. and Asia of hepatitis B and C, early, in the first five years of infection, long before the usual observance of liver cancer, which develops about fifteen to twenty-five years after infection. Relevant to both infectious hepatitis and HIV infections, transformed cells may be one form of safe haven for the virus: prolonging cell life and avoiding virus eviction, so that the virus remains inaccessible to anti-viral treatment.

Because administration of Replikins stimulates the immune system to produce antibodies having a cytotoxic effect, peptide vaccines based on the particular influenza virus Replikin or group of Replikins observed to be most concentrated over a given time period provide protection against the particular strain of influenza most likely to cause an outbreak in a given influenza season., e.g., an emerging strain or re-emerging strain For example, analysis of the influenza virus hemagglutinin amino acid sequence on a yearly or bi-yearly basis, provides data which are useful in formulating a specifically targeted influenza vaccine for that year. It is understood that such analysis may be conducted on a region-by-region basis or at any desired time period, so that strains emerging in different areas throughout the world can be detected and specifically targeted vaccines for each region can be formulated.

Influenza

Currently, vaccine formulations are changed twice yearly at international WHO and CDC meetings. Vaccine formulations are based on serological evidence of the most current preponderance of influenza virus strain in a given region of the world. However, prior to the present invention there has been no correlation of influenza virus strain specific amino acid sequence changes with occurrence of influenza epidemics or pandemics.

The observations of specific Replikins and their concentration in influenza virus proteins provides the first specific quantitative early chemical correlates of influenza pandemics and epidemics and provides for production and timely administration of influenza vaccines tailored specifically to treat the prevalent emerging or re-emerging strain of influenza virus in a particular region of the world. By analyzing the protein sequences of isolates of strains of influenza virus, such as the hemagglutinin protein sequence, for the presence, concentration and/or conservation of Replikins, influenza virus pandemics and epidemics can be predicted. Furthermore, the severity of such outbreaks of influenza can be significantly lessened by administering an influenza peptide vaccine based on the Replikin sequences found to be most abundant or shown to be on the rise in virus isolates over a given time period, such as about one to about three years.

An influenza peptide vaccine of the invention may include a single Replikin peptide sequence or may include a plurality of Replikin sequences observed in influenza virus strains. Preferably, the peptide vaccine is based on Replikin sequence(s) shown to be increasing in concentration over a given time period and conserved for at least that period of time. However, a vaccine may include a conserved Replikin peptide(s) in combination with a new Replikin(s) peptide or may be based on new Replikin peptide sequences. The Replikin peptides can be synthesized by any method, including chemical synthesis or recombinant gene technology, and may include non-Replikin sequences, although vaccines based on peptides containing only Replikin sequences are preferred. Preferably, vaccine compositions of the invention also contain a pharmaceutically acceptable carrier and/or adjuvant.

The influenza vaccines of the present invention can be administered alone or in combination with antiviral drugs, such as gancyclovir; interferon; interleukin; M2 inhibitors, such as, amantadine, rimantadine; neuraminidase inhibitors, such as zanamivir and oseltamivir; and the like, as well as with combinations of antiviral drugs.

Replikin Decoys in Malaria

Analysis of the primary structure of a *Plasmodium farciparum* malaria antigen located at the merozoite surface and/or within the parasitophorous vacuole revealed that this organism, like influenza virus, also contains numerous Replikins (Table 9). However, there are several differences between the observation of Replikins in *Plasmodium falciparum* and influenza virus isolates. For example, *Plasmodium falciparum* contains several partial Replikins, referred to herein as "Replikin decoys." These decoy structures contain an abundance of lysine residues, but lack the histidine required of Replikin structures. Specifically, these decoys contain many lysines 6 to 10 residues apart in overlapping fashion, similar to the true malaria recognins but without histidine residues. It is believed that the decoy structure maximizes the chances that an anti-malarial antibody or other agent will bind to the relatively less important structure containing the lysines, i.e., the Replikin decoys, rather than binding to histidine, which is present in Replikin structure, such as Replikins in respiratory enzymes, which could result in destruction of the trypanosome. For example, an incoming antibody, with specificity for Replikin structures, might attach to the Replikin decoy structure, leaving the true Replikin structure remains untouched.

Therefore, anti-Replikin treatment of malaria requires two phases (dual treatment): i) preliminary treatment with proteolytic enzymes that cleave the Replikin decoys, permitting 'safe passage' of the specific anti-Replikin treatment; and ii) attacking malaria Replikins either with specific antibodies or by cellular immunity engendered by synthetic malaria Replikin vaccines or by organic means targeting the malaria Replikins.

Repetition and Overlapping of Replikin Structures

Another difference seen in *Plasmodium falciparum* is a frequent repetition of individual Replikin structures within a single protein, which was not observed with influenza virus. Repetition may occur by (a) sharing of lysine residues between Replikins, and (b) by repetition of a portion of a Replikin sequence within another Replikin sequence.

A third significant difference between Replikin structures observed in influenza virus isolates and *Plasmodium falciparum* is a marked overlapping of Replikin structures throughout malarial proteins, e.g., there are nine overlapping Replikins in the 39 amino acid sequence of SEQ ID NO. 393 (Replikin concentration=23.1/100 amino acids); and 15 overlapping Replikins in the 41 amino acids of SEQ ID NO. 467 (Replikin concentration=36.6/100 amino acids). Both of these overlapping Replikin structures occur in blood stage trophozoites and schizonts. In contrast, influenza virus Replikins are more scattered throughout the protein and the maximum Replikin concentration is about 7.5/100 amino acids (FIG. 7); and tomato leaf curl gemini virus, which was also observed to have overlapping Replikins.

Replikins of Tomato Leaf Curl Gemini Virus

Tomato leaf curl Gemini virus has devastated tomato crops in China and in many other parts of the world. Its replikins reach high counts because of overlapping replikins as illustrated below in a virus isolated in Japan where the replikin count was 20.7

Replikin Analysis

```
Protein sequence; amino acid positions 1 to 135
m1 q2 p3 s4 s5 p6 s7 t8 s9 h10 c11 s12 q13 v14 s15
i16 k17 v18 q19 h20 k21 i22 a23 k24 k25 k26 p27
i28 r29 r30 k31 r32 v33 n34 l35 d36 c37 g38 c39
s40 y41 y42 l43 h44 l45 n46 c47 n48 n49 h50 g51
f52 t53 h54 r55 g56 t57 h58 h59 c60 s61 s62 s63
r64 e65 w66 r67 f68 y69 l70 g71 d72 k73 q74 s75
p76 l77 f78 q79 d80 n81 r82 t83 q84 p85 e86 a87
i88 s89 n90 e91 p92 r93 h94 h95 f96 h97 s98 d99
k100 i101 q102 p103 q104 h105 q106 e107 g108 t109
g110 d111 s112 q113 m114 f115 s116 q117 l118 p119
n120 l121 d122 d123 i124 t125 a126 s127 d128 w129
s130 f131 l132 k133 s134 i135 (SEQ ID NO: 862)
```

Amino-terminal replikins

```
                                     (SEQ ID NO. 757)
h10_c11_s12_q13_v14_s15_i16_k17_v18_q19_h20_k21_
i22_a23_k24
                                     (SEQ ID NO. 758)
h10_c11_s12_q13_v14_s15_i16_k17_v18_q19_h20_k21_
i22_a23_k24_k25_
                                     (SEQ ID NO. 759)
h10_c11_s12_q13_v14_s15_i16_k17_v18_q19_h20_k21_
i22_a23_k24_k25_k26
                                     (SEQ ID NO. 760)
h10_c11_s12_q13_v14_s15_i16_k17_v18_q19_h20_k21_
i22_a23_k24_k25_k26_p27_i28 r29_r30_k31
                                     (SEQ ID NO. 761)
k17_v18_q19_h20_k21_i22_a23_k24_k25_k26_p27_i28_
r29_r30_k31_r32_v33_n34_l35 d36_c37_g38_c39_s40_
y41_y42_l43_h44_l45_n46_c47_n48_n49_h50_

                                                      (SEQ ID NO. 762)
q19_h20_k21_i22_a23_k24_k25_k26_k27_i28_r29_r30_k31_r32_v33_n34_l35_d36_c37_
g38_c39_s40_y41_y42_l43_h44_l45_n46_c47_n48_n49_h50_g51_f52_t53_h54

                                                      (SEQ ID NO. 763)
k17_v18_q19_h20_k21_i22_a23_k24_k25_k26_p27_i28_r29_r30_k31_r32_v33_n34_l35_
d36_c37_g38_c39_s40_y41_y42_l43_h44_l45_n46_c47_n48_n49_h50_g51_f52_t53_h54_
r55_g56_t57_h58_

                                                      (SEQ ID NO. 764)
k17_v18_q19_h20_k21_i22_a23_k24_

                                                      (SEQ ID NO. 765)
k17_v18_q19_h20_k21_i22_a23_k24_k25_k26_p27_i28_r29_r30_k31_r32_v33_n34_l35_
d36_c37_g38_c39_s40_y41_y42_l43_h44_l45_n46_c47_n48_n49_h50_g51_f52_t53_h54_
r55_g56_t57_h58_h59_

                                                      (SEQ ID NO. 766)
k17_v18_q19_h20_k21_i22_a23_k24_k25_

                                                      (SEQ ID NO. 767)
k17_v18_q19_h20_k21_i22_a23_k24_k25_k26_p27_i28_r29_r30_k31_r32_v33_n34_l35_
d36_c37_g38_c39_s40_y41_y42_l43_h44_
```

-continued

```
                                                    (SEQ ID NO. 768)
k17_v18_q19_h20_k21_i22_a23_k24_k25_k26_

                                                    (SEQ ID NO. 769)
h20_k21_i22_a23_k24_k25_k26_p27_i28_r29_r30_k31_

                                                    (SEQ ID NO. 770)
k21_i22_a23_k24_k25_k26_p27_i28_r29_r30_k31_r32_v33_n34_l35_d36_c37_g38_c39_
s40_y41_y42_l43_h44_l45_n46_c47_n48_n49_h50_g51_f52_t53_h54_

                                                    (SEQ ID NO. 771)
k21_i22_a23_k24_k25_k26_p27_i28_r29_r30_k31_r32_v33_n34_l35_d36_c37_g38_c39_
s40_y41_y42_l43_h44_l45_n46_c47_n48_n49_h50_g51_f52_t53_h54_r55_g56_t57_h58_

                                                    (SEQ ID NO. 772)
k21_i22_a23_k24_k25_k26_p27_i28_r29_r30_k31_r32_v33_n34_l35_d36_c37_g38_c39_
s40_y41_y42_l43_h44_l45_n46_c47_n48_n49_h50_g51_f52_t53_h54_r55_g56_t57_h58_
h59_

                                                    (SEQ ID NO. 773)
k21_i22_a23_k24_k25_k26_p27_i28_r29_r30_k31_r32_v33_n34_l35_d36_c37_g38_c39_
s40_y41_y42_l43_h44_

                                                    (SEQ ID NO. 774)
k21_i22_a23_k24_k25_k26_p27_i28_r29_r30_k31_r32_v33_n34_l35_d36_c37_g38_c39_
s40_y41_y42_l43_h44_l45_n46_c47_n48_n49_h50_

                                                    (SEQ ID NO. 775)
k24_k25_k26_p27_i28_r29_r30_k31_r32_v33_n34_l35_d36_c37_g38_c39_s40_y41_y42_
l43_h44_l45_n46_c47_n48_n49_h50_g51_f52_t53_h54_r55_g56_t57_h58_

                                                    (SEQ ID NO. 776)
k24_k25_k26_p27_i28_r29_r30_k31_r32_v33_n34_l35_d36_c37_g38_c39_s40_y41_y42_
l43_h44_l45_n46_c47_n48_n49_h50_g51_f52_t53_h54_r55_g56_t57_h58_h59_

                                                    (SEQ ID NO. 777)
k24_k25_k26_p27_i28_r29_r30_k31_r32_v33_n34_l35_d36_c37_g38_c39_s40_y41_y42_
l43_h44_

                                                    (SEQ ID NO. 778)
k24_k25_k26_p27_i28_r29_r30_k31_r32_v33_n34_l35_d36_c37_g38_c39_s40_y41_y42_
l43_h44_l45_n46_c47_n48_n49_h50_

                                                    (SEQ ID NO. 779)
k24_k25_k26_p27_i28_r29_r30_k31_r32_v33_n34_l35_d36_c37_g38_c39_s40_y41_y42_
l43_h44_l45_n46_c47_n48_n49_h50_g51_f52_t53_h54_

                                                    (SEQ ID NO. 780)
k25_k26_p27_i28_r29_r30_k31_r32_v33_n34_l35_d36_c37_g38_c39_s40_y41_y42_l43_
h44_l45_n46_c47_n48_n49_h50_

                                                    (SEQ ID NO. 781)
k25_k26_p27_i28_r29_r30_k31_r32_v33_n34_l35_d36_c37_g38_c39_s40_y41_y42_l43_
h44_l45_n46_c47_n48_n49_h50_g51_f52_t53_h54_

                                                    (SEQ ID NO. 782)
k25_k26_p27_i28_r29_r30_k31_r32_v33_n34_l35_d36_c37_g38_c39_s40_y41_y42_l43_
h44_l45_n46_c47_n48_n49_h50_g51_f52_t53_h54_r55_g56_t57_h58_-

                                                    (SEQ ID NO. 783)
k25_k26_p27_i28_r29_r30_k31_r32_v33_n34_l35_d36_c37_g38_c39_s40_y41_y42_l43_
h44_l45_n46_c47_n48_n49_h50_g51_f52_t53_h54_r55_g56_t57_h58_h59_

                                                    (SEQ ID NO. 784)
k25_k26_p27_i28_r29_r30_k31_r32_v33_n34_l35_d36_c37_g38_c39_s40_y41_y42_l43_
h44_
```

The mechanism of lysine multiples is also seen in the Replikins of cancer proteins such as in gastric cancer transforming protein, ktkkgnrvsptmkvth (SEQ ID NO. 88), and in transforming protein P21B (K-RAS 2B) of lung, khkekmskdgkkkkkksk (SEQ ID NO. 89).

The relationship of higher Replikin concentration to rapid replication is also confirmed by analysis of HIV isolates. It was found that the slow-growing low titer strain of HIV (NSI, "Bru," which is prevalent in early stage HIV infection) has a Replikin concentration of 1.1 (±1.6) Replikins per 100 amino acids, whereas the rapidly-growing high titer strain of HIV (S1, "Lai", which is prevalent in late stage HIV infection) has a Replikin concentration of 6.8 (±2.7) Replikins per 100 amino acid residues.

The high concentration of overlapping Replikins in malaria, influenza virus and cancer cells is consistent with the legendary high and rapid replicating ability of malaria organisms. The multitude of overlapping Replikins in malaria also provides an opportunity for the organism to flood and confuse the immune system of its host and thereby maximize the chance that the wrong antibody will be made and perpetuated, leaving key malaria antigens unharmed.

As in the case of influenza virus, for example, peptide vaccines based on the Replikin structure(s) found in the malaria organism can provide an effective means of preventing and/or treating malaria. Vaccination against malaria can be achieved by administering a composition containing one or a mixture of Replikin structures observed in *Plasmodium falciparum*. Furthermore, antibodies to malaria Replikins can be generated and administered for passive immunity or malaria detection.

Replikins in Malaria

Malaria is a disease which accounts for more than 200 million cases annually world-wide and over 2 million deaths annually, and for which there is as yet no effective vaccine. Replikins have been found to be prominent in *Plasmodium falciparum,* the most common strain of trypanosome responsible for malaria.

High Replikin Count

In accord with the legendary high replication rate of trypanosomes, the highest replikin count yet observed in any species has been found in trypanosomes. In the trypanosome plasmodium falciparum, we found that for the ATPase protein recently determined to be the target of the effective antimalarial artemisinins, in the 1999 3D7 malaria pandemic year, the mean replikin count in the ATPase for all isolates was 57.6, and in one isolate the replikin count reached a record of 111.8 by repeating and overlaping replikins.

Repition and Overlapping of Replikin Structures

One characteristic seen in *Plasmodium falciparum* replikins which accounts for the high replikin count compared with influenza replikins, is a frequent repetition of individual replikin structures within a single protein, a feature which was not observed in influenza virus. Repetition may occur a) simply by repeating the entire replikin, (b) by sharing of lysine residues between replikins, and (c) by repetition of a portion of a replikin sequence combined with or within another replikin sequence.

(SEQ ID NO. 393)
ksdhnhksdhnhksdhnhksdhnhksdpnhkkknnnnnk (SEQ ID NO. 394)
ksdhnhksdhnhksdhnhksdpnhkkknnnnnk (SEQ ID NO. 395)
ksdhnbksdhnhksdpnhkkknnnnnk (SEQ ID NO. 396)
ksdhnhksdpnhkkkrmnnnk (SEQ ID NO. 397)
kkknnnnnkdnksdpnhk (SEQ ID NO. 398)
kknnnnnkdnksdpnhk (SEQ ID NO. 399)
knnnnnkdnksdpnhk (SEQ ID NO. 400)
kdnksdpnhk (SEQ ID NO. 401)
ksdpnhk -continued (SEQ ID NO. 743)
ksdhnhk (SEQ ID NO. 744)
ksdpnhkk (SEQ ID NO. 745)
ksdpnhkkk (SEQ ID NO. 746)
ksdpnhkk (SEQ ID NO. 747)
hkkknnnnnk (SEQ ID NO. 467)
kkdkekkkdsnenrkkkqkedkknpndnklkkieytnkith (SEQ ID NO. 468)
kdkekkkdsnenrkkkqkedkknpndnklkkieytnkith (SEQ ID NO. 469)
kekkkdsnenrkkkqkedkknpndnklkkieytnkith (SEQ ID NO. 470)
kkkdsnenrkkkqkedkknpndnklkkieytnkith (SEQ ID NO. 471)
kkdsnenrkkkqkedkknpndnklkkieytnkith (SEQ ID NO. 472)
kdsnenrkkkqkedkknpndnklkkieytnkith (SEQ ID NO. 473)
kkkqkedkknpndnklkkieytnkith (SEQ ID NO. 474)
kkqkedkknpndnklkkieytnkith (SEQ ID NO. 475)
kqkedkknpndnklkkieytnkith (SEQ ID NO. 476)
kedkknpndnklkkieytnkith (SEQ ID NO. 477)
kknpndnklkkieytnkith (SEQ ID NO. 478)
knpndnklkkieytnkith (SEQ ID NO. 479)
klkkieytnkith (SEQ ID NO. 480)
kkieytnkith (SEQ ID NO. 481)
kieytnkith Both of these overlapping replikin structures occur in blood stage trophozoites and schizonts. In contrast, influenza virus replikins are more scattered throughout the protein and the maximum replikin count (except in 1917-18) is about 7.5 (FIG. 7). As described earlier, tomato leaf curl gemini virus was also observed to have overlapping replikins raising the replikin count as high as 20.7.

TABLE 9

Replikin repeats, overlap, and conservation in one molecule, ATPase

Overlapping replikins, replikin repeats, and intramolecular conservation of replikin structure, were all found in the single molecule of Plasmodium Falciparum 3D7 ATPase, from amino acid positions 399 through 927 (full sequence embodiment below shown in SEQ ID NO: 863). As shown below, identical motifs of each replikin are conserved by the invariant initial 'k' and terminal 'hk' (shaded areas), whereas adjacent amino acids 'g/s/n' 'd/g/e' 's/c/n/h' and 's/n' are variable (clear). The last lysine for each replikin is also the first lysine for the next replikin, eg. k411, k417.:

| | | | | | | |
|---|---|---|---|---|---|---|
| k405 | s406 | d407 | s408 | n409 | h410 k411 | (SEQ ID NO. 785) |
| k411 | s412 | d413 | s414 | n415 | h416 k417 | |
| k417 | s418 | d419 | s420 | n421 | h422 k423 | |
| k423 | s424 | g425 | s426 | n427 | h428 k429 | (SEQ ID NO. 786) |
| k429 | s430 | d431 | c432 | n433 | h434 k435 | (SEQ ID NO. 787) |
| k435 | s436 | g437 | s438 | n439 | h440 k441 | |
| k459 | s460 | d461 | n462 | n463 | h464 k465 | (SEQ ID NO. 788) |
| k465 | s466 | d467 | s468 | s469 | h470 k471 | (SEQ ID NO. 789) |
| | | | | | | |
| k477 | s478 | d479 | s480 | s481 | h482 k483 | |
| k483 | s484 | g485 | s486 | n487 | h488 k489 | |
| k489 | s490 | d491 | n492 | n493 | h494 k495 | |
| k495 | s496 | d497 | s498 | s499 | h500 k501 | |
| k501 | s502 | g503 | s504 | n505 | h506 k507 | |
| k507 | s508 | d509 | h510 | n511 | h512 k513 | (SEQ ID NO. 790) |
| | | | | | | |
| k513 | s514 | d515 | s516 | n517 | h518 k519 | |
| k519 | s520 | d521 | s522 | n523 | h524 k525 | |
| k525 | n526 | e527 | s528 | n529 | h530 k531 | (SEQ ID NO. 791) |
| k531 | n532 | e533 | s534 | n535 | h536 k537 | |
| k537 | n538 | e539 | s540 | n541 | h542 k543 | |
| k543 | n544 | e545 | s546 | n547 | h548 k549 | |
| k549 | n550 | e551 | s552 | n553 | h554 k555 | |
| k555 | n556 | d557 | s558 | n559 | h560 k561 | (SEQ ID NO. 792) |
| k573 | s574 | d575 | n576 | n577 | h578 k579 | (SEQ ID NO. 793) |
| | | | | | | |
| k591 | s592 | d593 | n594 | n595 | h596 k597 | |
| k609 | s610 | d611 | n612 | n613 | h614 k615 | |
| k615 | s616 | d617 | n618 | n619 | h620 k621 | |
| k621 | s622 | d623 | n624 | n625 | h626 k627 | |
| k639 | s640 | d641 | n642 | n643 | h644 k645 | |
| k645 | s646 | d647 | n648 | n649 | h650 k651 | |
| k669 | s670 | d671 | n672 | n673 | h674 k675 | |
| k675 | s676 | d677 | n678 | n679 | h680 k681 | |
| | | | | | | |
| k681 | s682 | d683 | n684 | n685 | h686 k687 | |
| k687 | s688 | d689 | s690 | n691 | h692 k693 | |
| k693 | s694 | d695 | s696 | n697 | h698 k699 | |
| k699 | s700 | d701 | h702 | n703 | h704 k705 | |
| k723 | s724 | d725 | h726 | n727 | h728 k729 | |
| k729 | s730 | d731 | n732 | n733 | h734 k735 | |
| k735 | s736 | d737 | s738 | n739 | h740 k741 | |
| k741 | s742 | d743 | s744 | n745 | h746 k747 | |
| | | | | | | |
| k747 | s748 | d749 | h750 | n751 | h752 k753 | |
| k777 | s778 | d779 | h780 | n781 | h782 k783 | |
| k783 | s784 | d785 | n786 | n787 | h788 k789 | |
| k789 | s790 | d791 | s792 | n793 | h794 k795 | |
| k795 | s796 | d797 | s798 | n799 | h800 k801 | |
| k801 | s802 | d803 | s804 | n805 | h806 k807 | |
| k807 | s808 | d809 | h810 | n811 | h812 k813 | |
| k825 | s826 | d827 | n828 | n829 | h830 k831 | |
| k831 | s832 | d833 | h834 | n835 | h836 k837 | |
| k837 | s838 | d839 | n840 | n841 | h842 k843 | |
| | | | | | | |
| k843 | s844 | d845 | h846 | n847 | h848 k849 | |
| k849 | s850 | d851 | s852 | n853 | h854 k855 | |
| k855 | s856 | d857 | s858 | n859 | h860 k861 | |
| k861 | s862 | d863 | s864 | n865 | h866 k867 | |
| k867 | s868 | d869 | s870 | n871 | h872 k873 | |
| k873 | s874 | d875 | n876 | n877 | h878 k879 | |
| k897 | s898 | d899 | h900 | n901 | h902 k903 | |
| k903 | s904 | d905 | h906 | n907 | h908 k909 | |
| k909 | s910 | d911 | n912 | n913 | h914 k915 | |
| k915 | s916 | d917 | n918 | n919 | h920 k921 | |
| k921 | s922 | d923 | h924 | n925 | h926 k927 | |

Lysine Multiples

The phenomenon of lysine multiples in replikins, 'kk', 'kkk', etc., producing a high percent lysine, seen in the examples above in malaria, may be related to increased virulence and increased mortality, since it is also seen in the replikins of high mortality cancer proteins, such as in gastric cancer transforming protein, 'ktkkgnrvsptmkvth' (SEQ ID NO. 88), and in transforming protein P21B (K-RAS 2B) of lung 'khkekmskdgkkkkkksk' (SEQ ID NO. 89), and in high mortality SARS as in human SARS nucleocapsid protein 'khldayktfpptepkkdkkkk' (SEQ ID NO: 864), but is less commonly seen in lower mortality influenza, strains as in 1918 H1N1 human influenza 'kkgssypklsksyvnnkgkevlvlwgvhh' (SEQ ID NO: 832) (Table 7a).

The high concentration of overlapping Replikins in malaria, influenza virus and cancer cells is consistent with the legendary high and rapid replicating ability of malaria organisms. The multitude of overlapping Replikins in malaria also provides an opportunity for the organism to flood and confuse the immune system of its host and thereby maximize the chance that the wrong antibody will be made and perpetuated, leaving key malaria antigens unharmed.

As in the case of influenza virus, for example, peptide vaccines based on the Replikin structure(s) found in the malaria organism can provide an effective means of preventing and/or treating malaria. Vaccination against malaria can be achieved by administering a composition containing one or a mixture of Replikin structures observed in *Plasmodium falciparum*. Furthermore, antibodies to malaria Replikins can be generated and administered for passive immunity or malaria detection.

Replikin Decoys:

In another difference from influenza virus replikins, *Plasmodium falciparum* contains several repeating partial replikins, referred to herein as "replikin decoys." These decoys contain many lysines 6 to 10 residues apart in overlapping fashion, similar to the true malaria replikins but without histidine residues. It is believed that these decoy structure maximize the chances that an anti-malarial antibody or other agent will bind to the relatively less important structure containing the lysines, i.e., the replikin decoys, rather than the binding including histidine, which is present in replikin structure, such as replikins in respiratory enzymes, which could result in destruction of the trypanosome. For example, an incoming antibody, with specificity for replikin structures, might attach to the replikin decoy structure, leaving the true replikin structure untouched.

Therefore, anti-replikin treatment of malaria would require two phases (dual treatment): i) preliminary treatment with proteolytic enzymes that cleave the Replikin decoys, permitting 'safe passage' of the specific anti-Replikin treatment; and ii) attacking malaria Replikins either with specific antibodies or by cellular immunity engendered by synthetic malaria Replikin vaccines or by organic means targeting the malaria Replikins.

Table 10 provides a list of several *Plasmodium falciparum* Replikin sequences. It should be noted that this list is not meant to be complete. Different isolates of the organism may contain other Replikin structures.

TABLE 10

Malaria Replikins
a) Primary structure of a Plasmodium falciparum malaria antigen located at the merozoite surface and within the parasitophorous vacuole i) DECOYS:
(C-Terminal)
keeeekekekekekeekekeekekeekekekeekekekeekeeekk (SEQ ID NO. 293), or
keeeekekekekekeekekeekekeekekekeekekekeekeeekkek (SEQ ID NO. 294), or
keeeekekekekekeekekeekekekeekekeekekeekeekeeekk (SEQ ID NO. 295), or
keeeekekek (SEQ ID NO. 296)

ii) Replikins:
hkklikalkkniesiqnkk (SEQ ID NO. 297)
hkklikalkkniesiqnkm (SEQ ID NO. 298)
hkklikalkk (SEQ ID NO. 299)
hkklikalk (SEQ ID NO. 300)
katysfvntkkkiislksqghkk (SEQ ID NO. 301)
katysfvntkkkiislksqghk (SEQ ID NO. 302)
katysfvntkkkiislksqgh (SEQ ID NO. 303)
htyvkgkkapsdpqca dikeeckeilkek (SEQ ID NO. 304)
kiislksqghk (SEQ ID NO. 305)
kkkkfeplkngnvsetiklih (SEQ ID NO. 306)
kkkfeplkngnvsetiklih (SEQ ID NO. 307)
kkfeplkngnvsetiklih (SEQ ID NO. 308)
kngnvsetiklih (SEQ ID NO. 309)
klihlgnkdkk (SEQ ID NO. 310)
kvkkigvtlkkfeplkngnvsetiklihlgnkdkkh (SEQ ID NO. 311)
hliyknksynplllscvkkmnmlkenvdyiqnqnlfkelmnqkatysfvntkkkiislk (SEQ ID NO. 312)
hliyknksynplllscvkkmnmlkenvdyiqnqnlfkelmnqkatysfvntk (SEQ ID NO. 313)
hliyknksynplllscvkkmnmlkenvdyiqnqnlfkelmnqk (SEQ ID NO. 314)
hliyknksynplllscvkkmnmlkenvdyiqknqnlfk (SEQ ID NO. 315)
hliyknksynplllscvkkmnmlk (SEQ ID NO. 316)
ksannsanngkknnaeeniknlvnflqshkklikalkkniesiqnkkh (SEQ ID NO. 317)
kknnaeemknlvnflqshkklikalkkniesiqnkkh (SEQ ID NO. 318)
knlvnflqshkklikalkkniesiqnkkh (SEQ ID NO. 319)
kklikalkkniesiqnkkh (SEQ ID NO. 320)
klikalkkniesiqnkkh (SEQ ID NO. 321)
kkniesiqnkkh (SEQ ID NO. 322)
kniesiqnkkh (SEQ ID NO. 323)
knnaeemknlvnflqsh (SEQ ID NO. 324)
kklikalkkniesiqnkkqghkk (SEQ ID NO. 325)
kknnaeemknlvnflqshk (SEQ ID NO. 326)
knnaeemknlvnflqsh (SEQ ID NO. 327)
klikalkkniesiqnkkqghkk (SEQ ID NO. 328)
kvkkigvtlkkfeplkngnvsetiklih (SEQ ID NO. 329)
kngnvsetiklih (SEQ ID NO. 330)
klihlgnkdkk (SEQ ID NO. 331)
ksannsanngkknnaeemknlvnflqsh (SEQ ID NO. 332)
kknnaeemknlvnflqsh (SEQ ID NO. 333)
kklikalkkniesiqnkkh (SEQ ID NO. 334)
kalkkniesiqnkkh (SEQ ID NO. 335)
kkniesiqnkkh (SEQ ID NO. 336)
kelmnqkatysfvntkkkiislksqgh (SEQ ID NO. 337)
ksqghkk (SEQ ID NO. 338)
kkkiislksqgh (SEQ ID NO. 339)
kkiislksqgh (SEQ ID NO. 340)
kkniesiqnkkh (SEQ ID NO. 341)
kniesiqnkkh (SEQ ID NO. 342)
htyvkgkkapsdpqcadikeeckellkek (SEQ ID NO. 343)
htyvkgkkapsdpqcadikeeckellk (SEQ ID NO. 344)

b) "liver stage antigen-3" gene="LSA-3" Replikins
henvlsaalentqseeekkevidvieevk (SEQ ID NO. 345)
kenvvttilekveettaesvttfsnileeiqentitndtieekleelh (SEQ ID NO. 346)
hylqqmkekfskek (SEQ ID NO. 347)
hylqqmkekfskeknnnvievtnkaekkgnvqvtnktekttk (SEQ ID NO. 348)
hylqqmkekfskeknnnvievtnkaekkgnvqvtnktekttkvdknnk (SEQ ID NO. 349)
hylqqmkekfskeknnnvievtnkaekkgnvqvtnktekttkvdknnkvpkkrrtqk (SEQ ID NO. 350)
hylqqmkekfskeknnnvievtnkaekkgnvqvtnktekttkvdknnkvpkkrrtqksk (SEQ ID NO. 351)
hvdevmkyvqkidkevdkevskalesknd vtnvlkqnqdffskvknfvkkyk (SEQ ID NO. 352)
hvdevmkyvqkidkevdkevskalesknd vtnvlkqnqdffskvknfvkk (SEQ ID NO. 353)
hvdevmkyvqkidkevdkevskalesknd vtnvlkqnqdffsk (SEQ ID NO. 354)
hvdevmkyvqkidkevdkevskalesknd vtnvlk (SEQ ID NO. 355)
hvdevmkyvqkidkevdkevskalesk (SEQ ID NO. 356)
hvdevmkyvqkidkevdkevsk (SEQ ID NO. 357)
hvdevmkyvqkidkevdk (SEQ ID NO. 358)
hvdevmkyvqkidk (SEQ ID NO. 359)
kdevidlivqkekriekvkakkkklekkveegvsglkkh (SEQ ID NO. 360)
kvkakkkklekkveegvsglkkh (SEQ ID NO. 361)

TABLE 10-continued

```
kakkkklekkveegvsglkkh (SEQ ID NO. 362)
kkkklekkveegvsglkkh (SEQ ID NO. 363)
kkklekkveegvsglkkh (SEQ ID NO. 364)
kklekkveegvsglkkh (SEQ ID NO. 365)
klekkveegvsglkkh (SEQ ID NO. 366)
kkveegvsglkkh (SEQ ID NO. 367)
kveegvsglkkh (SEQ ID NO.368)
hveqnvyvdvdvpamkdqflgilneagglkemffnledvfksesdvitveeikdepvqk (SEQ ID NO. 369)
hikgleeddleevddlkgsildmlkgdmelgdmdkesledvttklgerveslk (SEQ ID NO. 370)
hikgleeddleevddlkgsildmlkgdmelgdmdkesledvttk (SEQ ID NO. 371)
hikgleeddleevddlkgsildmlkgdmelgdmdk (SEQ ID NO. 372)
hikgleeddleevddlkgsildmlk (SEQ ID NO. 373)
hlisgdadvlssalgmdeeqmktrkkaqrpk (SEQ ID NO. 374)
hditttldevvelkdveedkiek (SEQ ID NO. 375)
kkleevhelk (SEQ ID NO. 376)
kleevhelk (SEQ ID NO. 377)
ktietdileekkkeiekdh (SEQ ID NO. 378)
kkeiekdhfek (SEQ ID NO. 379)
kdhfek (SEQ ID NO. 380)
kfeeeaeeikh (SEQ ID NO. 381)

c) 28 KDA ookinete surface antigen precursor Replikins:
kdgdtkctlecaqgkkcikhksdhnhksdhnhksdpnhkkknnnnnk (SEQ ID NO. 382)
kdgdtkctlecaqgkkcikhksdhnhksdhnhksdpnhkk (SEQ ID NO. 383)
kdgdtkctlecaqgkkcikhksdhnhksdhnhksdpnhk (SEQ ID NO. 384)
kdgdtkctlecaqgkkcikhksdhnhksdhnhk (SEQ ID NO. 385)
kdgdtkctlecaqgkkcikhksdhnhk (SEQ ID NO. 386)
kdgdtkctlecaqgkkcikhk (SEQ ID NO. 387)
kdgdtkctlecaqgkk (SEQ ID NO. 388)
kdgdtkctlecaqgk (SEQ ID NO. 389)
kciqaecnykecgeqkcvwdgih (SEQ ID NO. 390)
kecgeqkcvwdgih (SEQ ID NO. 391)
hieckcnndyvltnryecepknkctsledtnk (SEQ ID NO. 392)

d) Blood stage trophozoites and schizonts Replikins:
ksdhnhksdhnhksdhnhksdhnhksdpnhkkknnnnnk (SEQ ID NO. 393)
ksdhnhksdhnhksdhnhksdpnhkkknnnnnk (SEQ ID NO. 394)
ksdhnhksdhnhksdpnhkkknnnnnk (SEQ ID NO. 395)
ksdhnhksdpnhkkknnnnnk (SEQ ID NO. 396)
kkknnnnnkdnksdpnhk (SEQ ID NO. 397)
kknnnnnkdnksdpnhk (SEQ ID NO. 398)
knnnnnkdnksdpnhk (SEQ ID NO. 399)
kdnksdpnhk (SEQ ID NO. 400)
ksdpnhk (SEQ ID NO. 401)
hslyalqqneeyqkvknekdqneikkikqlieknk (SEQ ID NO. 402)
hslyalqqneeyqkvknekdqneikkik (SEQ ID NO. 403)
hslyalqqneeyqkvknekdqneikk (SEQ ID NO. 404)
hslyalqqneeyqkvknekdqneik (SEQ ID NO. 405)
hklenleemdk (SEQ ID NO. 406)
khfddntneqk (SEQ ID NO. 407)
kkeddekh (SEQ ID NO. 408)
keennkkeddekh (SEQ ID NO. 409)
ktssgilnkeennkkeddekh (SEQ ID NO. 410)
knihikk (SEQ ID NO. 411)
hikkkegidigyk (SEQ ID NO. 412)
kkmwtcklwdnkgneitknih (SEQ ID NO. 413 )
kkgiqwnllkkmwtcklwdnkgneitknih (SEQ ID NO. 414 )
kekkdsnenrkkkqkedkknpnklkkieytnkithffkaknnkqqnnvth (SEQ ID NO. 415)
kkdsnenrkkkqkedkknpnklkkieytnkithffkaknnkqqnnvth (SEQ ID NO. 416)
kdsnenrkkkqkedkknpnklkkieytnkithffkaknnkqqnnvth (SEQ ID NO. 417)
kkqkedkknpnklkkieytnkithffkaknnkqqnnvth (SEQ ID NO. 418)
kqkedkknpnklkkieytnkithffkaknnkqqnnvth (SEQ ID NO. 419)
kedkknpnklkkieytnkithffkaknnkqqnnvth (SEQ ID NO. 420)
knpnklkkieytnkithffkaknnkqqnnvth (SEQ ID NO. 421)
kkieytnkithffkaknnkqqnnvth (SEQ ID NO. 422)
kieytnkithffkaknnkqqnnvth (SEQ ID NO. 423)
kithffkaknnkqqnnvth (SEQ ID NO. 424)
hknnedikndnskdikndnskdikndnskdikndnnedikndnskdik (SEQ ID NO. 425)
hknnedikndnskdikndnskdikndnskdikndnnedikndnsk (SEQ ID NO. 426)
hknnedikndnskdikndnskdikndnskdikndnnedik (SEQ ID NO. 427)
hknnedikndnskdikndnskdikndnskdik (SEQ ID NO. 428)
hknnedikndnskdikndnskdikndnsk (SEQ ID NO. 429)
hknnedikndnskdikndnskdik (SEQ ID NO. 430)
hknnedikndnskdikndnsk (SEQ ID NO. 431)
hknnedikndnskdik (SEQ ID NO. 432)
bknnedik (SEQ ID NO. 433)
kkyddlqnkynilnklknsleekneelkkyh (SEQ ID NO. 434)
kyddlqnkynilnklknsleekneelkkyh (SEQ ID NO. 435)
kynilnklknsleekneelkkyh (SEQ ID NO. 436)
```

TABLE 10-continued

| |
|---|
| klknsleekneelkkyh (SEQ ID NO. 437) |
| knsleekneelkkyh (SEQ ID NO. 438) |
| kneelkkyh (SEQ ID NO. 439) |
| hmgnnqdinenvynikpqefkeeeeedismvntkk (SEQ ID NO. 440) |
| knsnelkrindnffklh (SEQ ID NO. 441) |
| kpclykkckisqclykkckisqvwwcmpvkdtfntyernnvlnskienniekiph (SEQ ID NO. 442) |
| hinneytnknpkncllykneernyndnnikdyinsmnfkk (SEQ ID NO. 443) |
| hinneytnknpkncllykneernyndnnikdyinsmnfk (SEQ ID NO. 444) |
| hinneytnknpkncllyk (SEQ ID NO. 445) |
| knktnqskgvkgeyekkketngh (SEQ ID NO. 446) |
| ktnqskgvkgeyekkketngh (SEQ ID NO. 447) |
| kgvkgeyekkketngh (SEQ ID NO. 448) |
| kgeyekkketngh (SEQ ID NO. 449) |
| ksgmytnegnkscecsykkkssssnkvh (SEQ ID NO. 450) |
| kscecsykkkssssnkvh (SEQ ID NO. 451) |
| kkkssssnkvh (SEQ ID NO. 452) |
| kkssssnkvh (SEQ ID NO. 453) |
| kssssnkvh (SEQ ID NO. 454) |
| himlksgmytnegnkscecsykkkssssnk (SEQ ID NO. 455) |
| himlksgmytnegnkscecsykkk (SEQ ID NO. 456) |
| himlksgmytnegnkscecsykk (SEQ ID NO. 457) |
| himlksgmytnegnkscecsyk (SEQ ID NO. 458) |
| kplaklrkrektqinktkyergdviidnteiqkiiirdyhetlnvhkldh (SEQ ID NO. 459) |
| krektqinktkyergdviidnteiqkiiirdyhetlnvhkldh (SEQ ID NO. 460) |
| ktqinktkyergdviidnteiqkiiirdyhetlnvhkldh (SEQ ID NO. 461) |
| kplaklrkrektqinktkyergdviidnteiqkiiirdyhetlnvh (SEQ ID NO. 462) |
| kplaklrkrektqinktkyergdviidnteiqkiiirdyh (SEQ ID NO. 463) |
| klrkrektqinktkyergdviidnteiqkiiirdyh (SEQ ID NO. 464) |
| krektqinktkyergdviidnteiqkiiirdyh (SEQ ID NO. 465) |
| ktqinktkyergdviidnteiqkiiirdyh (SEQ ID NO. 466) |
| kkdkekkkdsnenrkkkqkedkknpndnklkkieytnkith (SEQ ID NO. 467) |
| kdkekkkdsnenrkkkqkedkknpndnklkkieytnkith (SEQ ID NO. 468) |
| kekkkdsnenrkkkqkedkknpndnklkkieytnkith (SEQ ID NO. 469) |
| kkkdsnenrkkkqkedkknpndnklkkieytnkith (SEQ ID NO. 470) |
| kkdsnenrkkkqkedkknpndnklkkieytnkith (SEQ ID NO. 471) |
| kdsnenrkkkqkedkknpndnklkkieytnkith (SEQ ID NO. 472) |
| kkkqkedkknpndnklkkieytnkith (SEQ ID NO. 473) |
| kkqkedkknpndnklkkieytnkith (SEQ ID NO. 474) |
| kqkedkknpndnklkkieytnkith (SEQ ID NO. 475) |
| kedkknpndnklkkieytnkith (SEQ ID NO. 476) |
| kknpndnklkkieytnkith (SEQ ID NO. 477) |
| knpndnklkkieytnkith (SEQ ID NO. 478) |
| klkkieytnkith (SEQ ID NO. 479) |
| kkieytnkith (SEQ ID NO. 480) |
| kieytnkith (SEQ ID NO. 481) |
| hgqikiedvnnenfnneqmknkyndeekmdisksksklksdflek (SEQ ID NO. 482) |
| hgqikiedvnnenfnneqmknkyndeekmdisksksklk (SEQ ID NO. 483) |
| hgqikiedvnnenfnneqmknkyndeekmdisksk (SEQ ID NO. 484) |
| hgqikiedvnnenfhneqmknkyndeekmdisk (SEQ ID NO. 485) |
| kkyddlqnkynilnklknsleekneelkkyh (SEQ ID NO. 486) |
| kyddlqnkynilnklknsleekneelkkyh (SEQ ID NO. 487) |
| kynilnklknsleekneelkkyh (SEQ ID NO. 488) |
| klknsleekneelkkyh (SEQ ID NO. 489) |
| knsleekneelkkyh (SEQ ID NO. 490) |
| kneelkkyh (SEQ ID NO. 491) |
| hmgnnqdinenvynikpqefkeeeeedismvntkkcddiqenik (SEQ ID NO. 492) |
| ktnlyniynnknddkdnildnenreglylcdvmknsnelkrindnffklh (SEQ ID NO. 493) |
| knsnelkrindnffklh (SEQ ID NO. 494) |
| krindnffklh (SEQ ID NO. 495) |
| hinneytnknpkncllykneernyndnnikdyinsmnfkk (SEQ ID NO. 496) |
| hinneytnknpkncllykneernyndnnikdyinsmnfk (SEQ ID NO. 497) |
| hinneytnknpkncllyk (SEQ ID NO. 498) |
| kpclykkckisqvwwcmpvkdtfhtyernnvlnskienniekiph (SEQ ID NO. 499) |
| kckisqvwwcmpvkdtfhtyemnvlnskienniekiph (SEQ ID NO. 500) |
| kienniekiph (SEQ ID NO. 501) |
| knktngskgvkgeyekkketngh (SEQ ID NO. 502) |
| ktngskgvkgeyekkketngh (SEQ ID NO. 503) |
| kgvkgeyekkketngh (SEQ ID NO. 504) |
| kgeyekkketngh (SEQ ID NO. 505) |
| ktiekinkskswffeeldeidkplaklrkrektqinktkyergdviidnteiqkiirdyh (SEQ ID NO. 506) |
| kinkskswffeeldeidkplaklrkrektqinktkyergdviidnteiqkiirdyh (SEQ ID NO. 507) |
| kplaklrkrektqinktkyergdviidnteiqkiirdyh (SEQ ID NO. 508) |
| himlksqmytnegnkscecsykkkssssnkvh (SEQ ID NO. 509) |
| klrkrektqinktkyergdviidnteiqkiirdyh (SEQ ID NO. 510) |
| krektqinktkyergdviidnteiqkiirdyh (SEQ ID NO. 511) |
| ktqinktkyergdviidnteiqkiirdyh (SEQ ID NO. 512) |
| kplaklrkrektqinktkyergdviidnteiqkiirdyhtlnvhkldh (SEQ ID NO. 513) |
| klrkrektqinktkyergdviidnteiqkiirdyhtlnvhkldh (SEQ ID NO. 514) |
| krektqinktkyergdviidnteiqkiirdyhtlnvhkldh (SEQ ID NO. 515) |

TABLE 10-continued

| |
|---|
| ktqinktkyergdviidnteiqkiirdyhtlnvhkldh (SEQ ID NO. 516) |
| kplaklrkrektqinktkyergdviidnteiqkiirdyhtlnvh (SEQ ID NO. 517) |
| klrkrektqinktkyergdviidnteiqkiirdyhtlnvh (SEQ ID NO. 518) |
| krektqinktkyergdviidnteiqkiirdyhtlnvh (SEQ ID NO. 519) |
| ktqinktkyergdviidnteiqkiirdyhtlnvh (SEQ ID NO. 520) |
| himlksqmytnegnkscecsykkkssssnkvh (SEQ ID NO. 521) |
| ksqmytnegnkscecsykkkssssnkvh (SEQ ID NO. 522) |
| kscecsykkkssssnkvh (SEQ ID NO. 523) |
| kkkssssnkvh (SEQ ID NO. 524) |
| kkssssnkvh (SEQ ID NO. 525) |
| kssssnkvh (SEQ ID NO. 526) |
| himlksqmytnegnkscecsykkkssssnk (SEQ ID NO. 527) |
| himlksqmytnegnkscecsykkk (SEQ ID NO. 528) |
| himlksqmytnegnkscecsykk (SEQ ID NO. 529) |
| himlksqmytnegnkscecsyk (SEQ ID NO. 530) |
| hnnhniqiykdkrinfmnphkvmyhdnmsknertek (SEQ ID NO. 531) |
| hnnhniqiykdkrinfmnphkvmyhdnmsk (SEQ ID NO. 532) |
| hnnhniqiykdkrinfminphk (SEQ ID NO. 533) |
| hkvmyhdnmsknertek (SEQ ID NO. 534) |
| hkvmyhdnmsk (SEQ ID NO. 535) |

Replikins in Structural Proteins

It has also been determined that some structural proteins include Replikin structures. Structural proteins are molecules involved in tissue and organ support, such as collagen in skin and connective tissue and in membrane structures, for example amyloid A4 precursor protein (APP) in brain. Overproduction of these proteins is associated with disease; specifically, scleroderma in the case of overproduction of collagen in skin (Table 11) and Alzheimer's Disease in the case of overproduction of APP in the brain (Table 12).

The association of scleroderma and malignancy has been a source of controversy during recent years. Several mechanisms of interrelationship have been suggested in earlier reports. Recent long-term studies suggest an increased association-ratio of scleroderma and malignancy. However, the underlying mechanisms remain elusive. (Wenzel, J. Eur. J. Dermatol. 20002 May-June; 12(3): 296-300).

Several proteins concerned with the excessive production of proteins in scleroderma have been found to contain Replikin structures. Thus, these provide further examples of unrecognized targets for inhibition or cessation of excessive collagen production. Table 11 provides a list of proteins in scleroderma and the associated Replikins.

The APP protein is the source of the amyloid beta A4 protein, which in excessive amounts forms plaques in the extracellular spaces in the brain, producing toxic effects associated with nerve cell loss in Alzheimer's Disease. Most studies to date have focused on the inability to clear the excessive deposits of A4, but have not considered that, rather than a waste clearance problem, this may actually be a problem of overproduction of the precursor protein APP. The high concentration of the Replikins in APP (3.3 Replikins per 100 amino acids) strongly suggest that overproduction may well be the cause of Alzheimer's Disease (Table 12). Therefore, the Replikins contained in Table 12 can be blocked or inhibited by the same methods as illustrated in detail for the glioma Replikin.

TABLE 11

| Proteins overproduced in scleroderma and associated Replikins: |
|---|
| PMC1 HUMAN: |
| hreictiqssggimllkdqvlrcskiagvkvaeitelilk (SEQ ID NO.536) |
| hreictiqssggimllkdqvlresk (SEQ ID NO.537) |
| 34KD nucleolar scleroderma antigen: |
| hreictiqssggimllkdqvlrcskiagvkvaeiteliklkalendqk (SEQ ID NO.538) |
| hreictiqssggimllkdqvlrcskiagvkvaeitelilk (SEQ ID NO.539) |
| Fibrillarin: |
| kkmqqenmkqpeqltlepyerdh (SEQ ID NO. 540) |
| kmqqenmkpqeqltlepyerdh (SEQ ID NO. 541) |
| SPOP HUMAN: |
| hemeeskknrveindvepevfkemmcfiytgkapnldk (SEQ ID NO.542) |
| hemeeskknrveindvepevfkemmcfiytgk (SEQ ID NO.543) |
| Centromere protein C: |
| khgelkvyk (SEQ ID NO.544) |
| klilgpqeekgkqh (SEQ ID NO. 545) |
| hnrihhk (SEQ ID NO. 546) |
| hhnssrkstkktnqssk (SEQ ID NO. 547) |
| hnssrkstkktnqssk (SEQ ID NO. 548) |
| khhnilpktlandkhshkph (SEQ ID NO.549) |
| hhnilpktlandkhshk (SEQ ID NO. 550) |
| hnilpktlandkhshk (SEQ ID NO. 551) |
| hnilpktlandk (SEQ ID NO. 552) |
| kntpdskkissrnindhh (SEQ ID NO.553) |
| kntpdskkissrnindh (SEQ ID NO. 554) |
| kdtciqspskecqkshpksvpvsskkk (SEQ ID NO. 555) |
| kdtciqspskecqkshpksvpvsskk (SEQ ID NO. 556) |
| hpksvpvsskkk (SEQ ID NO. 557) |
| hpksvpvsskk (SEQ ID NO. 558) |
| hpksvpvssk (SEQ ID NO. 559) |
| Factor CTCBF, KU antigen: |
| kalqekveikqlnh (SEQ 1ID NO. 560) |
| ktlfplieakkdqvtageifgdnhedgptakklktegggah (SEQ ID NO. 561) |
| ktlfplieakkkdqvtageifqdnb (SEQ ID NO. 562) |
| klcvfkkierhsih (SEQ ID NO. 563) |
| klcvfkkierh (SEQ ID NO. 564) |
| kgpsfplkgiteqqkegleivk (SEQ ID NO. 565) |

TABLE 11-continued

| Proteins overproduced in scleroderma and associated Replikins: |
|---|
| hgpsfplkgiteqqk (SEQ ID NO. 566) |
| ATP synthase subunit 6: |
| htllkilstflfk (SEQ ID NO. 567) |
| hllgnndknllpsk (SEQ ID NO. 568) |
| FBRL nuclear protein: |
| hrhegvficrgkedalvtk (SEQ ID NO. 569) |
| hegvficrgkedalvtk (SEQ ID NO. 570) |
| hsggnrgrgrggkrghqsgk (SEQ ID NO. 571) |
| krgnqsgknvmveph (SEQ ID NO. 572) |
| krgnqsgknvmvephrh (SEQ ID NO. 573) |
| kkmqqenmkpqeqltlepyerdh (SEQ ID NO.574) |
| kmqqenmkpqeqltlepyerdh (SEQ ID NO. 575) |
| HP1Hs-alpha protein: |
| haypedaenkeketak (SEQ ID NO. 576) |
| keanvkcpqiviafyeerltwh (SEQ ID NO. 577) |
| kvldrrvvkgqveyllkwkgfseeh (SEQ ID NO. 578) |
| kgqveyllkwkgfseeh (SEQ ID NO. 579) |
| FM/Scl nucleolar protein: |
| ksevaagvkksglpsaerlenvlfgphdcsh (SEQ ID NO.580) |
| ksevaagvkksgplpsaerlenvlfgph (SEQ ID NO. 581) |
| kaaeygkkaksetfrllhakniirpqlk (SEQ ID NO. 582) |
| kaaeygkkaksetfrllhak (SEQ ID NO. 583) |
| ksetfrllhak (SEQ ID NO. 584) |
| hakniirpqlk (SEQ ID NO. 585) |
| hmnlkiaeelpk (SEQ ID NO. 586) |
| hsldhllklycnvdsnk (SEQ ID NO. 587) |
| hllklycnvdsnk (SEQ ID NO. 588) |

TABLE 12

| Amyloid beta A4 precursor protein (APP) Replikins: | |
|---|---|
| kakerleakh | (SEQ ID NO. 589) |
| kdrqhtlk | (SEQ ID NO. 590) |
| kdrqhtlkh | (SEQ ID NO. 591) |
| ketcsekstnlh | (SEQ ID NO. 592) |
| kteeisevkmdaefgh | (SEQ ID NO. 593) |
| kteeisevkmdaefghdsgfevrh | (SEQ ID NO. 594) |
| kkyvraeqkdrqhtlkh | (SEQ ID NO. 595) |
| kyvraeqkdrqhtlkh | (SEQ ID NO. 596) |
| kkyvraeqkdrqh | (SEQ ID NO. 597) |
| kyvraeqkdrqht | (SEQ ID NO. 598) |
| hhvfnmlkkyvraeqk | (SEQ ID NO. 599) |
| hvfnmlkkyvraeqk | (SEQ ID NO. 600) |
| hhvfnmlkkyvraeqkdrqhtlkh | (SEQ ID NO. 601) |
| hvfnmlkkyvraeqkdrqhtlkh | (SEQ ID NO. 602) |
| hahfqkakerleakh | (SEQ ID NO. 603) |
| hahfqkakerleak | (SEQ ID NO. 604) |
| hfqkakerleak | (SEQ ID NO. 605) |

TABLE 12-continued

| Amyloid beta A4 precursor protein (APP) Replikins: | |
|---|---|
| hqermdvcethlhwhtvaketcsekstnlh | (SEQ ID NO. 606) |
| hqermdvcethlhwhtvaketcsek | (SEQ ID NO. 607) |
| hwhtvaketcsek | (SEQ ID NO. 608) |
| htvaketcsek | (SEQ ID NO. 609) |
| hlhwhtvaketcsek | (SEQ ID NO. 610) |
| hmnvqngkwesdpsgtktcigtk | (SEQ ID NO. 611) |
| hmnvqngkwesdpsgtk | (SEQ ID NO. 612) |

Passive Immunity

In another embodiment of the invention, isolated Replikin peptides may be used to generate antibodies, which may be used, for example to provide passive immunity in an individual. Passive immunity to the strain of influenza identified by the method of the invention to be the most likely cause of future influenza infections may be obtained by administering antibodies to Replikin sequences of the identified strain of influenza virus to patients in need. Similarly, passive immunity to malaria may be obtained by administering antibodies to *Plasmodium falciparum* Replikin(s).

Various procedures known in the art may be used for the production of antibodies to Replikin sequences. Such antibodies include but are not limited to polyclonal, monoclonal, chimeric, humanized, single chain, Fab fragments and fragments produced by an Fab expression library. Antibodies that are linked to a cytotoxic agent may also be generated. Antibodies may also be administered in combination with an antiviral agent. Furthermore, combinations of antibodies to different Replikins may be administered as an antibody cocktail.

For the production of antibodies, various host animals or plants may be immunized by injection with a Replikin peptide or a combination of Replikin peptides, including but not limited to rabbits, mice, rats, and larger mammals.

Monoclonal antibodies to Replikins may be prepared by using any technique that provides for the production of antibody molecules. These include but are not limited to the hybridoma technique originally described by Kohler and Milstein, (Nature, 1975, 256:495-497), the human B-cell hybridoma technique (Kosbor et al., 1983, Immunology Today, 4:72), and the EBV hybridoma technique (Cole et al., Monoclonal Antibodies and Cancer Therapy, Alan R. Liss, Inc., pp. 77-96). In addition, techniques developed for the production of chimeric antibodies (Morrison et al., 1984, Proc. Nat. Acad. Sci USA, 81:6851-6855) or other techniques may be used. Alternatively, techniques described for the production of single chain antibodies (U.S. Pat. No. 4,946,778) can be adapted to produce Replikin-specific single chain antibodies.

Particularly useful antibodies of the invention are those that specifically bind to Replikin sequences contained in peptides and/or polypeptides of influenza virus. For example, antibodies to any of peptides observed to be present in an emerging or re-emerging strain of influenza virus and combinations of such antibodies are useful in the treatment and/or prevention of influenza. Similarly, antibodies to any Replikins present on malaria antigens and combinations of such antibodies are useful in the prevention and treatment of malaria.

Antibody fragments which contain binding sites for a Replikin may be generated by known techniques. For example, such fragments include but are not limited to F(ab')2 fragments which can be produced by pepsin digestion of the antibody molecules and the Fab fragments that can be generated by reducing the disulfide bridges of the F(ab')2 fragments. Alternatively, Fab expression libraries can be generated (Huse et al., 1989, Science, 246:1275-1281) to allow rapid and easy identification of monoclonal Fab fragments with the desired specificity.

Figure 4A:
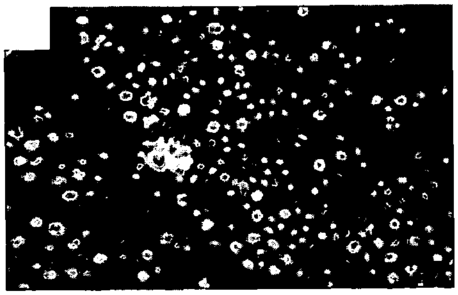
FIG. 4A is a photograph of a blood smear taken with ordinary and fluorescent light.
Figure 4B:
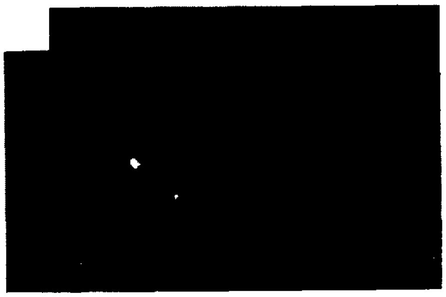
FIG. 4B is a photograph of a blood smear taken with ordinary and fluorescent light illustrating the presence of two leukemia cells.
Figure 4C:
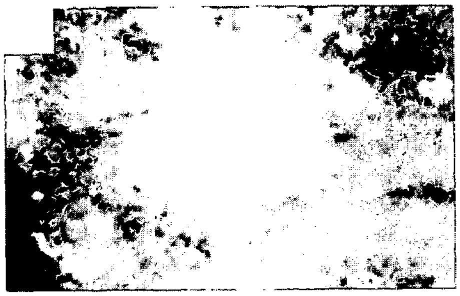
FIG. 4C is a photograph of a dense layer of glioma cells in the presence of antimalignin antibody.
Figure 4D:
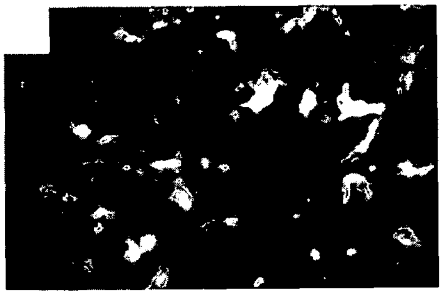
FIG. 4D and FIG. 4E are photographs of the layer of cells in FIG. 4C taken at 30 and 45 minutes following addition of antimalignin antibody.
Figure 4E:
Figure 4F:
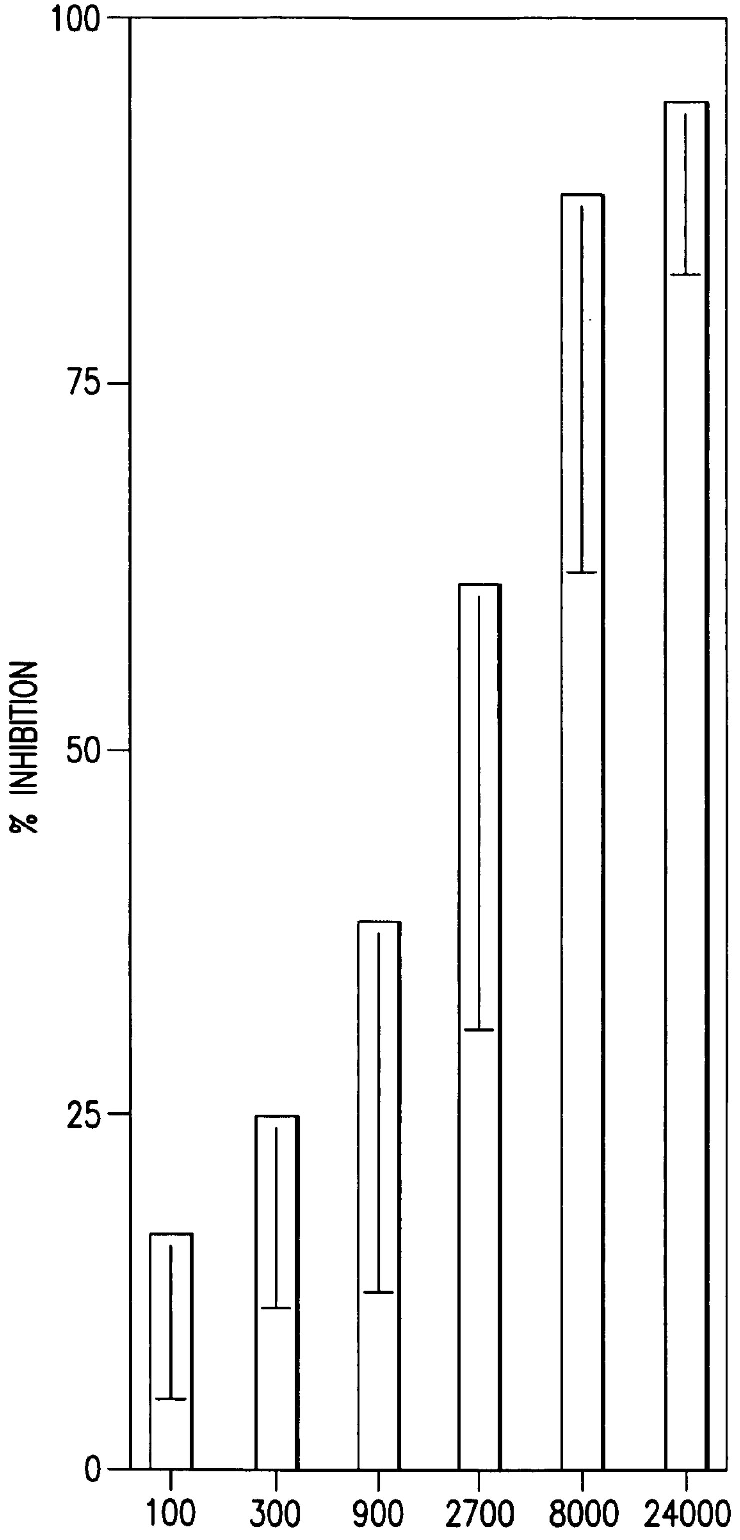
FIG. 4F is a bar graph showing the inhibition of growth of small cell lung carcinoma cells in vitro by antimalignin antibody.

The fact that antimalignin antibody is increased in concentration in human malignancy regardless of cancer cell type (FIG. 5), and that this antibody binds to malignant cells regardless of cell type now may be explained by the presence of the Replikin structures herein found to be present in most malignancies (FIG. 1 and Table 2). Population studies have shown that antimalignin antibody increases in concentration in healthy adults with age, and more so in high-risk families, as the frequency of cancer increases. An additional two-fold or greater antibody increase, which occurs in early malignancy, has been independently confirmed with a sensitivity of 97% in breast cancers 1-10 mm in size. Shown to localize preferentially in malignant cells in vivo, histochemically the antibody does not bind to normal cells but selectively binds to (FIG. 4*a,b*) and is highly cytotoxic to transformed cells in vitro (FIG. 4*c-f*). Since in these examples the same antibody is bound by several cell types, that is, brain glioma, hematopoietic cells (leukemia), and small cell carcinoma of lung, malignant Replikin class unity is again demonstrated.

Figure 5:
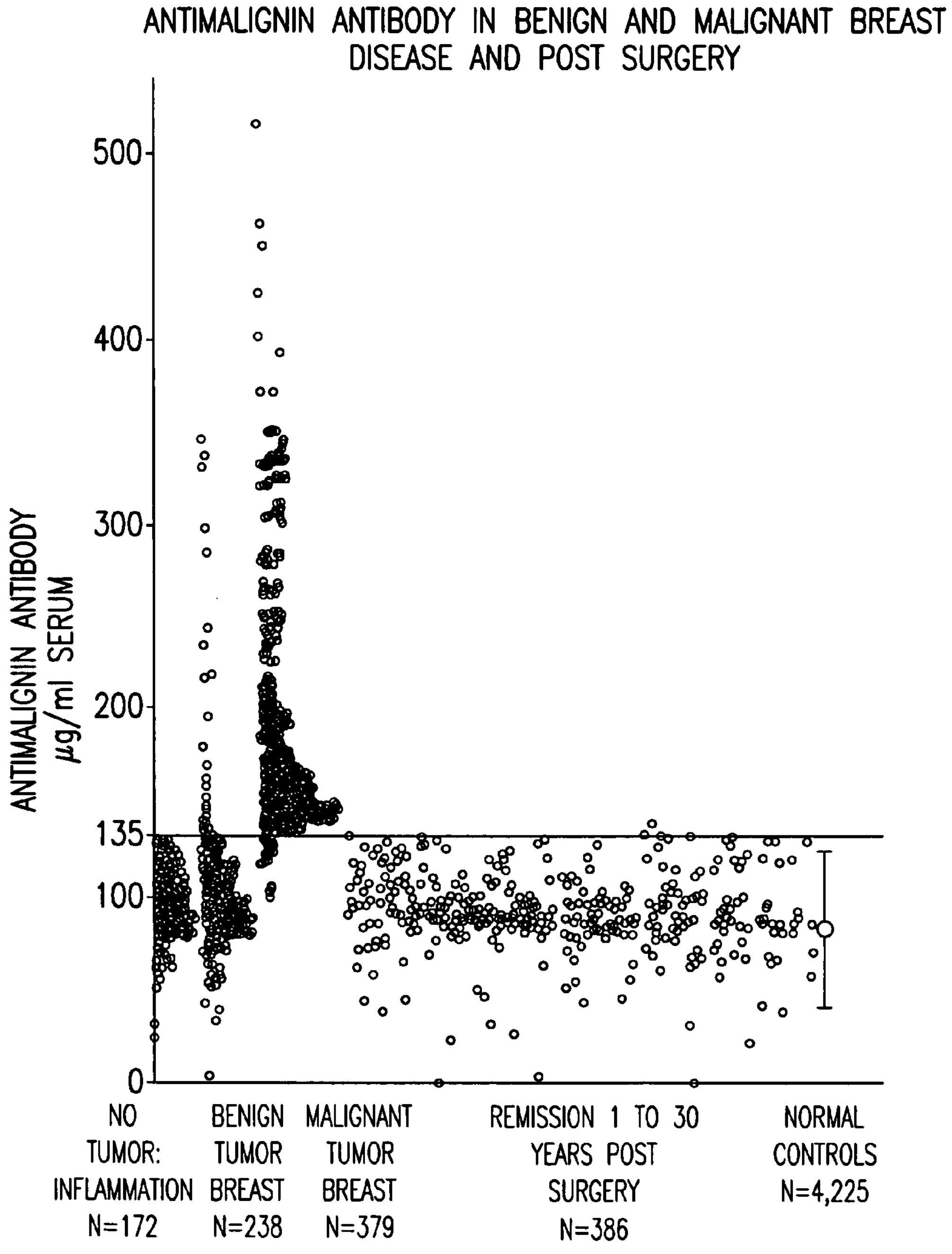
FIG. 5 is a plot of the amount of antimalignin antibody present in the serum of patients with benign or malignant breast disease pre-and post surgery.

Antimalignin does not increase with benign proliferation, but specifically increases only with malignant transformation and replication in breast in vivo and returns from elevated to normal values upon elimination of malignant cells (FIG. 5). Antimalignin antibody concentration has been shown to relate quantitatively to the survival of cancer patients, that is, the more antibody, the longer the survival. Taken together, these results suggest that anti-Replikin antibodies may be a part of a mechanism of control of cell transformation and replication. Augmentation of this immune response may be useful in the control of replication, either actively with synthetic Replikins as vaccines, or passively by the administration of anti-Replikin antibodies, or by the introduction of non-immune based organic agents, such as for example, carbohydrates, lipids and the like, which are similarly designed to target the Replikin specifically.

In another embodiment of the invention, immune serum containing antibodies to one or more Replikins obtained from an individual exposed to one or more Replikins may be used to induce passive immunity in another individual or animal. Immune serum may be administered via i.v. to a subject in need of treatment. Passive immunity also can be achieved by injecting a recipient with preformed antibodies to one or more Replikins. Passive immunization may be used to provide immediate protection to individuals who have been exposed to an infectious organism. Administration of immune serum or preformed antibodies is routine and the skilled practitioner can readily ascertain the amount of serum or antibodies needed to achieve the desired effect.

Synthetic Replikin Vaccines (Active Immunity)

Synthetic Replikin vaccines, based on Replikins such as the glioma Replikin (SEQ ID NO.: 1) "kagvaflhkk" or the hepatitis C Replikin (SEQ ID NO.: 18) "hyppkpgcivpak", or HIV Replikins such as (SEQ ID NO.: 5) "kcfncgkegh" or (SEQ ID NO.: 6) "kvylawvpahk" or preferably, an influenza vaccine based on conserved and/or emerging or re-emerging Replikin(s) over a given time period may be used to augment antibody concentration in order to lyse the respective virus infected cells and release virus extracellularly where chemical treatment can then be effective. Similarly, a malaria vaccine, based on Replikins observed in Plasmodium falciparum malaria antigens on the merozoite surface or within the parasitophorous vacuole, for example, can be used to generate cytotoxic antibodies to malaria. Table 7 shows the relation of shortening or compacting of Replikin sequences to mortality rate caused by the organisms which contain these Replikins, to as short as seven amino acids. This correlation has been found by us to be a general phenomenon regardless of the type of organism. We have also found that there may be a progression over time to the shortened Replikin structure, as in influenza and SARS viruses. There is abundant evidence that there are constant evolutionary and competitive pressures for the emergence of constantly increasing "efficacy" of each infectious organism. Based upon these observations, and by projection, it would appear that if evolutionary pressures are towards shorter and shorter Replikins, with higher and higher concentrations of lysine (k), to as high as 70% as in EEL leukemia (Table 7), then the projected theoretical ideal would be the shortest possible Replikin permitted by the algorithm which defines a Replikin, that is six amino acids (two ks six to ten amino acids apart), with the highest possible % k (see Example below in deduced Replikin "kkkkhk" (SEQ ID NO: 865), which contains 83.3% k, 5/6, and one obligatory "h"). We have therefore, so-to-speak, taken what appears to be, or might be, the next evolutionary step, not apparently as yet taken by the organisms themselves, and devised the resultant deduced Replikins to use as general vaccines. These Replikins which we have deduced have maximum % 'k's, therefore maximum potential binding capacity, plus the constituent 'h' by definition required for the Replikin, giving the potential for 'h' connection to redox energy systems. These devised Replikins are least likely to be cleaved by organisms because of their short length (proteins are cleaved to 6 to 10 amino acids long in processing for presentation to and recognition by immune cells), therefore most likely to present intact to immuneforming apparatuses in the organism to which they are administered, and, because of their high k content, they are most likely to generate a maximum immune response which mimics and may increase the maximum such response which can be generated against short homologous high mortality Replikins. Further, we have found that high % k Replikins generate the highest antibody responses when administered to rabbits. These synthetic peptides, designed by us, are designated as Universal synthetic epitopes, or "UTOPE"s , and the vaccines based upon these UTOPEs, are designated "UVAX"s. UVAXs, deduced synthetic vaccines, may be used as sole vaccines or as adjuvants when administered with more specific Replikin vaccines or other vaccines. The following are examples of deduced UTOPEs and UVAXs:

| DEVISED SYNTHETIC REPLIKIN (UTOPE OR UVAX) | SEQ ID NO: |
|---|---|
| kkkkhk | 732 |
| kkkhkk | 733 |
| kkhkkk | 734 |
| khkkkk | 735 |
| kkkkkkh | 736 |

-continued

| DEVISED SYNTHETIC REPLIKIN (UTOPE OR UVAX) | SEQ ID NO: |
|---|---|
| kkkkkhk | 737 |
| kkkkhkk | 738 |
| kkkhkkk | 739 |
| kkhkkkk | 740 |
| khkkkkk | 741 |
| hkkkkkk | 742 |

Recognin and/or Replikin peptides may be administered to a subject to induce the immune system of the subject to produce anti-Replikin antibodies. Generally, a 0.5 to about 2 mg dosage, preferably a 1 mg dosage of each peptide is administered to the subject to induce an immune response. Subsequent dosages may be administered if desired.

The Replikin sequence structure is associated with the function of replication. Thus, whether the Replikins of this invention are used for targeting sequences that contain Replikins for the purpose of diagnostic identification, promoting replication, or inhibiting or attacking replication, for example, the structure-function relationship of the Replikin is fundamental.

It is preferable to utilize only the specific Replikin structure when seeking to induce antibodies that will recognize and attach to the Replikin fragment and thereby cause destruction of the cell. Even though the larger protein sequence may be known in the art as having a "replication associated function," vaccines using the larger protein often have failed or proven ineffective.

Although the present inventors do not wish to be held to a single theory, the studies herein suggest that the prior art vaccines are ineffective because they are based on the use of the larger protein sequence. The larger protein sequence invariably has one or more epitopes (independent antigenic sequences that can induce specific antibody formation); Replikin structures usually comprise one of these potential epitopes. The presence of other epitopes within the larger protein may interfere with adequate formation of antibodies to the Replikin, by "flooding" the immune system with irrelevant antigenic stimuli that may preempt the Replikin antigens, See, e.g., Webster, R. G., J. Immunol., 97(2):177-183 (1966); and Webster et al., J. Infect. Dis., 134:48-58, 1976; Klenerman et al, Nature 394:421-422 (1998) for a discussion of this well-known phenomenon of antigenic primacy whereby the first peptide epitope presented and recognized by the immune system subsequently prevails and antibodies are made to it even though other peptide epitopes are presented at the same time. This is another reason that, in a vaccine formulation, it is important to present the constant Replikin peptide to the immune system first, before presenting other epitopes from the organism so that the Replikin is not preempted but lodged in immunological memory.

The formation of an antibody to a non-Replikin epitope may allow binding to the cell, but not necessarily lead to cell destruction. The presence of structural "decoys" on the C-termini of malaria proteins is another aspect of this ability of other epitopes to interfere with binding of effective anti-Replikin antibodies, since the decoy epitopes have many lysine residues, but no histidine residues. Thus, decoy epitopes may bind anti-Replikin antibodies, but may keep the antibodies away from histidine-bound respiratory enzymes. Treatment may therefore be most efficacious in two stages: 1) proteases to hydrolyze decoys, then; 2) anti-Replikin antibodies or other anti-Replikin agents.

It is well known in the art that in the course of antibody production against a "foreign" protein, the protein is first hydrolyzed into smaller fragments. Usually fragments containing from about six to ten amino acids are selected for antibody formation. Thus, if hydrolysis of a protein does not result in Replikin-containing fragments, anti-Replikin antibodies will not be produced. In this regard, it is interesting that Replikins contain lysine residues located six to ten amino acids apart, since lysine residues are known to bind to membranes.

Furthermore, Replikin sequences contain at least one histidine residue. Histidine is frequently involved in binding to redox centers. Thus, an antibody that specifically recognizes a Replikin sequence has a better chance of inactivating or destroying the cell in which the Replikin is located, as seen with anti-malignin antibody, which is perhaps the most cytotoxic anti-cancer antibody yet described, being active at picograms per cell.

One of the reasons that vaccines directed towards a particular protein antigen of a disease causing agent have not been fully effective in providing protection against the disease (such as foot and mouth vaccine which has been developed against the VP1 protein or large segments of the VP1 protein) is that the best antibodies have not been produced, that is—it is likely that the antibodies to the Replikins have not been produced. Replikins have not been produced. That is, either epitopes other than Replikins present in the larger protein fragments may interfere according to the phenomenon of antigenic primacy referred to above, and/or because the hydrolysis of larger protein sequences into smaller sequences for processing to produce antibodies results in loss of integrity of any Replikin structure that is present, e.g., the Replikin is cut in two and/or the histidine residue is lost in the hydrolytic processing. The present studies suggest that for an effective vaccine to be produced, the Replikin sequences, and no other epitope, should be used as the vaccine. For example, a vaccine of the invention can be generated using any one of the Replikin peptides identified by the three-point recognition system.

Particularly preferred peptides—for example—an influenza vaccine include peptides that have been demonstrated to be conserved over a period of one or more years, preferably about three years or more, and/or which are present in a strain of influenza virus shown to have the highest increase in concentration of Replikins relative to Replikin concentration in other influenza virus strains, e.g., an emerging strain. The increase in Replikin concentration preferably occurs over a period of at least about six months to one year, preferably at least about two years or more, and most preferably about three years or more. Among the preferred Replikin peptides for use in an influenza virus vaccine are those Replikins observed to "re-emerge" after an absence from the hemagglutinin amino acid sequence for one or more years.

The Replikin peptides of the invention, alone or in various combinations are administered to a subject, preferably by i.v. or intramuscular injection, in order to stimulate the immune system of the subject to produce antibodies to the peptide. Generally the dosage of peptides is in the range of from about 0.1 μg to about 10 mg, preferably about 10 μg to about 1 mg, and most preferably about 50 μg to about 500 ug. The skilled practitioner can readily determine the dosage and number of dosages needed to produce an effective immune response.

Quantitative Measurement Early Response(s) to Replikin Vaccines

The ability to measure quantitatively the early specific antibody response in days or a few weeks to a Replikin vaccine is a major practical advantage over other vaccines for which only a clinical response months or years later can be measured.

Adjuvants

Various adjuvants may be used to enhance the immunological response, depending on the host species, including but not limited to Freund's (complete and incomplete), mineral gels, such as aluminum hydroxide, surface active substances such as lysolecithin, pluronic polyols, polyanions, peptides, oil emulsions, key limpet hemocyanin, dintrophenol, and potentially useful human adjuvants such as BCG and Corynebacterium parvum. In addition to the use of synthetic UTOPEs as vaccines in themselves, UTOPEs can be used as adjuvants to other Replikin vaccines and to non-Replikin vaccines.

Replikin Nucleotide Sequences

Replikin DNA or RNA may have a number of uses for the diagnosis of diseases resulting from infection with a virus, bacterium or other Replikin encoding agent. For example, Replikin nucleotide sequences may be used in hybridization assays of biopsied tissue or blood, e.g., Southern or Northern analysis, including in situ hybridization assays, to diagnose the presence of a particular organism in a tissue sample or an environmental sample, for example. The present invention also contemplates kits containing antibodies specific for particular Replikins that are present in a particular pathogen of interest, or containing nucleic acid molecules (sense or antisense) that hybridize specifically to a particular Replikin, and optionally, various buffers and/or reagents needed for diagnosis.

Also within the scope of the invention are oligoribonucleotide sequences, that include antisense RNA and DNA molecules and ribozymes that function to inhibit the translation of Replikin- or recognin-containing mRNA. Both antisense RNA and DNA molecules and ribozymes may be prepared by any method known in the art. The antisense molecules can be incorporated into a wide variety of vectors for delivery to a subject. The skilled practitioner can readily determine the best route of delivery, although generally i.v. or i.m. delivery is routine. The dosage amount is also readily ascertainable.

Particularly preferred antisense nucleic acid molecules are those that are complementary to a Replikin sequence contained in a mRNA encoding, for example, an influenza virus polypeptide, wherein the Replikin sequence comprises from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to a Replikin present in the coding strand of the gene or to the mRNA encoding the influenza virus hemagglutinin protein, wherein the antisense nucleic acid molecule is complementary to a nucleotide sequence encoding a Replikin that has been demonstrated to be conserved over a period of six months to one or more years and/or which are present in a strain of influenza virus shown to have an increase in concentration of Replikins relative to Replikin concentration in other influenza virus strains. The increase in Replikin concentration preferably occurs over a period of at least six months, preferably about one year, most preferably about two or three years or more.

Similarly, antisense nucleic acid molecules that are complementary to mRNA those that are complementary to a mRNA encoding bacterial Replikins comprising a Replikin sequence of from 7 to about 50 amino acids including (1) at least one lysine residue located six to ten residues from a second lysine residue; (2) at least one histidine residue; and (3) at least 6% lysine residues. More preferred are antisense nucleic acid molecules that are complementary to the coding strand of the gene or to the mRNA encoding a protein of the bacteria.

Diagonostic Applications

For organisms such as diatom plankton, foot and mouth disease virus, tomato leaf curl gemini virus, hepatitis B and C, HIV, influenza virus and malignant cells, identified constituent Replikins are useful as vaccines, and also may be usefully targeted for diagnostic purposes. For example, blood collected for transfusions may be screened for contamination of organisms, such as HIV, by screening for the presence of Replikins shown to be specific for the contamination organism. Also, screening for Replikin structures specific for a particular pathological organism leads to diagnostic detection of the organism in body tissue or in the environment.

Replikin Stimulation of Growth

In another embodiment of the invention, Replikin structures are used to increase the replication rate of cells, tissues or organs. A method is available to increase replication rates by the addition of specific Replikin structures for other cells, tissues or organs that it is desired to replicate more rapidly, together with or without appropriate stimulae to cell division know in the art for said cells, tissues or organs to increase the rate of replication and yield. This may be accomplished, for example, by methods known in the art, by modifying or transforming a gene encoding for or associated with a protein or enzyme having a replication function in the organism with at least one Replikin structure.

In another aspect of the invention, Replikin structures are used to increase the replication of organisms. The present invention demonstrates that in influenza virus, for example, increased replication associated with epidemics is associated with increased concentration of Replikins. The increase is due to 1) the reappearance of particular Replikin structures, which were present in previous years, but which then disappeared for one or more years; and/or 2) by the appearance of new Replikin compositions. In addition, in malaria Replikins, repetition of the same Replikin in a single protein occurs. Further, UTOPEs can be used to stimulation growth of an organism or to increase replication of organisms.

Thus, the present invention provides methods and compositions for increasing the replication of organisms. Similarly, in the manner that Replikins of different organisms can be targeted to inhibit replication of any organism, Replikins can be used to increase the replication of any organism. For example, production of rice, maize, and wheat crops, which are critical to feeding large populations in the world, can be improved, for example, by increasing the concentration (number of Replikins/100 amino acid residues) of any particular strain of rice.

As an example, in the *Oryza sativa* strain of rice, catalase isolated from immature seeds was observed to contain the following different Replikins within the 491 amino acid sequence of the protein:

```
                                        (SEQ ID NO. 638)
kfpdvihafkpnprsh

                                        (SEQ ID NO. 639)
kfpdvihafk
```

```
karyvkfhwk                                   (SEQ ID NO. 640)

                                             (SEQ ID NO. 641)
hpkvspelraiwvnylsqedeslgvkianlnvk

katihkqndfk                                  (SEQ ID NO. 642)

                                             (SEQ ID NO.643)
happtpitprpvvgrrqkatihkqndfk

                                             (SEQ ID NO. 644)
kfrpsssfdtkttttnagapvwndnealtvgprgpilledyhliekvah

                                             (SEQ ID NO. 645)
kfrpsssfdtkttttnagapvwndnealtvgprgpilledyn
```

Thus, by using recombinant gene cloning techniques well known in the art, the concentration of Replikin structures in an organism, such as a food crop plant, can be increased, which will promote increased replication of the organism. For example, inserting additional Replikin sequences, like the Replikins identified above, into the *Oryza sativa* catalase gene by methods well know in the art will promote this organism's replication.

Similarly, in the NBS-LRR protein of *Oryza sativa* Oaponica cultivar group), the following Replikins were found:

```
                                             (SEQ ID NO. 647)
kvkahfqkh

                                             (SEQ ID NO. 648)
kvkahfqk

                                             (SEQ ID NO. 648)
kdyeidkddlih

                                             (SEQ ID NO. 650)
hmkqcfafcavfpk

                                             (SEQ ID NO. 651)
hvfwelvwrsffqnvkqigsifqrkvyrygqsdvttskihdlmhdlavh

                                             (SEQ ID NO. 652)
kqigsifqrkvrygpsdvttskihdlmhdlavh

                                             (SEQ ID NO. 653)
kqigsifqrkvyrygpsdvttskihdlmh

                                             (SEQ ID NO. 654)
kqigsifqrkvyrygqsdvttskih
```

Further, for aspartic proteinase oryzasin 1 precursor protein, the following Replikins were found:

```
    khgvsagik              (SEQ ID NO. 655)

    htvfdygkmrvgfak        (SEQ ID NO. 657)

    hsryksgqsstyqkngk      (SEQ ID NO. 658)
```

Similarly, in the MADS-box protein FDRMADS3 transcription factor of *Oryza sativa* (indica cultivar-group), the following Replikins were found:

```
                                             (SEQ ID NO. 659)
    kqeamvlkqeinllqkglryiygnraneh

                                             (SEQ ID NO. 660)
    kqeinllqkglryiygnraneh

                                             (SEQ ID NO. 661)
    kskegmlkaaneilqekiveqnglidvgmmvadqqngh

                                             (SEQ ID NO. 662)
    kaaneilqekiveqnglidvgmmvadqqngh
```

Similarly, in LONI MAIZE (ATP-binding redox associated Hydrolase; Serine protease; Multigene family; Mitochondrion), the following Replikins were found:

```
                                             (SEQ ID NO. 663)
    kvlaahrygik

                                             (SEQ ID NO. 664)
    klkiamkhliprvleqh

                                             (SEQ ID NO. 665)
    klkiamkh

                                             (SEQ ID NO. 666)
    ktslassiakalnrkfirislggvkdeadirgh

                                             (SEQ ID NO. 667)
    kalnrkfirislggvkdeadirgh

                                             (SEQ ID NO. 668)
    kfirislggvkdeadirgh

                                             (SEQ ID NO. 669)
    kvrlskatelvdrhlqsilvaekitqkvegqlsksqk

                                             (SEQ ID NO. 670)
    hlqsilvaekitqkvegglsksqk

                                             (SEQ ID NO. 671)
    kvrlskatelvdrh

                                             (SEQ ID NO. 672)
    kvggsavesskqdtkngkepihwhskgvaaralh

                                             (SEQ ID NO. 673)
    kvggsavesskqdtkngkepihwh

                                             (SEQ ID NO. 674)
    kvggsavesskqdtkngkepih

                                             (SEQ ID NO. 675)
    kqdtkngkepihwhskgvaaralh

                                             (SEQ ID NO. 676)
    kqdtkngkepih
```

Similarly, for Glyceraldehyde 3-phospate dehydrogenase A, a chloroplast precursor, the following Replikins are found:

```
                                             (SEQ ID NO. 677)
    hrdlrraraaalnivptstgaakavslvlpnlk

                                             (SEQ ID NO. 678)
    kvlddqkfgiikgtmttth

                                             (SEQ ID NO. 679)
    hiqagakkvlitapgk

                                             (SEQ ID NO. 680)
    hgrgdaspldviaindtggvkqashllk

                                             (SEQ ID NO. 710)
    kqashllk
```

Further, examples of rust resistance-like protein RP1-4 (*Zea mays*) found include the following Replikins:

(SEQ ID NO. 681)
kvrrvlskdysslkqlmtlmmdddiskhlqiiesgleeredkvwmkeniik (SEQ ID NO. 682)
kvrrvlskdysslkqlmtlmmdddiskh (SEQ ID NO.683)
hlqiiesgleeredkvwmkeniik (SEQ ID NO. 684)
hdlreniimkaddlask (SEQ ID NO. 685)
hvqnlenvigkdealask (SEQ ID NO. 686)
kkqgyelrqlkdlnelggslh (SEQ ID NO. 687)
kqgyelrqlkdlnelggslh (SEQ ID NO. 688)
klylksrlkelilewssengmdamnilh (SEQ ID NO. 689)
hlqllqlngmverlpnkvcnlsklrylrgykdqipnigk (SEQ ID NO. 690)
hlqllqlngmverlpnkvcnlskrylrgyk (SEQ ID NO. 691)
hlqllqlngmverlpnkvcnlsk (SEQ ID NO. 692)
hnsnklpksvgelk (SEQ ID NO. 693)
klpkvgelkh (SEQ ID NO. 694)
hlsvrvesmqkhkeiiyk (SEQ ID NO. 695)
khkeiiyk (SEQ ID NO. 696)
klrdilqesqkfllvldlalfkh (SEQ ID NO. 697)
hafsgaeikdqllrmklqdtaeeiakrlgqcplaakvlgsrmcrrk (SEQ ID NO. 698)
hafsgaeikdqllrmk (SEQ ID NO. 699)
klqdtaeeiakrlgqclaakvlgsrmcrrkdiaewkaadvwfeksh (SEQ ID NO. 700)
kvlgsrmcrrkdiaewkaadvwfeksh (SEQ ID NO. 701)
kdiaewkaadvwfeksh (SEQ ID NO. 702)
kaadvwfeksh (SEQ ID NO. 703)
hvptttslptskvfgrnsdrdrivkfllgktttaeasstk (SEQ ID NO. 704)
kailteakqlrdllglph (SEQ ID NO. 705)
kakaksgkgpllredessstattvmkpfh (SEQ ID NO. 706)
ksphrgkleswlrrlkeafydaedlldeh -continued (SEQ ID NO. 707)
ksphrgkleswlrrlk (SEQ ID NO. 708)
hrgkleswlrrlk (SEQ ID NO. 709)
ksphrgk As discussed previously, the Replikin in wheat ubiquitin activating enzyme E (SEQ ID Nos. 614-616) is conserved. This conservation of Replikin structure provides reliable targets for stimulation of plant growth.

The close relationship of Replikins to redox enzymes is also clearly indicated in this structure in wheat. Thus, this wheat ubiquitin activating enzyme E activates ubiquitin by first adenylating with ATP its carboxy-terminal glycine residue and, thereafter, linking this residue to the side chain of a cysteine residue in E1 (SEQ ID NO. 614), yielding an ubiquitin-E1 thiolester and free AMP.

A further example of the relationship of wheat Replikins to redox enzymes was also found in the PSABWheat Protein, Photosystem I P700 chlorophyll A apoprotein A2 (PsaB) (PSI-B) isolated from bread Chinese spring wheat *Chloroplast Triticum aestivum*. This protein functions as follows: PsaA and PsaB bind 9700, the primary electron donor of photosystem I (PSI), as well as the electron acceptors A0, A1, and FX. PSI functions as a plastocyanin/cytochrome c6-ferredoxin oxidoreductase. Cofactor P700 is a chlorophyll A dimer, A0 is chlorophyll A, A1 is a phylloquinone and FX is a 4Fe-4S iron-sulfur center. The subunit A psaA/S heterodimer binds the P700 chlorophyll special pair and subsequent electron acceptors. The PSI reaction center of higher plants and algae is composed of one at least 11 subunits. This is an integral membrane protein of the Chloroplast thylakoid membrane. The 4Fe-4S iron-sulfur"center" to which 'h' bind is critical; hence the significance of 'h' in Replikin structure. Next to bacterial Replikins, these wheat Replikins and plant Replikins are the most primitive evolutionary illustrations of the importance of the Replikin structure to replication and the energy source needed for replication. This basic relationship carries through algae, virus Replikins, bacteria, cancer cells, and apparently all organisms with regard to replication.

Further examples of Replikins were found in the PSAB Wheat protein, which is critical for wheat growth. These include:

(SEQ ID NO. 617)
hlqpkwkpslswfknaesrlnhh (SEQ ID NO. 618)
hlqpkwkpslswfk (SEQ ID NO. 619)
kwkpslswfknaesrlnhh (SEQ ID NO. 620)
kwkpslswfknaesrlnh (SEQ ID NO. 621)
kpslswfknaesrlnhh (SEQ ID NO. 622)
kpslswfknaesrlnh (SEQ ID NO. 623)
hhaialglhtttlilvkgaldargsklmpdkk -continued (SEQ ID NO. 624)
haialglhtttlilvkgaldargsklmpdkk (SEQ ID NO. 625)
hhaialglhtttlilvkgaldargsk (SEQ ID NO. 626)
haialglhtttlilvkgaldargsk (SEQ ID NO. 627)
htttlilvkgaldargsklmpdkk (SEQ ID NO. 628)
htttlilvkgaldargsklmpdk (SEQ ID NO. 629)
htttlilvkgaldargsk A further example of the relationship of wheat Replikins to redox is provide in the PSAA_WHEAT Photosystem I 9700 chlorophyll A apoprotein A1, that include:

(SEQ ID NO. 630)
hhhlaiailfliaghmyrtnwgighglkdileahkgpftgqghk (SEQ ID NO. 631)
hhlaiailfliaghmyrtnwgighglkdileahkgpftgqghk (SEQ ID NO. 632)
hlaiailfliaghmyrtnwgighglkdileahkgpftgqghk (SEQ ID NO. 633)
hmyrtnwgighglkdileahkgpftgqghk (SEQ ID NO. 634)
hglkdileahkgpftgqghk (SEQ ID NO. 635)
hdileahkgpftgqghk (SEQ ID NO. 636)
hkgpftgqghk (SEQ ID NO. 637)
kgpftgqghk Computer Software for Identifying Replikins The present invention also provides methods for identifying Replikin sequences in an amino acid or nucleic acid sequence. Visual scanning of over four thousand sequences was performed in developing the present 3-point-recognition methods. However, data banks comprising nucleotide and/or amino acid sequences can also be scanned by computer for the presence of sequences meeting the 3 point recognition requirements.

Figure 6:
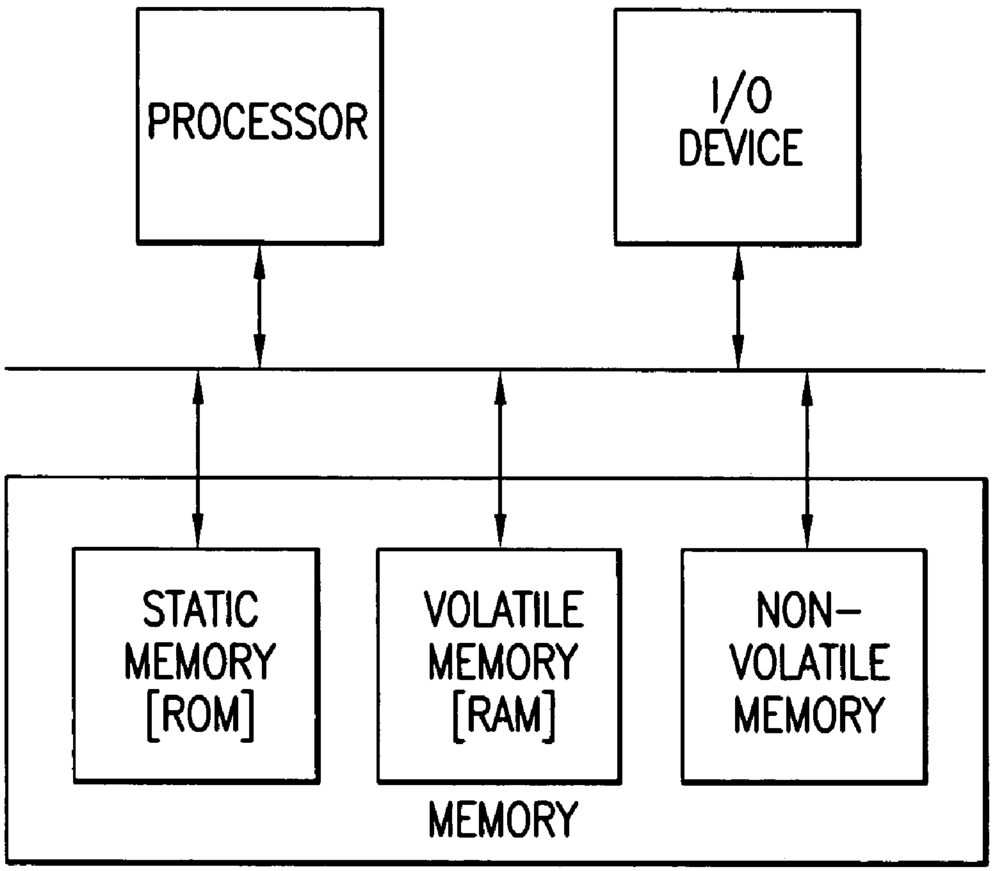
FIG. 6 is a box diagram depicting an embodiment of the invention wherein a computer is used to carry out the 3-point-recognition method of identifying Replikin sequences.

According to another embodiment of the invention, three-point recognition methods described herein may be performed by a computer. FIG. 6 is a block diagram of a computer available for use with the foregoing embodiments of the present invention. The computer may include a processor, an input/output device and a memory storing executable program instructions representing the 3-point-recognition methods of the foregoing embodiments. The memory may include a static memory, volatile memory and/or a nonvolatile memory. The static memory conventionally may be a read only memory ("ROM") provided on a magnetic, or an electrical or optical storage medium. The volatile memory conventionally may be a random accessmemory ("RAM") and may be integrated as a cache within the processor or provided externally from the processor as a separate integrated circuit. The non-volatile memory may be an electrical, magnetic or optical storage medium.

From a proteomic point of view the construction of a "3-point recognition" template based on the new glioma peptide sequence led directly to identification of a biology-wide class of proteins having related structures and functions. The operation of the 3-point-recognition method resembles identification by the use of a "keyword" search; but instead of using the exact spelling of the keyword "kagvaflhkk" (SEQ ID NO.: 1) as in a typical sequence homology search, or in the nucleotide specification of an amino acid, an abstraction of the keyword delimited by the "3-point-recognition" parameters is used. This delimited abstraction, although derived from a single relatively short amino acid sequence leads to identification of a class of proteins with structures that are defined by the same specifications. That particular functions, in this case transformation and replication, in addition to structures, turn out also to be shared by members of the exposed class suggests that these structures and functions are related. Thus, from this newly identified short peptide sequence, a molecular recognition 'language' has been formulated, which previously has not been described. Further, the sharing of immunological specificity by diverse members of the class, as here demonstrated for the cancer Replikins, suggests that B cells and their product antibodies recognize Replikins by means of a similar recognition language.

Other Uses of the Three Point Recognition Method

Since "3-point-recognition" is a proteomic method that specifies a particular class of proteins, using three or more different recognition points for other peptides similarly should provide useful information concerning other protein classes. Further, the "3-point-recognition" method is applicable to other recognins, for example to the TOLL 'innate' recognition of lipopolyssacharides of organisms. The three point recognition method may also be modified to identify other useful compounds of covalently linked organic molecules, including other covalently linked amino acids, nucleotides, carbohydrates, lipids or combinations thereof. In this embodiment of the invention a sequence is screened for subsequences containing three or more desired structural characteristics. In the case of screening compounds composed of covalently linked amino acids, lipids or carbohydrates the subsequence of 7 to about 50 covalently linked units should contain (1) at least one first amino acid, carbohydrate or lipid residue located seven to ten residues from a second of the first amino acid, carbohydrate or lipid residue; (2) encoding at least one second amino acid, lipid or carbohydrate residue; and (3) at least 6% of the first amino acid, carbohydrate or lipid residue. In the case of screening nucleotide sequences, the subsequence of about 21 to about 150 nucleotides should contain (1) at least one codon encoding a first amino acid located within eighteen to thirty nucleotides from a second codon encoding the first amino acid residue; (2) at least one second amino acid residue; and (3) encodes at least 6% of said first amino acid residue.

Several embodiments of the present invention are specifically illustrated and described herein. However, it will be appreciated that modifications and variations of the present invention are encompassed by the above teachings and within the purview of the appended claims without departing from the spirit and intended scope of the invention.

EXAMPLE 1

Process for Extraction, Isolation and Identification of Replikins and the Use of Replikins to Target, Label or Destroy Replikin-Containing Organisms a) Algae The following algae were collected from Bermuda water sites and either extracted on the same day or frozen at −20 degrees C. and extracted the next day. The algae were homogenized in a cold room (at 0 to 5 degrees C.) in 1 gram aliquots in neutral buffer, for example 100 cc. of 0.005M phosphate buffer solution, pH 7 ("phosphate buffer") for 15 minutes in a Waring blender, centrifuged at 3000 rpm, and the supernatant concentrated by perevaporation and dialyzed against phosphate buffer in the cold to produce a volume of approximately 15 ml. The volume of this extract solution was noted and an aliquot taken for protein analysis, and the remainder was fractionated to obtain the protein fraction having a pK range between 1 and 4.

The preferred method of fractionation is chromatography as follows: The extract solution is fractionated in the cold room (4° C.) on a DEAE cellulose (Cellex-D) column 2.5×11.0 cm, which has been equilibrated with 0.005M phosphate buffer. Stepwise eluting solvent changes are made with the following solutions:

Solution 1-4.04 g. NaH2PO4 and 0.5g NaH2PO4 are dissolved in 15 liters of distilled water (0.005 molar, pH 7);

Solution 2-8.57 g. NaH2PO4 is dissolved in 2,480 ml. of distilled water;

Solution 3-17.1 g. of NaH2PO4 is dissolved in 2480 ml of distilled water (0.05 molar, pH 4.7);

Solution 4-59.65 g. of NaH2PO4 is dissolved in 2470 ml distilled water (0.175 molar);

Solution 5-101.6 g. of NaH2PO4 is dissolved in 2455 ml distilled water (pH 4.3);

Solution 6-340.2 g. of NaH2PO4 is dissolved in 2465 of distilled water (1.0 molar, pX-i 4.1);

Solution 7-283.63 g. of 80% phosphoric acid (H3P04) is made up in 2460 ml of distilled water (1.0 molar, pH 1.0).

The extract solution, in 6 to 10 ml volume, is passed onto the column and overlayed with Solution 1, and a reservoir of 300 ml of Solution 1 is attached and allowed to drip by gravity onto the column. Three ml aliquots of eluant are collected and analyzed for protein content at OD 280 until all of the protein to be removed with Solution 1 has been removed from the column. Solution 2 is then applied to the column, followed in succession by Solutions 3, 4, 5, 6 aid 7 until all of the protein which can, be removed with each Solution is removed from the column. The eluates from Solution 7 are combined, dialyzed against phosphate buffer, the protein content determined of both dialysand and dialyzate, and both analyzed by gel electrophoresis. One or two bands of peptide or protein of molecular weight between 3,000 and 25,000 Daltons are obtained in Solution 7. For example the algae *Caulerpa mexicana, Laurencia obtura, Cladophexa prolifera, Sargassum natans, Caulerpa verticillata, Halimeda tuna,* and *Penicillos capitatus,* after extraction and treatment as above, all demonstrated in Solution 7 eluates sharp peptide bands in this molecular weight region with no contaminants. These Solution 7 proteins or their eluted bands are hydrolyzed, and the amino acid composition determined. The peptides so obtained, which have a lysine composition of 6% or greater are Replikin precursors. These Replikin peptide precursors are then determined for amino acid sequence and the Replikins are determined by hydrolysis and mass spectrometry as detailed in U.S. Pat. No. 6,242,578 B1. Those that fulfill the criteria defined by the "3-point-recognition" method are identified as Replikins. This procedure can also be applied to obtain yeast, bacterial and any plant Replikins.

b) Virus

Using the same extraction and column chromatography separation methods as above in a) for algae, Replikins in virus-infected cells are isolated and identified.

c) Tumor Cells In Vivo and In Vitro Tissue Culture

Using the same extraction and column chromatography separation methods as above in a) for algae, Replikins in tumor cells are isolated and identified. For example, Replikin precursors of Astrocytin isolated from malignant brain tumors, Malignin (Aglyco 1OB) isolated from glioblastoma tumor cells in tissue culture, MCF7 mammary carcinoma cells in tissue culture, and P3J Lymphoma cells in tissue culture each treated as above in a) yielded Replikin precursors with lysine content of 9.1%, 6.7%, 6.7%, and 6.5% respectively. Hydrolysis and mass spectrometry of Aglyco lOB as described in Example 10 U.S. 6,242,578 B1 produced the amino acid sequence, ykagvaflhkkndiide (SEQ ID NO: 866) the 16-mer Replikin.

EXAMPLE 2

As an example of diagnostic use of Replikins: Aglyco 1OB or the 16-mer Replikin may be used as antigen to capture and quantify the amount of its corresponding antibody present in serum for diagnostic purposes are as shown in FIGS. 2, 3, 4 and 7 of U.S. Pat. No. 6,242,578 B1.

As an example of the production of agents to attach to Replikins for labeling, nutritional or destructive purposes: Injection of the 16-mer Replikin into rabbits to produce the specific antibody to the 16-mer Replikin is shown in Example 6 and FIGS. 9A and 9B of U.S. Pat. No. 6,242,578 B1.

As an example of the use of agents to label Replikins: The use of antibodies to the 16-mer Replikin to label specific cells which contain this Replikin is shown in FIG. 5 and Example 6 of U.S. Pat. No. 6,242,578 B1.

As an example of the use of agents to destroy Replikins: The use of antibodies to the 16-mer Replikin to inhibit or destroy specific cells which contain this Replikin is shown in FIG. 6 of U.S. Pat. No. 6,242,578 B1.

EXAMPLE 3

Analysis of sequence data of isolates of influenza virus hemagglutinin protein or neuraminidase protein for the presence and concentration of Replikins is carried out by visual scanning of sequences or through use of a computer program based on the 3-point recognition system described herein. Isolates of influenza virus are obtained and the amino acid sequence of the influenza hemagglutinin and/or neuraminidase protein is obtained by any art known method, such as by sequencing the hemagglutinin or neuraminidase gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause of influenza in upcoming flu seasons, and that form the basis for seasonal influenza peptide vaccines or nucleic acid based vaccines. Observation of an increase in concentration, particularly a stepwise increase in concentration of Replikins in a given strain of influenza virus for a period of about six months to about three years or more is a predictor of emergence of the strain as a likely cause of influenza epidemic or pandemic in the future.

Peptide vaccines or nucleic acid-based vaccines based on the Replikins observed in the emerging strain are generated. An emerging strain is identified as the strain of influenza virus having the highest increase in concentration of Replikin sequences within the hemagglutinin and/or neuraminidase sequence during the time period. Preferably, the peptide or nucleic acid vaccine is based on or includes any Replikin sequences that are observed to be conserved in the emerging strain. Conserved Replikins are preferably those Replikin sequences that are present in the hemagglutinin or neuraminidase protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

The influenza vaccine is preferably administered to a patient in need thereof prior to the onset of "flu season." Influenza flu season generally occurs in late October and lasts through late April. However, the vaccine may be administered at any time during the year. Preferably, the influenza vaccine is administered once yearly, and is based on Replikin sequences observed to be present, and preferably conserved in the emerging strain of influenza virus. Another preferred Replikin for inclusion in an influenza vaccine is a Replikin demonstrated to have re-emerged in a strain of influenza after an absence of one or more years.

EXAMPLE 4

Analysis of sequence data of isolates of coronavirus nucleocapsid, or spike, or envelope, or other protein for the presence and concentration of Replikins is carried out by visual scanning of sequences or through use of a computer program based on the 3-point recognition method described herein. Isolates of coronavirus are obtained and the amino acid sequence of the coronavirus protein is obtained by any method known in the art, such as by sequencing the protein's gene and deriving the protein sequence therefrom. Sequences are scanned for the presence of new Replikins, conservation of Replikins over time and concentration of Replikins in each isolate. Comparison of the Replikin sequences and concentrations to the amino acid sequences obtained from isolates at an earlier time, such as about six months to about three years earlier, provides data that are used to predict the emergence of strains that are most likely to be the cause an outbreak or pandemic, and that form the basis for coronavirus peptide vaccines or nucleic acid based vaccines. Observation of an increase in concentration, particularly a stepwise increase in concentration of Replikins in a given class, or strain, of coronavirus for a period of about six months to about three years or more is a predictor of emergence of the strain as a likely cause of an epidemic or pandemic, such as SARS, in the future.

Peptide vaccines or nucleic acid-based vaccines based on the Replikins observed in the emerging strain of coronaviruses are generated. An emerging strain is identified as the strain of coronovirus having the highest increase in concentration of Replikin sequences within the nucleocapsid sequence during the time period. Preferably, the peptide or nucleic acid vaccine is based on or includes any Replikin sequences that are observed to be conserved in the strain. Conserved Replikins are preferably those Replikin sequences which are present in the nucleocapsid protein sequence for about two years and preferably longer. The vaccines may include any combination of Replikin sequences identified in the emerging strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

The coronavirus vaccine may be administered to a patient at any time of the year. Preferably, the coronavirus vaccine is administered once and is based on Replikin sequences observed to be present, and preferably conserved, in the classes of coronavirus.

EXAMPLE 5

Analysis of sequence data of isolates of *Plasmodium falciparum* antigens for the presence and concentration of Replikins is carried out by visual scanning of sequences or through use of a computer program based on the 3-point recognition method described herein. Isolates of *Plasmodium falciparum* are obtained and the amino acid sequence of the protein is obtained by any art known method, such as by sequencing the gene and deriving the protein sequence therefrom. Sequences are scanned for the presence of Replikins, conservation of Replikins over time and concentration of Replikins in each isolate. This information provides data that are used to form the basis for anti-malarial peptide vaccines or nucleic acid based vaccines.

Peptide vaccines or nucleic acid-based vaccines based on the Replikins observed in the malaria causing organism are generated. Preferably, the peptide or nucleic acid vaccine is based on or includes any Replikin sequences that are observed to be present on a surface antigen of the organism. The vaccines may include any combination of Replikin sequences identified in the malaria causing strain.

For vaccine production, the Replikin peptide or peptides identified as useful for an effective vaccine are synthesized by any method, including chemical synthesis and molecular biology techniques, including cloning, expression in a host cell and purification therefrom. The peptides are preferably admixed with a pharmaceutically acceptable carrier in an amount determined to induce a therapeutic antibody reaction thereto. Generally, the dosage is about 0.1 µg to about 10 mg.

Then malaria vaccine is preferably administered to a patient in need thereof at any time during the year, and particularly prior to travel to a tropical environment.

Another embodiment includes an antisense nucleic acid molecule complementary to the coding strand of the gene or the mRNA encoding organism for the replikins in organisms including, but not limited to, viruses, trypanosomes, bacteria, fungi, algae, amoeba, and plants, wherein said antisense nucleic acid molecules is complementary to a nucleotide sequence of a replikin containing organism.

What is claimed is:

1. An isolated or synthesized coronavirus peptide consisting of 7 to about 50 amino acids wherein said peptide is isolated or synthesized by identifying a motif consisting of:

(1) at least one lysine residue located at a first terminus of said motif and at least one lysine residue or at least one histidine residue located at a second terminus of said motif;

(2) a first lysine residue located six to ten residues from a second lysine residue;

(3) at least one histidine residue; and (4) at least 6% lysine residues, selecting said identified motif and isolating or synthesizing said coronavirus peptide comprising said identified motif wherein said motif is selected from the group consisting of SEQ ID NO: 712, SEQ ID NO: 717, SEQ ID NO: 718, SEQ ID NO: 719, and SEQ ID NO: 720.

2. The peptide according to claim 1 wherein said coronavirus peptide comprises the amino acid sequence set forth in SEQ ID NO: 712.

3. The peptide according to claim 1 wherein said coronavirus peptide comprises the amino acid sequence set forth in SEQ ID NO: 717.

4. The peptide according to claim 1 wherein said coronavirus peptide comprises the amino acid sequence set forth in SEQ ID NO: 718.

5. The peptide according to claim 1 wherein said coronavirus peptide comprises the amino acid sequence set forth in SEQ ID NO: 719.

6. The peptide according to claim 1 wherein said coronavirus peptide comprises the amino acid sequence set forth in SEQ ID NO: 720.

7. The peptide according to claim 1 wherein said coronavirus peptide consists of the amino acid sequence set forth in SEQ ID NO: 712.

8. The peptide according to claim 1 wherein said coronavirus peptide consists of the amino acid sequence set forth in SEQ ID NO: 717.

9. The peptide according to claim 1 wherein said coronavirus peptide consists of the amino acid sequence set forth in SEQ ID NO: 718.

10. The peptide according to claim 1 wherein said coronavirus peptide consists of the amino acid sequence set forth in SEQ ID NO: 719.

11. The peptide according to claim 1 wherein said coronavirus peptide consists of the amino acid sequence set forth in SEQ ID NO: 720.

12. A method of stimulating the immune system of a subject to produce antibodies to coronavirus comprising administering an effective amount of at least one isolated or synthesized coronavirus peptide of claim 1.

13. An immunogenic composition comprising a pharmaceutically acceptable carrier and at least one isolated or synthesized coronavirus Replikin peptide wherein said isolated or synthesized coronavirus Replikin peptide consists of 7 to about 50 amino acids and wherein said coronavirus Replikin peptide is isolated or synthesized by identifying a motif consisting of:

(1) at least one lysine residue located at a first terminus of said motif and at least one lysine residue or at least one histidine residue located at a second terminus of said motif;

(2) a first lysine residue located six to ten residues from a second lysine residue;

(3) at least one histidine residue; and (4) at least 6% lysine residues, selecting said identified motif and isolating or synthesizing said coronavirus peptide comprising said identified motif and wherein said identified motif is selected from the group consisting of SEQ ID NO: 712, SEQ ID NO: 717, SEQ ID NO: 718, SEQ ID NO: 719, and SEQ ID NO: 720.

14. The immunogenic composition of claim 13 wherein the immunogenic composition comprises a plurality of isolated Replikin peptides.

15. The immunogenic composition of claim 13 wherein the at least one isolated or synthesized Replikin peptide comprises the amino acid sequence of SEQ ID NO: 712.

* * * * *

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Column 5, line 49, “lysine residues” should be changed to --lysine residue--;

Column 8, line 53, “at least on” should be changed to --at least one--;

Column 9, lines 58-59, there should be no line break between “step” and “(3)”;

Column 10, line 63, “BACTERIA” should be on a separate line as it is the section title;

Column 12, line 55, the following missing paragraphs should be inserted:

--Two important sub-species of bacteria, classified under mycobacteria, are Mycobacterium leprae (leprosy) whose 30-s ribosomal protein has a C-terminal Replikin and Mycobacterium tuberculosis (tuberculosis) whose ATPase has three Replikins.

Replikin in 30s Ribosomal Protein s6 of Mycobacterium leprae (leprosy) is: kvmrtdkh (SEQ ID NO: 797).--;

Column 13, line 10, “kncnikcpaglttqeafNgdpralaqylmniah” should be changed to --kncnikcpaglttqeafngdpralaqylmniah--;

Column 13, line 58 “bindspecifically” should be changed to --bind specifically--;

Column 16, line 21, “role to rapid” should be changed to --role in rapid--;

Column 18, line 17, “know” should be changed to --known--;

Table 2, line 2 (columns 19-20),

“35 Isolepisprolifera kagaetgeikgh” should be changed to

--35 Isolepis prolifera kaqaetgeikgh--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 2, line 10 (columns 19-20),
"Diseula dcstructiva" should be changed to --Diseula destructiva--;

Table 2, line 31 (columns 21-22),
"98 *Bacillus anthracis* haerlkvgknapk" should be changed to
--98 *Bacillus anthracis* haerlkvqknapk--;

Table 2, line 36 (columns 21-22),
"46 Arabidopsis thaliana, kelssttgeksh" should be changed to
--46 Arabidopsis thaliana, kelssttqeksh--;

Table 2, line 51 (columns 21-22),
"101 Small Pox Virus (Variola) hyddvnikndivvsrck" should be changed to
--101 Small Pox Virus (Variola) hyddvrikndivvsrck--;

Table 2, line 97 (columns 23-24), "tyrosine kinasc" should be changed to
--tyrosine kinase--;

Column 25, lines 11-13, the following repeated text should be deleted:
"members of the coronavirus class and, more specifically, are also present in the nucleocapsid protein sequence from these coronaviruses.";

Table 3, line 4 (columns 27-28),
"hekyggink (SEQ ID NO. 107)" should be changed to
--hekygglnk (SEQ ID NO. 107)--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 3, line 20 (columns 27-28),
"klygdskpqkflssangvtth (SEQ ID NO. 130)" should be changed to
--klygdskpqkftssangvtth (SEQ ID NO. 130)--;

Table 4, lines 43-44 (columns 31-32),
"h(k/n)(g/q)kssfy(r/k)nllwltekng(l/s) 1948, 79, 89, 96
yp(n/t)lsksyannkek (SEQ ID NO. 165)"
should be changed to
--h(k/n)(g/q)kssfy(r/k)nllwltekng(l/s) 1948, 79, 89, 96
yp(n/t)lsksyannkek (SEQ ID NO. 165)--;

Table 4, line 45 (columns 31-32),
"h(k/n)(g/q)kssfy(r/k)nllwltek (SEQ ID NO. 166) 1948, 79, 89, 96"
should be changed to
--h(k/n)(g/q)kssfy(r/k)nllwltek (SEQ ID NO. 166) 1948, 79, 89, 96--;

Column 48, line 34, "proceeds" should be changed to --precedes--;

Column 49, line 26, "(see paragraph [0109])" should be changed to
--(see columns 16-17)--;

Table 7, line 5 (columns 49-50), "Goose Replik in" should be changed to
--Goose Replikin--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 7, line 10 (columns 49-50),

"1kedlypklrksvvhnkkkevlvlwgihh 29 1919-2001 H1N1" should be changed to

--1kedlypklrksvvhnkkkevlviwgihh 29 1919-2001 H1N1--;

Table 7, line 11 (columns 49-50),

"lkensypklrksiiinkkkevlvlwgihh H3N2 Influenza" should be changed to

--lkensypklrksiiinkkkevlviwgihh H3N2 Influenza--;

Table 7, line 88 (columns 51-52),

"khkkgivk 8 Plasm. Falciparum" should be changed to

--khkkqivk 8 Plasm. Falciparum--;

Table 7a.

Goose Replikin (GR) sequences in different influenza strains from 1917 to 2003; SARS and H3N2-Fujian appearance 2002-2003.

| Replikins related to the Goose Replikin<br>Continuous amino acid sequences<br>Shared motif and/or position not underlined<br>Amino acid substitutions underlined<br>'Condensed' indicates condensation of sequence length in H1N2 and H3N2-Fujian | SEQ ID NO. | Replikin Length (Number of amino acids) | Virus or other organism containing replikin (complete Replikins except for Fujian strain) |
|---|---|---|---|
| kkgtsypklsksytnnkgkevlvlwgvhh | 831 | 29 | **1917 H1N_ Influenza Goose Replikin (GR)** |
| kkgssypklsksyvnnkgkevlvlwgvhh | 832 | 29 | **1918 GR in H1N1 Human Influenza** |
| kkgsnypvakgsynntsgeqmliiwgvhh | 875 | 29 | 1958 GR H2N2 Influenza |
| kkgpnypvakgsynntsgeqmliiwgvhh | 867 | 29 | 1964,1965,1968 GR in H2N2 Influenza |
| kkgtsypklsksytnnkgkevlvlwgvhh | 833 | 29 | 1976,'77,'80,'81,'85 GR in H1N1 Influenza |

UNITED STATES PATENT AND TRADEMARK OFFICE
CERTIFICATE OF CORRECTION

PATENT NO.        : 7,442,761 B2
APPLICATION NO.   : 10/860050
DATED             : October 28, 2008
INVENTOR(S)       : Bogoch et al.

It is certified that error appears in the above-identified patent and that said Letters Patent is hereby corrected as shown below:

| Sequence | No. | Len | Description |
|---|---|---|---|
| kknsayptikrsynntnqedllvlwgihh | 834 | 29 | 1996-2001 GR in H5N1 Influenza |
| kkgdsypklsksytnnkgkevlvlwgvhh | 868 | 29 | 1996 GR in H1N1 Influenza |
| kkgssypklsksyvnnkgkevlvlwgvhh | 869 | 29 | 1997,1998 GR in H1N1 Influenza |
| kkgnsypkisksyinnkekevlvlwgihh | 870 | 29 | 1999 GR in H1N2 Influenza |
| kkgnsypklsksyinnkkkevlviwgihh | 871 | 29 | 2000 GR in H1N2 Influenza |
| kkgnsypklsksyinnkgkkvlvlwgihh | 872 | 29 | 2001 GR in H1N2 Influenza |
| kkgtsypklsksytnnkkkevlvlwgvhh | 835 | 29 | 2001 GR in H1N2 Influenza |
| knglypnlsksyannkekevlilwgvhh | 836 | 28 | 2002 GR in H1N2 Influenza (condensed) |
| khldayktfpptepkkdkkkk | 837 | 21 | 2002-3 Human SARS nucleocapsid protein |
| kkensypklrksiiinkkkevlviwgihh | 751 | 29 | 1968-2001 GR in H3N2 Influenza (complete) |
| kleykypalnvtmpnndkfdklyiwgvhh | 752 | 29 | 1996 H3N2 Fujian Influenza (incomplete) |
| kykypalnvtmpnnekfdklyiwgvhh | 753 | 27 | 2003 H3N2 Fujian(condensed, incomplete) |
| ktgnaklqrkkekknkrettlqqh | 838 | 24 | Porcine epidemic diarrhea coronavirus |
| kkinspgpkfegsgvpdnenlktsqqh | 839 | 27 | Avian bronchitis coronavirus |
| kknvksakqlphlkvlldvrgakqlph | 754 | 27 | 2000 shrimp white spot syndrome virus |
| kkinspgpkfegsgvpdnenlktsqqh | 840 | 27 | Avian bronchitis coronavirus |
| khlrefvfknkdgflyvykk | 755 | 20 | 2002-3 Human SARS spike protein |
| kkgakllhkpivwh | 756 | 14 | 2002-3 Human SARS nucleocapsid protein |
| khlrefvfknkdgflyvykk | 841 | 20 | 2002-3 Human SARS spike protein |
| kkgakllhkpivwh | 842 | 14 | 2002-3 Human SARS nucleocapsid protein |

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

| | | | |
|---|---|---|---|
| keeldkyfknh | 843 | 11 | 2002-3 Human SARS spike protein |
| kkgakllhk | 844 | 9 | 2002-3 Human SARS envelope protein |
| kyrylrhgk | 845 | 9 | 2002-3 Human SARS spike protein |
| khldayk | 846 | 7 | 2002-3 Human SARS nucleocapsid protein |
| ksrgipikkgh | 847 | 11 | Nipah virus, v-protein |
| ksrimpikkgh | 848 | 11 | Hendra virus, v-protein |
| kkflngfkhh | 849 | 10 | Sindbis virus |
| kkkskkhkdk | 850 | 10 | EEL leukemia |
| khhpkdnlik | 851 | 10 | BRCA-1 breast cancer |
| khkrkkfrqk | 852 | 10 | Ovarian cancer |
| kagvaflhkk | 853 | 10 | Glioma Replikin |
| kihlisvkk | 854 | 9 | Smallpox virus |
| krfilhakk | 855 | 9 | HIV TAT protein |
| klisihek | 856 | 8 | Smallpox virus |
| klreehck | 857 | 8 | B.anthracis, HATPase |
| kkhatvlk | 858 | 8 | Ebola virus polymerase |

Table 7a, line 3 (columns 55-56),

"kkgsnypvakgsynntsqeqmliiwgvhh 875 29 1958 GR H2N2 Infuenza"

should be changed to

--kkgsnypvakgsynntsgeqmliiwgvhh 875 29 1958 GR H2N2 Influenza--;

Table 7a, line 4, (columns 55-56),

"kkgpnypvakgsynntsqeqmliiwgvhh 867 29 1964, 1965, 1968 GR in H2N2 infuenza" should be changed to --kkgpnypvakgsynntsgeqmliiwgvhh 867 29 1964, 1965, 1968 GR in H2N2 Influenza--;

UNITED STATES PATENT AND TRADEMARK OFFICE
CERTIFICATE OF CORRECTION

PATENT NO. : 7,442,761 B2 Page 7 of 14
APPLICATION NO. : 10/860050
DATED : October 28, 2008
INVENTOR(S) : Bogoch et al.

It is certified that error appears in the above-identified patent and that said Letters Patent is hereby corrected as shown below:

Table 7a, line 11, (columns 55-56),

"kkgnsypksksyinnkgkkvlwgihh 872 29 2001 GR in H1N2 Influenza"

should be changed to

--kkgnsypklsksyinnkgkkevlvlwgihh 872 29 2001 GR in H1N2 Influenza--;

Table 7a, line 12, (columns 55-56),

"kkgtsypklsksytnnkkkeylvlwgihh 835 29 2001 GR in H1N2 Influenza"

should be changed to

--kkgtsypklsksytnnkkkevlvlwgihh 835 29 2001 GR in H1N2 Influenza--;

Table 7a, line 15, (columns 55-56),

"kkensypklrksiiihkkkevlvlwgihh 751 29 1968-2001 GR in H3N2 Influenza (complete)" should be changed to --kkensypklrksiiinkkkevlviwgihh 751 29 1968-2001 GR in H3N2 Influenza (complete)--

Table 7a, line 39 (columns 55-56), "Smalpox" should be changed to --Smallpox.--;

Column 60, lines 60-61,

"hqn(s/e)(e/q)g(t/s)g(q/y)aad(l/q)kstq(a/n)a(i/l)d(q/g)l(n/t)(g/n)k,(I/v)n(r/s) vi(e/c)l" (SEQ ID NO. 276)"

should be changed to

--hqn(s/e)(e/q)g(t/s)g(q/y)aad(l/q)kstq(a/n)a(i/l)d(q/g)i(n/t)(g/n)k(l/v)n(r/s)vi(e/c)l" (SEQ ID NO. 276)--;

UNITED STATES PATENT AND TRADEMARK OFFICE
CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Column 61, lines 36-37, "(SEQ ID NO.: 5) "kcfficgkegh"" should be changed to --(SEQ ID NO.: 5) "kcfncgkegh"--;

Column 63, line 9, "(SEQ ID NO.: 5) "kcfficgkegh"" should be changed to --(SEQ ID NO.: 5) "kcfncgkegh"--;

Column 66, after line 16, the following missing paragraph should be inserted:
--Description: The first occurrence of tomato yellow leaf curl virus in tomato (specific host Lycopersicon esculentum Mill.), in Japan
Isolated: 1998 Source: Tomato yellow leaf curl virus-[Aichi] Strain: Aichi--;

Column 66, after line 44, the following missing paragraph should be inserted before (SEQ ID NO. 762):
--Analysis of this sequence showed that amino acids 1-163 of this "replicating protein" contain five Replikins, namely: (SEQ ID NO.: 13) kfrinaknyfltyph, (SEQ ID NO.: 14) knletpvnklfiricrefh, (SEQ ID NO.: 15) hpniqaaksstdvk, (SEQ ID NO.: 16) ksstdvkaymdkdgdvldh, and (SEQ ID NO.: 17) kasalnilrekapkdfvlqfh.--;

Column 67, after (SEQ ID NO. 784), the following missing paragraphs should be inserted:
--Mid-molecule: Zero replikins.
Carboxy-terminal: Zero replikins.
Replikin Count=Number of Replikins per 100 amino acids=28/135=20.7
Even higher replikin counts are seen to be achieved by overlapping replikins in malaria.--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Column 69, line 45, before (SEQ ID NO. 393), the following missing paragraph should be inserted:

--In addition to repeats of replikin structures, another significant difference between replikin structures observed in influenza virus proteins and those in Plasmodium falciparum proteins is a marked overlap of replikins throughout malarial proteins. For example, overlapping replikin structures occur in blood stage trophozoites and schizonts as seen in the following:

1) in the 39 amino acid sequence of SEQ ID NO. 393, in addition to the four exact repeats of ‘ksdhnhk’, there are fourteen overlapping replikins (replikin concentration or Replikin Count=18/39=46.2/100 amino acids):--;

Column 69, lines 51-52, “(SEQ ID NO. 395) ksdhnbksdhnhksdpnhkkknnnnnk” should be changed to --(SEQ ID NO. 395) ksdhnhksdhnhksdpnhkkknnnnnk--;

Column 69, lines 53-54, “(SEQ ID NO. 396) ksdhnhksdpnhkkkrmnnnk” should be changed to --(SEQ ID NO. 396) ksdhnhksdpnhkkknnnnnk--;

Column 70, line 45, before (SEQ ID NO. 467), the following missing paragraph should be inserted:

--and 2) 15 overlapping Replikins occur in the 41 amino acids of SEQ ID NO. 467 (Replikin concentration or replikin count=36.6/100 amino acids).--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 9 should be replaced with the following table, which has underlining instead of shading so the text is readable:

| | | | | | | | |
|---|---|---|---|---|---|---|---|
| k405 | s406 | d407 | s408 | n409 | h410 | k411 | (SEQ ID NO. 785) |
| k411 | s412 | d413 | s414 | n415 | h416 | k417 | |
| k417 | s418 | d419 | s420 | n421 | h422 | k423 | |
| k423 | s424 | g425 | s426 | n427 | h428 | k429 | (SEQ ID NO. 786) |
| k429 | s430 | d431 | c432 | n433 | h434 | k435 | (SEQ ID NO. 787) |
| k435 | s436 | g437 | s438 | n439 | h440 | k441 | |
| k459 | s460 | d461 | n462 | n463 | h464 | k465 | (SEQ ID NO. 788) |
| k465 | s466 | d467 | s468 | s469 | h470 | k471 | (SEQ ID NO. 789) |
| k477 | s478 | d479 | s480 | s481 | h482 | k483 | |
| k483 | s484 | g485 | s486 | n487 | h488 | k489 | |

| | | | | | | | |
|---|---|---|---|---|---|---|---|
| k489 | s490 | d491 | n492 | n493 | h494 | k495 | |
| k495 | s496 | d497 | s498 | s499 | h500 | k501 | |
| k501 | s502 | g503 | s504 | n505 | h506 | k507 | |
| k507 | s508 | d509 | h510 | n511 | h512 | k513 | (SEQ ID NO. 790) |
| k513 | s514 | d515 | s516 | n517 | h518 | k519 | |
| k519 | s520 | d521 | s522 | n523 | h524 | k525 | |
| k525 | n526 | e527 | s528 | n529 | h530 | k531 | (SEQ ID NO. 791) |
| k531 | n532 | e533 | s534 | n535 | h536 | k537 | |
| k537 | n538 | e539 | s540 | n541 | h542 | k543 | |
| k543 | n544 | e545 | s546 | n547 | h548 | k549 | |
| k549 | n550 | e551 | s552 | n553 | h554 | k555 | |
| k555 | n556 | d557 | s558 | n559 | h560 | k561 | (SEQ ID NO. 792) |
| k573 | s574 | d575 | n576 | n577 | h578 | k579 | (SEQ ID NO. 793) |
| k591 | s592 | d593 | n594 | n595 | h596 | k597 | |

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

k609 s610 d611 n612 n613 h614 k615
k615 s616 d617 n618 n619 h620 k621
k621 s622 d623 n624 n625 h626 k627
k639 s640 d641 n642 n643 h644 k645
k645 s646 d647 h648 n649 h650 k651
k669 s670 d671 h672 n673 h674 k675
k675 s676 d677 h678 n679 h680 k681
k681 s682 d683 n684 n685 h686 k687
k687 s688 d689 s690 n691 h692 k693
k693 s694 d695 s696 n697 h698 k699
k699 s700 d701 h702 n703 h704 k705 k723 s724 d725 h726 n727 h728 k729
k729 s730 d731 n732 n733 h734 k735
k735 s736 d737 s738 n739 h740 k741
k741 s742 d743 s744 n745 h746 k747
k747 s748 d749 h750 n751 h752 k753
k777 s778 d779 h780 n781 h782 k783
k783 s784 d785 n786 n787 h788 k789
k789 s790 d791 s792 n793 h794 k795
k795 s796 d797 s798 n799 h800 k801
k801 s802 d803 s804 n805 h806 k807

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

| | | | | | | |
|---|---|---|---|---|---|---|
| k807 | s808 | d809 | h810 | n811 | h812 | k813 |
| k825 | s826 | d827 | n828 | n829 | h830 | k831 |
| k831 | s832 | d833 | h834 | n835 | h836 | k837 |
| k837 | s838 | d839 | n840 | n841 | h842 | k843 |
| k843 | s844 | d845 | h846 | n847 | h848 | k849 |
| k849 | s850 | d851 | s852 | n853 | h854 | k855 |
| k855 | s856 | d857 | s858 | n859 | h860 | k861 |
| k861 | s862 | d863 | s864 | n865 | h866 | k867 |
| k867 | s868 | d869 | s870 | n871 | h872 | k873 |
| k873 | s874 | d875 | n876 | n877 | h878 | k879 |
| k897 | s898 | d899 | h900 | n901 | h902 | k903 |
| k903 | s904 | d905 | h906 | n907 | h908 | k909 |
| k909 | s910 | d911 | n912 | n913 | h914 | k915 |
| k915 | s916 | d917 | n918 | n919 | h920 | k921 |
| k921 | s922 | d923 | h924 | n925 | h926 | k927 |

Table 10, line 18 (columns 73-74),

“htyvkgkkapsdpqca dikeeckeilkek (SEQ ID NO. 304)” should be changed to

--htyvkgkkapsdpqcadikeeckellkek (SEQ ID NO. 304)--;

Table 10, line 31 (columns 73-74),

“ksannsanngkknnaeeniknlvnflqshkkikalkkniesiqnkkh (SEQ ID NO. 317)”

should be changed to

--ksannsanngkknnaeemknlvnflqshkklikalkkniesiqnkkh (SEQ ID NO. 317)--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 10, line 89 (columns 75-76),
“hlisgdadvlssalgmdeeqmktrkkaqrpk (SEQ ID NO. 374)” should be changed to
--hiisgdadvlssalgmdeeqmktrkkaqrpk (SEQ ID NO. 374)--;

Table 10, line 150 (columns 75-76),
“bknnedik (SEQ ID NO. 433)” should be changed to
--hknnedik (SEQ ID NO. 433)--;

Table 10, line 202 (columns 77-78),
“hgqikiedvnnenfhneqmknkyndeekmdisk (SEQ ID NO. 485)” should be changed to
--hgqikiedvrnnenfnneqmknkyndeekmdisk (SEQ ID NO. 485)--;

Table 10, line 216 (columns 77-78),
“kpclykkckisqvwwcmpvkdtfhtyernnvlnskienniekiph (SEQ ID NO. 499)” should be changed to
--kpclykkckisqvwwcmpvkdtfntyernnvlnskienniekiph (SEQ ID NO. 499)--;

Table 10, line 217 (columns 77-78),
“kckisqvwwcmpvkdtfhtyemnvlnskienniekiph (SEQ ID NO. 500)” should be changed to
--kckisqvwwcmpvkdtfntyernnvlnskienniekiph (SEQ ID NO. 500)--;

UNITED STATES PATENT AND TRADEMARK OFFICE

CERTIFICATE OF CORRECTION

PATENT NO. : 7,442,761 B2
APPLICATION NO. : 10/860050
DATED : October 28, 2008
INVENTOR(S) : Bogoch et al.

It is certified that error appears in the above-identified patent and that said Letters Patent is hereby corrected as shown below:

Table 10, line 250 (columns 77-78),
“hnnhniqiykdkrinfminphk (SEQ ID NO. 533)” should be changed to
--hnnhniqiykdkrinfmnphk (SEQ ID NO. 533)--;

Column 84, line 40, “immuneforming” should be changed to
--immume-forming--; and
Column 89, line 27, “Opapnica” should be changed to --(japonica--.

Signed and Sealed this

Tenth Day of November, 2009

David J. Kappos
*Director of the United States Patent and Trademark Office*